(12) United States Patent
Wessjohann et al.

(10) Patent No.: US 8,865,863 B2
(45) Date of Patent: Oct. 21, 2014

(54) MCR DENDRIMERS

(75) Inventors: Ludger A. Wessjohann, Halle (DE); Michael Henze, Freiburg (DE); Oliver Kreye, Königsback (DE); Daniel Garcia Rivera, Playa Ciudad Habana (CU)

(73) Assignee: Leibniz-Institut fur Pflandzenbiochemie, Halle (Saale) (DE)

( * ) Notice: Subject to any disclaimer, the term of this patent is extended or adjusted under 35 U.S.C. 154(b) by 118 days.

(21) Appl. No.: 13/695,053

(22) PCT Filed: Apr. 14, 2011

(86) PCT No.: PCT/EP2011/001905
§ 371 (c)(1),
(2), (4) Date: Apr. 15, 2013

(87) PCT Pub. No.: WO2011/134607
PCT Pub. Date: Nov. 3, 2011

(65) Prior Publication Data
US 2013/0203960 A1  Aug. 8, 2013

(30) Foreign Application Priority Data
Apr. 30, 2010  (DE) .......................... 10 2010 018 882

(51) Int. Cl.
C07K 1/06 (2006.01)
C07K 14/00 (2006.01)
C07K 5/02 (2006.01)
C07K 5/062 (2006.01)
C08G 83/00 (2006.01)
A61K 38/00 (2006.01)

(52) U.S. Cl.
CPC .............. C07K 1/061 (2013.01); A61K 38/00 (2013.01); C07K 14/001 (2013.01); C07K 5/0202 (2013.01); C07K 5/06069 (2013.01); C08G 83/003 (2013.01)

USPC .......................................... 530/300; 530/335

(58) Field of Classification Search
CPC .................. C12Q 2537/157; C12Q 2565/632; C07K 16/2863; C07K 1/061
See application file for complete search history.

(56) References Cited

FOREIGN PATENT DOCUMENTS

WO    WO 2006/105043 A2 * 10/2006 ............. A61K 48/00

OTHER PUBLICATIONS

Ivar Ugi. Recent progress in the chemistry of multicomponent reactions. Pure Appl. Chem., vol. 73, No. 1, pp. 187-191, 2001.*
International Search Report and Written Opinion dated Jul. 27, 2011, for corresponding International Patent Application No. PCT/EP2011/001905.
International Preliminary Report on Patentability dated Nov. 6, 2012, for corresponding International Patent Application No. PCT/EP2011/001905.
Izabela Bury, et al.: "Interfacial Behavior of a Series of Amphiphilic Block Co-dendrimers", Langemuir, American Chemical Society, Jan. 1, 2007, vol. 23, No. 2, pp. 619-625.

(Continued)

Primary Examiner — Karlheinz R Skowronek
Assistant Examiner — Jia-Hai Lee
(74) Attorney, Agent, or Firm — Pergamant Gilman & Cepeda LLP; Milagros A. Cepeda; Edward D. Pergament

(57) ABSTRACT

The invention relates to a method for producing peptoidic, peptidic and chimeric peptidic-peptoidic dendrimers by multiple iterative multi-component reactions (MCR), in particular Ugi or Passerini multi-component reactions, to compounds produced in this way and to the use thereof.

14 Claims, 38 Drawing Sheets

(56) References Cited

OTHER PUBLICATIONS

Nachiket S Dighe, et al.: "Covergent synthesis: A strategy to synthesize compounds of biological interest", Pharmacia Lettre, 2010, vol. 2, No. 1, Issn: 0974-248X, pp. 318-328.

Oliver Kreye: "Zyklisierende und verzweigte mehrfache Ugi-Reaktionen", 2009, Retrieved from the Internet: URL: http://nbn-resolving.de/urn:nbn:de:gbv:3:4-2618.

Oliver Kreye: "Zyklisierende und verzweigte mehrfache Ugi-Reaktionen", 2009, Retrieved from the internet: URL: http://nbn-resolving.de/urn:nbn:de:gbv:3:4-2618, English Translation of Abstract.

Oleg Lukin, et al.: "Designer Dendrimers: Branched Oligosulfonimides with Controllable Molecular Architectures", Journal of the American Chemical Society, Jul. 1, 2006, vol. 128, No. 27, Issn: 0002-7863, pp. 8964-8974.

Daniel G. Rivera, et al.: "Architectural Chemistry: Synthesis of Topologically Diverse Macromulticycles by Sequential Multiple Multicomponent Macrocyclizations", Journal of the American Chemical Society, Mar. 18, 2009, vol. 131, No. 10, Issn: 0002-7863, pp. 3721-3732.

\* cited by examiner

| 1st generation (protected) | 1st generation (functionalized) |
|---|---|
|  |  |

1st generation (protected)

1st generation (functionalized)

| 1st generation (protected) | 1st generation (functionalized) |
|---|---|
|  | |

Figure 5 continued

3rd generation (functionalized)

MCR DENDRIMERS

This application is a National Stage Application under U.S.C. §371 of PCT International Application No. PCT/EP2011/001905 filed Apr. 14, 2011, which claims priority to DE 10 2010 018 882.4, filed on Apr. 30, 2010; both of which are hereby incorporated herein by reference in their entirety.

BACKGROUND

The present invention relates to a process for preparing peptoidic, peptidic and chimeric peptide-peptoidic dendrimers by multiple iterative multicomponent reactions (MCRs), especially UGI or PASSERINI multicomponent reactions, to compounds thus obtained and to their use.

Dendrimers are supramolecular, branched architectures of well-defined molecular weight. These molecules branch outwardly from multifunctional core units to form more or less regular three-dimensional shells, the peripheral end groups of which form the surface (cf. FIG. 1). Having a high degree of molecular uniformity, low polydispersity and properties making them attractive materials for the developments in nanomedicine in particular, dendrimers are very interesting in many respects. The high diversity and molecular sizes achievable with this method exceed previously known techniques and their possibilities. Dendrimers show potential for use in targeting, for example, as contrast media, coating, drug display, drug delivery, light-harvesting or energy transfer, and for use in nanobiosystems.

The most common and simple method of constructing dendrimers employs so-called divergent methods of synthesis. This refers to the construction strategy which starts with the core unit and produces the dendrimer in a synthesis "from in to out". Divergent syntheses are generally simple to do and therefore are employed with preference. Yet there is one immense disadvantage in that complete reactions are often impossible in higher generations due to steric hindrances, resulting in the formation of so-called "mistakes". The product mixtures obtained are then difficult to purify by chromatography. There are also convergent syntheses, wherein the dendrimers are constructed "from out to in". Although convergent syntheses are less common than divergent syntheses, this strategy does have certain advantages. The formation of "mistakes" is minimized and the dendrons produced are easier to purify. However, one disadvantage consists in the binding of dendrons to core units, which is frequently unsuccessful owing to steric hindrance.

Divergent and convergent syntheses aside, there are also more recent methods in existence, such as orthogonal synthesis, the convergent two-step method, the doubly exponential method, solid-phase synthesis and also coordination-chemical synthesis.

The syntheses mentioned all have the disadvantage of minimal scope for variation in constructing the dendrimers, since the reagents used, such as acrylonitrile, acrylic esters and dihydroxybenzyl alcohols for example, cannot be modified in their basic structure owing to their chemical reaction characteristics.

SUMMARY

Based on these monotonous/problematical strategies of construction, the present invention has for its object to synthesize designable, highly varied and flexible dendrimers by multicomponent reactions which by producing high diversity have appreciable advantages over the standard methods mentioned.

This object is achieved by the embodiments characterized in the claims.

DETAILED DESCRIPTION

The present invention more particularly provides a process for preparing chimeric peptide-peptoidic dendrimers, including peptoid, peptidic and depsipeptoidic dendrimers, by multiple iterative multicomponent reactions, especially UGI and PASSERINI multicomponent reactions.

The process of the present invention comprises reacting a polyfunctionalized core unit with two to six further components which each have different functionalities with different reactivities or protective groups, wherein this multicomponent reaction leads to a branched compound by reactively branching the 3 to 7 components,
activating the less reactive functionalities and/or deprotecting the protective groups to generate a functionalized first generation of a branched dendrimer,
reacting the functionalized first generation of the branched dendrimer with further components which each have different functionalities with different reactivities or protective groups, wherein this multicomponent reaction leads to a subsequent branched compound by reactively branching the 3 to 7 components, and
iteratively repeating the aforementioned steps to obtain peptide-peptoidic dendrimers of higher generations.

A preferred embodiment of the present process according to the invention employs UGI and/or PASSERINI multicomponent reactions wherein the polyfunctionalized core unit has UGI-reactive functionalities and is reacted with bifunctional components which each have a first UGI-reactive functionality and a second terminal UGI-reactive functionality which is in protected form (PURG, protected UGI-reactive group) in a UGI or PASSERINI multicomponent reaction, wherein the second protected UGI-reactive functionality is activable after the reaction by deprotecting the PURGs back to UGI-reactive groups.

UGI multicomponent reactions (hereinafter abbreviated as UGI-4CR) are based on four-component reactions of synthons which each have an UGI-reactive group (URG) from reactive groupings such as isonitriles, carboxylic acids, primary amines or oxo groups, such as aldehyde groups or keto groups, and generate N-branched dipeptide (peptide-peptoid) units. In the case of PASSERINI reactions, the amino component is omitted, and a three-component reaction produces a depsipeptide unit. For the purposes of the present invention, UGI-4CRs include PASSERINI reactions.

Figure 1:
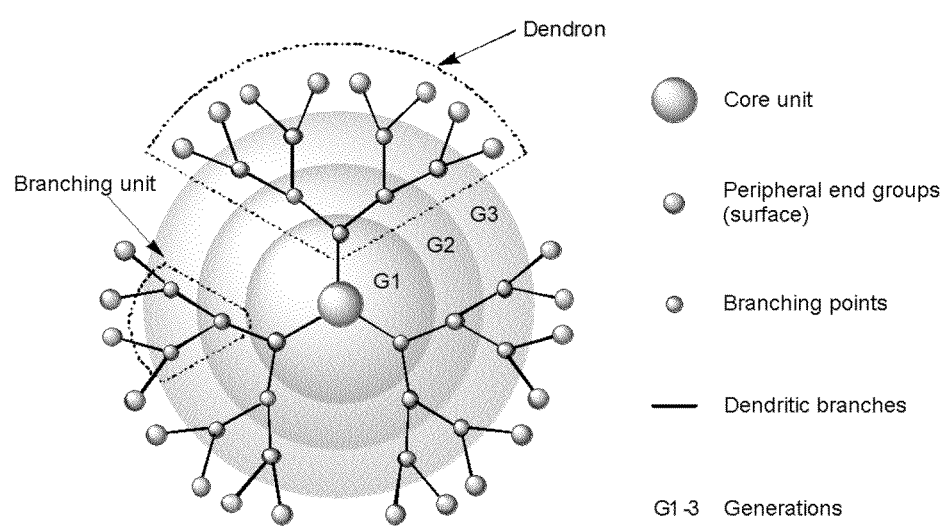
FIG. 1 shows the structural built-up of dendrimers.
Figure 2:
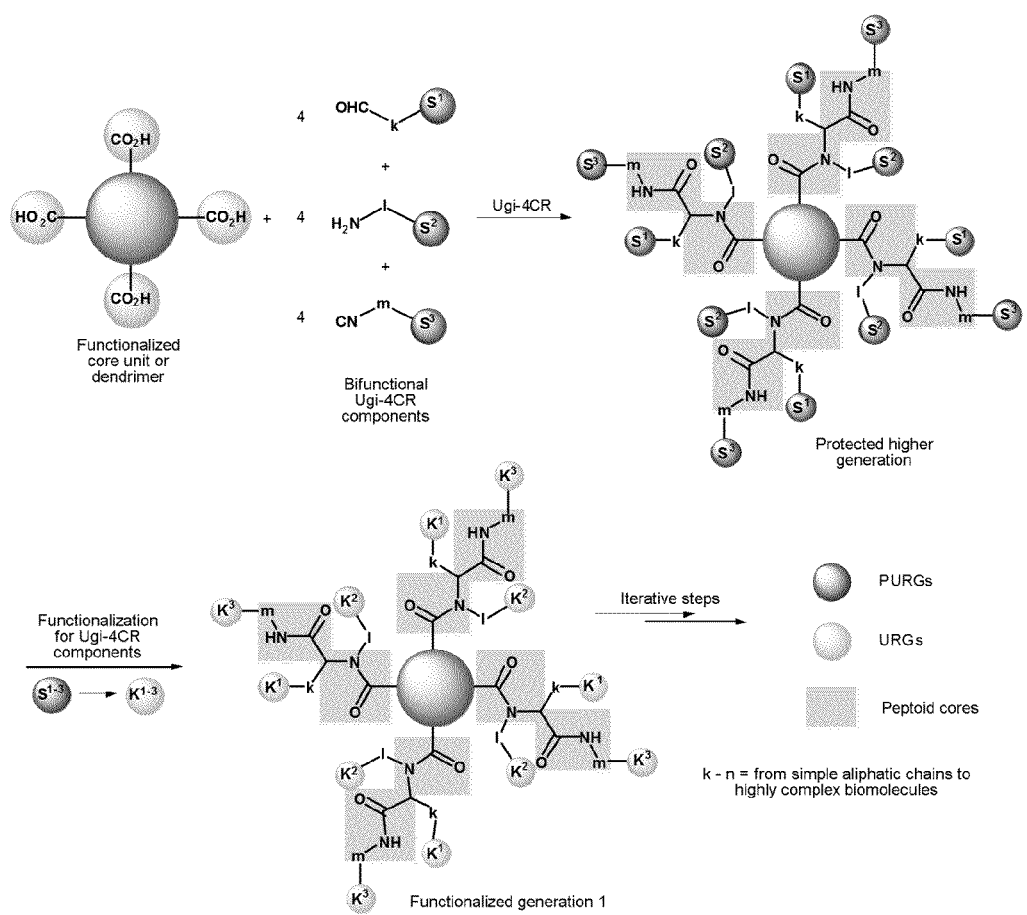
FIG. 2 shows the process according to the present invention in a simplified manner.

The process of the present invention is depicted in simplified form in FIG. 2, where by way of example a tetracarboxylic acid core unit undergoes a fourfold UGI-4CR with bifunctional isonitriles, primary amines and aldehydes to generate the branching. Subsequent activation of protected functionalities finally affords the up to threefold number of functional groups of the first generation, which in turn are capable of forming a highly branched second generation in UGI-4CRs.

However, the process of the present invention is not, as shown in FIG. 2, limited to the core unit having carboxylic acid groups as URGs; instead the core unit can also have some other URG.

The process of the present invention preferably utilizes monoprotected bifunctional synthons constructed from different organic moieties (k, l, m and n) to construct α-aminoacylamide units which makes it possible to produce an unending diversity of products. A UGI (4CR) four-component reaction is concerned here in that an amine derivative, a carbonyl component (aldehyde or ketone), a carboxylic acid (or other Ugi-reactive acids such as $HN_3$ or acidic phenols) and an isocyanide derivative (also called isonitriles) react to form α-aminoacylamide derivatives. The organic moieties may be simple aliphatic chains as well as functionalized chains through to highly complex biomolecules. Decisively, there are no further reactive groupings likewise capable of reacting in UGI-4CRs.

The process of the present invention allows the use of bifunctional synthons comprising PURGs, wherein any groupings can be used as protected function (PURG, S) which can be converted into URGs in simple reactions. Possible functionalizations and methods therefor are shown below in table 1.

The reaction procedure involved in the process according to the present invention can be engineered such that the synthesis can be carried out not only in solution but also in solid phase. The inevitable escalation which results therefrom to a high degree of automation and is obvious to a person skilled in the art is an essential characteristic of the process according to the present invention.

TABLE 1

| S PURG | F URG | Possibilities and conditions |
|---|---|---|
| —$CO_2$PG | —$CO_2$H | cleaving of ester functions ($CO_2$Me, $CO_2$Et, $CO_2$t-Bu, $CO_2$Bn, $CO_2$All, etc.) under different conditions (acidic, basic, reductive, catalytic, enzymatic etc.) |
| —CO—NH—PG | —$CO_2$H | hydrolysis of amides, preferably indolylamides under weak basic conditions |
| —$CH_2$OH or | —$CO_2$H or | oxidation of primary alcohols to |

TABLE 1-continued

| S PURG | F URG | Possibilities and conditions |
|---|---|---|
| —$CH_2$O—PG | —CHO | aldehydes or carboxylic acids in various ways |
| —CH(OR)$_2$ | —CHO | cleaving of acetals to aldehydes under acidic conditions (ketals/ketones analogously) |
| —NH—CHO | —NC | conversion of formamides into isonitriles with water-withdrawing reagents under base influence |
| —NH—PG | —$NH_2$ | detachment of amino protective groups (Boc, Cbz, Fmoc, Alloc, etc.) under different conditions (acidic, basic, reductive, catalytic, etc.) |
| —$N_3$ or —$NO_2$ | —$NH_2$ | reduction of azides or nitro compounds to primary amines by various methods |
| —CN | —$CH_2NH_2$ | reduction of nitriles to primary amines |

Functional groups useful in the context of the present invention are listed hereinbelow by way of example on/in Ugi dendrimers (UBU=UGI-type branching unit; peptoid-peptide branching element formed in a UGI reaction).

Carboxylic Acids/Carboxylic Esters:

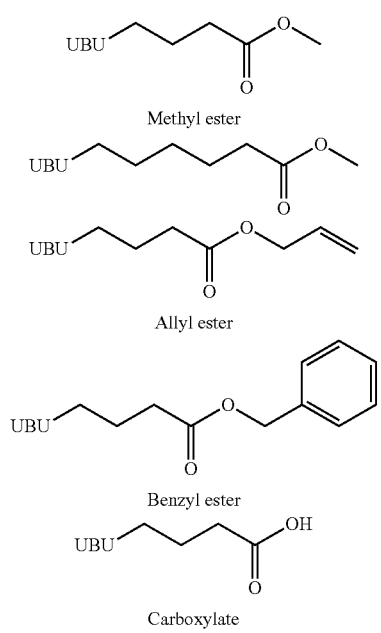

Methyl ester

Allyl ester

Benzyl ester

Carboxylate

Amines/Protected Amines:

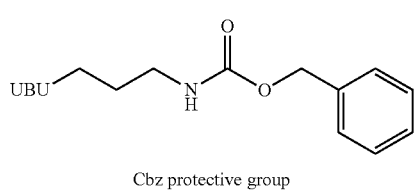

Cbz protective group

5

-continued

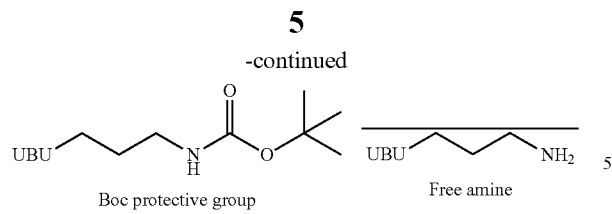

Boc protective group | Free amine

Thiols:

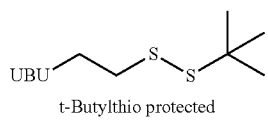

t-Butylthio protected

Alcohols:

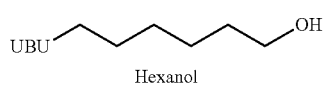

Hexanol

Aromatics:

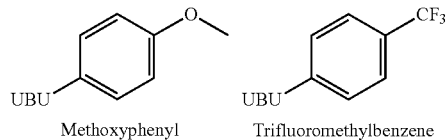

Methoxyphenyl | Trifluoromethylbenzene

Alkyl Chains:

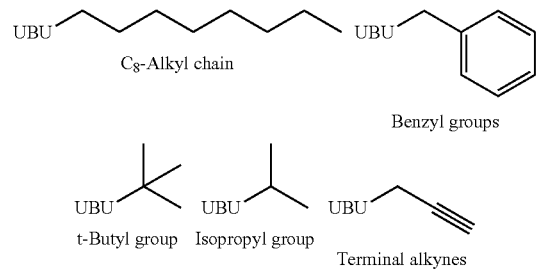

$C_8$-Alkyl chain | Benzyl groups t-Butyl group | Isopropyl group | Terminal alkynes Sugar Derivatives:

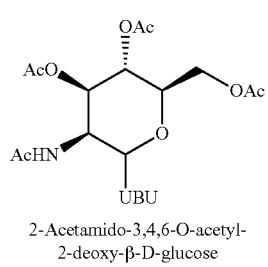

2-Acetamido-3,4,6-O-acetyl-
2-deoxy-β-D-glucose

6

-continued

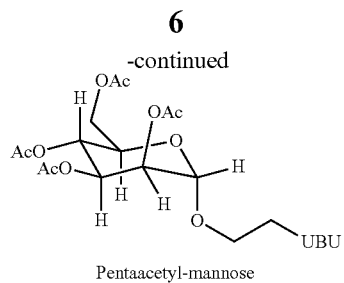

Pentaacetyl-mannose

PEG Units:

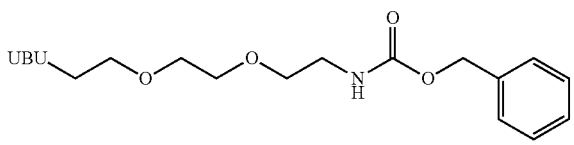

Convertible Isocyanide Precursor:

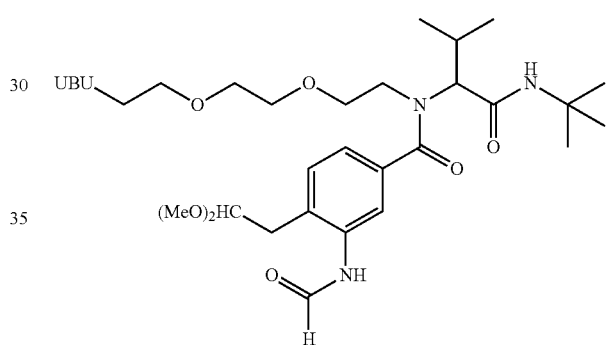

Protected Amino Acids:

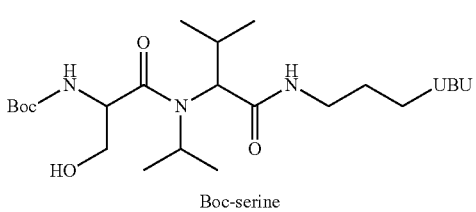

Boc-serine

Dopamine Derivatives:

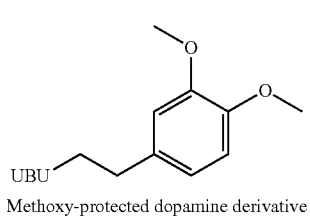

Methoxy-protected dopamine derivative

Fluorescent Dyes:

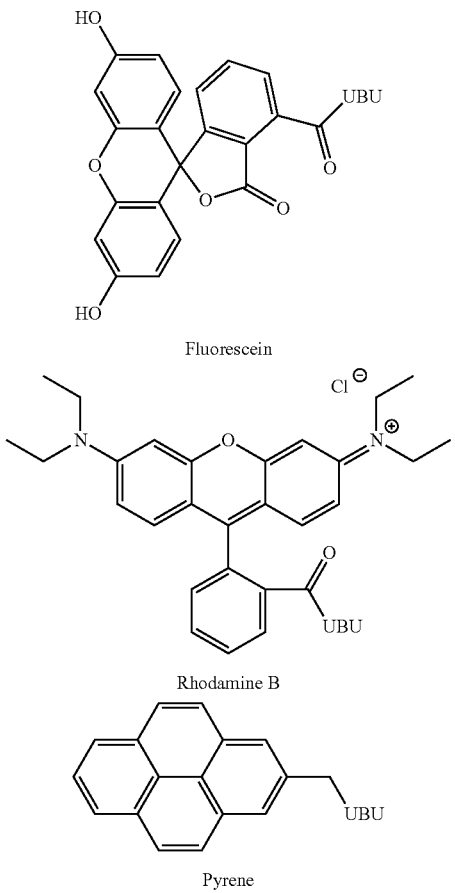

Fluorescein

Rhodamine B

Pyrene

Exemplary components for the UGI dendrimer synthesis as per the present invention are as follows:

Protective groups (PG)/precursor groups for PURG (similarly also protective groups for FG (functional unit)/NBU (nonbranching unit))

Ester Protective Groups for Carboxyl Functions:

methyl, ethyl, n-propyl, isopropyl, n-butyl, isobutyl, methoxymethyl, methylthiomethyl, tetrahydropyranyl, benzyloxymethyl, phenacyl, N-phthalimidomethyl, 2,2,2-trichloroethyl, 2-haloethyl, 2-(p-toluene-4-sulfonyl)-ethyl, tert-butyl, cinnamyl, benzyl, triphenylmethyl(trityl), bis(o-nitrophenyl)methyl, 9-anthrylmethyl, 2-(9,10-dioxo) anthrylmethyl, piperonyl, trimethylsilyl, 4-nitrobenzyl, 4-methoxybenzyl, pyridyl-4-methyl (4-picolyl), 4-methoxyphenacyl, diphenylmethyl(benzhydryl), cyclohexyl, 9-fluorenylmethyl, 1-adamantyl, 2-adamantyl, allyl, dicyclopropylmethyl, tert-butyldimethylsilyl esters.

Amides and Hydrazides as Protective Group for the Carboxyl Function:

indolylamides and precursors thereof, e.g. N-[2-(2',2'-dialkoxyethyl)phenyl], cyclohexenyl among others, which according to (*Synlett* 2007, 3188-3192) emanate from so-called convertible isonitriles, N,N-dimethylamide, N-7-nitroindolylamides, hydrazide, N-phenylhydrazide, N,N'-diisopropylhydrazide.

Amino Protective Groups of the Urethane Type:

benzyloxycarbonyl (Z or Cbz), tert-butyloxycarbonyl (Boc), fluorenyl-9-methoxycarbonyl (Fmoc), 4-methoxybenzyloxycarbonyl, 2, 3 and 4-nitrobenzyloxycarbonyl, 2, 3 and 4-chlorobenzyloxycarbonyl, 3,5-dimethoxybenzyloxycarbonyl, α,α-dimethyl-3,5-dimethoxybenzyloxycarbonyl, 2-nitro-4,5-dimethoxybenzyloxycarbonyl (6-nitroveratryloxycarbonyl), furyl-2-methoxycarbonyl(furfuryloxycarbonyl), 2-(4-tolylsulfonyl)ethoxycarbonyl, 4-phenylazobenzyloxycarbonyl, 2-iodoethoxycarbonyl, 2-cyano-tert-butyloxycarbonyl, 2,2,2-trichloro-tert-butyloxycarbonyl, isonicotinyloxycarbonyl, tert-amyloxycarbonyl, adamantyl-1-oxycarbonyl, 1-(1-adamantyl)-1-methylethoxycarbonyl, isobornyloxycarbonyl, 2-[biphenyl-(4)]-propyl-2-oxycarbonyl, piperidinooxycarbonyl, cyclopentyloxycarbonyl, α-methyl-2,4,5-trimethylbenzyloxycarbonyl, 5-benzisoxazolylmethyloxycarbonyl, (4-phenylazophenyl)isopropyloxycarbonyl, methyloxycarbonyl, 2,2,2-trichloroethyloxycarbonyl, 2-trimethylsilylethyloxycarbonyl, 1,1-dimethylpropynyloxycarbonyl, 1-methyl-1-phenylethyloxycarbonyl, 1-methyl-1-(4-biphenyl)ethyloxycarbonyl, 1,1-dimethyl-2-haloethyloxycarbonyl, 1,1-dimethyl-2-cyanoethyloxycarbonyl, cyclobutyloxycarbonyl, 1-methylcyclobutyloxycarbonyl, vinyloxycarbonyl, allyloxycarbonyl, cinnamyloxycarbonyl, 8-quinolyloxycarbonyl, N-hydroxypiperidinyloxycarbonyl, 2,4-dichlorobenzyloxycarbonyl, 9-anthrylmethyloxycarbonyl, 2-[4-(methylsulfonyl)phenylsulfonyl]ethyloxycarbonyl, 2,2-bis(4'-nitrophenyl)ethyloxycarbonyl, 2-(2,4-dinitrophenyl) ethyloxycarbonyl, methylsulfonylethyloxycarbonyl, diphenylmethyloxycarbonyl protective groups.

Amides as Amino Protective Groups:

N-formyl, N-acetyl, N-chloroacetyl, N-trichloroacetyl, N-trifluoroacetyl, N-o-nitrophenylacetyl, N-o-nitrophenoxyacetyl, N-acetoacetyl, N-3-phenylpropionyl, N-3-(p-hydroxyphenyl)propionyl, N-3-methyl(o-nitrophenoxy)propionyl, N-2-methyl-2-(o-phenylazophenoxy)propionyl, N-4-chlorobutyryl, N-o-nitrocinnamoyl, N-picolinoyl, N-(N'-acetylmethionyl), N-benzoyl, N-phthaloyl, N-dithiasuccinoyl protective groups.

Special Amino Protective Groups:

N-allyl, N-phenacyl, N-3-acetoxypropyl, N-methoxymethyl, N-benzyloxymethyl, N-pivaloyloxymethyl, N-tetrahydropyranyl, N-2,4-dinitrophenyl, N-benzyl, N-o-nitrobenzyl, N-di(p-methoxyphenyl)methyl, N-triphenylmethyl(N-trityl), N-(p-methoxyphenyl)diphenylmethyl, N-diphenyl-4-pyridylmethyl, N-2-picolyl-N'-oxide, N,N'-isopropylidene, N-benzylidene, N-p-nitrobenzylidene, N-salicylidene, N-(5,5-dimethyl-3-oxo-1-cyclohexenyl), N-nitro, N-oxide, N-diphenylphosphinyl, N-dimethylthiophosphinyl, N-benzenesulfonyl, N-o-nitrobenzenesulfonyl, N-toluenesulfonyl (N-tosyl), N-benzylsulfonyl, N-trifluoromethylsulfonyl, N-phenacylsulfonyl protective groups and the protection of amino groups as quaternary ammonium salts.

Protective Groups for Carbonyl Functions (Aldehydes and Ketones):

dialkyl, bis(2,2,2-trichloroethyl), S,O- and S,S'-dialkyl acetyls and ketals, 1,3-dioxane, 5-methylene-1,3-dioxane, 5,5-dibromo-1,3-dioxane, 1,3-dioxolane, 4-bromomethyl-1,3-dioxolane, 4-o-nitrophenyl-1,3-dioxolane, 1,3-dithiane, 1,3-dithiolane, 1,3-oxathiolane, O-trimethylsilylcyanohydrin, N,N-dimethylhydrazone, 2,4-dinitrophenylhydrazone, O-phenylthiomethyloxime, substituted methylene derivatives, bismethylenedioxo derivatives.

Groups Convertible into Isonitrile:
N-formamide, N-formamide orthoester

Groups Convertible with CN Reagents into an Isonitrile:
—Cl, —Br, —I, OTs, O-Ms, —O-TFA, epoxide Further Protective Groups (PGs)

Many other functional groups in general rarely need protection in UGI reactions. However, specific functionalization reactions may necessitate some protection, for example for the hydroxyl function or sulfhydryl group.

Protection of Hydroxyl Groups as Ethers:

methyl, methoxymethyl (MOM), methylthiomethyl (MTM), 2-methoxyethoxymethyl (MEM), bis(2-chloroethoxy)methyl, tetrahydropyranyl (THP), tetrahydrothiopyranyl, 4-methoxytetrahydropyranyl, 4-methoxytetrahydrothiopyranyl, tetrahydrofuranyl, tetrahydrothiofuranyl, 1-ethoxyethyl, 1-methyl-1-methoxyethyl, 2-(phenylselenyl)ethyl, tert-butyl, allyl, benzyl, o-nitrobenzyl, triphenylmethyl (trityl), α-naphthyldiphenylmethyl, p-methoxyphenyldiphenylmethyl, 9-(9-phenyl-10-oxo)anthryl, trimethylsilyl (TMS), isopropyldimethylsilyl, tert-butyldimethylsilyl (TBDMS), tert-butyldiphenylsilyl, tribenzylsilyl, triisopropyl silyl ethers.

Protection of Hydroxyl Groups as Esters:

formate, acetate, trichloroacetate, phenoxyacetate, isobutyrate, pivaloate, adamantoate, benzoate, 2,4,6-trimethylbenzoate (mesitoate), methylcarbonate, 2,2,2-trichloroethylcarbonate, allylcarbonate, p-nitrophenylcarbonate, benzylcarbonate, p-nitrobenzylcarbonate, S-benzylthiocarbonate, N-phenylcarbonate, nitrate, 2,4-dinitrophenylsulfenate.

Examples of FGs, NBUs, that are Relevant to the Properties of Polymers:

Biomolecules and natural products such as peptides, lipids, saccharides, steroids, nucleotides, terpenes and alkaloids may also be synthons for dendrimer synthesis. Since complete recitation of all possible organic moities is not possible, some examples will be presented at this point.

Alkyl:

Saturated disubstituted hydrocarbon-derived radicals (alkyl radicals): methyl, ethyl, n-propyl, isopropyl, n-butyl, sec-butyl, tert-butyl, n-pentyl and isomeric pentyl radicals (e.g., neopentyl radicals), n-hexyl radicals and isomeric structures, n-heptyl and isomeric structures, n-octyl and isomeric structures, n-nonyl and isomeric structures, n-decyl and isomeric structures, $C_{11}$ to $C_{>100}$ chains (linear and branched)

Alkenyl and Alkynyl Radicals and Polyunsaturated Hydrocarbon-Derived Radicals (Dienes, Trienes, Polyenes, Diynes, Triynes and Polyines May be Cumulated, Conjugated and Isolated):

Ethenyl (vinyl), propenyl (allyl), 1-butenyl, 2-butenyl, isobutenyl (2-methylpropenyl), 1-pentenyl, 2-pentenyl, 3-pentenyl and isomeric structures, linear and branched hexenyl radicals, linear and branched heptenyl radicals, linear and branched octenyl radicals, linear and branched nonenyl radicals, linear and branched deceenyl radicals, $C_{11}$ to $C_{>100}$ chains (linear and branched), ethynyl, propynyl (propargyl), 1-butynyl, 2-butynyl, linear and branched pentynyl radicals, linear and branched hexynyl radicals, linear and branched heptynyl radicals, linear and branched octynyl radicals, linear and branched nonynyl radicals, linear and branched dodecynyl radicals, $C_{11}$ to $C_{>100}$ chains (linear and branched), radicals derived from using $C_{12-22}$ fatty acids having 1-5 double bonds, specifically from stearic acid, oleic acid, linoleic acid, linolenic acid, arachidonic acid, e.g. Z-heptadec-8-enyl from oleic acid as UGI carboxylic acid component, butadienyl, pentadienyl, linear and branched hexadienyl, hexatrienyl, linear and branched heptadienyl, heptatrienyl, linear and branched octadienyl and octatrienyl, octatetraenyl Cyclic Hydrocarbons (Saturated, Unsaturated, Polyunsaturated and Aromatic):

Cyclopropyl, cyclobutyl, cyclopentyl, cyclohexyl, cycloheptyl, cyclooctyl, cyclononyl, cyclo-$C_{10}$ radicals up to macrocyclic systems ($C_{>100}$), cyclopropenyl, cyclobutenyl, cyclopentenyl, cyclohexenyl, cycloheptenyl, cyclooctenyl, cyclononenyl, unsaturated cyclo-$C_{10}$ radicals up to macrocyclic systems ($C_{>100}$), cyclopentadienyl, cyclohexadienyl, cycloheptadienyl, cycloheptatrienyl, cyclooctadienyl, cyclooctatrienyl, cyclooctatetraenyl, mono- and polyunsaturated cyclo-$C_9$ radicals up to macrocyclic systems ($C_{>100}$), bicyclic, disubstituted hydrocarbons such as camphor, camphene, bornane, norbornane, norbornene and spiro compounds, aromatic systems such as disubstituted benzenes, toluenes, naphthalenes, anthracenes, phenanthrenes, pyrenes, chrysenes, fluorenes, indenes, acenaphthenes, azulenes, biphenyls, estradiol, bile acids derived sterols, phytosterols, phytosterans, and many other polycyclic compounds Heterocyclic Systems (Saturated, Unsaturated, Polyunsaturated and Aromatic:

Furans, pyrans, dioxanes, benzofurans, pyrones, chromenes, dibenzofurans, xanthenes, pyrroles, pyrazoles, imidazoles, triazoles, pyridines, pyridazines, pyrimidines, pyrazines, triazines, tetrazoles, indoles, quinolines, isoquinolines, carbazoles, acridines, phenanthridines, indazoles, benzimidazoles, cinnolines, quinazolines, quinoxalines, phenazines, benzocinnolines, phenanthrolines, purines, thiophenes, thiopyrans, benzothiophenes, thioxanthenes, isoxazoles, oxazoles, isothiazoles, thiazoles, benzoxazoles and phenoxazines and many further heterocycles Alcohols and Ethers:

PEG-OH, PEG-OMe, etc.

Sugars, Protected Sugars and Linker-Linked Sugars:

e.g., glucosyl, mannosyl, galactosyl, etc.

glucosylalkyl, mannosylalkyl, etc.

glucosyl-PEGyl, mannosyl-PEGyl, etc.

N-acetylglucoaminyl, N-acetylglucosaminylalkyl, N-acetylglucosaminyl-PEGyl sialyl, sialylalkyl, sialyl-PEGyl Thiols, Sulfides, Disulfides, Selenides and their Oxidation Products (Sulfoxides, Sulfones, Sulfonic Acids, Sulfates), (PG=H, Protective Group):

e.g., —S-PG, —S-alkyl, —S-aryl, —Se—PG, —Se-alkyl, —Se-aryl, —S(=O)alkyl, —$SO_2$-alkyl, —S(=O)aryl, —$SO_2$-aryl, —$SO_3$—PG, —$OSO_3$—PG, —S—S-alkyl, —S—S-aryl.

Dyes (Including Fluorescent Dyes):

e.g., rhodaminyl, fluoresceinyl, cyanine dyes, perylenyl, coumarinyl (including derivatives), BODIPY dyes, etc.

Chelators for Complexing Metal Ions, Specifically Lanthanides for MRT Contrasting (Gd):

EDTA, DOTA, DTPA, etc.

Sidechains and Protected Sidechains of Amino Acids, their Homologous and Nor Compounds, N-Protected or carboxylate-protected amino acids which undergo the UGI Reaction Via the Free Carboxylate or, Respectively, Amino Function (PG=H or One or More Protective Groups—Function Conformed), Comprising for Example:

Cysteine/Cysteine Homologs:

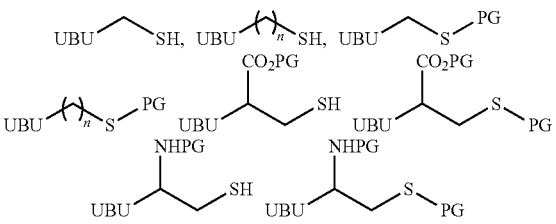

Methionine:
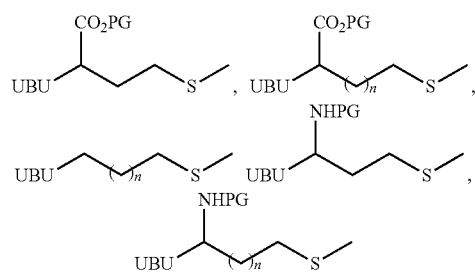
Serine
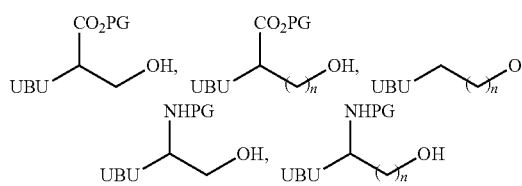
Threonine
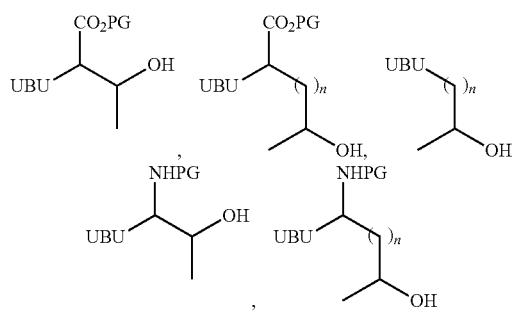
Arginine
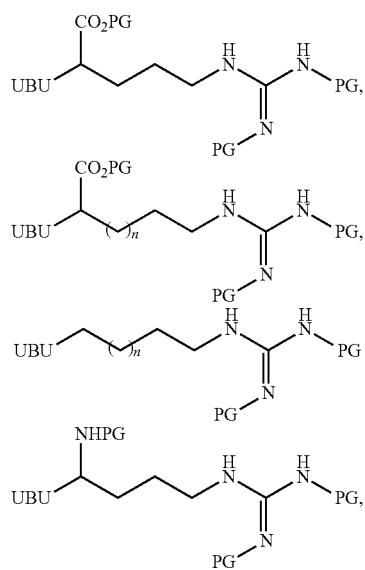
-continued
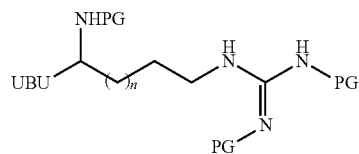
Lysine
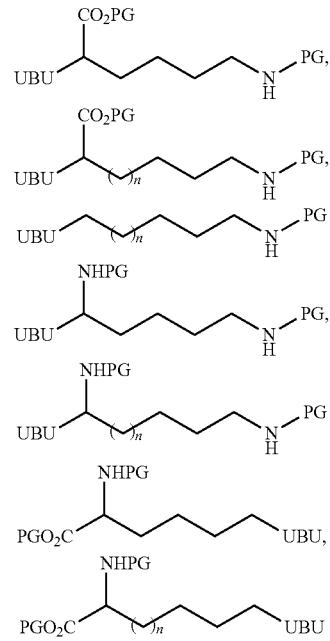
Asparagine
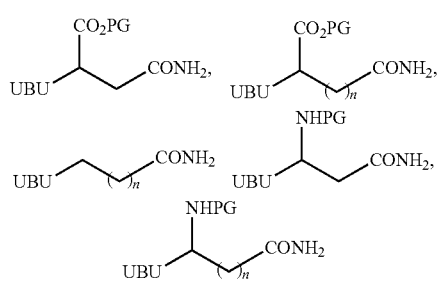
Aspartic Acid
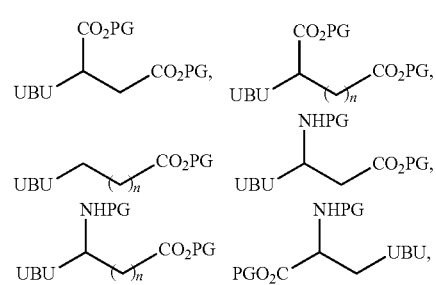

-continued
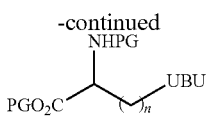
Glutamine
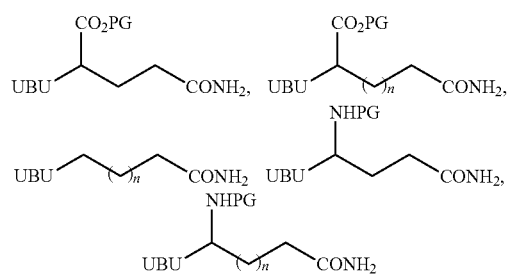
Glutamic Acid
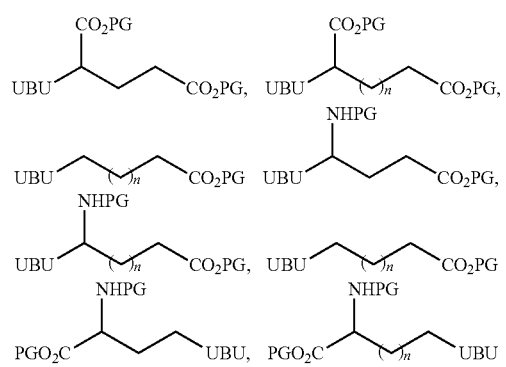
Phenylalanine
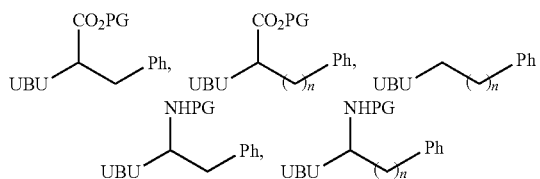
Thyrosine
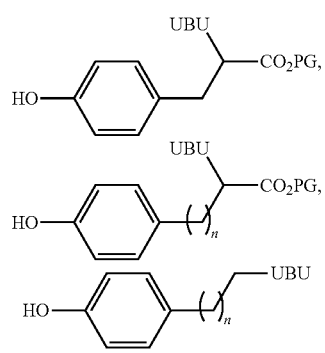
-continued
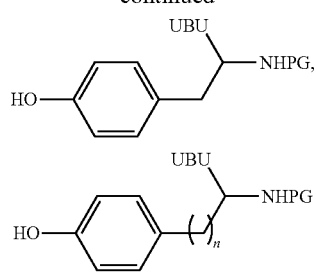
Tryptophan
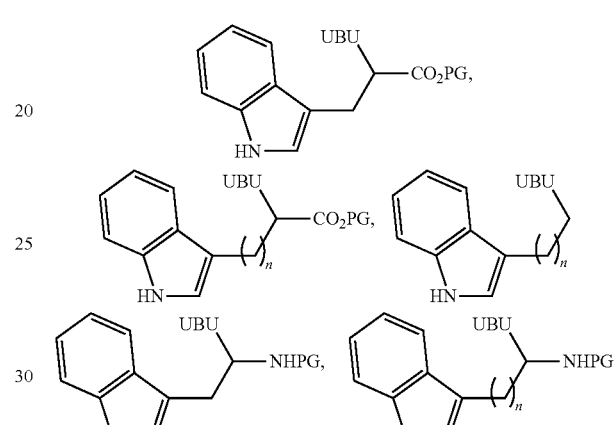
Histidine
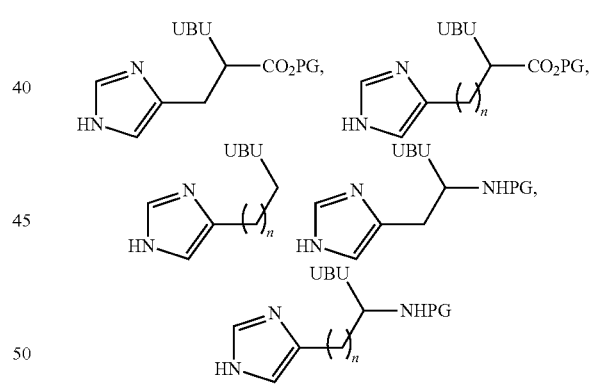
Proline/Hydroxyproline
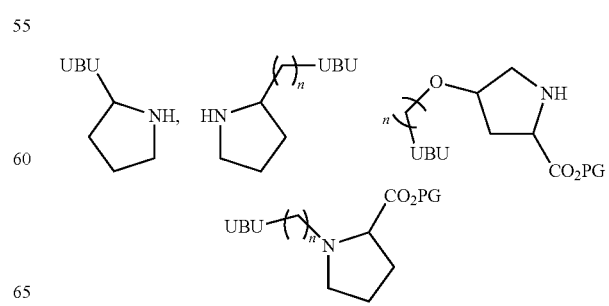

Amino Acids with Alkyl Chains

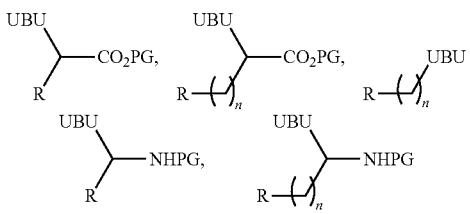

R=—H(glycine), —CH₃(alanine), —CH(CH₃)₂(valine), —CH₂—CH(CH₃)₂(leucine), —CH(CH₃)—CH₂CH₃(isoleucine)

Linkers

Alkylidene groups, arylidene, —PEG-, etc., including especially all synthons listed as FG, as "di-yl"

PEG linkers: n=0, 1, 2, 3 ...

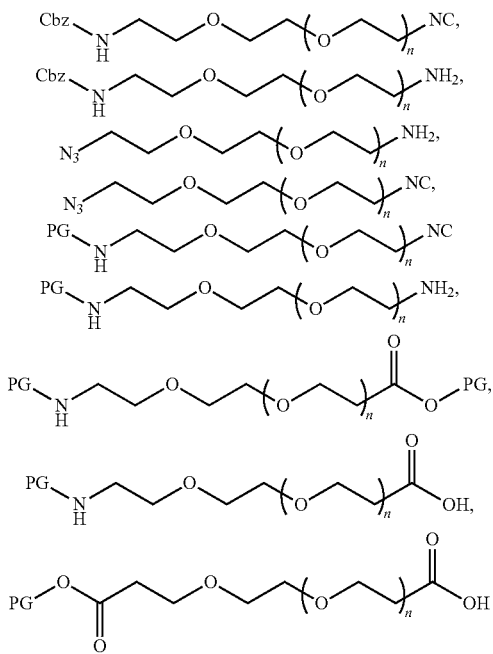

Figure 3:
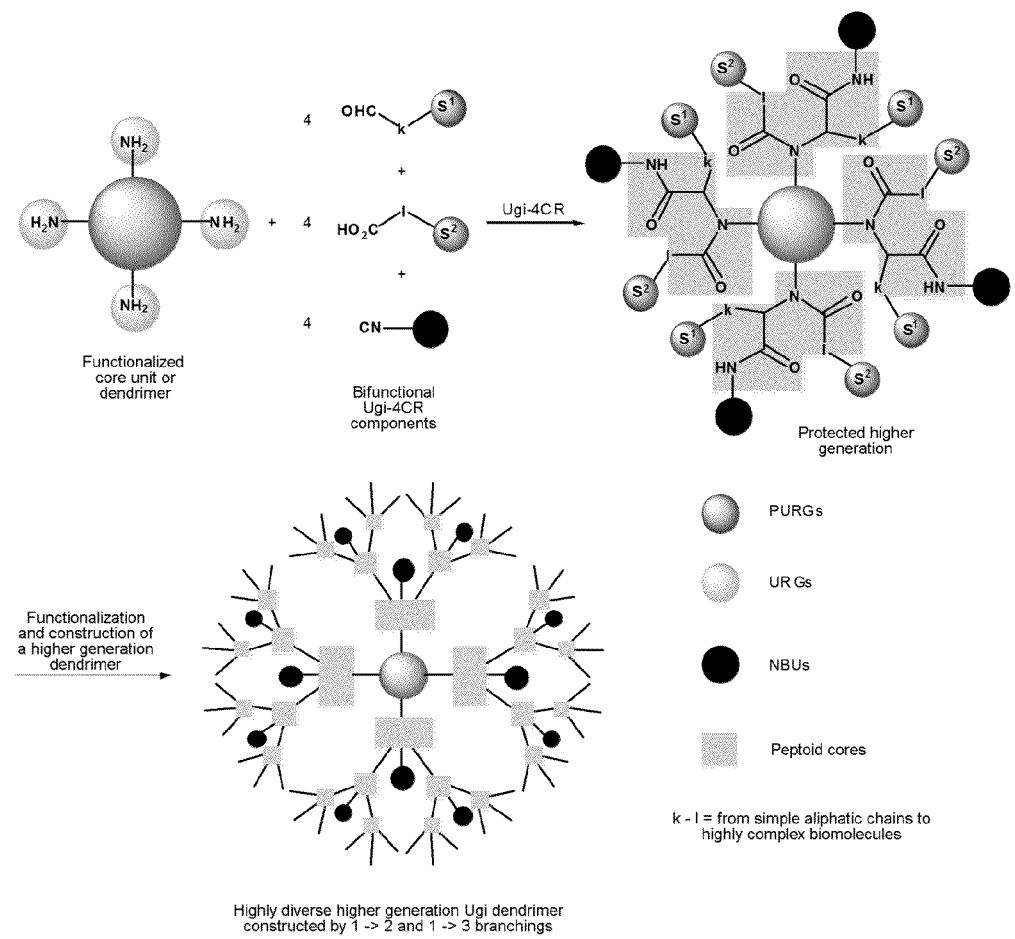
FIG. 3 shows an embodiment of the process according to the present invention using bifunctional synthons comprising a non-branching unit.

In a preferred embodiment, bifunctional synthons used comprise a nonbranching unit (NBU) whereby 1→2 branching or linear prolongation is freely generatable in every generation. Using a variety of NBUs as UGI-4CR components in the process of the present invention makes it possible to influence the peptide-peptoidic structure of the constructed dendrimer. This realization further enhances the diversity in the synthesis of UGI dendrimers considerably, as shown in FIG. 3.

Figure 4:
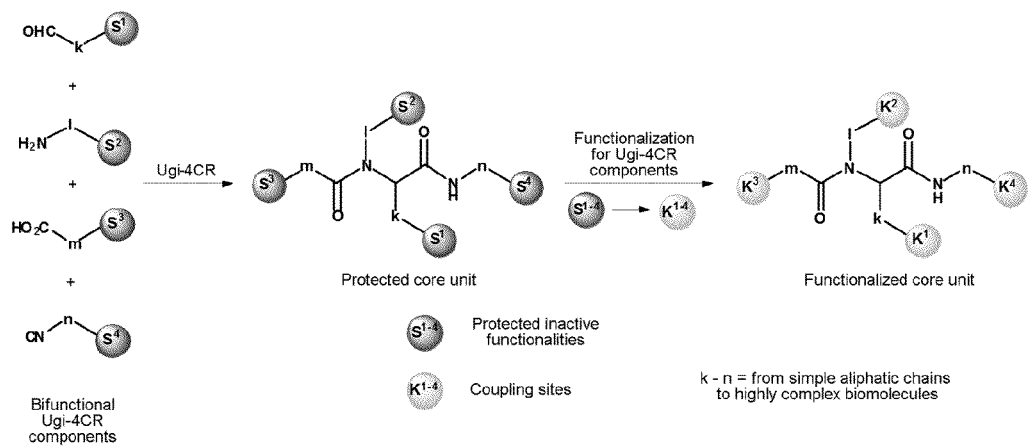
FIG. 4 shows another embodiment of the process according to the present invention using multifunctional core units.

In a further preferred embodiment, the process of the present invention comprises using multifunctional core units which may consist of known polyfunctional molecules with URG on the surface, or which are likewise synthesized via UGI-4CRs (which correspond to a union of core unit and 1ˢᵗ generation). In the latter embodiment, the single reaction with four bifunctional components yields, after activation, a tetrafunctional core unit with an α-aminoacylamide unit. Since the components can likewise be varied in any desired manner, high diversity can be generated even at the stage of the core unit, as is clear from FIG. 4.

The rule that the four components do not all have to be of bifunctional construction but that the use of NBUs can provide di- or trifunctionalized core units also applies here, as will be appreciated. UGI-monofunctionalized peptide-peptoids can be used as anchor unit of dendrons in convergent syntheses. The given asymmetry of α-aminoacylamides makes it possible, depending on a nonbranching component used, to produce fundamentally different peptide-peptoidic structures in the core. In the core or anchor unit alone, 15 structurally different functionalized α-aminoacylamides can be formulated. Tetra- and trifunctional core units are very useful for the divergent construction of dendrimers. Bifunctional α-aminoacylamides can likewise be used in the divergent method of the present invention.

In a preferred embodiment, esters function to convert the protected functionalities (S) into reactive coupling sites (K) which, after the first generation for example has been prepared, are transformed by hydrolysis into active carboxyl groups which can then be reused in UGI-4CRs.

Figure 5:
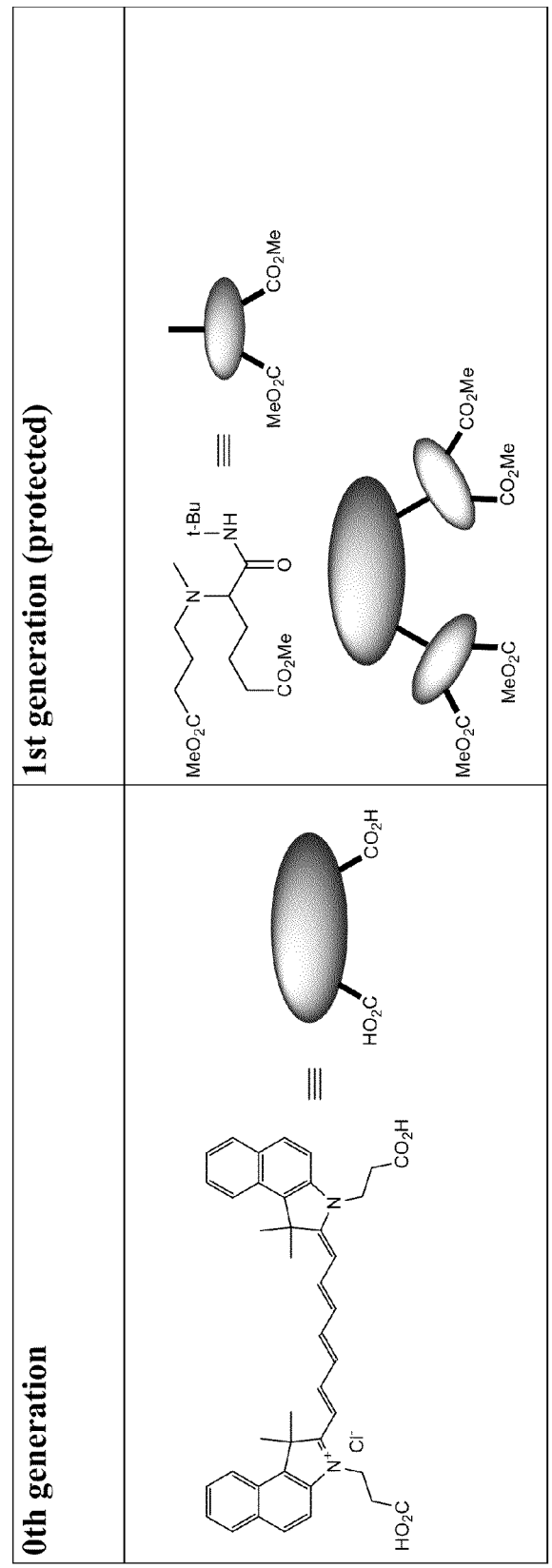
FIG. 5 exemplifies respective core units ("0th generation") as well as first generation dendrimers emanating therefrom and being in accordance with the present invention.
Figure 5:
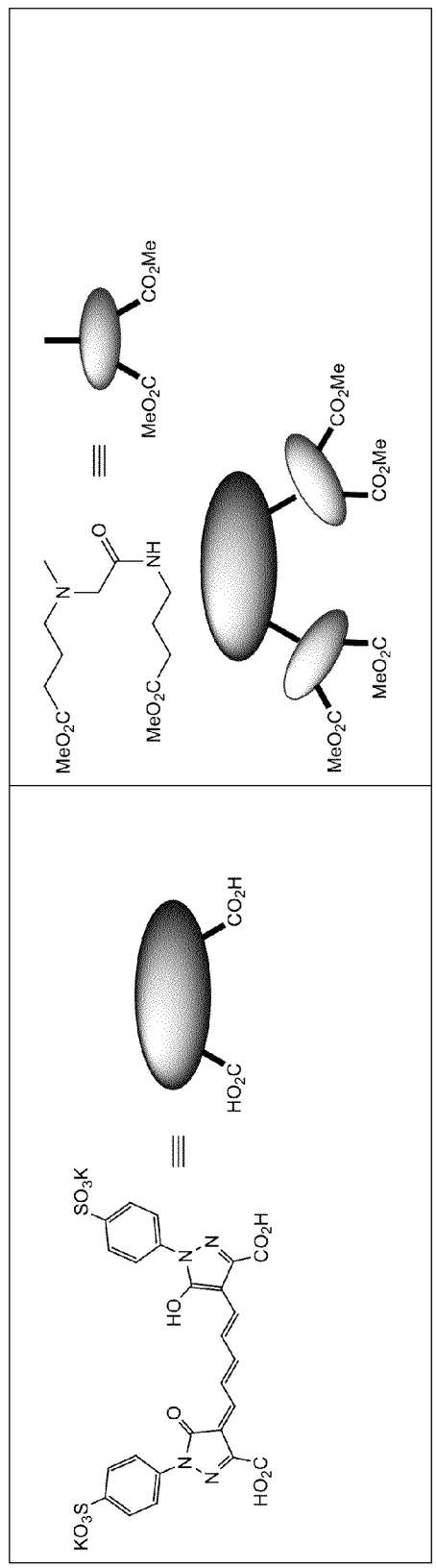
Figure 5:
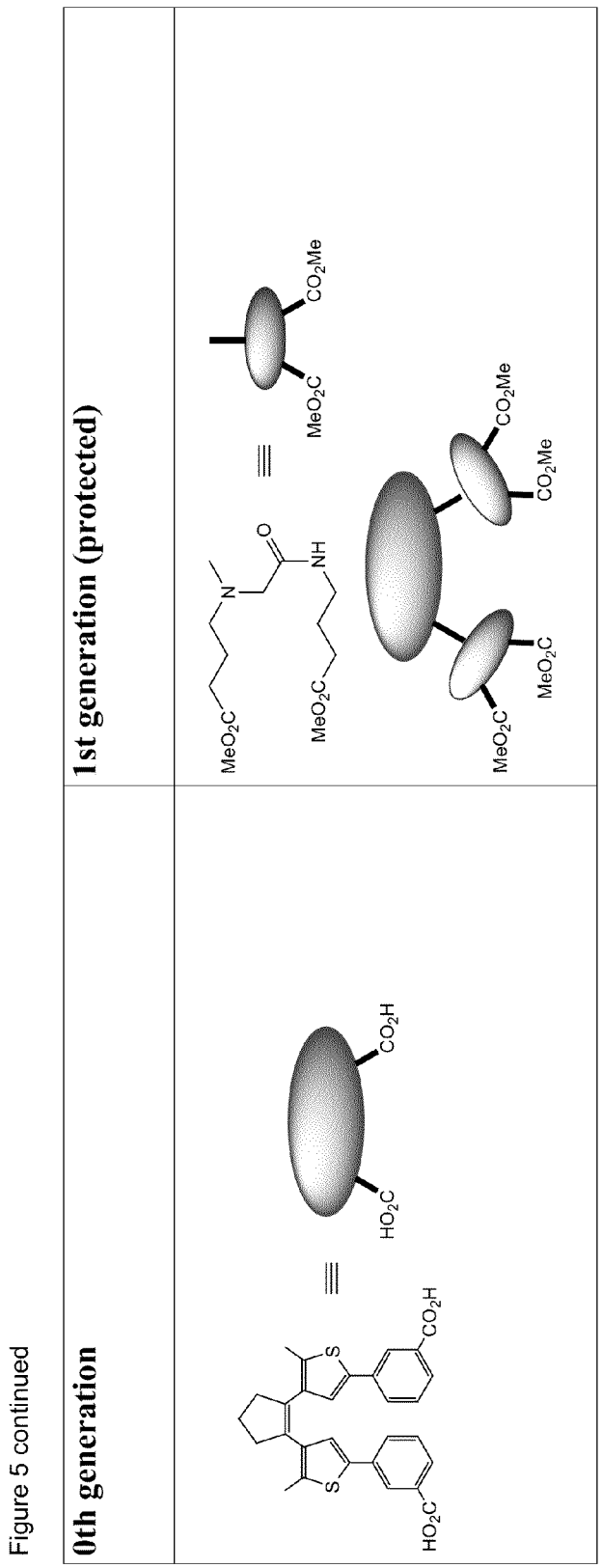
Figure 5:
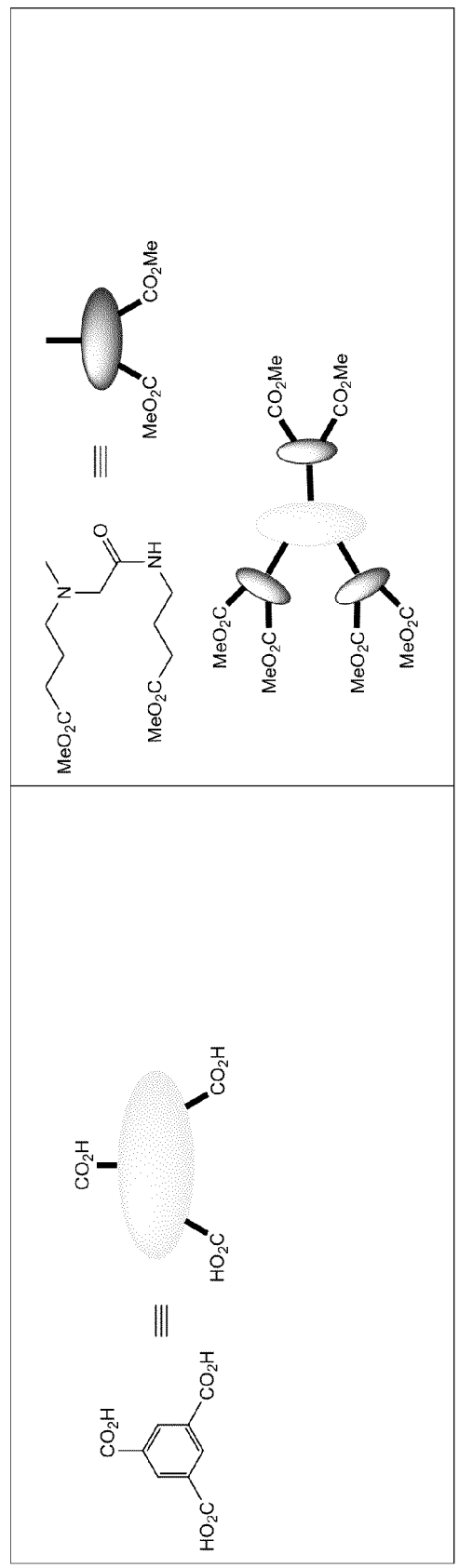
Figure 5:
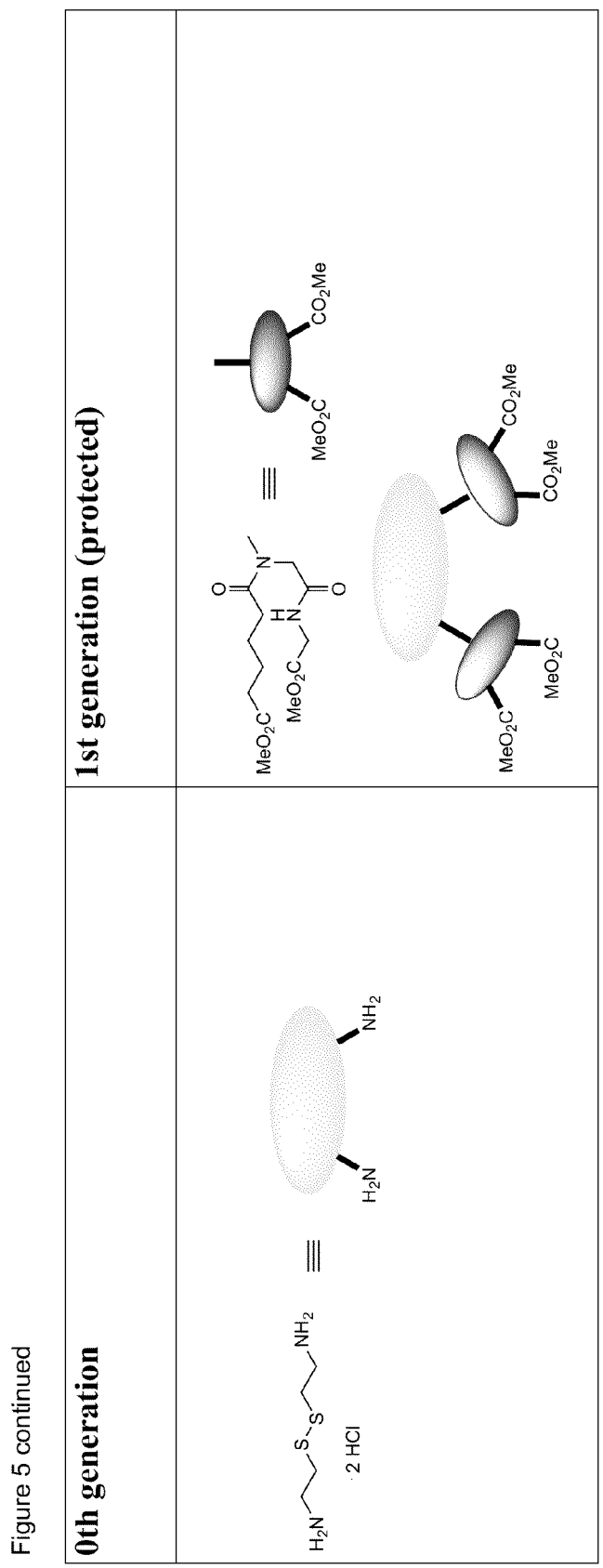
Figure 5:
Figure 5:
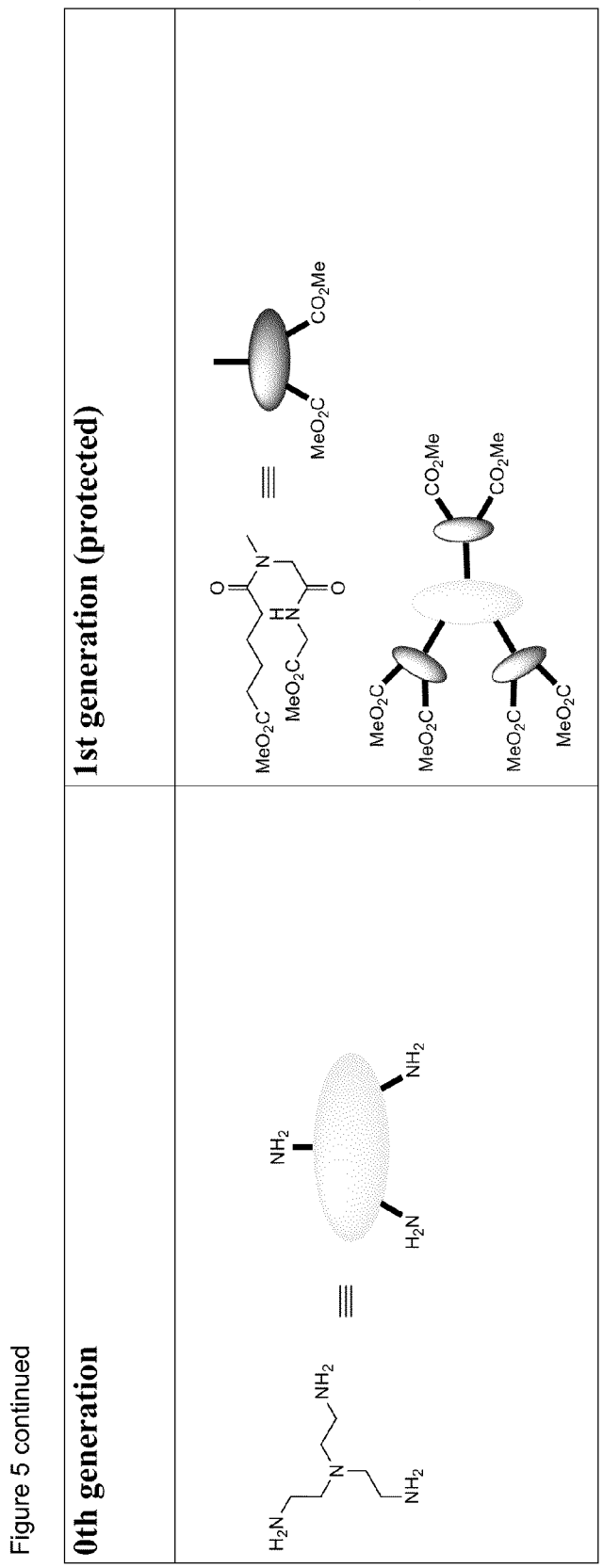
Figure 5:
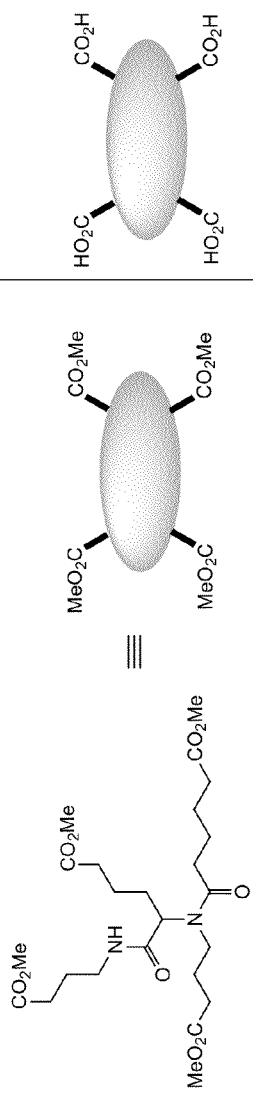
Figure 5:
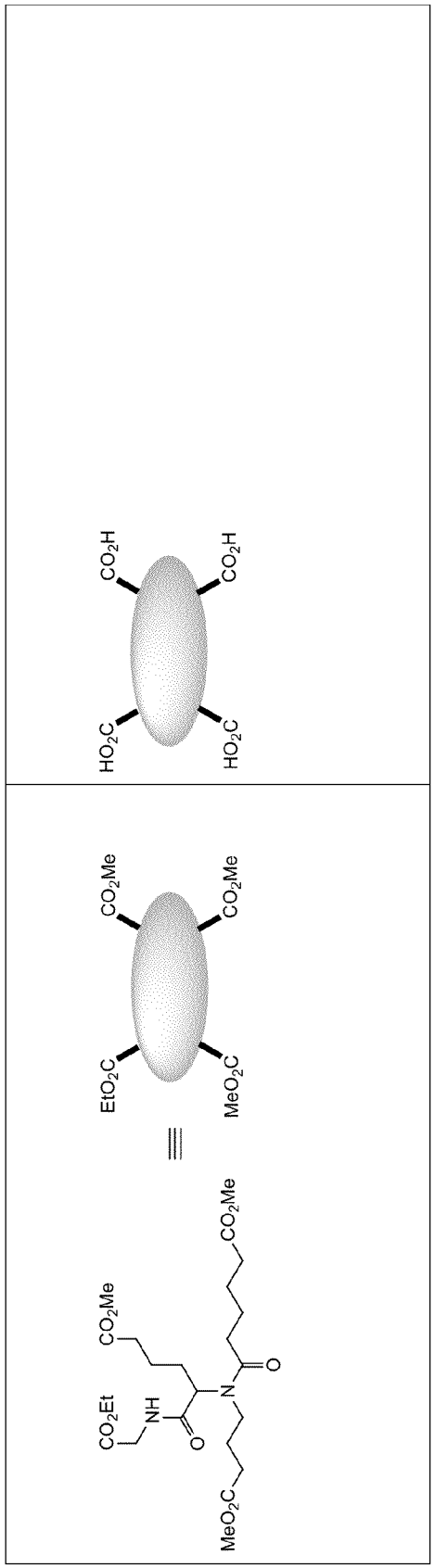
Figure 5:
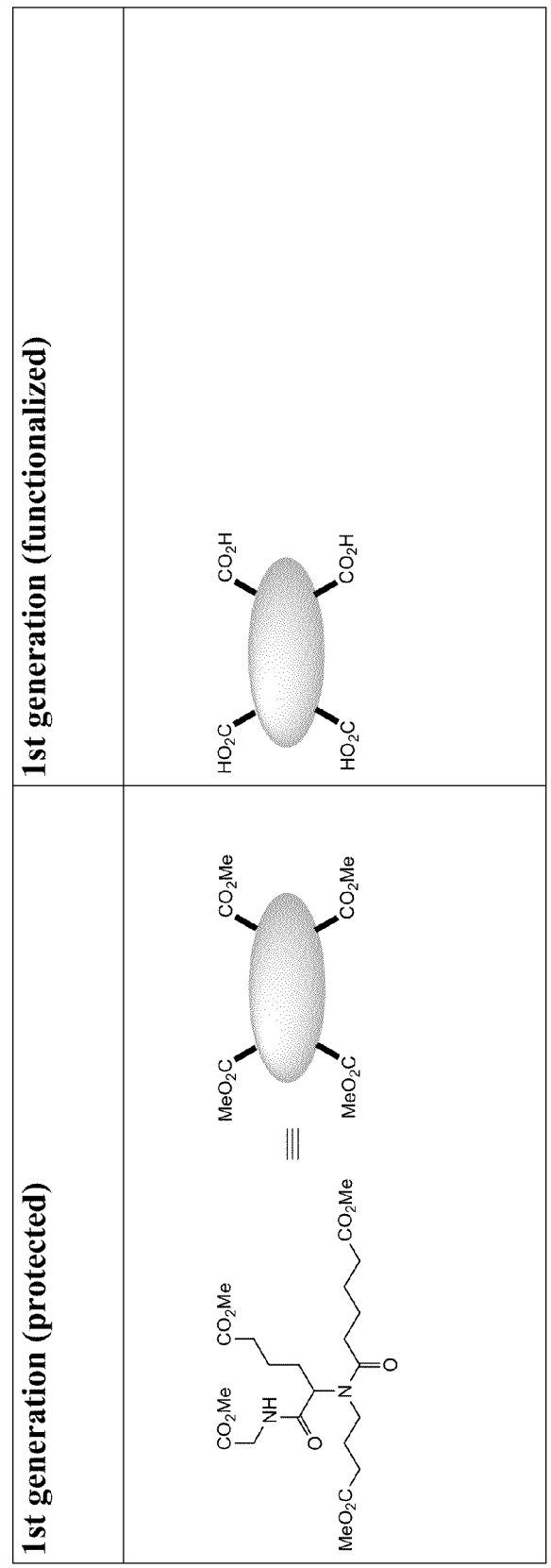
Figure 5:
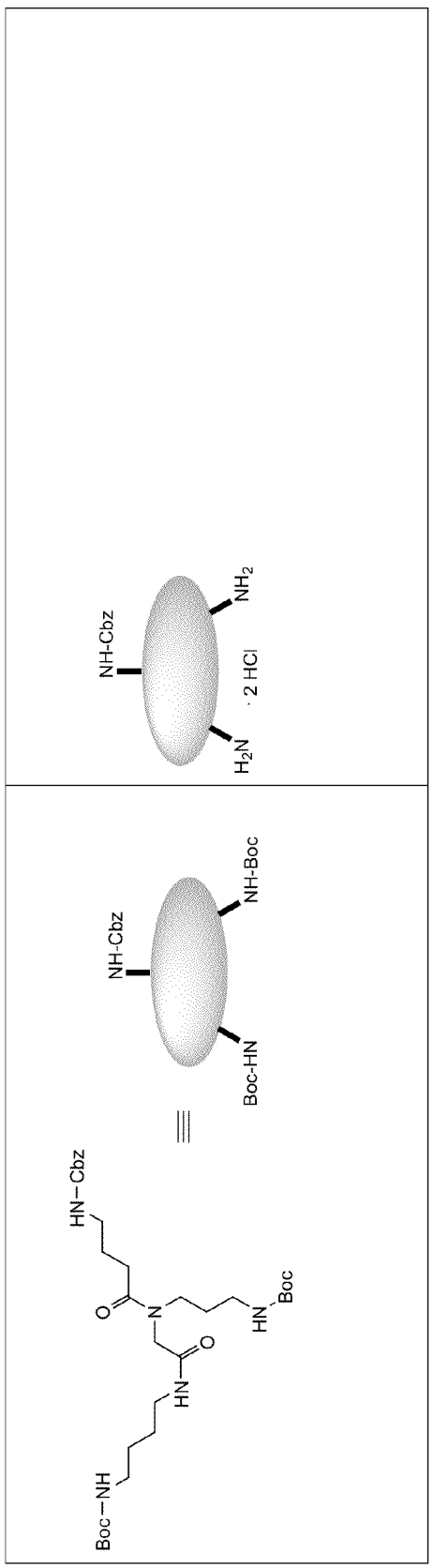
Figure 5:
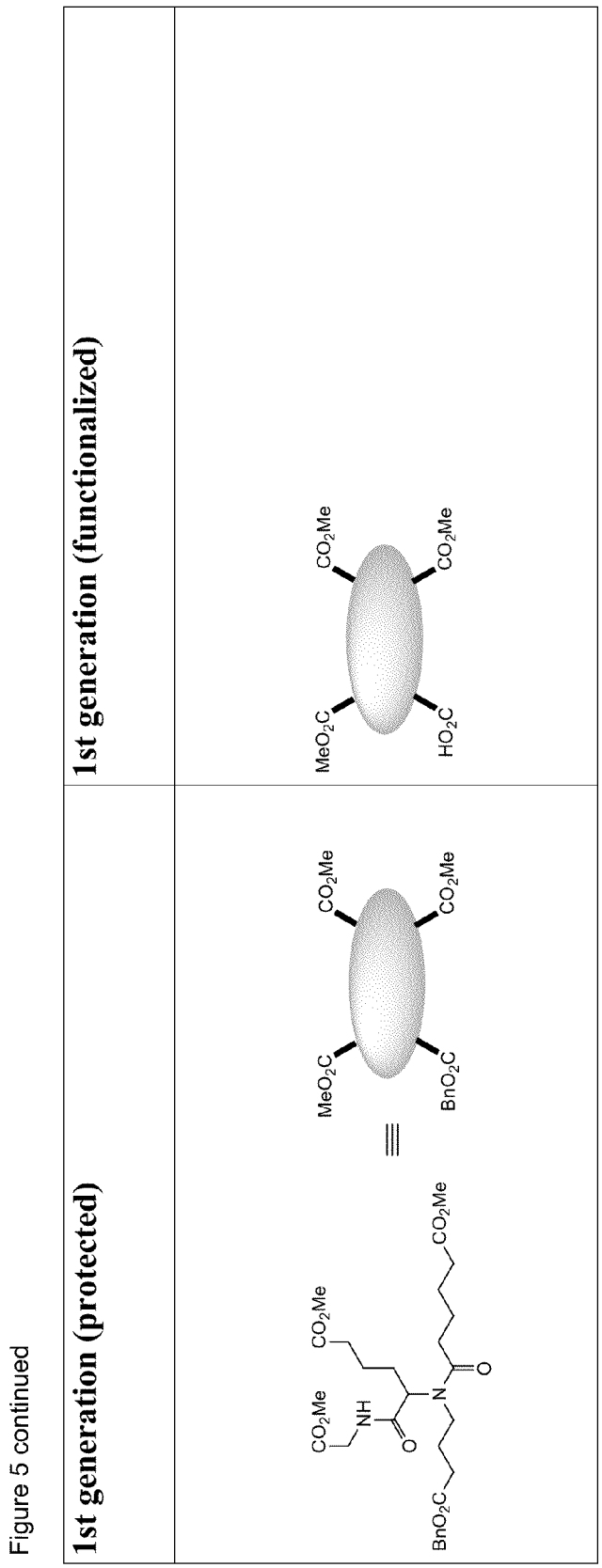
Figure 5:
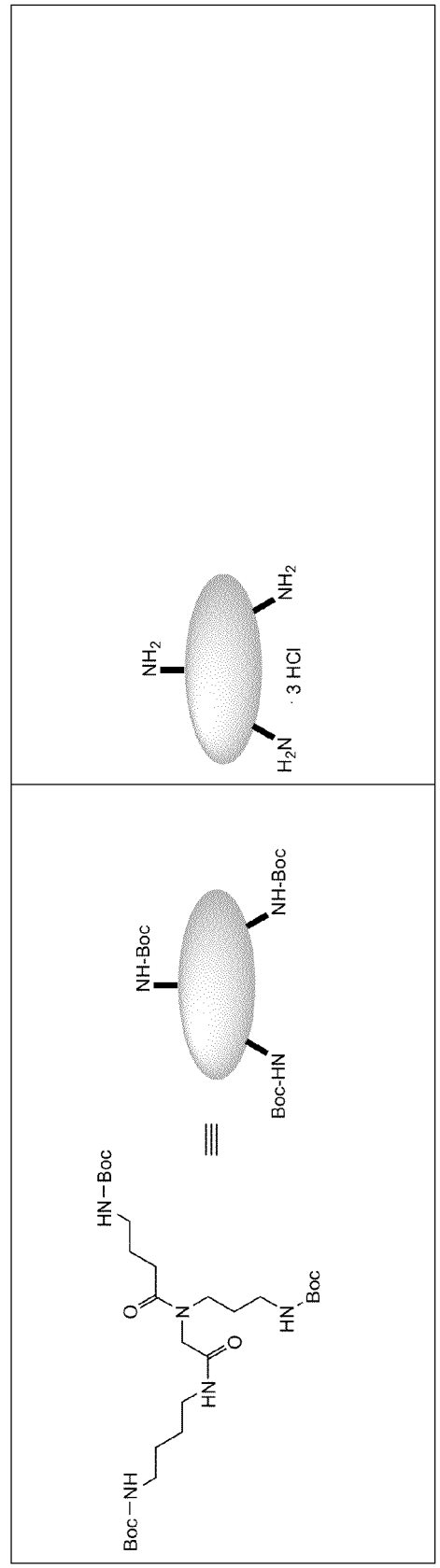
Figure 5:
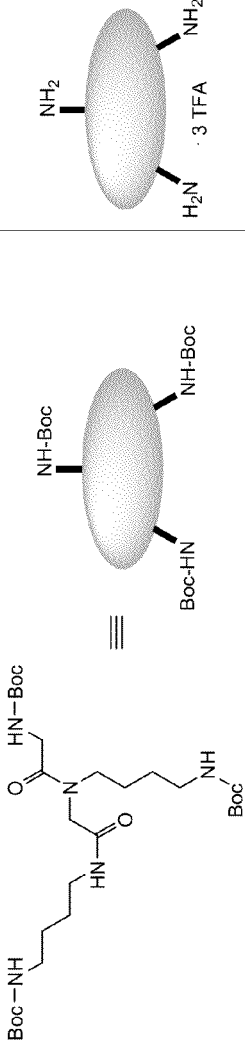
Figure 5:
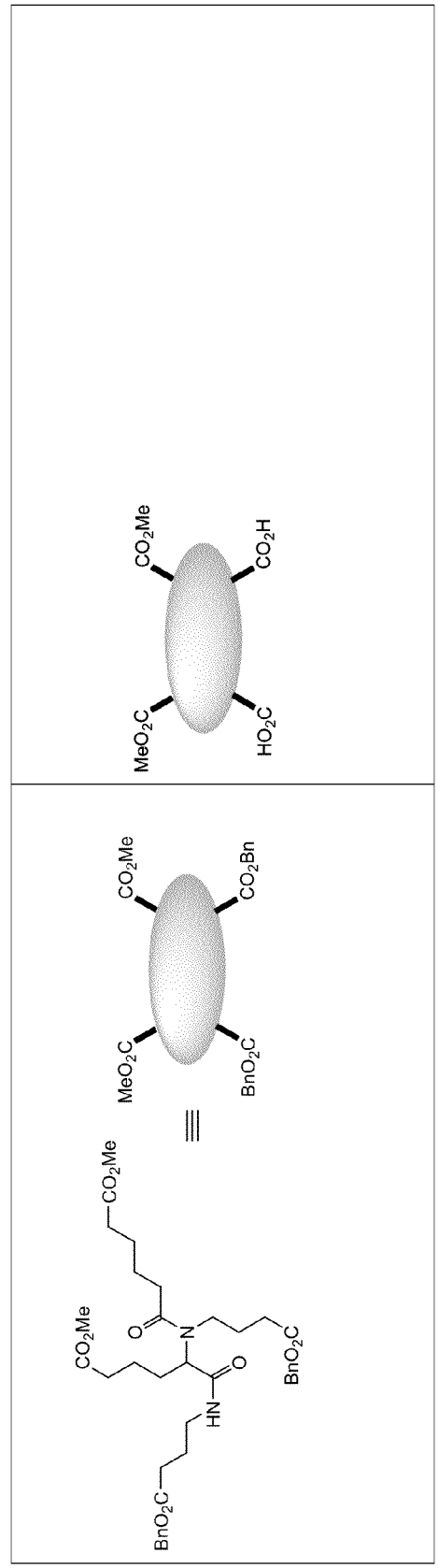
Figure 5:
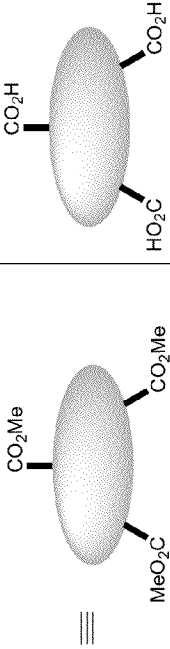
Figure 5:
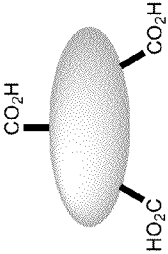
Figure 5:
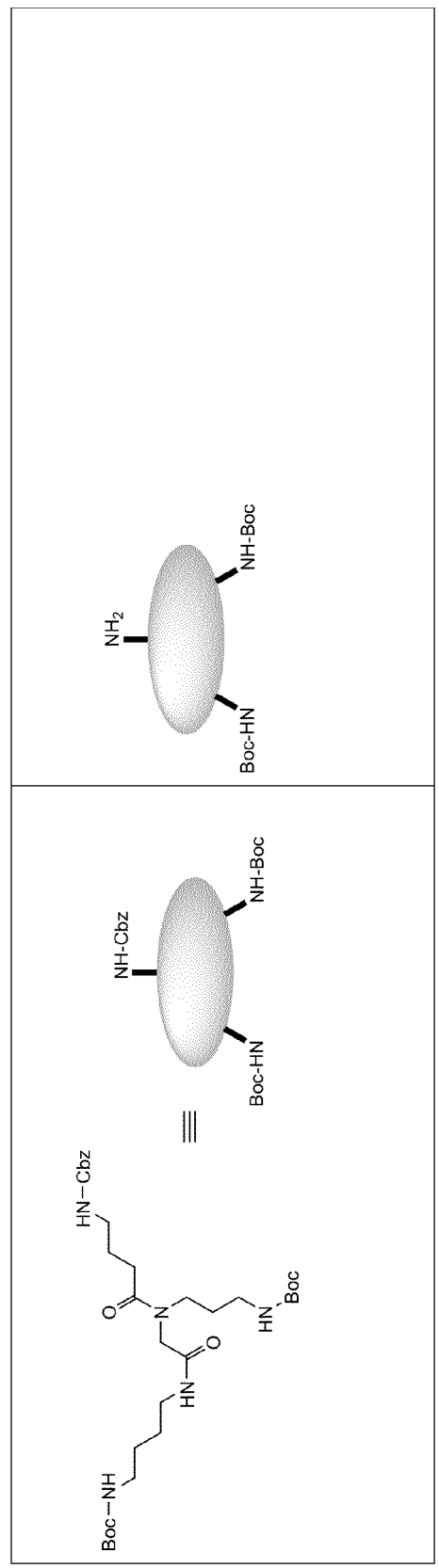
Figure 5:
Figure 5:
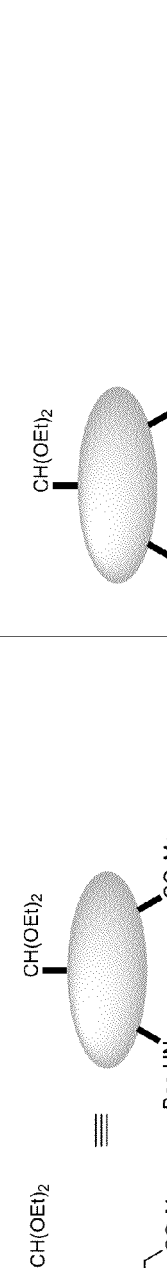
Figure 5:
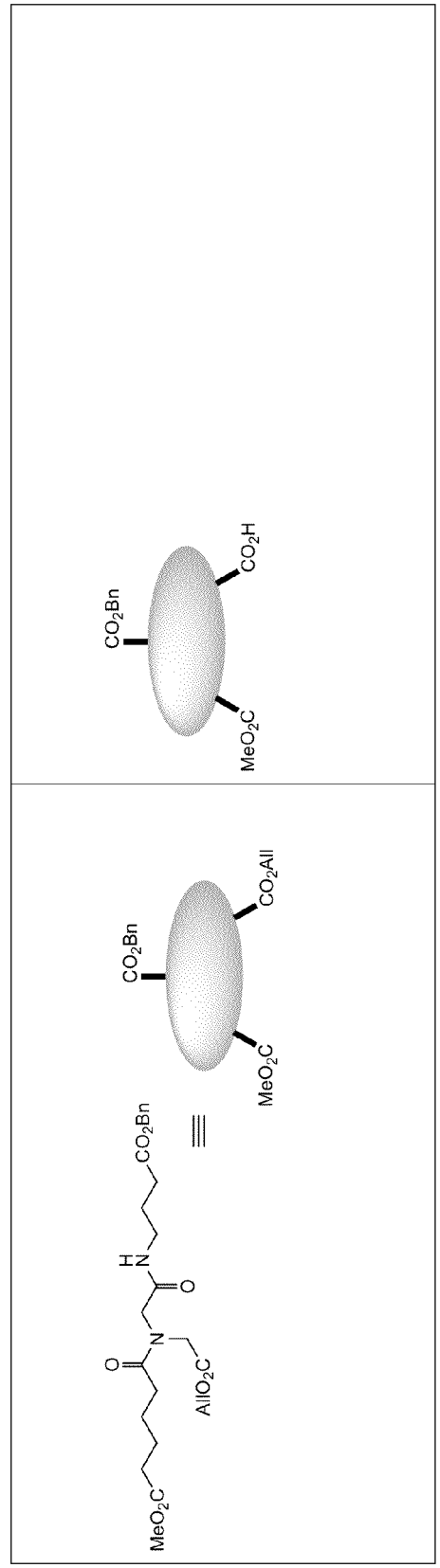
Figure 5:
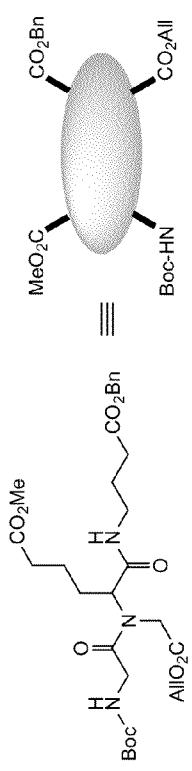
Figure 5:
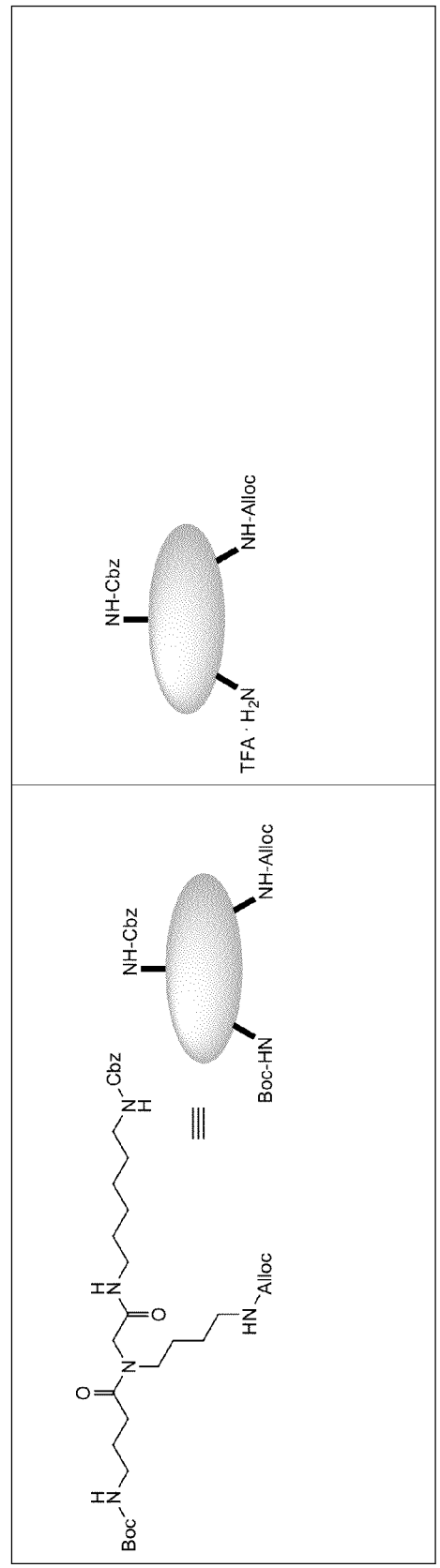
Figure 5:
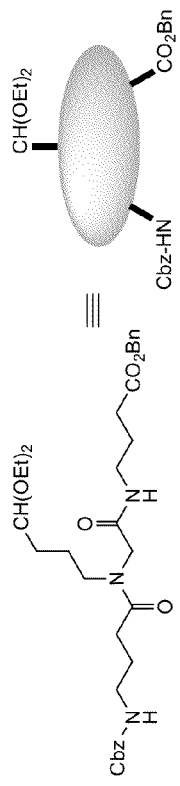
Figure 5:
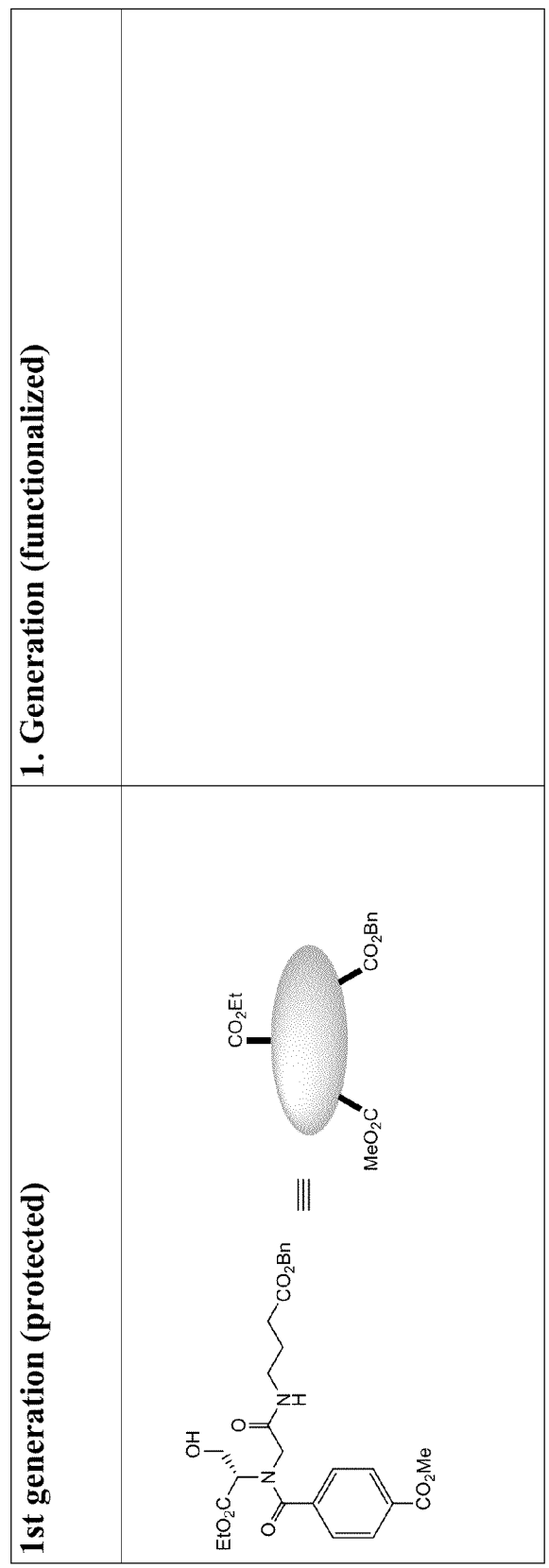
Figure 5:
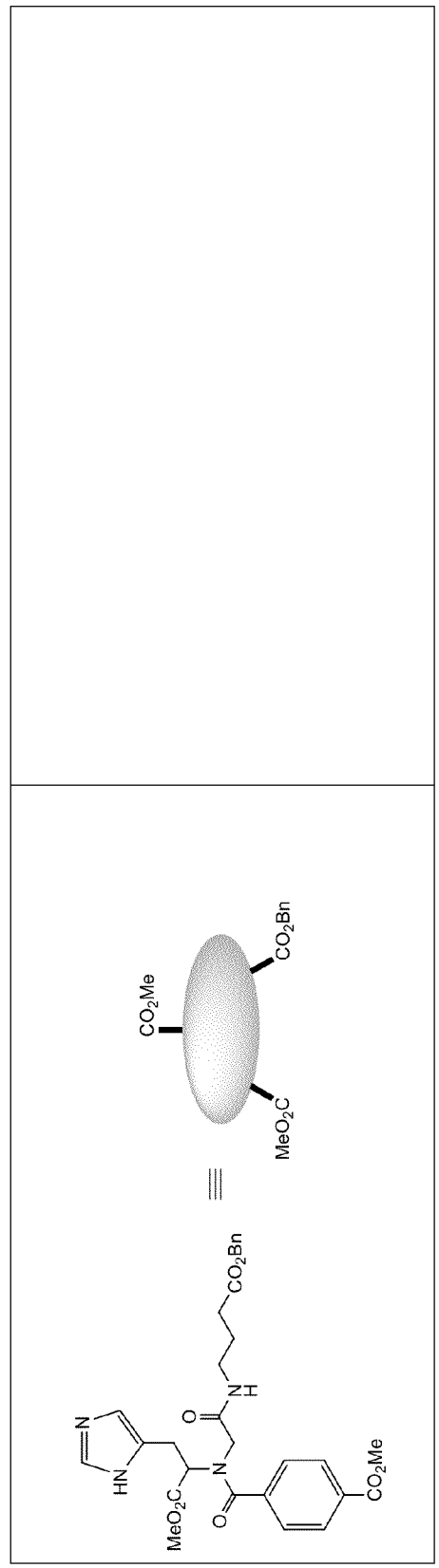
Figure 5:
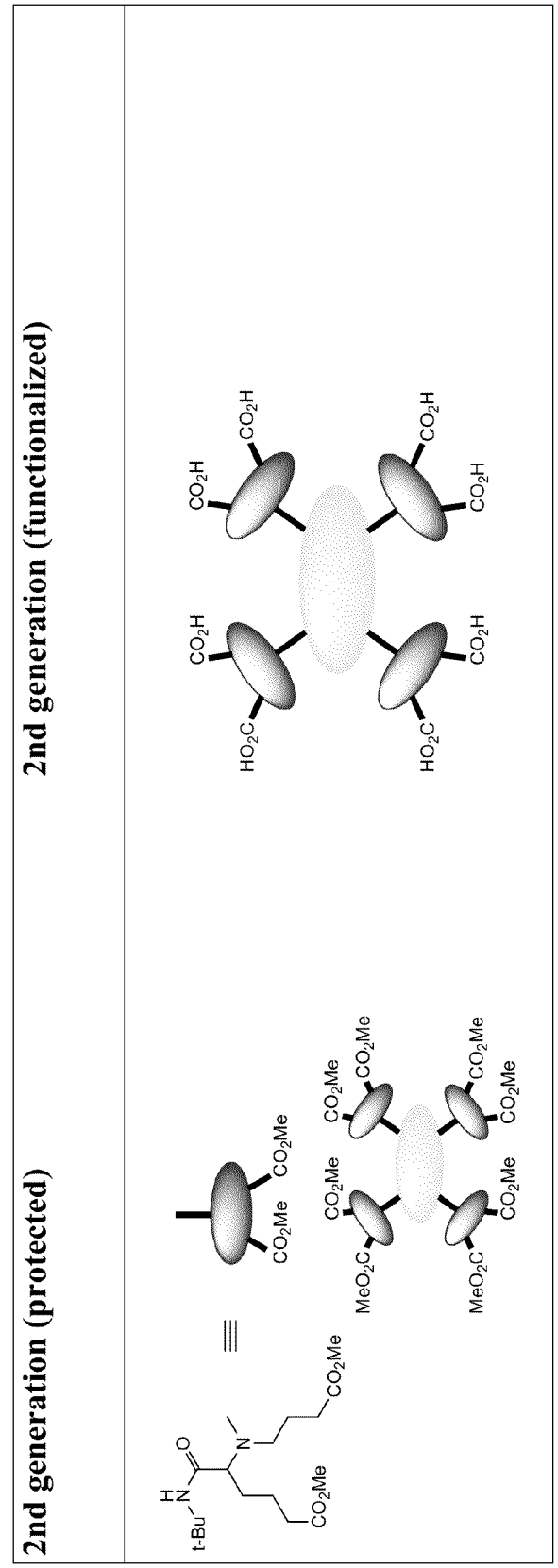
Figure 5:
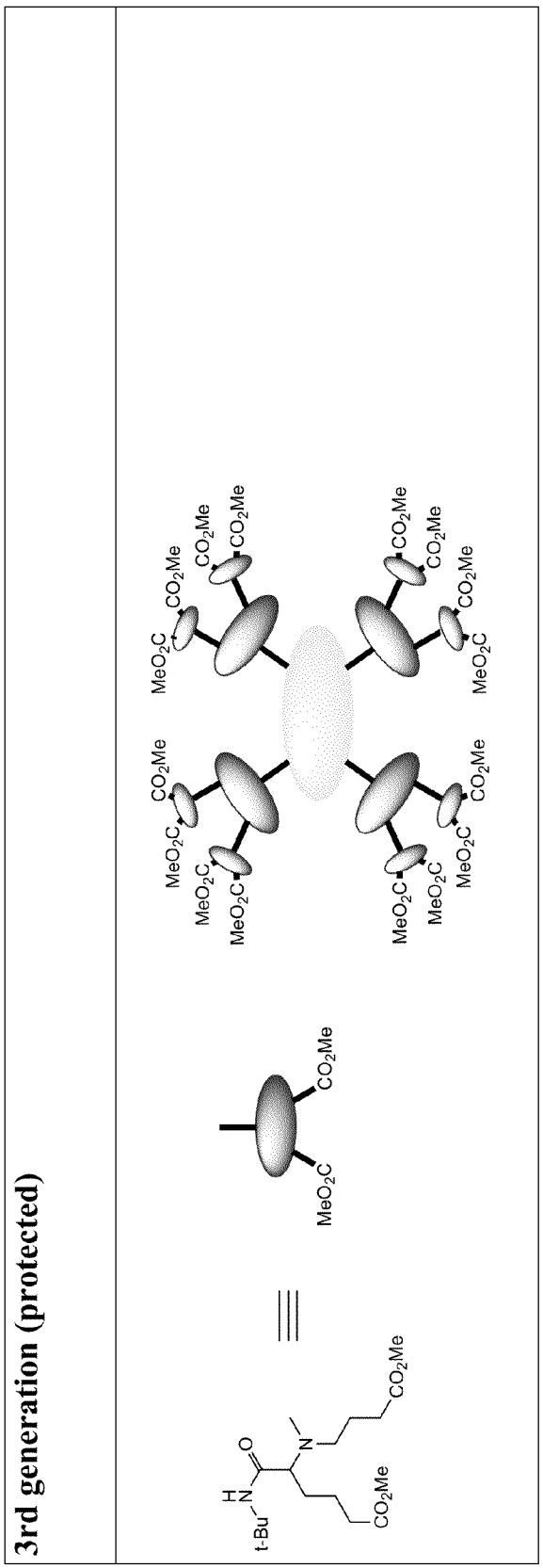
Figure 5:
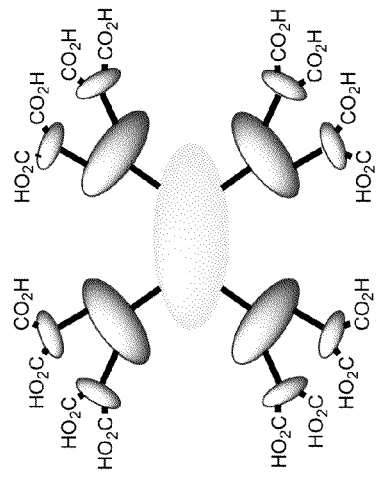

FIG. 5 shows by way of example the "0$^{th}$ generation", i.e., core units not prepared by branched UGI reaction, e.g., (functionalized) polyacids and polyamines, and also the 1$^{st}$ generation dendrimers which emanate therefrom and are in accordance with the present invention.

In a further preferred embodiment, suitable protective-group tactics are used to specifically activate protected functions selectively in each generation of the divergently constructed dendrimer or in the core unit. It is crucial that protective groups and reaction conditions are chosen such that other protected functions remain unchanged and do not undergo any secondary reactions (orthogonal protection). This requires, depending on the complexity desired, appropriate protective-group tactics known to a person skilled in the art, but then affords the synthesis of highly complex, "designed" dendrimers by the divergent method, for example the synthesis of janus dendrimers.

In a further preferred embodiment, the process of the present invention comprises forming stereogenic sites in every α-aminoacylamide unit. This makes it possible to formulate even at the stage of the first generation 32 different stereoisomers from five stereogenic sites. The process of the present invention enables for example artificial enzymes to be synthesized in order that active sites may be specifically generated with necessary flexibility and accessibility for substrates.

In a further preferred embodiment, the process of the present invention further comprises activating the surface of resulting peptide-peptoidic dendrimers in a further UGI-4CR to generate higher generation peptide-peptoidic dendrimers having different functionalities at their surface.

The process of the present invention has appreciable advantages over conventional processes:

- The radicals derived from the bifunctional synthons used may comprise any desired structure (from simple aliphatic chains to highly complex biomolecules). There is a proviso in that there are no further UGI-reactive groups in the radical.
- The maximum degree of branching is three (four when ketones are used), emanating from each functional group of the core unit. These 1→3 branchings are possible, but not necessary. By using NBUs it is possible to generate 1→2 branchings, linear prolongations or non-(P)URG-functionalized segments.
- The asymmetry of the α-aminoacylamide branching points obtained makes it possible to produce almost at will different structures in the branching unit (various lengths for example) by using different nonbranching components.

Homogeneous functionalities in the periphery may differ in their protected form (for example, various ester groupings) which are selectively activatable and enable the dendrimer to be constructed sectionally.

Heterogeneous protected functionalities in the periphery are likewise possible (for example, ester functions in the presence of protected primary amines), which are selectively activatable and enable the dendrimer to be constructed sectionally with structurally different branching points.

The present invention thus also provides peptoidic, depsipeptidic and preferably chimeric peptide-peptoidic dendrimers and also corresponding janus dendrimers which are obtainable by multiple iterative multicomponent reactions, especially UGI or PASSERINI multicomponent reactions. The peptoidic dendrimers of the present invention are not subject to any special restrictions provided they are obtained by the process described above.

First generation peptide-peptoidic dendrimers are included among these according to the present invention, provided they are based on a "zero-th generation" core unit. Core units are of "zero-th generation" when the core unit does not come from an Ugi or Passerini reaction. Core units of this type are classic polyfunctional core units of dendrimers or classic commercial dendrimers themselves, which bear Ugu-reactive groups, preferably carboxylic acid or amino functions, on the surface.

Included are more particularly second, third, fourth and further generation peptide-peptoidic dendrimers as exemplified hereinbelow. Janus dendrimers as exemplified hereinbelow are similarly included.

The present inventors determined that the peptide-peptoidic dendrimers obtainable by the process of the present invention can be employed as pharmaceutically usable products or biological auxiliaries. More particularly, these peptoidic dendrimers can be employed in the following sectors: drug delivery, imaging, protein-labeling and -separation, DNA/RNA delivery, surface recognition, cell recognition and tissue recognition, and as macroamphiphile.

The examples which follow serve to further illustrate the present invention without limiting it in any way.

Synthesis Sequence for Second Generation
Dendrimer 7 as Starting Point for Further Syntheses

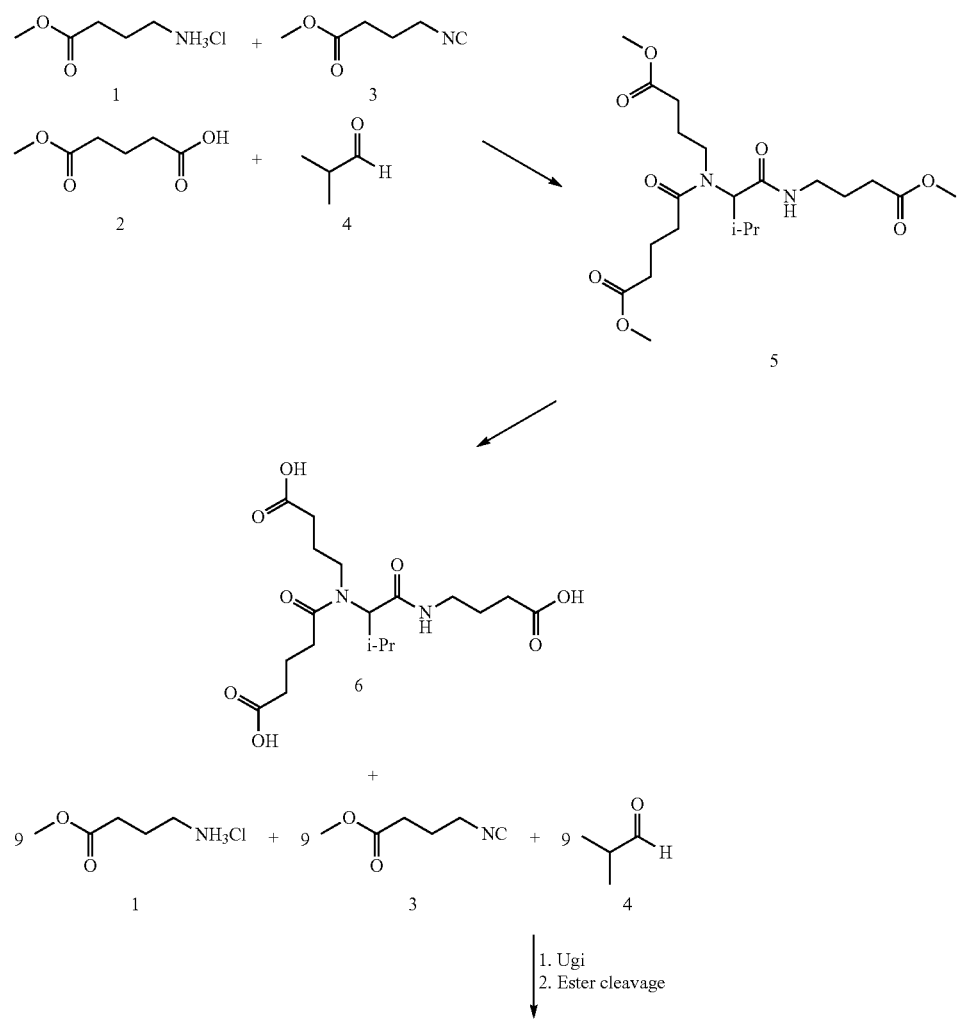

-continued

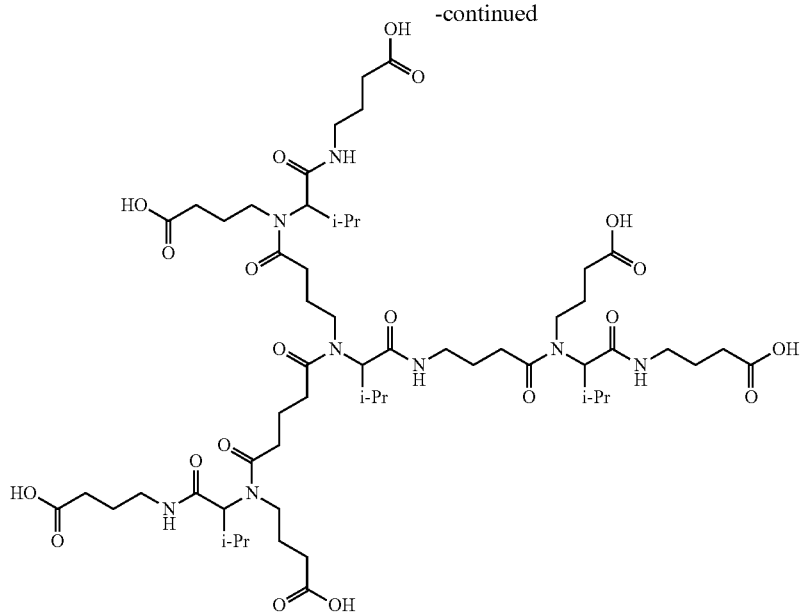

7

Methyl 4-(chloramino)butanoate 1

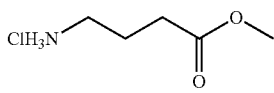

γ-Aminobutyric acid (20.0 g, 193 mmol) was dissolved in 320 mL of methanol and cooled down to 0° C. using an ice bath. Thionyl chloride (43.5 mL, 600 mmol) was then added dropwise using a dropping funnel. The ice bath was removed and the mixture was stirred overnight after warming to room temperature.

Volatiles were removed in a rotary evaporator, 300 mL of $Et_2O$ were then added before storing at −30° C. for 30 min. The solid material was filtered off and thoroughly washed with $Et_2O$. Drying in vacuo left a white solid (29.0 g, 97%).

MS (ESI): $[M+H]^+$=118.6

Formamide of methyl 4-(chloramino)butanoate

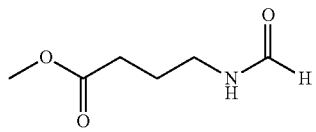

Methyl 4-(chloramino)butanoate 1 (15.0 g, 98.0 mol) was dissolved in 100 ml of trimethyl orthoformate followed by heating under reflux for 4 hours. The solvent was removed in a rotary evaporator. The product was obtained as a white solid (14.2 g, quant.).

$^1$H NMR ($CDCl_3$): δ [ppm]=8.16 (s, 1H, CHO); 3.68 (s, 3H, O—$CH_3$); 3.33 (m, 2H, $CH_2$); 2.40 (t, 2H, $^3J$=7 Hz, $CH_2$); 1.87 (q, 2H, $^3J$=7 Hz, $CH_2$).

4-Isocyanomethyl butyrate 3

The formamide of methyl 4-(chloramino)butanoate (12.9 g, 89.0 mol) was initially charged in 300 mL of dry $CH_2Cl_2$. Diisopropylamine (37.0 mL, 266 mmol) was then added. The solution was cooled down to 0° C. (ice bath). Phosphoryl chloride (9.76 mL, 107 mmol) was then slowly added dropwise. On completion of the addition the solution was stirred at RT for 2 h.

The reaction was ended by addition of 20 g of $Na_2CO_3$ dissolved in 100 mL of $H_2O$. After 30 min stirring at RT the reaction solution was diluted with 100 mL of $CH_2Cl_2$ and also 100 mL of $H_2O$ and then extracted 3× with 100 mL of $CH_2Cl_2$ each time. The combined organic phases were dried over $Na_2SO_4$ and concentrated in vacuo. Column-chromatographic purification with $CH_2Cl_2$/MeOH (9.75/0.25, v/v) yielded a dark brown oil (8.30 g, 73%).

$^1$H NMR ($CDCl_3$): δ [ppm]=3.70 (s, 3H, O—$CH_3$); 3.51 (m, 2H, $CH_2$); 2.52 (t, 2H, $^3J$=7 Hz, $CH_2$); 1.87 (m, 2H, $CH_2$).

Synthesis of First Generation Methyl Ester-Functionalized (5)

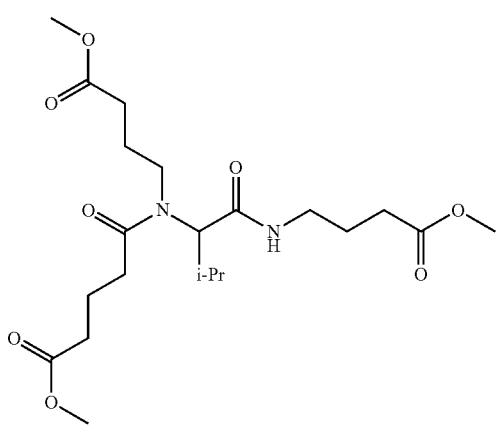 [SMILES: COC(=O)CCCNC(=O)C(C(C)C)N(CCCC(=O)OC)C(=O)CCCC(=O)OC]

Methyl 4-(chloramino)butanoate 1 (2.00 mg, 13.0 mmol) and isobutyraldehyde 4 (1.18 mL, 13.0 mmol) were added to a solution of triethylamine (1.8 mL, 13.0 mmol) in 50 mL of methanol. The solution was stirred at RT for 2 h. Then, methyl 4-isocyanobutanoate 3 (1.65 g, 13.0 mmol) and monomethyl glutarate 2 (1.63 mL, 13.0 mmol) were added, followed by stirring at RT overnight. The solution was concentrated in a rotary evaporator and the residue was purified by column chromatography (MeOH/EE, 1/39). Product 5 was obtained as colorless oil (5.07 g, 88%).

MS (ESI): $[M+Na]^+=467.4$

Synthesis of First Generation Carboxy-Functionalized (6)

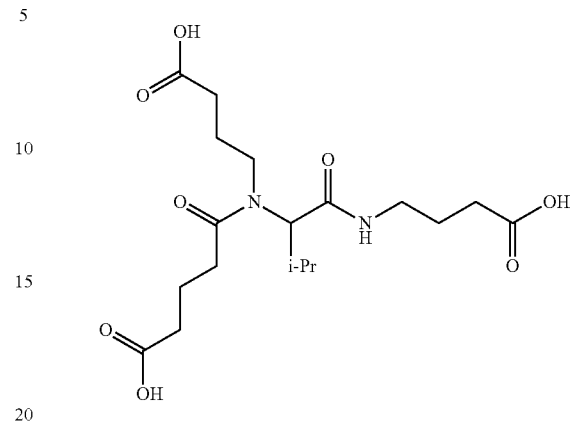

First generation methyl ester-functionalized 5 (2.50 g, 5.80 mmol) was dissolved in 75 ml of THF/H$_2$O (2/1) and cooled down to 0° C. with an ice bath. Then, lithium hydroxide monohydrate (1.82 g, 43.4 mmol) was added. The ice bath was removed followed by stirring at RT overnight. The solution was strongly acidified with saturated NaHSO$_4$ and extracted 3× with 150 mL of ethyl acetate each time. The combined organic phases were dried over Na$_2$SO$_4$ and concentrated in a rotary evaporator. Product 6 was obtained as colorless oil (2.30 mg, 98%).

MS (ESI): $[M+H]^+=401.3$

Synthesis of Second Generation Methyl Ester-Functionalized (7a)

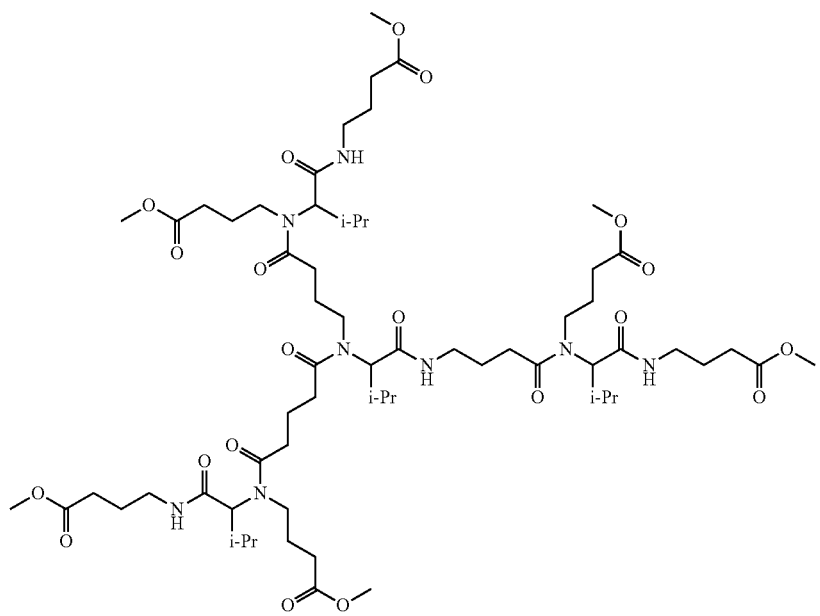

Methyl 4-(chloramino)butanoate 1 (1.00 g, 7.50 mmol) and isobutyraldehyde 4 (0.69 mL, 7.50 mmol) were added to a solution of triethylamine (1.04 mL, 7.50 mmol) in 50 mL of methanol. The solution was stirred at RT for 2 h. Then, methyl 4-isocyanobutanoate 3 (1.15 mg, 7.50 mmol) and 6 (1.00 g, 2.50 mmol) were added, followed by stirring at RT overnight. The solution was concentrated in a rotary evaporator and the residue was purified by column chromatography (MeOH/EE, 1/19). The product was obtained as colorless oil (2.89 g, 89%).

MS (ESI): [M+Na]$^+$=1320.1

Synthesis of Second Generation Carboxylate-Functionalized (7)

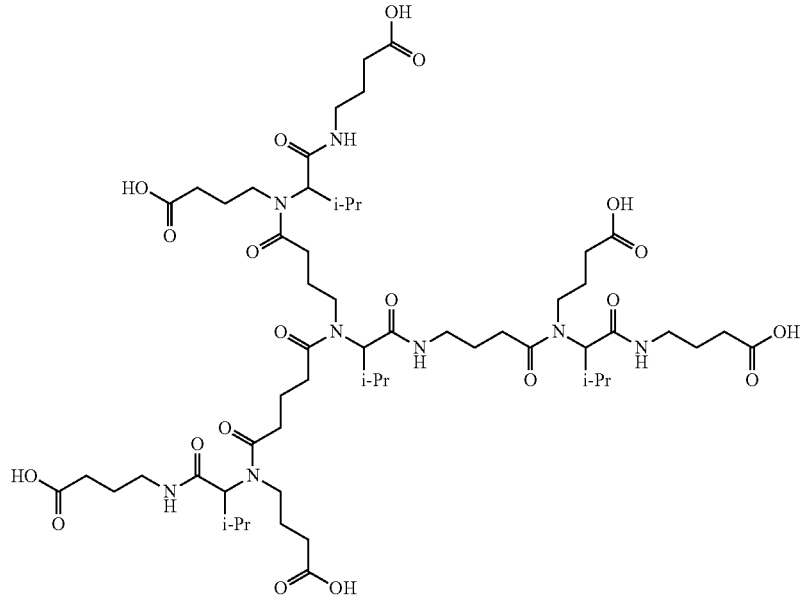 [SMILES: CC(C)C(C(=O)NCCCC(=O)O)N(CCCC(=O)O)C(=O)CCCNC(=O)C(C(C)C)N(CCCC(=O)N(CCCC(=O)O)C(C(=O)NCCCC(=O)O)C(C)C)C(=O)CCCC(=O)N(CCCC(=O)O)C(C(=O)NCCCC(=O)O)C(C)C]

Second generation methyl ester-functionalized (2.73 g, 2.11 mmol) was dissolved in 120 ml of THF/H$_2$O (2/1) and cooled down to 0° C. with an ice bath. Then, lithium hydroxide monohydrate (1.32 g, 31.6 mmol) was added. The ice bath was removed followed by stirring at RT overnight. The solution was strongly acidified with saturated NaHSO$_4$ and extracted 3× with 150 mL of ethyl acetate each time. The combined organic phases were dried over Na$_2$SO$_4$ and concentrated in a rotary evaporator. Product 7 was obtained as colorless oil (2.40 mg, 94%).

MS (ESI): [M+H]$^+$=1235.9

Synthesis of 3$^{rd}$ Generation Methyl Ester-Functionalized (8)

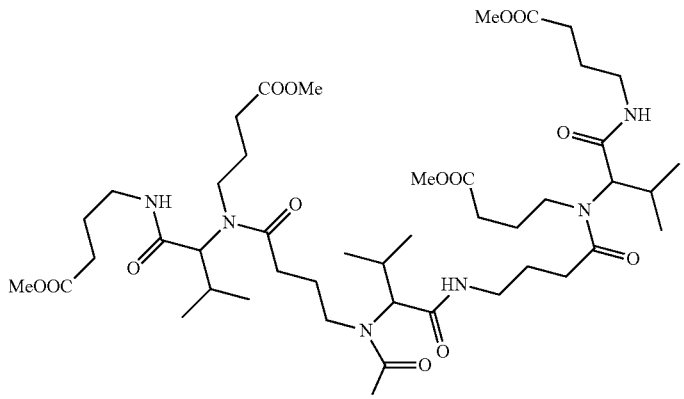

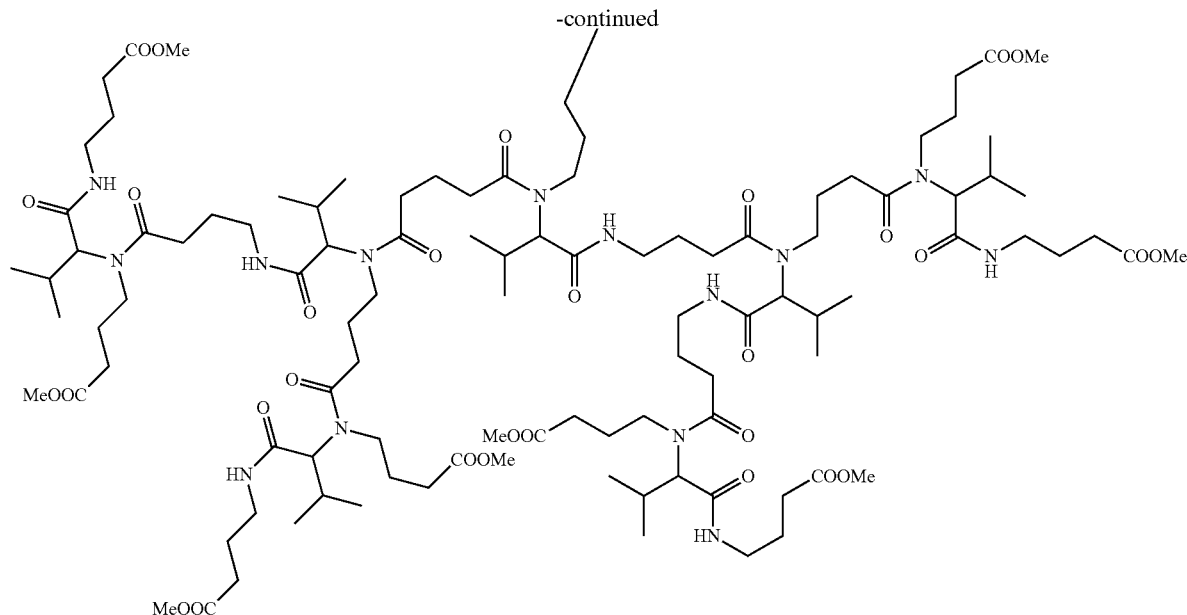

Methyl 4-(chloramino)butanoate 1 (553 g, 3.60 mmol) and isobutyraldehyde 4 (0.33 mL, 3.60 mmol) were added to a solution of triethylamine (0.50 mL, 3.60 mmol) in 20 mL of methanol. The solution was stirred at RT for 2 h. Then, methyl 4-isocyanobutanoate 3 (458 mg, 3.60 mmol) and 7 (480 mg, 0.39 mmol) were added, followed by stirring at RT overnight. The solution was concentrated in a rotary evaporator and the residue was purified by column chromatography (MeOH/EE, 1/19). Product 8 was obtained as colorless oil (1.00 g, 89%).
MS (ESI): [M+2Na]$^{2+}$=1524.9

Allyl 4-(paratoluenesulfonylamino)butanoate 9

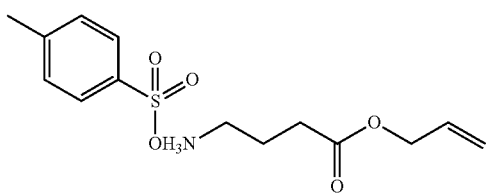

γ-Aminobutyric acid (25.8 g, 250 mmol), allyl alcohol (100 mL, 1.50 mol) and p-toluenesulfonic acid (48.5 g, 255 mmol) were suspended in 100 mL of toluene and the suspension was refluxed for 16 h under a water separator. Subsequently, the orange solution was concentrated under reduced pressure. Following complete crystallization of the residue, it was thoroughly washed with diethyl ether (4×300 ml). The product was obtained as a colorless solid (77.8 g, 99%).

$^1$H NMR (CD$_3$OD), 300 MHz): δ=1.92 (quint., J=7.5 Hz, 2H, CH$_2$), 2.36 (s, 3H, CH$_3$), 2.46 (t, J=7.3 Hz, 2H, CH$_2$), 2.96 (t, J=7.7 Hz, 2H, CH$_2$), 4.58 (dt, J=5.8, 1.3 Hz, 2H, CH$_2$), 5.18-5.34 (m, 2H, CH$_2$), 5.86-6.00 (m, 1H, CH), 7.23 (d, J=7.7 Hz, 2H, CH), 7.71 (d, J=8.1 Hz, 2H, CH) ppm.

Synthesis of 3$^{rd}$ Generation Allyl Ester/Benzyl Ester-Functionalized (Orthogonally Protected Surface) (10)

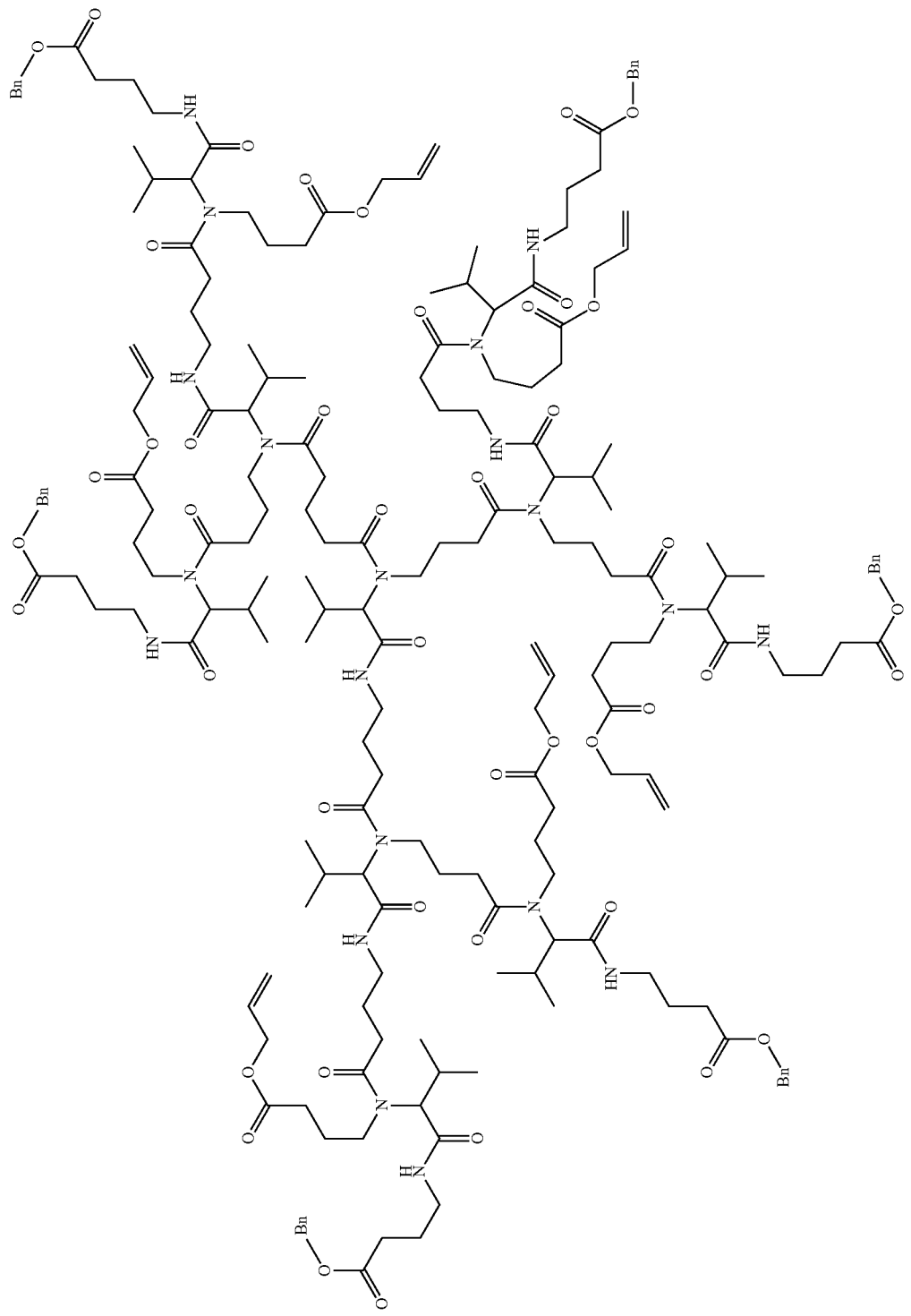

Allyl 4-(paratoluenesulfonylamino)butanoate 9 (233 mg, 0.74 mmol) and isobutyraldehyde 4 (67.5 μl, 0.74 mmol) were added to a solution of triethylamine (103 μl, 0.74 mmol) in 15 mL of methanol. The solution was stirred at RT for 2 h. Then, benzyl 4-isocyanobutanoate (151 mg, 0.74 mmol) and 7 (100 mg, 0.08 mmol) were added followed by stirring at RT overnight. The solution was concentrated in a rotary evaporator and the residue was purified by column chromatography (MeOH/EE, 1/39). Product 10 was obtained as a colorless oil (215 mg, 73%).

MS (ESI): $[M+2Na]^{2+}=1830.9$

Synthesis of $3^{rd}$ Generation Allyl Ester/Benzyl Ester-Functionalized (11)

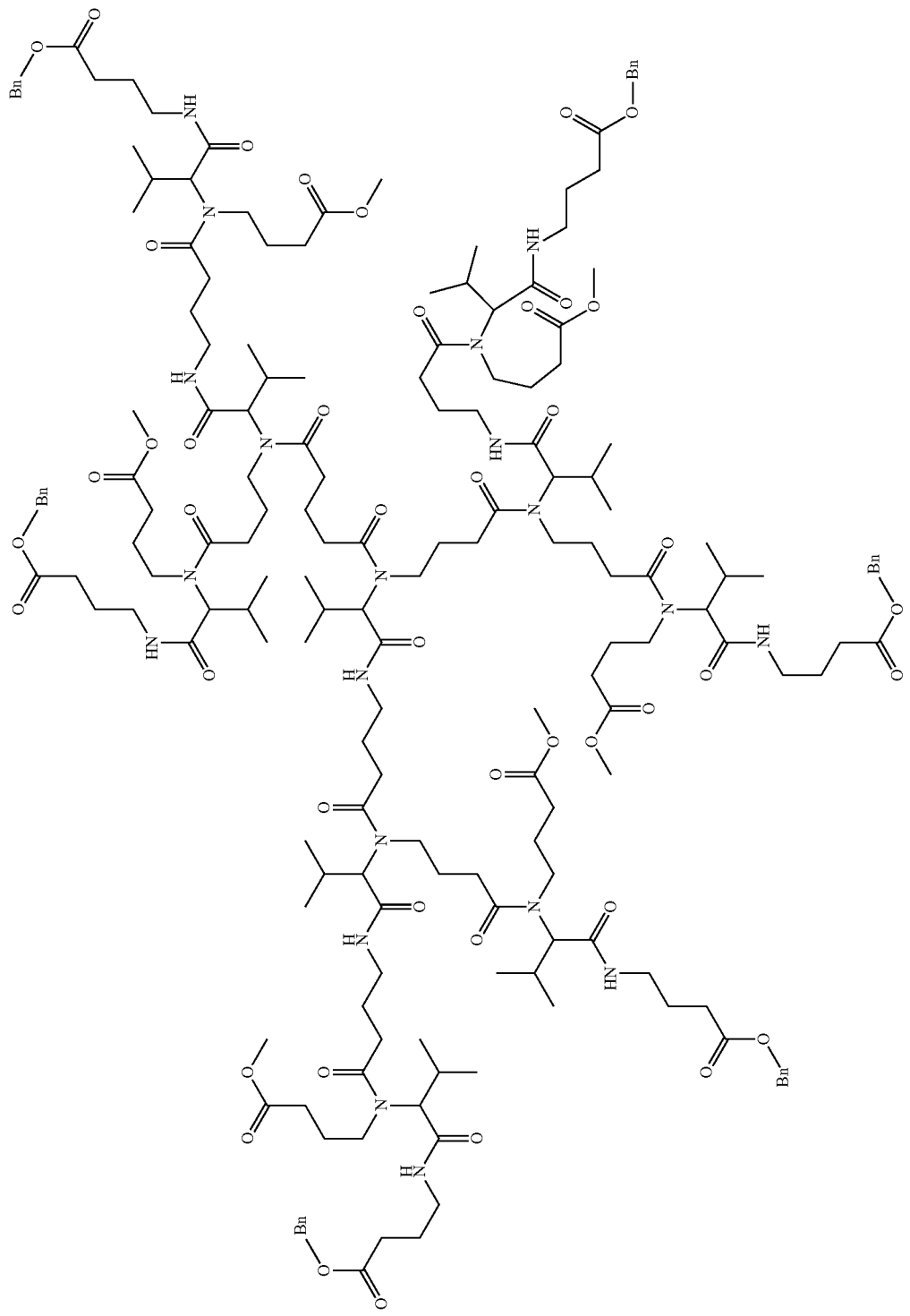

Methyl 4-(chloramino)butanoate 1 (114 mg, 0.74 mmol) and isobutyraldehyde 4 (67.5 μl, 0.74 mmol) were added to a solution of triethylamine (103 μl, 0.74 mmol) in 15 mL of methanol. The solution was stirred at RT for 2 h. Then, benzyl 4-isocyanobutanoate (151 mg, 0.74 mmol) and 7 (100 mg, 0.08 mmol) were added followed by stirring at RT overnight. The solution was concentrated in a rotary evaporator and the residue was purified by column chromatography (MeOH/EE, 1/39). Product 11 was obtained as a colorless oil (214 mg, 75%).

MS (ESI): $[M+Na]^{2+}=1752.8$

Synthesis of Dendrimers with Amine Surface

Synthesis of benzyl phenyl carbonate (*Synthesis,* 2002, 15, 2195-2202)

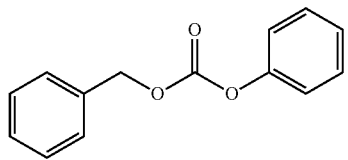 [SMILES: O=C(OCc1ccccc1)Oc1ccccc1]

Benzyl alcohol (10.8 g, 100.0 mol) was dissolved in 100 mL of $CH_2Cl_2$. The solution was cooled down to 0° C. and phenyl chloroformate (15.7 g, 100 mol) was slowly added dropwise. The solution was stirred at RT overnight. Addition of 100 mL of $H_2O$ was followed by 2× washes with 100 mL of 2M $H_2SO_4$ each time. The organic phase was separated off and dried over $Na_2SO_4$. The solvent was removed in vacuo to obtain a colorless liquid (22.5 g, 99%).

$^1$H NMR ($CDCl_3$, 300 MHz): δ=7.45-7.31 (m, 6H, CH, aromat.), 7.25-7.14 (m, 4H, CH, aromat.), 5.25 (s, 2H, $CH_2$, benzyl).

Benzyl 3-aminopropylcarbamate (12) (*Synthesis,* 2002, 15, 2195-2202)

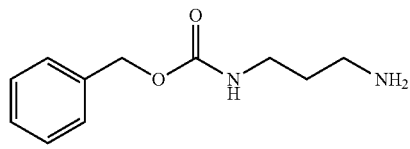 [SMILES: NCCCNC(=O)OCc1ccccc1]

To a solution of 1,3-propanediamine (6.50 g, 87.0 mol) in 250 mL of abs. EtOH was added benzyl phenyl carbonate (20.0 g, 87.0 mmol). The solution was stirred overnight. A white precipitate formed. The solvent was removed in a rotary evaporator, and the residue was taken up with 100 ml of distilled $H_2O$. This was followed by acidification with 2M HCl to pH 1-2, and 4× extracting with 250 mL of $CH_2Cl_2$ each time. The aqueous phase was rendered strongly alkaline with 2M NaOH and extracted 4× with 250 mL of $CH_2Cl_2$ each time. The combined organic phases were dried over $Na_2SO_4$, subsequently the solvent was removed in a rotary evaporator to obtain the product as a viscid white mass (4.70 g, 26%).

ESI-MS: $[M+H]^+=209.1$

Benzyl [3-(formylamino)propyl]carbamate

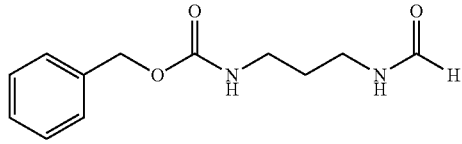 [SMILES: O=CNCCCNC(=O)OCc1ccccc1]

Benzyl 3-aminopropylcarbamate 12 (8.00 g, 36.0 mmol) was dissolved in 250 mL of ethyl formate. The solution was refluxed for 4 h. Following complete conversion of the amine, the solution was concentrated to dryness in a rotary evaporator to obtain the formamide as a colorless oil (8.90 g, 99%).

ESI-MS: $[M+Na]^+=259.2$

Benzyl 3-isocyanopropylcarbamate (13)

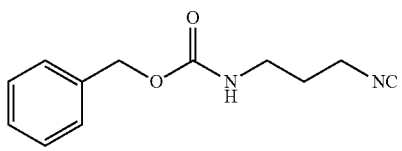

To a solution of benzyl [3-(formylamino)propyl]-carbamate (15.8 g, 67.0 mmol) in 300 mL of dry $CH_2Cl_2$ was added diisopropylamine (29.6 mL, 211 mmol). The solution was cooled down to 0° C. using an ice bath. Then, $POCl_3$ (7.36 mL, 80.0 mmol) was slowly added dropwise. After warming to room temperature, the solution was stirred for a further 3 h. Addition of 20 g of $Na_2CO_3$, dissolved in 100 mL of distilled $H_2O$, was followed by further stirring at RT for 30 min. The reaction mixture was subsequently diluted with 100 mL of $CH_2Cl_2$ and also 100 mL of distilled $H_2O$ and the aqueous phase was extracted 3× with 150 mL of $CH_2Cl_2$ each time. The combined organic phases were dried over $Na_2SO_4$ and concentrated in a rotary evaporator. Purification by column chromatography (MeOH/$CH_2Cl_2$, 1/9, v/v) gave a dark brown liquid (13.0 g, 89%).

ESI-MS: $[M+Na]^2=241.1$ 4-(((Benzyloxy)carbonyl)amino)butanoic acid (14)

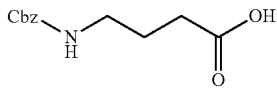 [SMILES: O=C(O)CCCNC(=O)OCc1ccccc1]

To a solution of γ-aminobutryric acid (10.0 g, 103 mmol) in 150 mL of $CH_2Cl_2$ and 400 mL of 5% $Na_2CO_3$ was added benzyloxycarbonyl chloride (17.4 mL, 103 mmol) by gradual dropwise addition. The solution was stirred at room temperature for 6 h and then acidified with 10% HCl. The solution was extracted with ethyl acetate (4×200 mL). The combined organic phases were dried over $Na_2SO_4$ and concentrated in a rotary evaporator to obtain product 14 as colorless oil (19.0 g, 78%)

MS (ESI): $[M-H]^-=236.0$.

35

Benzyl (4-(4-[([(benzyloxy)carbonyl]amino/bu-tanoyl)-5-(1-methylethyl)-6,12-dioxo-14-phenyl-13-oxa-4,7,11-triazatetradec-1-yl]carbamate (15a)

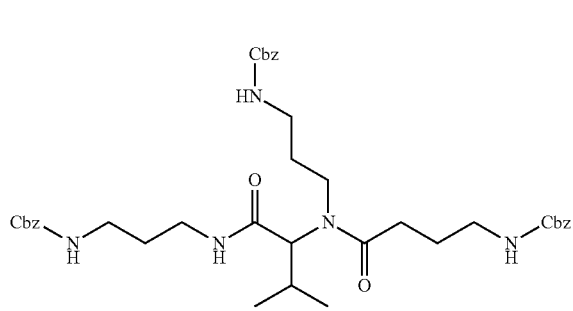 [SMILES: CC(C)C(C(=O)NCCCNC(=O)OCc1ccccc1)N(CCCNC(=O)OCc1ccccc1)C(=O)CCCNC(=O)OCc1ccccc1]

To a solution of benzyl 3-aminopropylcarbamate 12 (208 mg, 1.00 mmol) in MeOH was added isobutyraldehyde 4 (72 mg, 1.00 mmol). This solution was stirred at room temperature for 2 hours. Then, benzyl 3-isocyanopropylcarbamate 13 (218 mg, 1.00 mmol) and 4-[(benzyloxy)carbonyl]aminobutanoic acid 14 (237 mg, 1.00 mmol) were added. The solution was stirred at room temperature overnight. The solvent was removed in a rotary evaporator and the residue was purified by column chromatography (MeOH/CH$_2$Cl$_2$, 1/19, v/v) to obtain product 15a as colorless oil (623 mg, 87%).

MS (ESI): [M+H]$^+$=718.7, [M+Na]$^+$=740.7

36

N$^2$-(4-Aminobutanoyl)-N,N$^2$-bis(3-aminopropyl) valinamide (15)

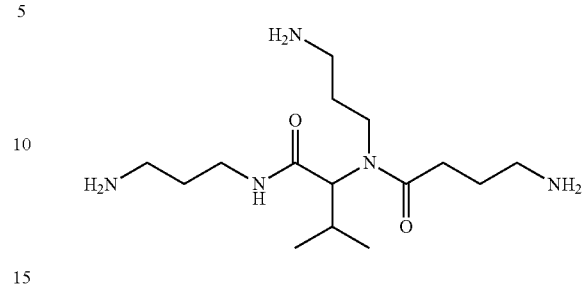

To a solution of compound 15 (546 mg, 0.76 mmol) in MeOH was added Pd(OH)$_2$/C (55 mg). The solution was 3× devolatilized and bubbled with hydrogen from a balloon. The solution was vigorously stirred under hydrogen overnight. The solution was filtered through a Celite pad and the solvent was removed in a rotary evaporator to leave amine 15 as colorless oil (231 mg, 97%).

MS (ESI): [M+H]$^+$=316.1 [M+Na]$^+$=338.4

Second Generation Dendrimer (16a)

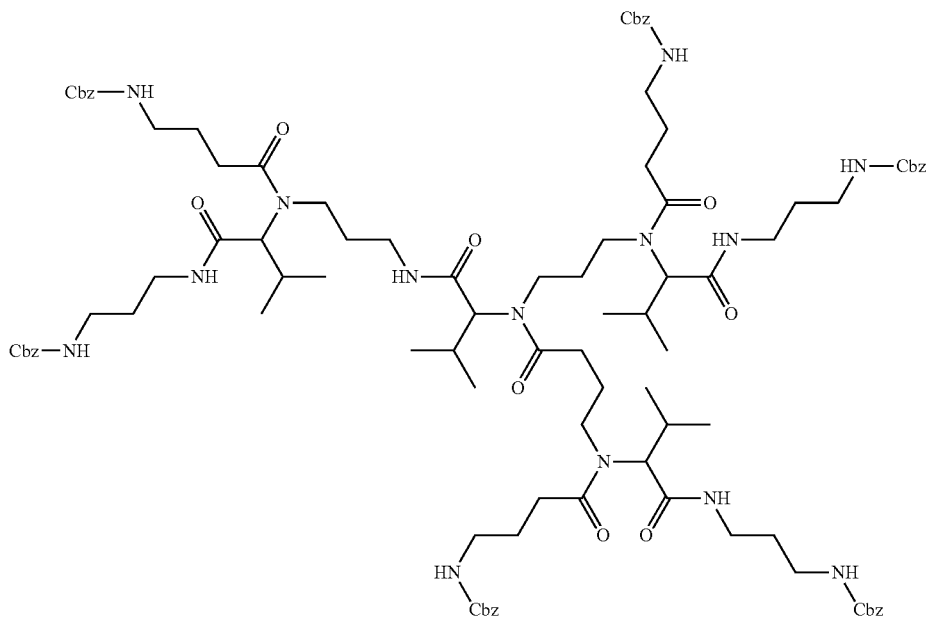 [SMILES: CC(C)C(C(=O)NCCCNC(=O)OCc1ccccc1)N(CCCNC(=O)C(C(C)C)N(CCCN(C(=O)CCCNC(=O)OCc1ccccc1)C(C(=O)NCCCNC(=O)OCc1ccccc1)C(C)C)C(=O)CCCN(C(=O)CCCNC(=O)OCc1ccccc1)C(C(=O)NCCCNC(=O)OCc1ccccc1)C(C)C)C(=O)CCCNC(=O)OCc1ccccc1]

To a solution of triamine 15 (190 mg, 0.60 mmol) in 5 mL of MeOH was added isobutyraldehyde 4 (129.8 mg, 1.80 mmol). The solution was stirred at room temperature for 2 hours. Then, benzyl 3-isocyanopropylcarbamate 13 (393 mg, 1.80 mmol) and 4-[(benzyloxy)carbonyl]aminobutanoic acid 14 (428 mg, 1.80 mmol) were added. The solution was stirred at room temperature overnight. The solvent was concentrated in a rotary evaporator and the residue was purified by column chromatography (MeOH/CH$_2$Cl$_2$, 1/19, v/v) to obtain product 16a as colorless oil (790 mg, 71%).

MS (ESI): [M+2Na]$^{2+}$=945.2, [M+Na]$^+$=1867.9

Functionalized Second Generation Dendrimer (16)

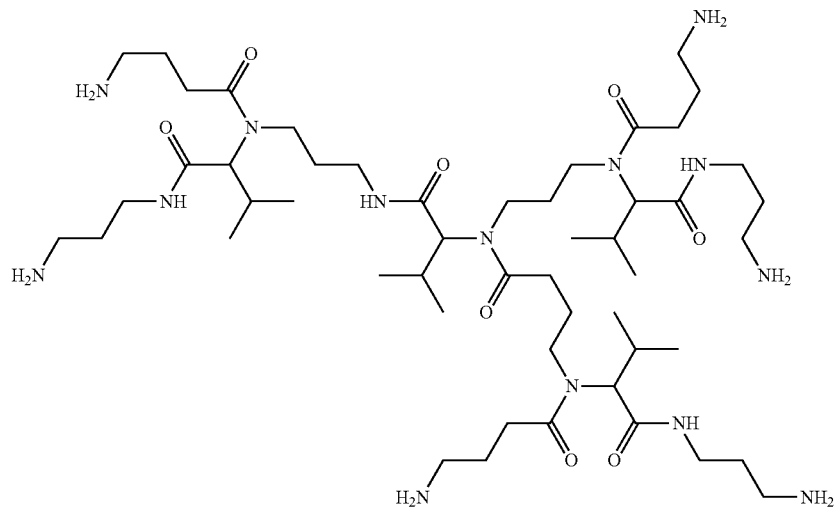 [SMILES: CC(C)C(C(=O)NCCCN)N(CCCNC(=O)C(C(C)C)N(CCCN(C(=O)CCCN)C(C(=O)NCCCN)C(C)C)C(=O)CCCN(C(=O)CCCN)C(C(=O)NCCCN)C(C)C)C(=O)CCCN]

To a solution of compound 16a (710 mg, 0.39 mmol) in 5 mL of MeOH was added Pd (OH)$_2$/C (70 mg). The solution was 3× devolatilized and bubbled with hydrogen from a balloon. The solution was vigorously stirred under hydrogen overnight. The solution was filtered through a Celite pad and the solvent was removed in a rotary evaporator to leave amine 16 as colorless oil (400 mg, 97%). MS (ESI): [M+2H]$^{2+}$= 521.0 [M+H]$^+$=1039.9

Changing the Functional Surface Groups

A dendrimer with amino surface can also be constructed using a carboxy-functionalized 2$^{nd}$ dendrimer generation. For this, an UGI reaction is carried out with compounds 13, 12, 4 and 7 to obtain dendrimer 17 as product. It can be shown here that changing between various reactive groups in the individual generations is possible.

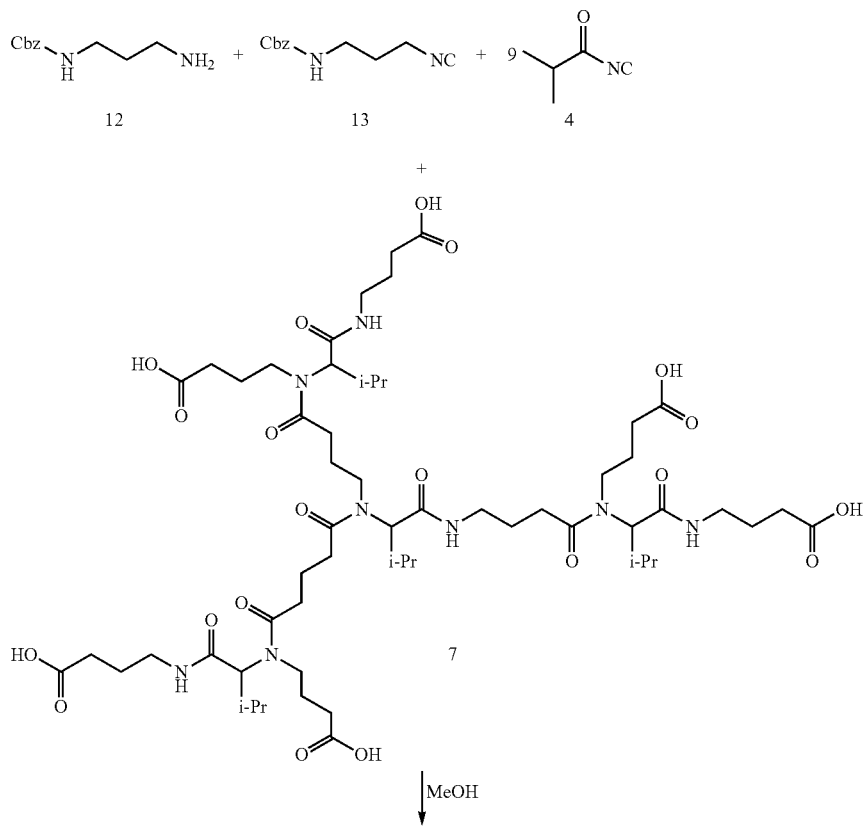

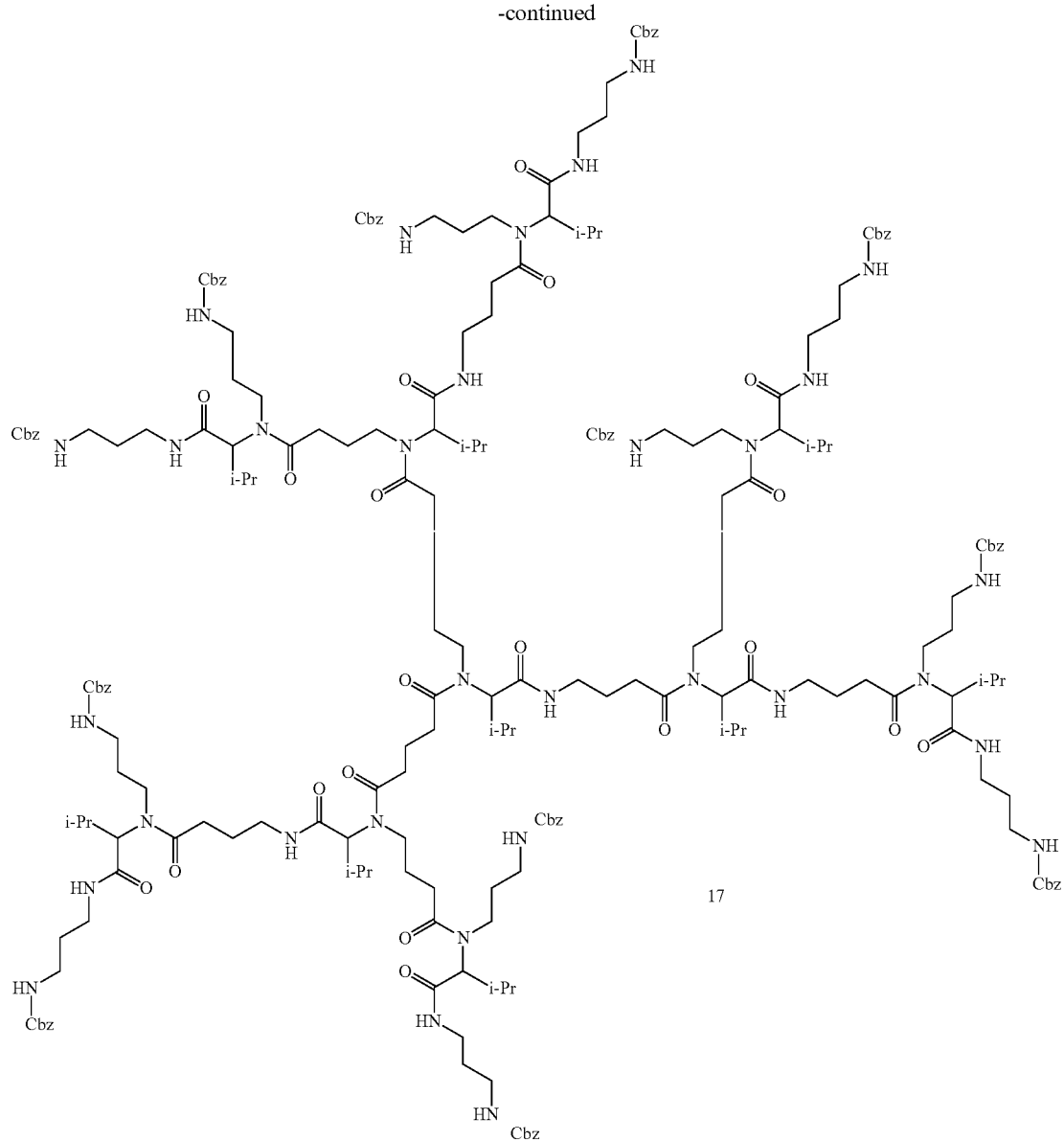

17

Synthesis of 3$^{rd}$ Generation Dendrimer (17)

To a solution of benzyl 3-aminopropylcarbamate 12 (625 mg, 3.00 mmol) in 5 mL of MeOH was added isobutyraldehyde 4 (274 µL, 3.00 mmol). The solution was stirred at room temperature for 2 hours. Then, benzyl 3-isocyanopropylcarbamate 13 (655 mg, 3.00 mmol) and also dendrimer 7 (400 mg, 0.33 mmol) were added. The solution was stirred at RT for 20 h. The solvent was removed in a rotary evaporator and the residue was purified by column chromatography (MeOH/EE, 1/20) to obtain product 17 as colorless oil (1.13 g, 84%).

MS (ESI): [M+3Na]$^{3+}$=1388.8

Synthesis of S-t-Bu-Protected Dendrimers with Sulfur Surface

A sulfur-functionalized second generation dendrimer can be synthesized from the known literature compound 18. Carboxy-functionalized second generation 7 serves as basis. The UGI reaction with 9 equivalents each of 18 and isobutyraldehyde 4, 9 equivalents of t-butyl isocyanide 19 and 1 equivalent 7 affords the S-t-bu-protected sulfur-functionalized dendrimer 20 of the 3$^{rd}$ generation in 89% yield.

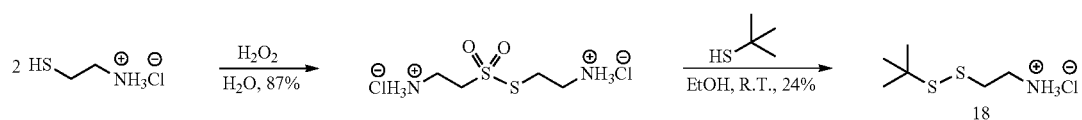

-continued

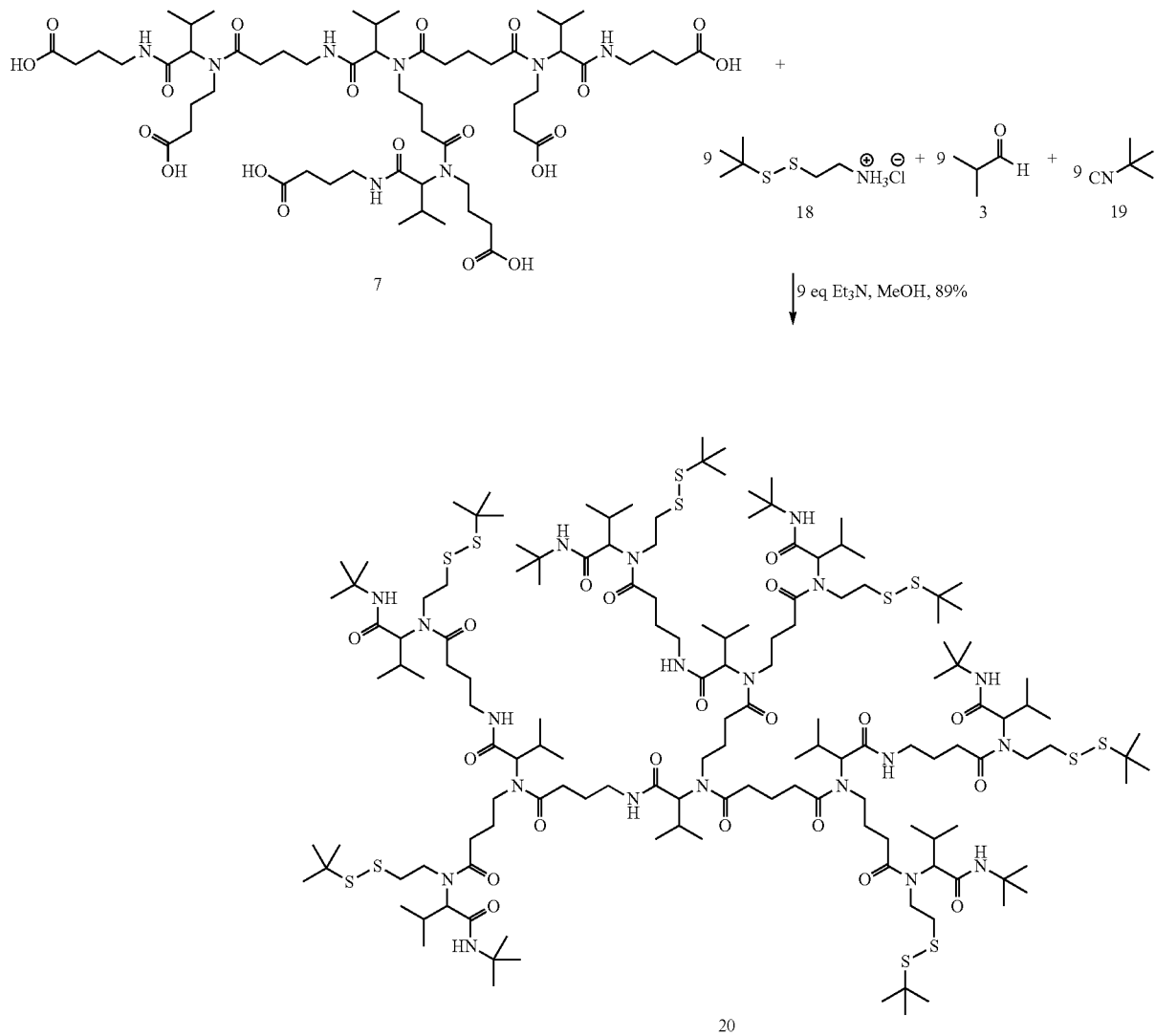

Synthesis of 18 (see JACS, 83, 1961, 4416-4417)

Cysteamine hydrochloride (5.00 g, 44.0 mmol) was dissolved in 50 ml of distilled $H_2O$ and cooled down to 0° C. with an ice bath. A 30% $H_2O_2$ solution (7.30 mL, 72.6 mmol) was slowly added dropwise. A few crystals of KI were then added as catalyst. The solution was stirred at RT for 20 h. The solvent was removed in a rotary evaporator and the residue was taken up in 30 ml of glacial acetic acid. A colorless precipitate formed on 2 hours' storage in a refrigerator and was filtered off and thoroughly washed with glacial acetic acid to obtain the dihydrochloride as colorless solid (5.30 g, 94%) which was further reacted without further purification. Dihydrochloride (5.30 g, 20.6 mmol) was dissolved in 10 ml of distilled $H_2O$. Then, t-BuSH (2.06 mL, 20.6 mmol) in 10 mL of EtOH was added and the solution was stirred at RT for 20 h. The solution was concentrated in a rotary evaporator and the residue was taken up with a mixture of 20 mL of distilled $H_2O$ and 20 mL of $Et_2O$. The solution was neutralized with $NaHCO_3$. The ether phase was then separated off and washed with distilled $H_2O$. The organic phase was extracted 2× with 6 mL of conc. HCl each time. The acidic aqueous phase was concentrated in a rotary evaporator to obtain hydrochloride 18 as colorless solid (700 mg, 17%).

$^1$H NMR (300 MHz, $CD_3OD$): δ=1.33 (s, 9H, $CH_3$), 2.94 (t, 2H, $CH_2$), 3.22 (t, 2H, $CH_2$) ppm.

Synthesis of (20)

Hydrochloride 18 (150 mg, 0.74 mmol), isobutyraldehyde 4 (68.0 µl, 0.74 mmol) and $Et_3N$ (103 µl, 0.74 mmol) were dissolved in 5 mL of MeOH followed by stirring at RT for 2 h. Then, dendrimer 7 (100 mg, 0.08 mmol) and t-butyl isocyanide 19 (84.0 µl, 0.74 mmol) were added. The solution was stirred at RT for 20 h. The solvent was removed in a rotary evaporator and the residue was purified by column chromatography (EE/MeOH, 20/1). Product 20 was obtained as colorless solid (200 mg, 89%). MS (ESI): $[M+2Na]^+$=1537.6

Synthesis of an N-Boc Serine-Functionalized Dendrimer

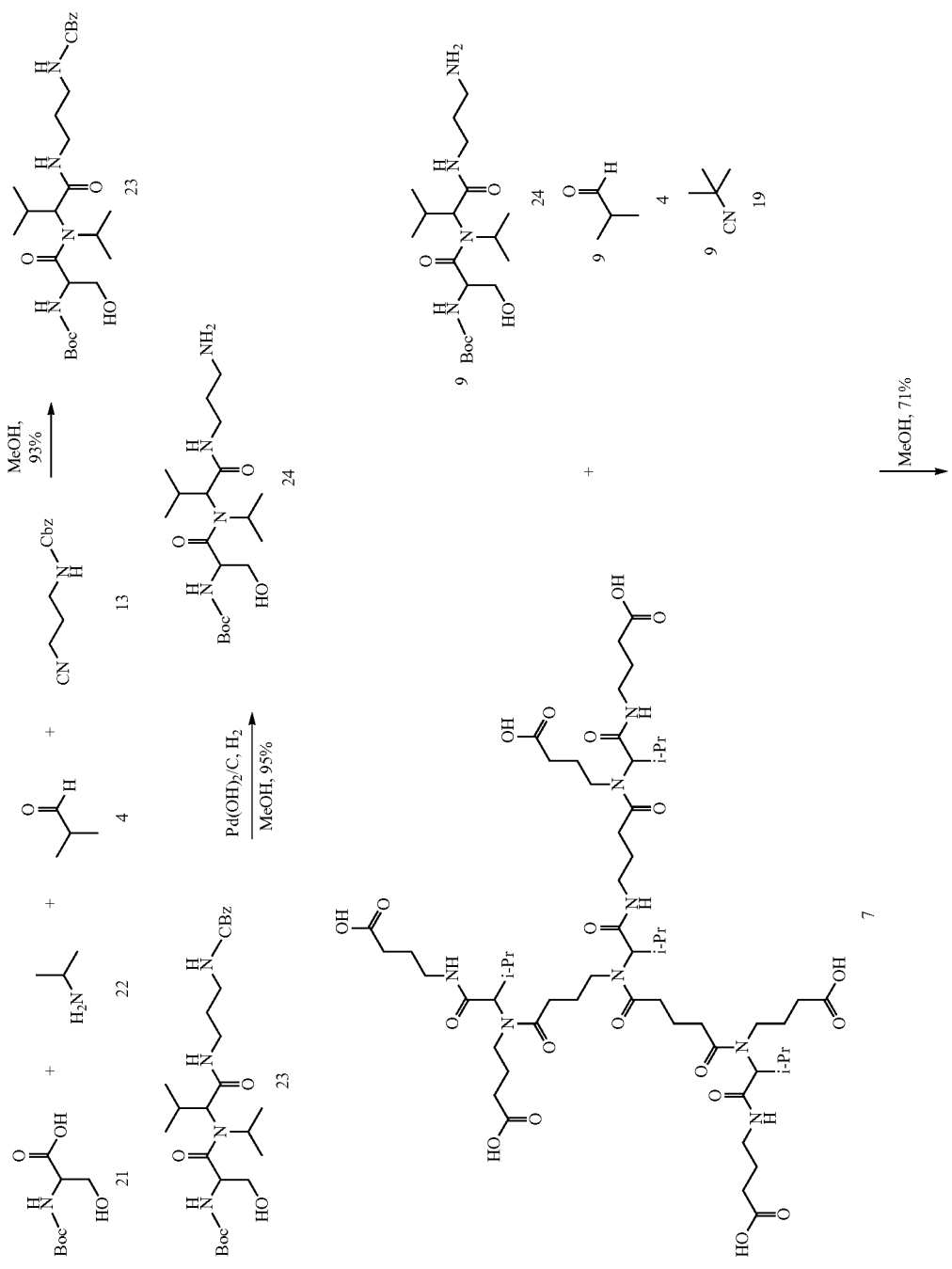

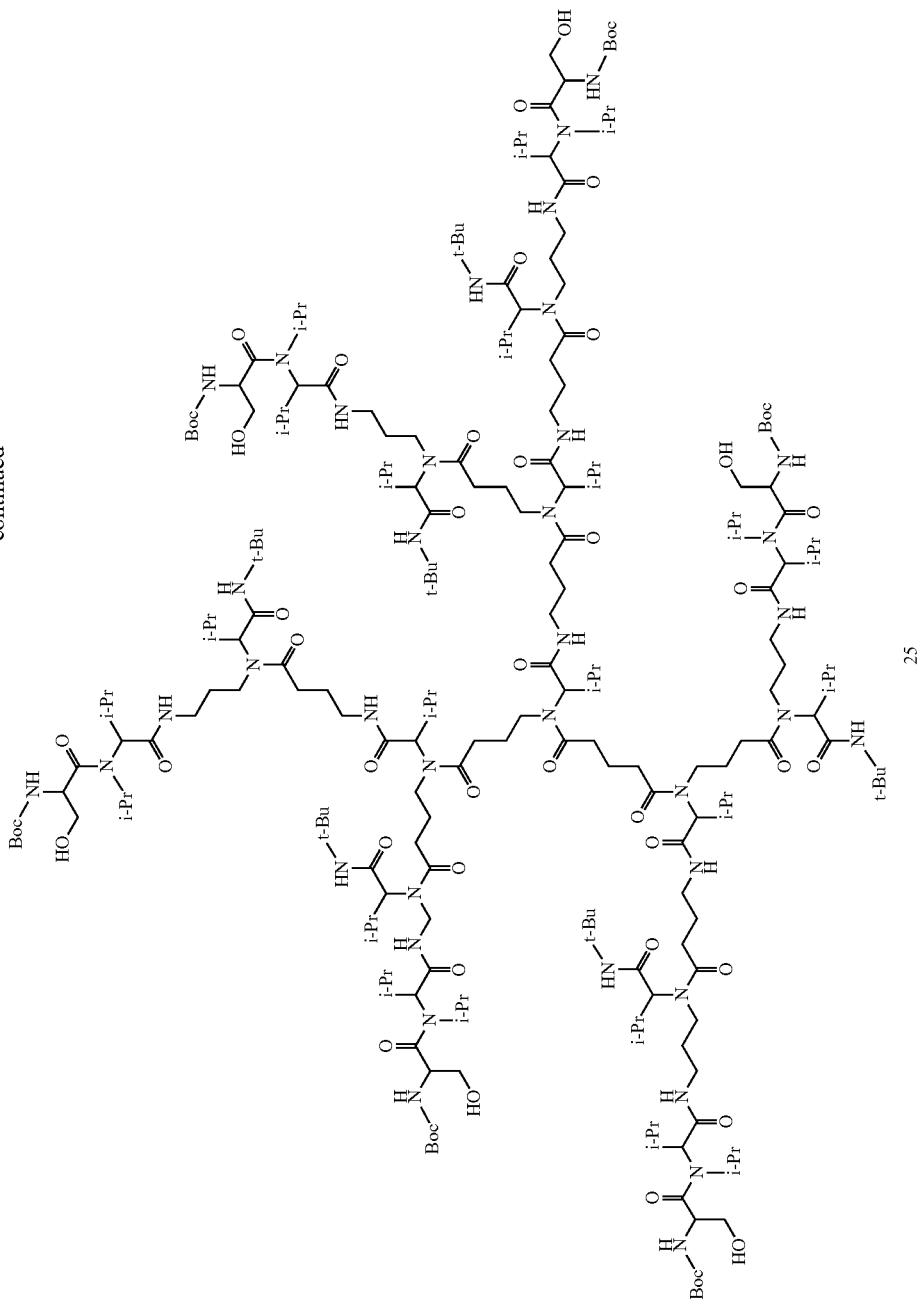

The carboxy-functionalized 2nd dendrimer generation 7 can be used as starting material to construct an N-Boc serine-functionalized 3rd generation dendrimer. For this purpose, N-Boc serine 21 was UGI-reacted with isopropylamine 22, isobutyraldehyde 4 and isonitrile 19 to form compound 23. Subsequent hydrogenolysis affords the amine 24 which is subsequently UGI-reacted with 7 to form dendrimer 25.

Synthesis of UGI Product 23

Isopropylamine 22 (827 µl, 9.70 mmol) and isobutyraldehyde 4 (885 µl, 9.70 mmol) were dissolved in 10 mL of MeOH followed by stirring at RT for 2 h. N-Boc-Ser-OH 21 (2.00 g, 9.70 mmol) and benzyl 3-isocyanopropylcarbamate 13 (2.10 g, 9.70 mmol) were added and the solution was stirred at RT for 20 h. The solvent was subsequently removed in a rotary evaporator and the residue purified by column chromatography (EE/hexane, 4/1) to obtain product 23 as colorless oil (4.85 g, 93%).
MS (ESI): [M+H]$^+$=537.6 [M+Na]$^+$=559.1

Synthesis of Amine (24)

UGI product 23 (4.35 g, 8.10 mmol) was dissolved in 50 mL of MeOH. Then, 300 mg of Pd(OH)$_2$/C were added. Under vigorous agitation, the solution was 3× devolatilized and bubbled with hydrogen from a balloon. The solution was vigorously stirred at RT for 4 h. The catalyst was then filtered off on a Celite pad. The solvent was concentrated in a rotary evaporator and product 24 was obtained as colorless oil (3.10 g, 95%).
ESI-MS: calc. 403.5, obs. 403.7
MS (ESI): [M+H]$^+$=403.6

Synthesis of Dendrimer (25)

Amine 24 (1.50 g, 3.69 mmol) and isobutyraldehyde 4 (340 µL, 3.69 mmol) were dissolved in 20 mL of MeOH followed by stirring at RT for 2 h. Then, dendrimer 7 (500 mg, 0.41 mmol) and t-butyl isocyanide 19 (422 µL, 3.69 mmol) were added and the solution was stirred at RT for 20 h. The solvent was removed in a rotary evaporator and the residue purified by column chromatography (MeOH/EE, 1/15) to obtain product 25 as colorless oil (1.30 g, 71%). MS (ESI): [M+3Na]$^{3+}$=1505.6, [M+2Na]$^{2+}$=2248.7

Synthesis of Amino Dendrimers with Other UGI Components

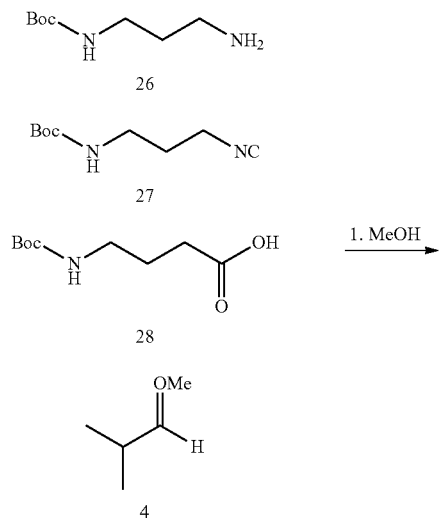

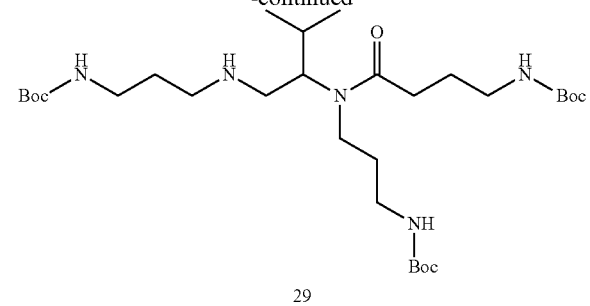

29

Synthesis of t-butyl 3-aminopropylcarbamate 26* (see Synthesis, 2002, 15, 2195-2202).

Synthesizing the Formamide of t-Butyl 3-Aminopropylcarbamate (26)

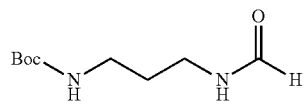 [SMILES: CC(C)(C)OC(=O)NCCCNC=O]

Amine 26* (8.30 g, 47.0 mmol) was dissolved in ethyl formate (150 mL) followed by refluxing for 3 h. The solvent was removed in a rotary evaporator to obtain the product (9.1 g, 95%) as yellow oil. The formamide was further reacted without further purification. MS (ESI): [M+Na]$^+$=225.3 t-Butyl 3-isocyanopropylcarbamate (27)

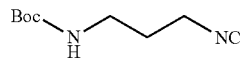

The formamide (9.1 g, 45 mmol) was dissolved in 250 mL of dry CH$_2$Cl$_2$ and cooled down to 0° C. using an ice bath. Then, diisopropylamine (18.8 mL, 134 mmol) was added and phosphoryl chloride (4.89 mL, 53.8 mmol) was slowly added dropwise. The solution was stirred at room temperature for 2 h. Then, Na$_2$CO$_3$ (10.0 g in 100 mL H$_2$O) was added followed by stirring at R.T. for 30 min. The phases were separated and the aqueous phase was extracted with CH$_2$Cl$_2$ (3×100 mL). The organic phases were dried over Na$_2$SO$_4$ and concentrated to dryness in a rotary evaporator. The residue was purified by column chromatography (CH$_2$Cl$_2$/MeOH, 40/1) to obtain product 27 as brown oil (6.56 g, 79%). MS (ESI): [M+Na]$^+$=207.1

Synthesis of 4-(((t-butyloxy)carbonyl)amino)butanoic Acid (28)

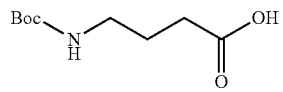

γ-Aminobutyric acid (10.0 g, 97.0 mmol) was dissolved in 100 mL of MeOH and triethylamine (84.0 mL, 600 mmol) was added. Boc$_2$O (43.7 g, 200 mmol) was added and the solution was refluxed overnight. The reaction solution was concentrated to dryness and the residue dissolved in saturated NaHCO₃ (200 mL). The solution was extracted with petroleum ether (3×150 mL). The aqueous phase was acidified with 2M HCl and extracted with ethyl acetate (3×150 mL). The organic phases were combined and dried over Na₂SO₄. The solution was concentrated in a rotary evaporator and the product was obtained as a colorless solid (16.0 g, 78.8 mmol). Melting point: 58° C.

Synthesis of Boc-Protected First Generation (29)

Amine 26 (87.1 mg, 0.50 mmol) and isobutyraldehyde 4 (46 µL, 0.50 mmol) were dissolved in 10 mL of MeOH followed by stirring at RT for 2 h. Carboxylic acid 28 (109 mg, 0.50 mmol) and t-butyl 3-isocyanopropylcarbamate 27 (292.1 mg, 0.50 mmol) were added and the solution was stirred at RT for 20 h. The solvent was then removed in a rotary evaporator and the residue purified by column chromatography (CH₂Cl₂/MeOH, 20/1) to obtain product 29 as colorless oil (194 mg, 63%). MS (ESI): [M+H]⁺=616.4

Synthesis of First Generation (30)

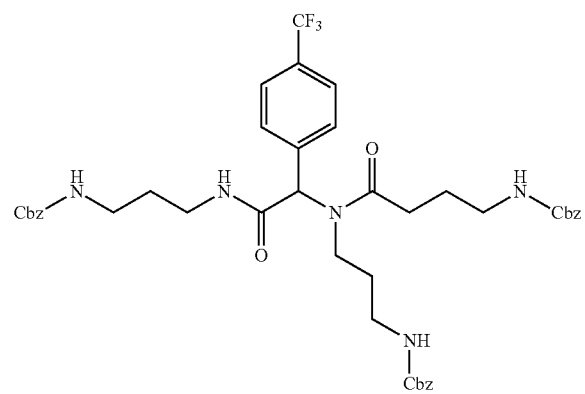

Amine 12 (2.70 g, 13.0 mmol) and p-trifluoromethylbenzaldehyde (1.78 mL, 13.0 mmol) were dissolved in 50 ml of MeOH followed by stirring at RT for 2 h. Carboxylic acid 14 (3.08 g, 13.0 mmol) and isocyanide 13 (2.80 g, 13.0 mmol) were added and the solution was stirred at RT for 20 h. The solvent was then removed in a rotary evaporator and the residue purified by column chromatography (EE/PE, 1/4) to obtain product 30 as colorless oil (7.32 g, 69%).

Synthesis of First Generation (31)

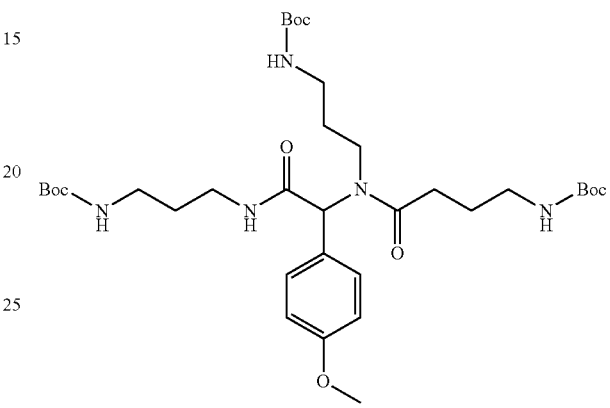

Amine 26 (87.1 mg, 0.50 mmol) and p-methoxybenzaldehyde (60.3 µL, 0.50 mmol) were dissolved in 10 mL of MeOH followed by stirring at RT for 2 h. Carboxylic acid 28 (109 mg, 0.50 mmol) and t-butyl 3-isocyanopropylcarbamate 27 (292.1 mg, 0.50 mmol) were added and the solution was stirred at RT for 20 h. The solvent was then removed in a rotary evaporator and the residue purified by column chromatography (CH₂Cl₂/MeOH, 20/1) to obtain product 31 as colorless oil (194 mg, 63%). MS (ESI): [M+H]⁺=680.8

Synthesis of Dendrimers with Sugar Functions Via Click Reactions

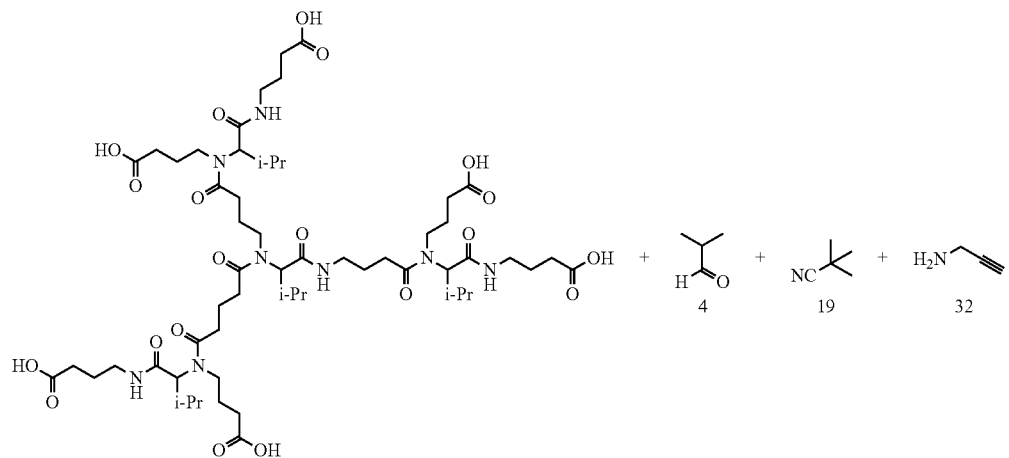

-continued
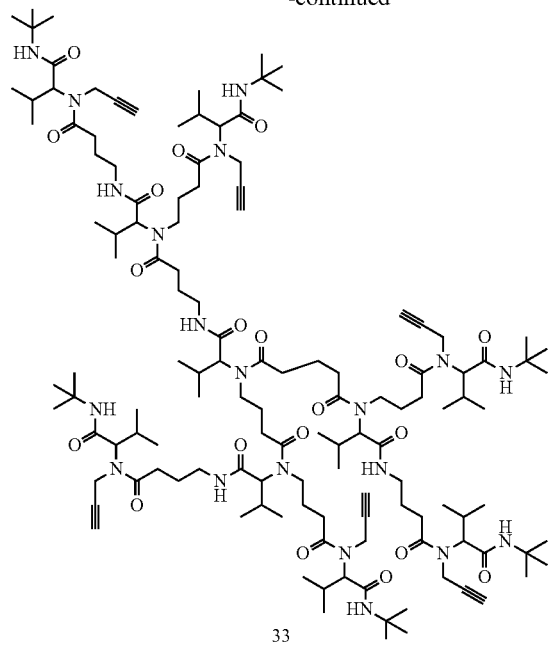
33

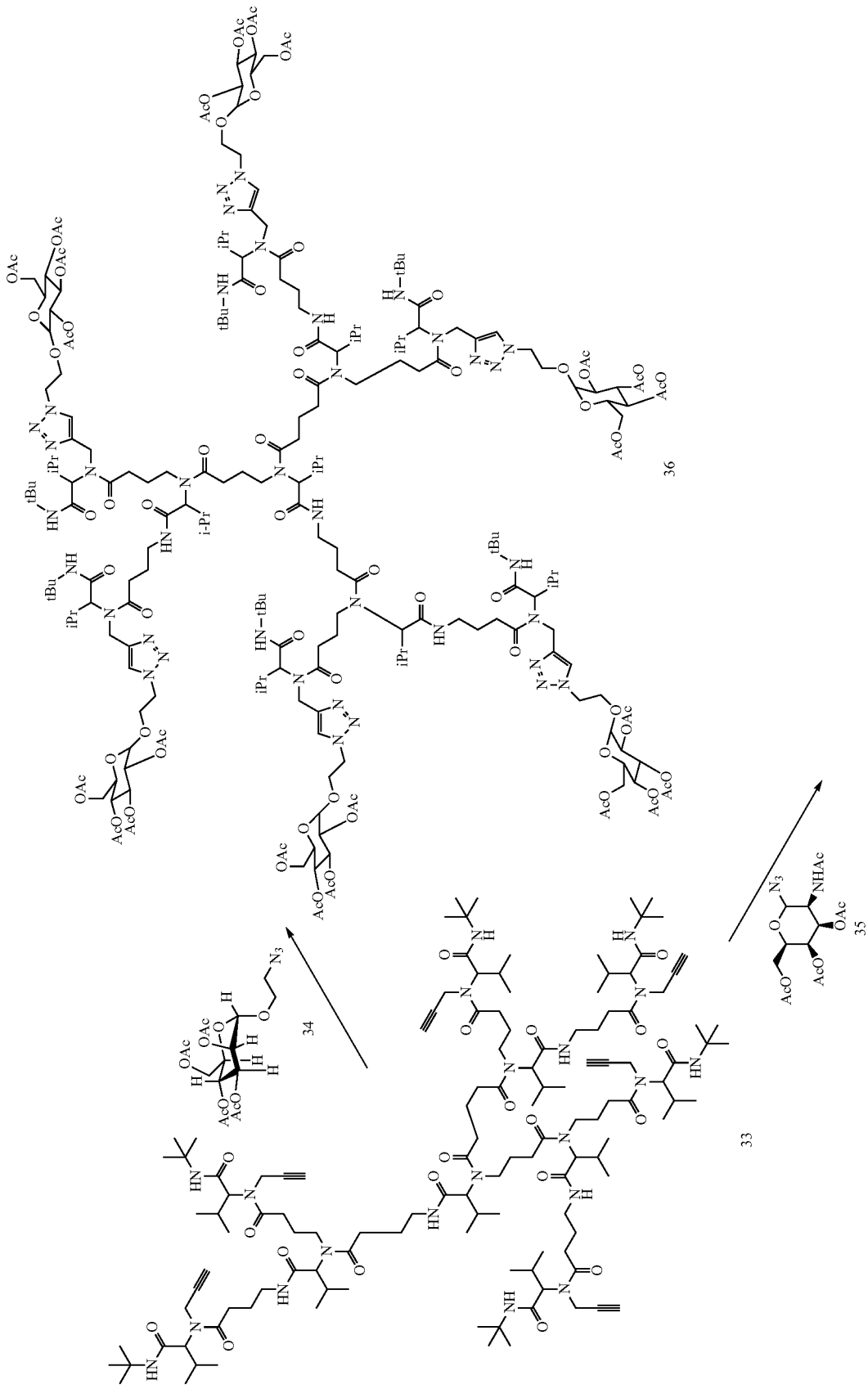

-continued
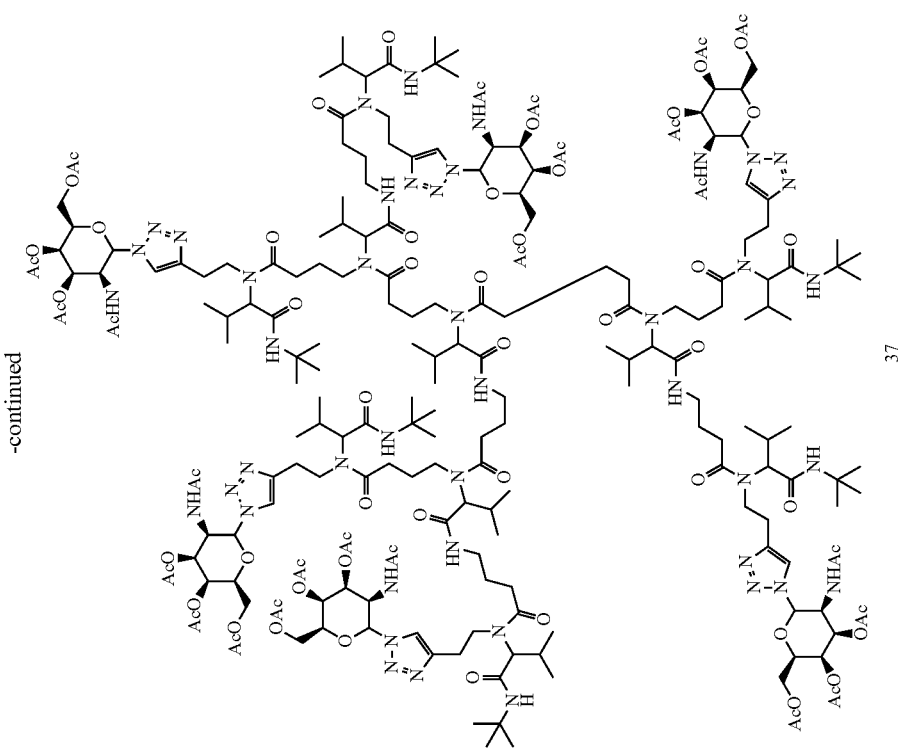
37

Synthesis of 3$^{rd}$ Generation Alkyne-Functionalized (33)

Propargylamine 32 (97.0 μl, 1.50 mmol) and isobutyraldehyde 4 (137 μl, 1.50 mmol) were dissolved in 5 ml of MeOH followed by stirring at R.T. for 2. Then, dendrimer 7 (200 mg, 165 μmol) and t-butyl isocyanide 19 (170 μl, 150 mmol) were added. The solution was stirred at R.T. overnight. The solvent was concentrated to dryness in a rotary evaporator and the residue was purified by column chromatography (EE/MeOH, 20/1) to obtain product 33 as yellow oil (230 mg, 59%). MS (ESI): [M+Na]$^+$=2390.2

Synthesis of compound 34 is known from the literature: *J. Chem. Soc.: Perkin Trans. I*, 2001, 823. Compound 35 is commercially available.

Synthesis of Mannose-Modified Dendrimer (36)

Dendrimer 33 (190 mg, 0.08 mmol) and mannose derivative 34 (201 mg, 0.48 mmol) were dissolved in t-BuOH. Then, Cu(II)SO$_4$ (18.0 mg, 0.10 mmol), dissolved in 2.5 mL of H$_2$O, and also sodium ascorbate (38.0 mg, 0.20 mmol), dissolved in 5 mL of H$_2$O, were added. The solution was stirred at R.T. overnight. The reaction solution was diluted with H$_2$O and CH$_2$Cl$_2$ (10 mL each). The organic phase was separated off and the aqueous phase was extracted with CH$_2$Cl$_2$ (3×20 mL). The combined organic phases were dried over Na$_2$SO$_4$ and the solvent was concentrated in a rotary evaporator. Subsequent column-chromatographic purification yielded product 36 as colorless oil (200 mg, 51%). MS (ESI): [M+3Na]=1647.2

Synthesis of GlucNAc-Modified Dendrimer (37)

Dendrimer 33 (190 mg, 0.08 mmol) and N-acetylglucose derivative 35 (180 mg, 0.48 mmol) were dissolved in t-BuOH. Then, Cu(II)SO$_4$ (18.0 mg, 0.10 mmol), dissolved in 2.5 mL of H$_2$O, and also sodium ascorbate (38.0 mg, 0.20 mmol), dissolved in 5 mL of H$_2$O, were added. The solution was stirred at R.T. overnight. The reaction solution was diluted with H$_2$O and CH$_2$Cl$_2$ (10 mL each). The organic phase was separated off and the aqueous phase was extracted with CH$_2$Cl$_2$ (3×20 mL). The combined organic phases were dried over Na$_2$SO$_4$ and the solvent was concentrated in a rotary evaporator. Subsequent column-chromatographic purification yielded product 37 as colorless oil (190 mg, 52%). MS (ESI): [M+3Na]$^{3+}$=1556.5

Synthesis of Dendrimers with Terminal Hydroxyl Groups

Carboxy-functionalized second generation 7 can be reacted with isobutyraldehyde 4, t-butyl isocyanide 19 and 6-aminohexanol 38 to synthesize the 3$^{rd}$ generation dendrimer 39.

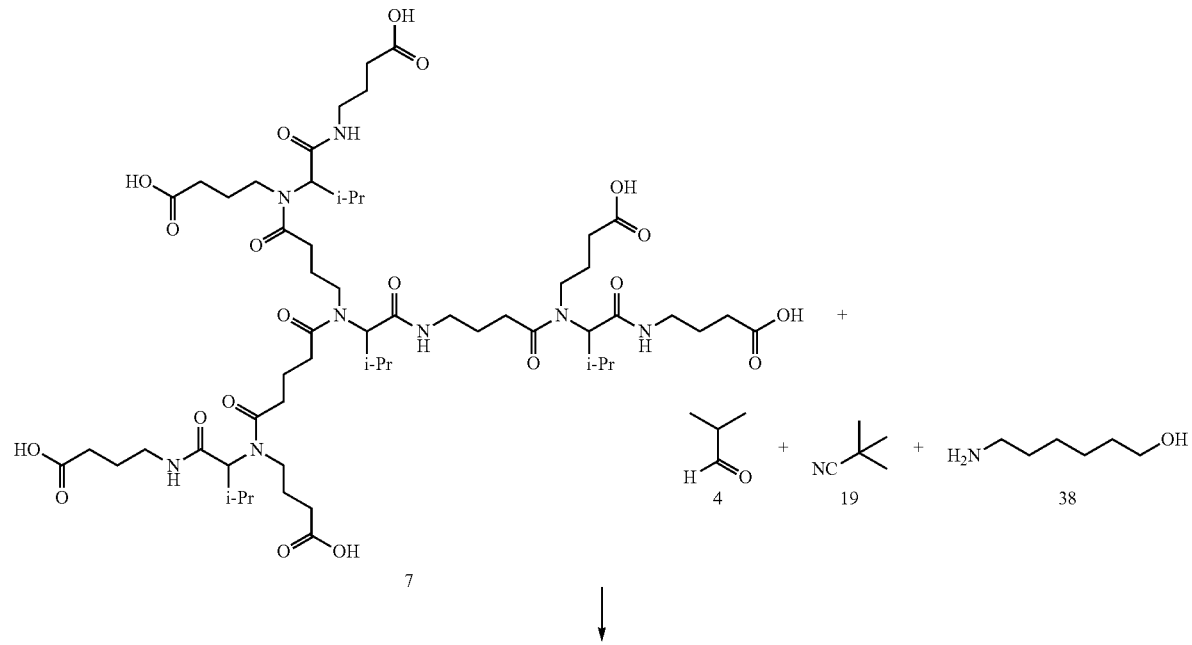

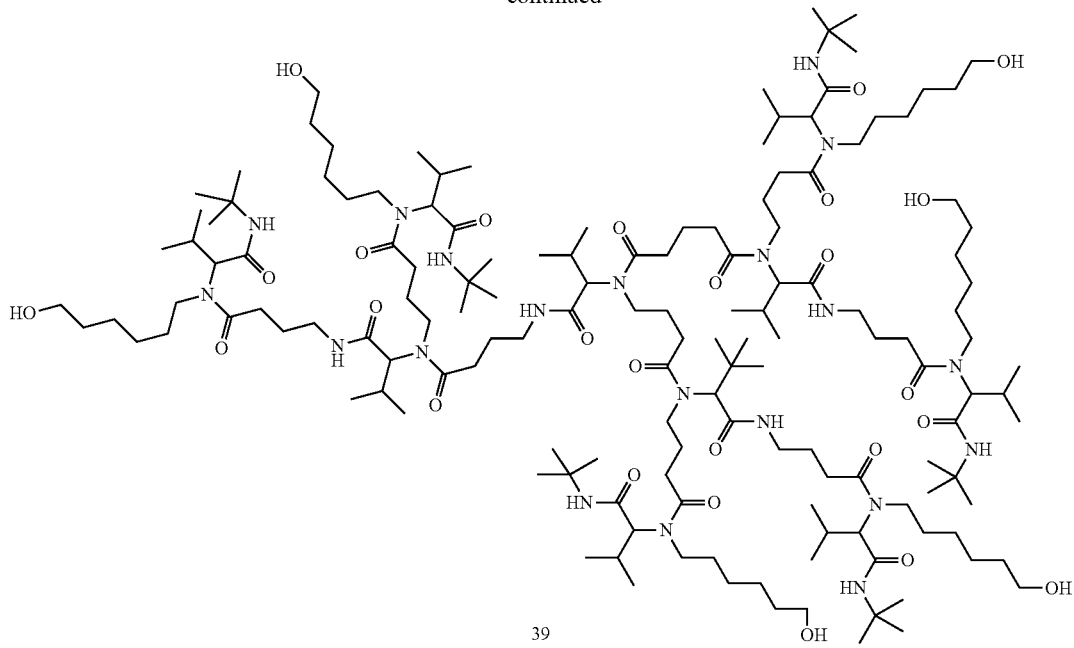

39

Synthesis of Dendrimer 39

6-Aminohexanol 38 (522 mg, 4.45 mmol) and isobutyraldehyde 4 (406 μl, 4.45 mmol) were dissolved in 10 mL of MeOH followed by stirring at R.T. for 2 h. Then, dendrimer 7 (300 mg, 0.25 mmol) and t-butyl isocyanide 19 (503 μl, 4.45 mmol) were added. The solution was stirred at R.T. overnight. The solution was concentrated to dryness in a rotary evaporator and the residue was purified by column chromatography to obtain the product as colorless oil (588 mg, 86%).

MS (ESI): [M+Na]$^+$=2763.6

Synthesis of Dendrimers with Fluorescent Dyes

The fluorescent dyes used were 5(6)-carboxyfluorescein, a pyrene derivative and rhodamine B.

Synthesis of Fluorescein-Labeled Dendrimers

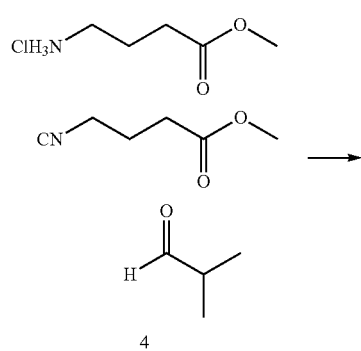

40

Synthesis of (40)

Methyl 4-(chloramino)butanoate 1 (41.5 mg, 0.27 mmol), triethylamine (37.4 μL, 0.27 mmol) and isobutyraldehyde 4 (24.6 μl, 0.27 mmol) were dissolved in 5 mL of MeOH followed by stirring at R.T. for 2 h. Then, 5(6)-carboxyfluorescein (100 mg, 0.27 mmol) and methyl 4-(isocyano)butanoate 3 (34.0 μl, 0.27 mmol) were added. The solution was stirred at R.T. overnight. The solution was concentrated to dryness in a rotary evaporator and the residue purified by column chromatography to obtain the product as orange oil (80 mg, 44%). MS (ESI): [M+H]$^+$=675.5

Synthesis of Dendrimers with Pyrene Dyes
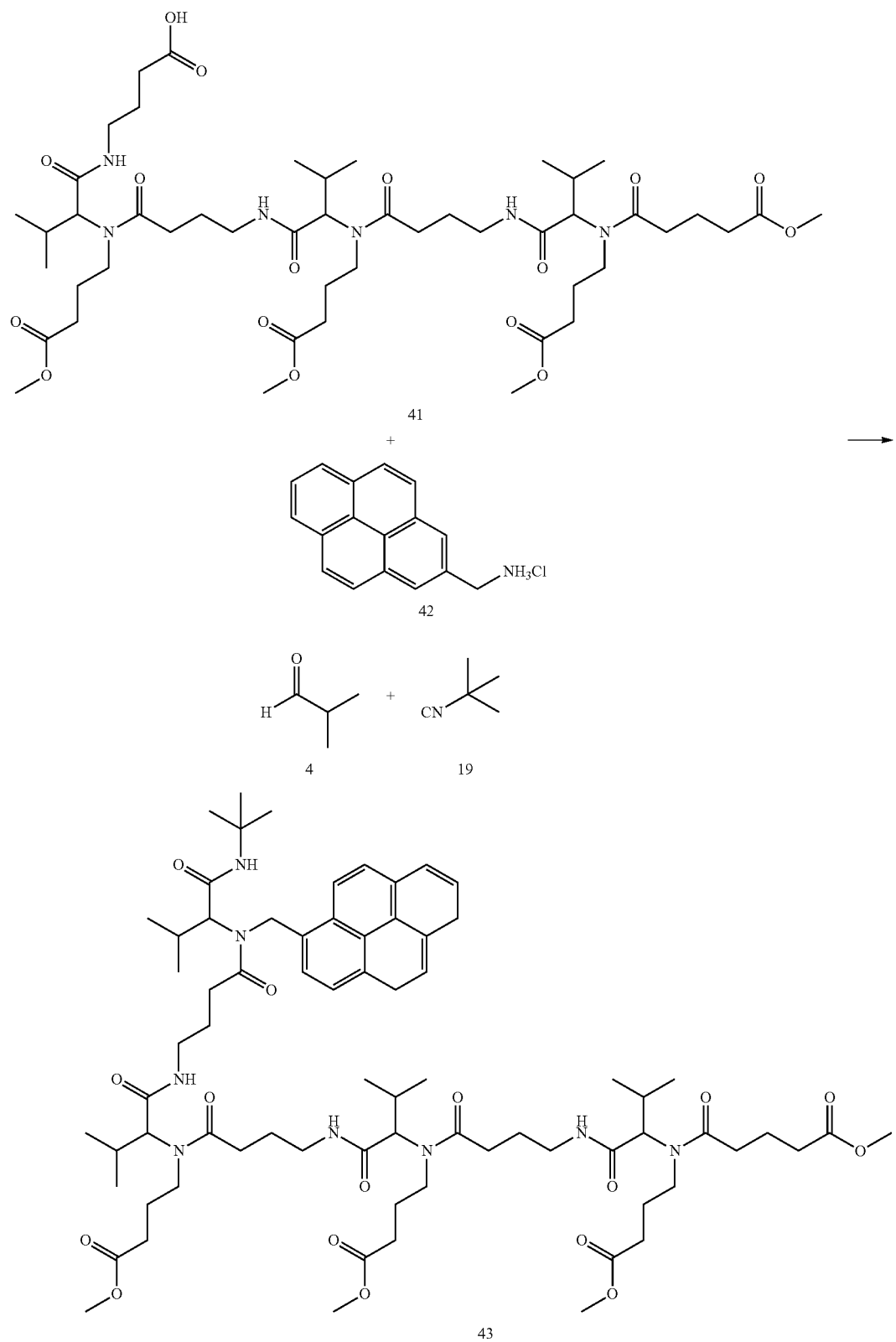

Synthesis of (43)

1-Pyrenemethylamine hydrochloride 42 (26.8 mg, 0.10 mmol), triethylamine (14.0 µl, 0.10 mmol) and isobutyraldehyde 4 (10.0 µl, 0.10 mmol) were dissolved in 5 mL of MeOH followed by stirring at R.T. for 2 h. Then, dendrimer 41 (100 mg, 0.10 mmol) and t-butyl isocyanide 19 (11 µl, 0.10 mmol) were added. The solution was stirred at R.T. overnight. The solution was concentrated to dryness in a rotary evaporator and the residue purified by column chromatography (EE/hex., 10/1) to obtain the product as colorless oil (70.0 mg, 57%).

MS (ESI): [M+Na]$^+$=1391.0

Synthesis of Rhodamine B-Labeled Dendrimers

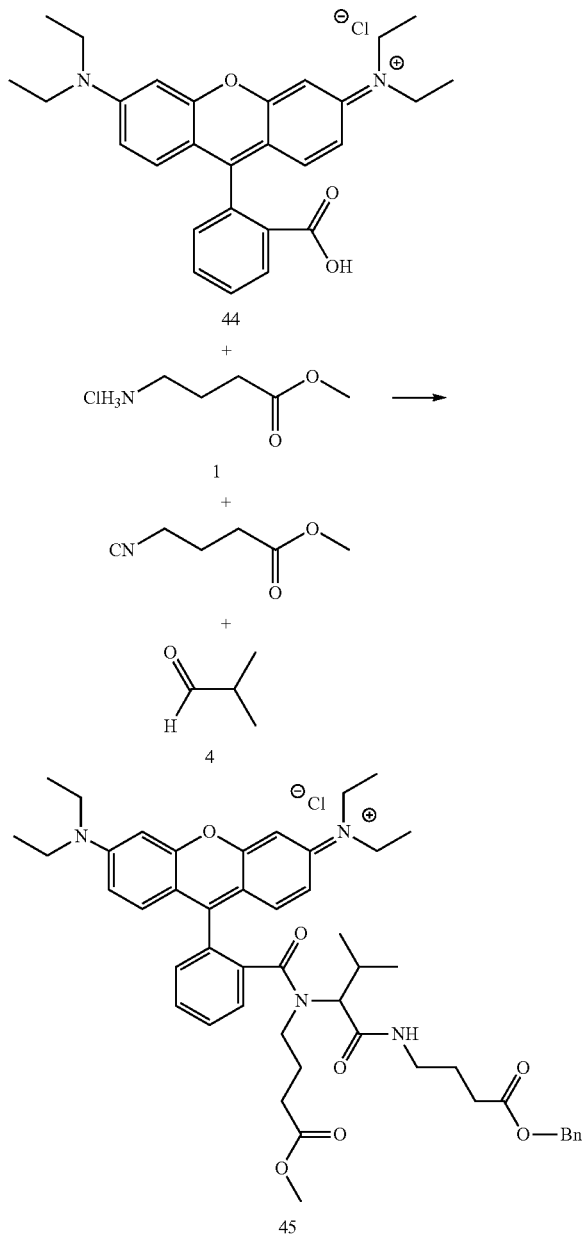

Synthesis of (45)

Methyl 4-(chloramino)butanoate 1 (644 mg, 4.20 mmol), triethylamine (583 µL, 4.20 mmol) and isobutyraldehyde 4 (382 µl, 4.20 mmol) were dissolved in 20 mL of MeOH followed by stirring at R.T. for 2 h. Then, rhodamine B (2.00 g, 4.20 mmol) and benzyl 4-(isocyano)butanoate (854 mg, 4.20 mmol) were added. The solution was stirred at R.T. overnight. The solution was concentrated to dryness in a rotary evaporator and the residue purified by column chromatography (CH$_2$Cl$_2$/MeOH, 20/1) to obtain the product as a violet oil (2.69 g, 55%).

MS (ESI): [M]$^+$=817.5

Synthesis of Core Units Via UGI-4CRs

General Method for UGI-4CRs with Primary Alkylammonium Chlorides:

The aldehyde or keto component (6.50 mmol), the primary ammonium chloride (6.50 mmol) and triethylamine (6.50 mmol) in MeOH (10 mL) are stirred at room temperature for two hours to form the imine intermediate. Then, the carboxylic acid component (6.50 mmol) and the isonitrile component (6.50 mmol) are added in succession. The reaction proceeds at room temperature on stirring for one day and the course is policed via TLC. After the reaction has ended, the methanolic solution is evaporated and the crude product obtained purified by column chromatography.

Methyl 5-[(5-methoxy-1-{[(4-methoxy-4-oxobutyl)amino]-carbonyl}-5-oxopentyl)-(4-methoxy-4-oxobutyl)amino]-5-oxopentanoate (50)

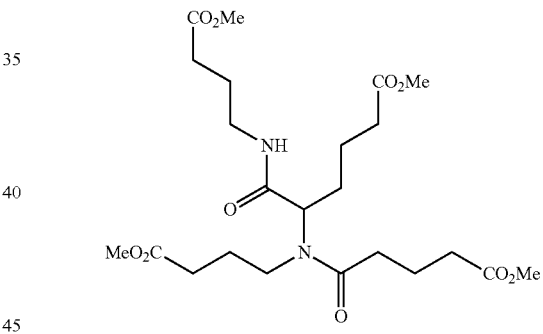

The Ugi-4CR of monomethyl glutarate (0.95 g, 6.51 mmol) with methyl 5-oxopentanoate (0.85 g, 6.51 mmol), methyl 4-aminobutyrate hydrochloride (1.00 g, 6.51 mmol) and methyl 4-isocyanobutyrate (0.83 g, 6.51 mmol) yields the methyl ester-protected core unit 50 after column-chromatographic purification (ethyl acetate/MeOH 4:1) as slightly yellowish oil (0.82 g, 25%). TLC (ethyl acetate) $R_f$=0.40; $^1$H NMR (CDCl$_3$, 300 MHz) δ=1.54-1.61 (m, 2H, CH$_2$), 1.71-2.04 (m, 8H, 4CH$_2$), 2.24-2.44 (m, 8H, 4CH$_2$), 2.51 (t, J=7.2 Hz, 2H, CH$_2$), 3.20-3.35 (m, 4H, 2CH$_2$), 3.66, 3.67, 3.68, 3.69 (4s, 12H, 4CH$_3$), 4.80 (t, J=7.6 Hz, 1H, CH), 6.83 (t, J=5.8 Hz, 1H, NH) ppm; $^{13}$C NMR (CDCl$_3$, 75 MHz) δ=19.97, 20.61, 20.89, 21.55, 24.61, 24.78, 27.49, 30.81, 31.32, 31.46, 31.54, 32.25, 32.81, 32.89, 33.01, 33.05, 33.15, 33.51, 35.42, 38.68, 38.93, 44.46, 51.55, 51.59, 51.62, 51.71, 57.19, 170.93, 172.71, 173.14, 173.21, 173.31, 173.46, 173.88, 175.67 ppm; ESI-MS of C$_{23}$H$_{38}$N$_2$O$_{10}$ (M+H$^+$=502.8; M+Na$^+$=525.6; M−H$^-$=501.5); IR (ATR) ν=2953.1, 2917.1, 2851.3, 1728.5 (CO$_2$Me), 1672.6, 1633.2 (amide), 1531.1, 1435.4, 1365.9, 1253.1, 1195.1, 1167.6, 1091.9, 1059.4, 992.2, 866.8, 731.7 cm$^{-1}$; HRMS of C$_{23}$H$_{38}$N$_2$O$_{10}$ [M+Na]$^+$ calc. 525.24242 obs. 525.24111.

General Method for Saponifications of Methyl Esters:

The methyl ester derivative (1.50 mmol) in a mixture of THF (20 mL) and water (10 mL) is cooled to 0° C. by means of an ice bath. Then, LiOH monohydrate is added (at 2.5 equivalents per methyl ester group) and the reaction mixture is allowed to warm to room temperature. Reaction is allowed to proceed for about one day while the course of the reaction is policed via TLC. After the reaction has ended, the reaction mixture is acidified (pH 2) with 2M NaHSO$_4$ and extracted with ethyl acetate (5×30 mL). The combined organic solutions are dried over Na$_2$SO$_4$, filtered and concentrated to dryness in vacuo to obtain the generally pure carboxylic acid derivative.

5-[(4-Carboxy-1-{[(3-carboxypropyl)amino]carbonyl}-butyl)(3-carboxypropyl)amino]-5-oxopentanoic acid (51) (First Generation Self-Generated Core Unit)

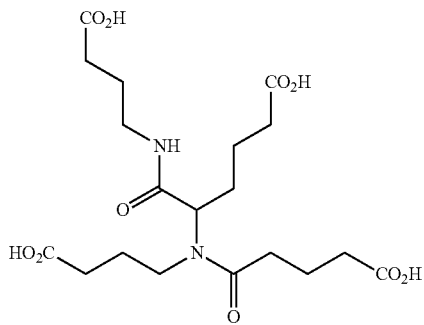 [SMILES: O=C(O)CCCNC(=O)C(CCCC(=O)O)N(CCCC(=O)O)C(=O)CCCC(=O)O]

Saponifying the methyl ester groups of core unit 50 (0.76 g, 1.51 mmol) yields the tetracarboxylic acid derivative 51 as a slightly yellowish oil (0.61 g, 90%). TLC (ethyl acetate/MeOH/H$_2$O 5:2:1) R$_f$=0.36; $^1$H NMR (CD$_3$OD, 300 MHz) δ=1.54-1.62 (m, 2H, CH$_2$), 1.73-1.97 (m, 8H, 4CH$_2$), 2.29-2.41 (m, 8H, 4CH$_2$), 2.55 (t, J=7.4 Hz, 2H, CH$_2$), 3.19-3.42 (m, 4H, 2CH$_2$), 4.75 (t, J=6.6 Hz, 1H, CH) ppm; $^{13}$C NMR (CD$_3$OD, 75 MHz) δ=21.38, 21.73, 21.97, 22.95, 25.59, 26.24, 29.44, 30.57, 31.77, 32.24, 32.62, 33.39, 33.66, 33.91, 34.04, 34.40, 39.92, 40.10, 46.48, 59.19, 61.86, 171.90, 172.82, 175.20, 175.74, 176.13, 176.59, 176.66, 176.70, 176.77, 176.81, 176.94 ppm; ESI-MS C$_{19}$H$_{30}$N$_2$O$_{10}$ (M+H$^+$=447.4; M+Na$^+$=469.6; M−H$^-$=445.7); IR (ATR) ν=3324.8, 2944.2, 2833.3, 1708.5 (CO$_2$H), 1626.2 (amide), 1543.2, 1412.7, 1201.8, 1018.9 cm$^{-1}$; HRMS C$_{19}$H$_{30}$N$_2$O$_{10}$ [M+Na]$^+$ calc. 469.17981 obs. 469.18014.

Methyl N-(6-methoxy-6-oxohexyl)-N-(5-methoxy-5-oxopentanoyl)phenylalanyl-β-alaninate (52)

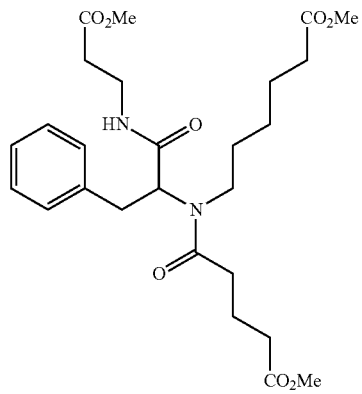 [SMILES: COC(=O)CCCCCN(C(=O)CCCC(=O)OC)C(Cc1ccccc1)C(=O)NCCC(=O)OC]

The Ugi-4CR of monomethyl glutarate (2.00 g, 13.7 mmol) with phenylacetaldehyde (1.64 g, 13.7 mmol), methyl 6-aminohexanoate hydrochloride (2.49 g, 13.7 mmol) and methyl 3-isocyanopropionate (1.55 g, 13.7 mmol) yields the methyl ester-protected core unit 52 following column-chromatographic purification (ethyl acetate/MeOH 19:1) as yellowish oil (1.87 g, 27%). TLC (ethyl acetate) R$_f$=0.49; $^1$H NMR (CDCl$_3$, 300 MHz) δ=1.20-1.63 (m, 4H, 2CH$_2$), 1.86-2.00 (m, 4H, 2CH$_2$), 2.26-2.57 (m, 8H, 4CH$_2$), 3.02-3.30 (m, 4H, 2CH$_2$), 3.45 (q, J=6.2 Hz, 2H, CH$_2$), 3.66, 3.66, 3.67 (3s, 9H, 3CH$_3$), 4.79 (br, t, J=7.4 Hz, 1H, CH), 7.10-7.29 (m, 5H, 5CH) ppm; $^{13}$C NMR (CDCl$_3$, 75 MHz) δ=19.86, 20.33, 24.35, 26.30, 26.92, 29.09, 32.38, 32.87, 32.91, 33.55, 33.67, 33.87, 34.20, 34.98, 46.86, 51.47, 51.50, 51.53, 51.65, 60.57, 126.37, 128.23, 128.79, 137.17, 170.67, 172.11, 173.13, 173.37, 173.47, 173.58, 176.85 ppm; ESI-MS of C$_{26}$H$_{38}$N$_2$O$_8$ (M+H$^+$=507.2; M+Na$^+$=529.3; 2M+Na$^+$=1036.1; M−H$^-$=505.4); IR (ATR) ν=3352.7, 2951.7, 1730.9 (CO$_2$Me), 1644.3 (amide), 1530.9, 1436.8, 1367.3, 1196.7, 1172.0, 1062.1, 1024.7, 842.8, 752.0, 701.5 cm$^{-1}$; HRMS of C$_{26}$H$_{38}$N$_2$O$_8$ (M+Na]$^+$ calc. 529.25259 obs. 529.25267.

N-(4-Carboxybutanoyl)-N-(5-carboxypentyl)phenylalanyl-β-alanine (53)

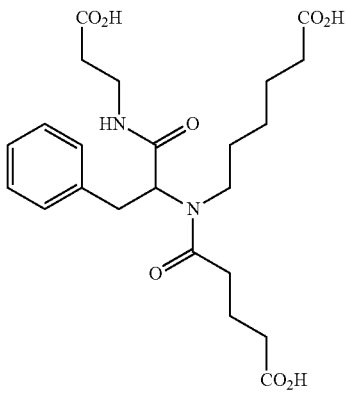 [SMILES: O=C(O)CCCCCN(C(=O)CCCC(=O)O)C(Cc1ccccc1)C(=O)NCCC(=O)O]

Saponifying the methyl ester groups of core unit 52 (1.10 g, 2.17 mmol) affords the tricarboxylic acid derivative 53 as yellowish oil (0.97 g, 96%). TLC (ethyl acetate/MeOH/H$_2$O 5:2:1) R$_f$=0.59; $^1$H NMR (CD$_3$OO, 300 MHz). δ=1.20-1.64 (m, 4H, 2CH$_2$), 1.80-1.92 (m, 4H, 2CH$_2$), 2.22-2.50 (m, 8H, 4CH$_2$), 3.00-3.32 (m, 4H, 2CH$_2$), 3.35-3.43 (m, 2H, CH$_2$), 4.63-4.69 (m, 1H, CH), 7.16-7.29 (m, 5H, 5CH) ppm; $^{13}$C NMR (CD$_3$OD, 75 MHz) δ=21.37, 21.69, 25.60, 27.32, 30.05, 33.51, 33.91, 34.30, 34.65, 35.48, 36.41, 62.68, 127.53, 129.37, 130.19, 139.05, 172.38, 174.93, 175.17, 175.26, 176.60, 176.73, 177.21 ppm; ESI-MS of C$_{23}$H$_{32}$N$_2$O$_8$ (M+H$^+$=465.2; M+Na$^+$=487.3; 2M+Na$^+$=951.8; M−H$^-$=463.6); IR (ATR) ν=2940.7, 1703.4 (CO$_2$H), 1538.2, 1496.1, 1409.5, 1190.8, 1056.8, 864.9, 752.4, 701.7 cm$^{-1}$; HRMS C$_{23}$H$_{32}$N$_2$O$_8$ [M+Na]$^+$ calc. 487.20563 obs. 487.20562.

Methyl 6-methoxy-N-(6-methoxy-6-oxohexyl)-N-(5-methoxy-5-oxopentanoyl)-6-oxonorleucyl-β-alaninate (54)

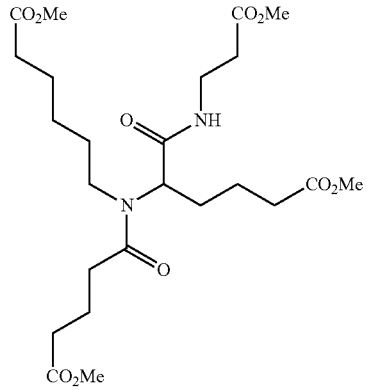 [SMILES: COC(=O)CCCCCN(C(=O)CCCC(=O)OC)C(CCCC(=O)OC)C(=O)NCCC(=O)OC]

The Ugi-4CR of monomethyl glutarate (2.00 g, 13.7 mmol) with methyl 5-oxopentanoate (1.78 g, 13.7 mmol), methyl 6-aminohexanoate hydrochloride (2.49 g, 13.7 mmol) and methyl 3-isocyanopropionate (1.55 g, 13.7 mmol) yields the methyl ester-protected core unit 54 after column-chromatographic purification (ethyl acetate/MeOH 9:1) as brown oil (1.95 g, 28%). TLC (ethyl acetate/MeOH 19:1) R$_f$=0.71; $^1$H NMR (CDCl$_3$, 300 MHz) δ=1.23-1.34 (m, 2H, CH$_2$), 1.48-1.77 (m, 8H, 4CH$_2$), 1.93-2.03 (m, 2H, CH$_2$), 2.28-2.45 (m, 8H, 4CH$_2$), 2.51 (t, J=6.3 Hz, 2H, CH$_2$), 3.22 (t, J=8.2 Hz, 2H, CH$_2$), 3.42-3.50 (m, 2H, CH$_2$), 3.66, 3.67, 3.68, 3.68, (4s, 12H, 4CH$_3$), 4.76 (t, J=7.6 Hz, 1H, CH), 6.99 (t, J=5.8 Hz, 1H, NH) ppm; $^{13}$C NMR (CDCl$_3$, 75 MHz) δ=20.27, 20.40, 21.47, 24.30, 26.43, 27.33, 29.44, 32.21, 32.94, 33.09, 33.43, 33.65, 33.68, 34.90, 36.96, 45.20, 51.42, 51.46, 51.49, 51.63, 57.13, 170.86, 171.96, 173.23, 173.37, 173.41, 173.47, 176.37 ppm; ESI-MS of C$_{24}$H$_{40}$N$_2$O$_{10}$ (M+H$^+$=517.2; M+Na$^+$=539.4; 2M+Na$^+$=1055.6; M−H$^-$=515.6; IR (ATR) ν=3372.9, 2951.5, 2835.4, 1731.4 (CO$_2$Me), 1625.5 (amide), 1533.0, 1437.4, 1367.8, 1198.1, 1173.5, 1024.4, 1024.4, 842.0 cm$^{-1}$; HRMS of C$_{24}$H$_{40}$N$_2$O$_{10}$ (M+Na)$^+$ calc. 539.25752 obs. 539.25756.

N-(4-Carboxybutanoyl)-N-(5-carboxypentyl)-6-oxidanyl-6-oxidanylidenenorleucyl-β-alanine (55)

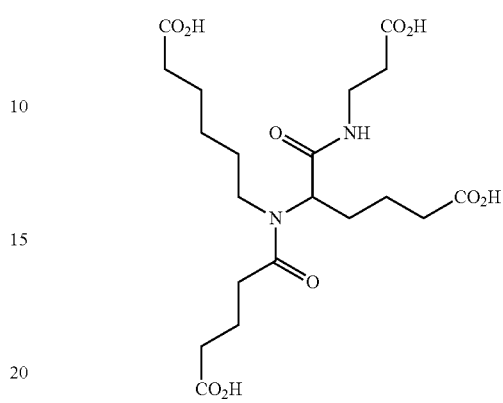

Saponifying the methyl ester groups of core unit 54 (1.87 g, 3.62 mmol) yields the tetracarboxylic acid derivative 55 as reddish brown oil (1.55 g, 93%). TLC (ethyl acetate/MeOH/H$_2$O 5:2:1) R$_f$=0.40; $^1$H NMR (CDCl$_3$, 300 MHz) δ=1.21-1.41 (m, 2H, CH$_2$), 1.53-1.75 (m, 8H, 4CH$_2$), 1.84-1.99 (m, 2H, CH$_2$), 2.26-2.40 (m, 8H, 4CH$_2$), 2.43-2.55 (m, 2H, CH$_2$), 3.10-3.38 (m, 2H, CH$_2$), 3.40-3.47 (m, 2H, CH$_2$), 4.75 (t, J=6.7 Hz, 1H, CH) ppm; $^{13}$C NMR (CD$_3$OD, 75 MHz) δ=21.39, 21.78, 21.88, 22.86, 25.61, 27.56, 29.26, 30.80, 33.38, 33.93, 34.00, 34.39, 34.44, 34.76, 36.45, 47.08, 59.02, 172.81, 175.04, 175.14, 175.56, 176.64, 176.85, 177.28 ppm; ESI-MS C$_{20}$H$_{32}$N$_2$O$_{10}$ (M+H$^+$=461.3; M+Na$^+$=483.0; M−H$^-$=459.5); IR (ATR) ν=3338.5, 2944.2, 2834.3, 1708.7 (CO$_2$H), 1662.7, 1621.8 (amide), 1537.6, 1410.4, 1198.4, 1019.5 cm$^{-1}$; HRMS of C$_{20}$H$_{32}$N$_2$O$_{10}$ (M+Na)$^+$ calc. 483.19547 obs. 483.19500.

Divergent Construction of Dendimers Via UGI-4CRs

Preparation of First Generation Dendrimers

Methyl Ester-Protected Second Generation (1→2 Branching) (60)

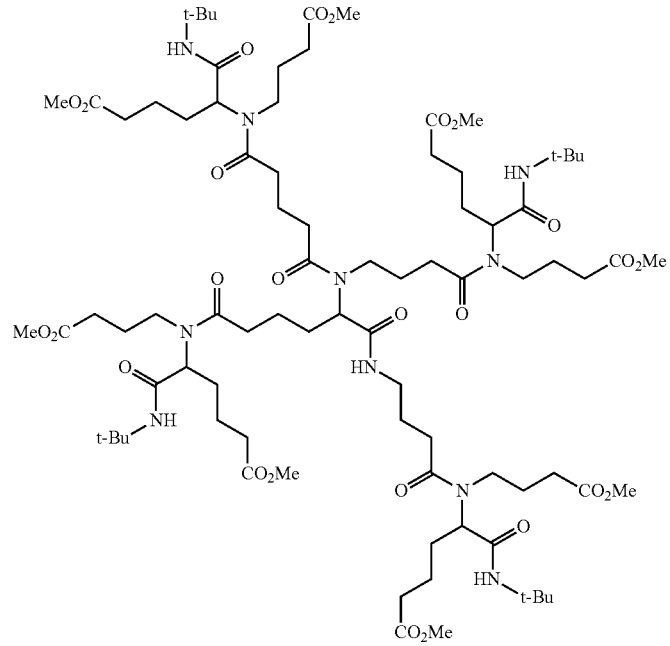

Figure 6:
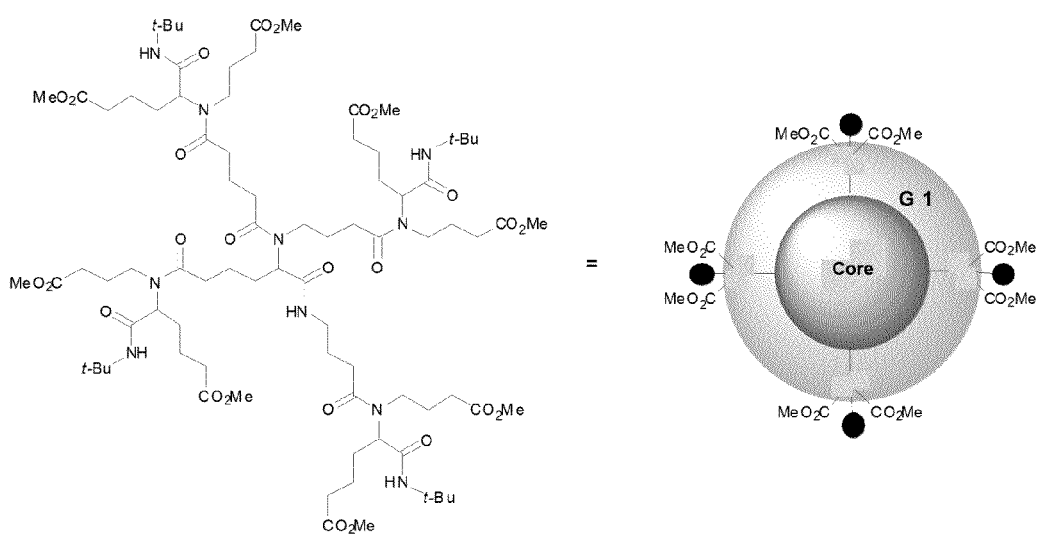
FIG. 6 shows the structure of compound (60) (methyl ester-protected second generation (1→2 branching) as prepared in accordance with the present invention.

= see FIG. 6

The fourfold Ugi-4CR of tetracarboxylic acid core unit (0.84 g, 1.88 mmol) with excesses of methyl 5-oxopentanoate (2.94 g, 22.6 mmol), methyl 4-aminobutyrate hydrochloride (3.47 g, 22.6 mmol) and t-butylisonitrile (1.88 g, 22.6 mmol) yields the methyl ester-protected second generation 60 after column-chromatographic purification (ethyl acetate/MeOH 19:1) as slightly yellowish oil (2.12 g, 66%). TLC (ethyl acetate/MeOH 19:1) $R_f$=0.64; $^1$H NMR (CDCl$_3$, 300 MHz) δ=1.24-1.37 (m, 36H, 12CH$_3$), 1.52-1.90 (m, 38H, 19CH$_2$), 2.26-2.63 (m, 24H, 12CH$_2$), 3.25-3.41 (m, 10H, 5CH$_2$), 3.62-3.68 (m, 24H, 8CH$_3$), 4.70-4.83 (m, 5H, 5CH), 6.46-6.50 (m, 5H, 5NH) ppm; $^{13}$C NMR (CDCl$_3$, 75 MHz) δ=21.00, 21.47, 24.74, 27.38, 28.50, 28.66, 30.83, 30.95, 33.50, 43.65, 50.89, 51.45, 51.64, 53.38, 56.98, 60.24, 169.90, 172.70, 173.25, 173.70 ppm; ESI-MS of $C_{83}H_{142}N_{10}O_{26}$ (M+H$^+$=1697.4; M+Na$^+$=1718.2; M+2Na$^{2+}$=870.9; M−H$^-$=1694.8; M+Cl$^-$=1730.6); IR (ATR) ν=3318.6, 2953.9, 2246.8, 1731.7 (CO$_2$Me), 1673.3 (amide), 1624.1 (amide), 1532.8, 1435.2, 1363.8, 1258.6, 1196.9, 1168.3, 1076.3, 918.0, 728.1 cm$^{-1}$; HRMS of $C_{83}H_{142}N_{10}O_{26}$ exact mass=1695.00967 m/z (z=2) [M+2Na]$^{2+}$ calc. 870.49461, obs. 870.49746.

Second Generation as Octacarboxylic Acid (61)

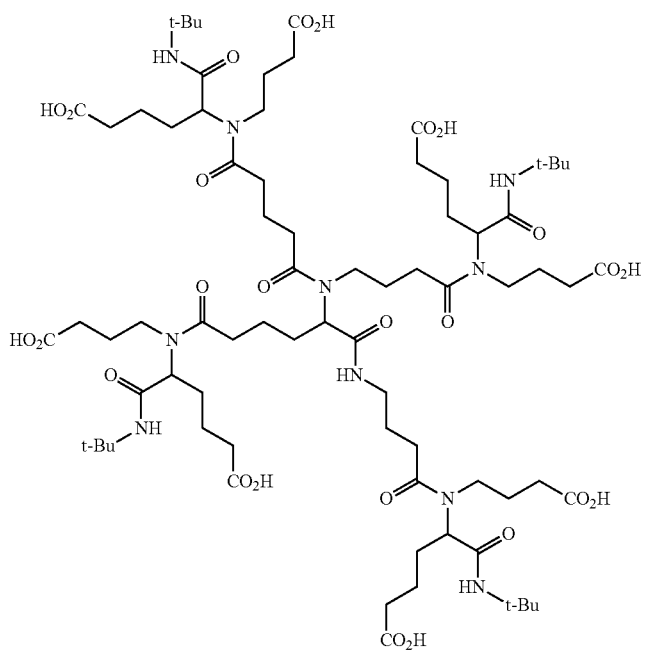

Figure 7:
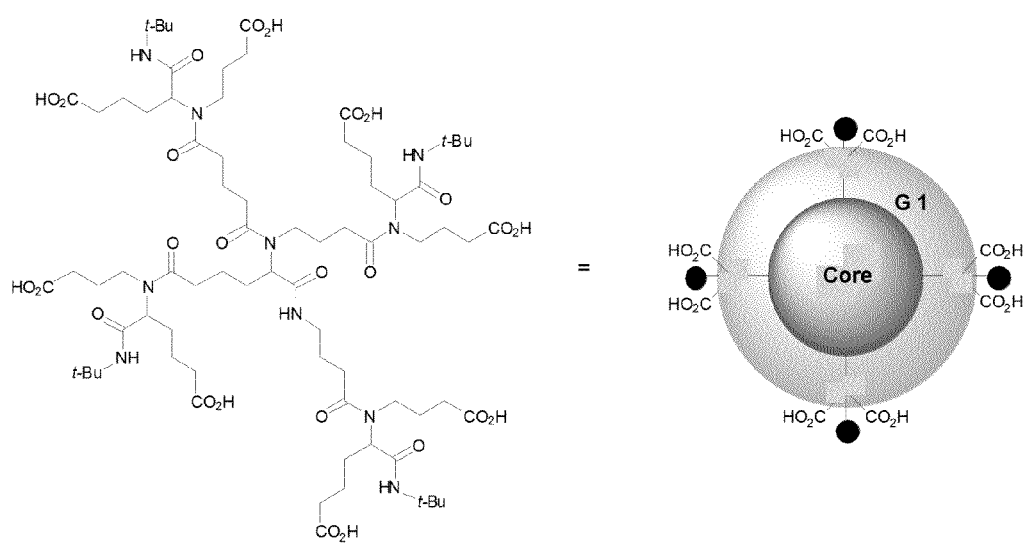
FIG. 7 shows the structure of compound (61) (second generation as octacarboxylic acid) as prepared in accordance with the present invention.

= see FIG. 7

Saponifying the methyl ester groups of second generation 60 (2.00 g, 1.18 mmol) yields the octacarboxylic acid derivative 61 as colorless solid (1.74 g, 93%). TLC (ethyl acetate/MeOH/H$_2$O 2:2:1) $R_f$=0.80; mp. 75-76° C. (ethyl acetate); $^1$H NMR (CD$_3$OD, 300 MHz) δ=1.21-1.39 (m, 36H, 12CH$_3$), 1.53-1.94 (m, 38H, 19CH$_2$), 2.24-2.54 (m, 24H, 12CH$_2$), 3.24-3.39 (m, 10H, 5CH$_2$), 4.75-4.78 (m, 5H, 5CH) ppm; $^{13}$C NMR (CD$_3$OD, 75 MHz) δ=22.76, 22.90, 25.28, 26.30, 28.85, 29.43, 31.77, 32.69, 33.87, 34.39, 45.51, 52.20, 52.52, 58.97, 61.78, 171.95, 176.05, 176.54, 176.67 ppm; ESI-MS of $C_{75}H_{126}N_{10}O_{26}$ (M+H$^+$=1585.4; M+Na$^+$=1606.0; M−H$^-$=1582.1, M+2Na$^{2+}$=814.7, M−H$^{2-}$=791.0); IR (ATR) ν=3335.3, 2964.2, 1713.2 (CO$_2$H), 1620.4 (amide), 1538.9, 1455.3, 1417.4, 1365.9, 1218.4, 1027.2, 864.6, 754.3 cm$^{-1}$; HRMS of $C_{75}H_{126}N_{10}O_{26}$ exact mass=1582.88447 m/z (z=2) [M−2H]$^{2-}$ calc. 790.43441, obs. 790.43280.

Methyl Ester-Protected Second Generation (1→2 Branching) (62)

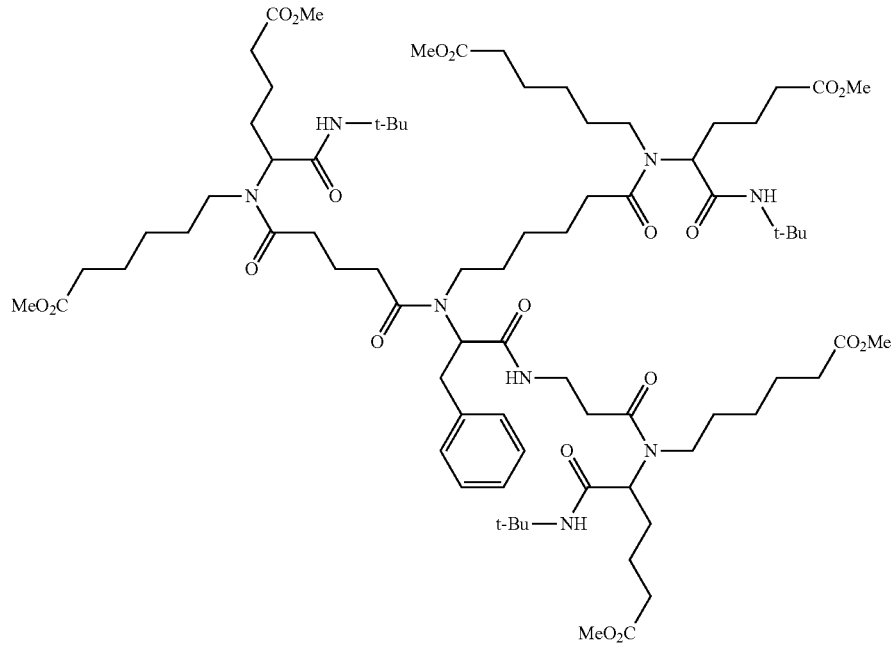 [SMILES: COC(=O)CCCCCN(C(=O)CCCCCN(C(=O)CCCC(=O)N(CCCCCC(=O)OC)C(CCCC(=O)OC)C(=O)NC(C)(C)C)C(Cc1ccccc1)C(=O)NCCC(=O)N(CCCCCC(=O)OC)C(CCCC(=O)OC)C(=O)NC(C)(C)C)C(CCCC(=O)OC)C(=O)NC(C)(C)C]

The threefold Ugi-4CR of tricarboxylic acid core unit 53 (0.18 g, 0.38 mmol) with excesses of methyl 5-oxapentanoate (0.45 g, 3.42 mmol), methyl 6-aminohexanoate hydrochloride (0.62 g, 3.42 mmol) and t-butylisonitrile (0.28 g, 3.42 mmol) yields the methyl ester-protected second generation 62 after column-chromatographic purification (ethyl acetate/MeOH 19:1) as yellowish oil (0.36 g, 64%). TLC (ethyl acetate/MeOH 19:1) $R_f$=0.64; $^1$H NMR (CDCl$_3$, 300 MHz) δ=1.24-1.94 (m, 65H, 9CH$_3$, 19CH$_2$), 2.25-2.41 (m, 20H, 10CH$_2$), 3.19-3.30 (m, 12H, 6CH$_2$), 3.65, 3.66, 3.67 (3s, 18H, 6CH$_3$), 4.65-4.80 (m, 4H, 4CH), 6.40-6.62 (m, 4H, 4NH), 7.16-7.24 (m, 5H, 5CH) ppm; $^{13}$C NMR (CDCl$_3$, 75 MHz) δ=21.49, 24.39, 24.58, 25.03, 26.54, 26.84, 27.35, 27.54, 28.55, 29.69, 32.68, 33.26, 33.51, 33.77, 44.57, 50.85, 50.91, 51.46, 53.39, 57.22, 128.17, 128.82, 169.68, 169.95, 173.30, 173.50, 173.78 ppm; ESI-MS of C$_{77}$H$_{128}$N$_8$O$_{20}$ (M+H$^+$= 1486.3; M+Na$^+$=1509.2; M+2Na$^{2+}$=766.2; M–H$^-$= 1484.3); IR (ATR) ν=3316.5, 2950.8, 2867.1, 1732.2 (CO$_2$Me), 1677.0 (amide), 1622.5 (amide), 1536.6, 1453.6, 1435.3, 1364.0, 1198.0, 1171.0, 1077.0, 1009.7, 883.2, 752.9, 702.3 cm$^{-1}$; HRMS of C$_{77}$H$_{128}$N$_8$O$_{20}$ exact mass=1484.92449 m/z (z=2) [M+2Na]$^{2+}$ calc. 765.45202, obs. 765.45117.

Second Generation as Hexacarboxylic Acid (63)

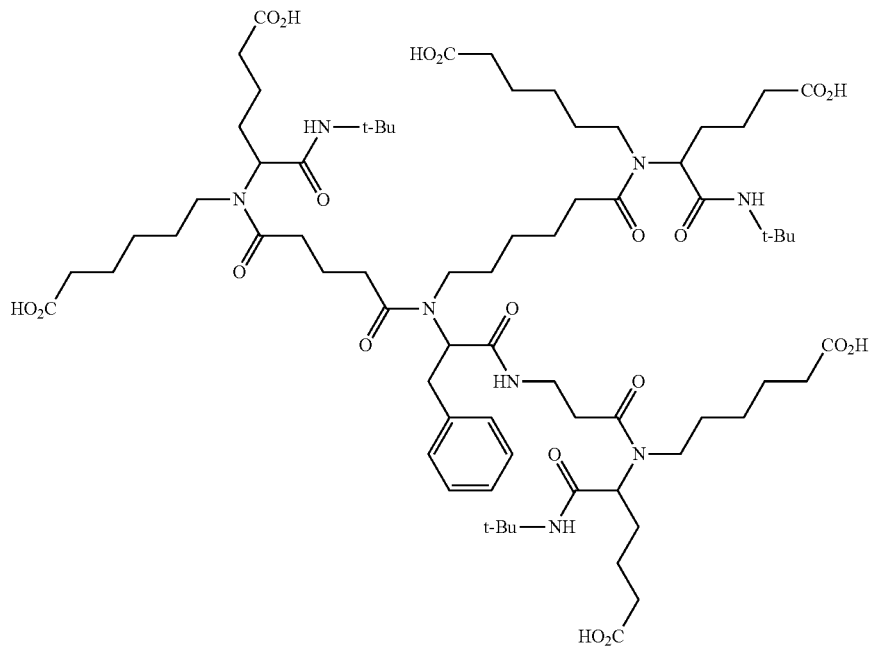 [SMILES: CC(C)(C)NC(=O)C(CCCC(=O)O)N(CCCCCC(=O)O)C(=O)CCCCCN(C(=O)CCCC(=O)N(CCCCCC(=O)O)C(CCCC(=O)O)C(=O)NC(C)(C)C)C(Cc1ccccc1)C(=O)NCCC(=O)N(CCCCCC(=O)O)C(CCCC(=O)O)C(=O)NC(C)(C)C]

Saponifying the methy ester groups of second generation 62 (0.18 g, 0.12 mmol) yields the hexacarboxylic acid derivative 63 as colorless oil (0.15 g, 93%). TLC (ethyl acetate/MeOH/H$_2$O 3:2:1) R$_f$=0.81; $^1$H NMR (CD$_3$OD, 300 MHz) δ=1.25-1.88 (m, 65H, 9CH$_3$, 19CH$_2$), 2.26-2.64 (m, 20H, 10CH$_2$), 3.13-3.54 (m, 12H, 6CH$_2$), 4.73-4.76 (m, 4H, 4CH), 7.16-7.24 (m, 5H, 5CH) ppm; $^{13}$C NMR (CD$_3$OD, 75 MHz) δ=22.73, 24.21, 25.65, 25.77, 27.57, 27.84, 28.82, 29.38, 31.00, 34.39, 34.80, 46.25, 52.15, 59.06, 129.54, 130.38, 172.21, 176.75, 176.90, 177.25 ppm; ESI-MS of C$_{71}$H$_{116}$N$_8$O$_{20}$ (M+H$^+$=1402.2; M+Na$^+$=1424.4; M−H$^−$=1400.3); IR (ATR) ν=3331.5, 2941.6, 2831.5, 1713.0 (CO$_2$H), 1661.5 (amide), 1621.0 (amide), 1541.6, 1455.1, 1425.6, 1366.1, 1221.4, 1090.1, 1022.1 cm$^{-1}$; HRMS of C$_{71}$H$_{116}$N$_8$O$_{20}$ [M+Na]$^+$ calc. 1423.82036, obs. 1423.81896.

Methyl Ester-Protected Second Generation (1→2 Branching) (64)

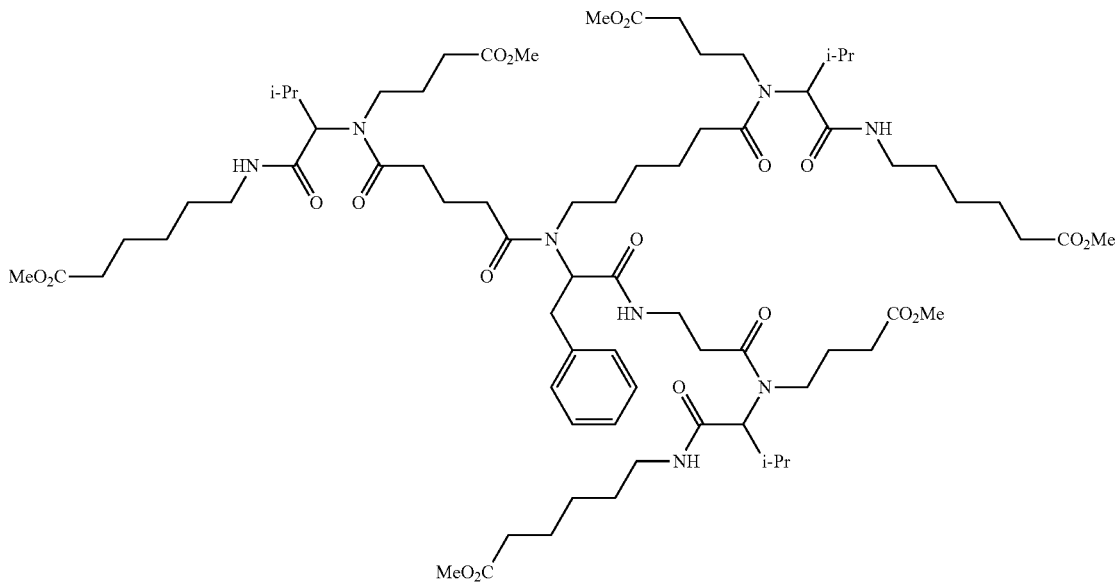 [SMILES: COC(=O)CCCCCNC(=O)C(C(C)C)N(CCCC(=O)OC)C(=O)CCCCCN(C(=O)CCCC(=O)N(CCCC(=O)OC)C(C(=O)NCCCCCC(=O)OC)C(C)C)C(Cc1ccccc1)C(=O)NCCC(=O)N(CCCC(=O)OC)C(C(=O)NCCCCCC(=O)OC)C(C)C]

The threefold Ugi-4CR of tricarboxylic acid core unit 53 (0.18 g, 0.38 mmol) with excesses of isobutyraldehyde (0.25 g, 3.42 mmol), methyl 4-aminobutyrate hydrochloride (0.53 g, 3.42 mmol) and methyl 6-isocyanohexanoate (0.53 g, 3.42 mmol) yields the methyl ester-protected second generation 64 after column-chromatographic purification (ethyl acetate/MeOH 19:1) as colorless oil (0.35 g, 63%). TLC (ethyl acetate/MeOH 19:1) R$_f$=0.49; $^1$H NMR (CDCl$_3$, 300 MHz) δ=0.74-0.99 (m, 18H, 6CH$_3$), 1.21-1.95 (m, 32H, 16CH$_2$), 2.27-2.65 (m, 23H, 10CH$_2$, 3CH), 3.15-3.59 (m, 18H, 9CH$_2$), 3.65, 3.67, 3.68 (3s, 18H, 6CH$_3$), 4.06-4.40 (m, 4H, 4CH), 6.67-7.05 (m, 4H, 4NH), 7.17-7.26 (m, 5H, 5CH) ppm; $^{13}$C NMR (CDCl$_3$, 75 MHz) δ=18.84, 19.77, 24.44, 26.29, 26.33, 29.03, 30.77, 30.92, 33.80, 38.92, 39.00, 51.39, 51.63, 128.15, 128.77, 172.64, 172.84, 173.63 ppm; ESI-MS of C$_{74}$H$_{122}$N$_8$O$_{20}$ (M+H$^+$=1444.1; M+Na$^+$=1466.3; M+2Na$^{2+}$=744.6; M−H$^−$=1442.3; M+Cl$^−$=1478.6); IR (ATR) ν=3307.2, 2949.9, 2870.9, 1732.1 (CO$_2$Me), 1621.1 (amide), 1537.8, 1435.3, 1366.8, 1196.3, 1162.4, 1102.1, 1029.3, 924.9, 865.9, 731.9, 701.0 cm$^{-1}$; HRMS of C$_{74}$H$_{122}$N$_8$O$_{20}$ exact mass=1442.87754 m/z (z=2) [M+2Na]$^{2+}$ calc. 744.42854, obs. 744.42727.

Second Generation as Hexacarboxylic Acid (65)

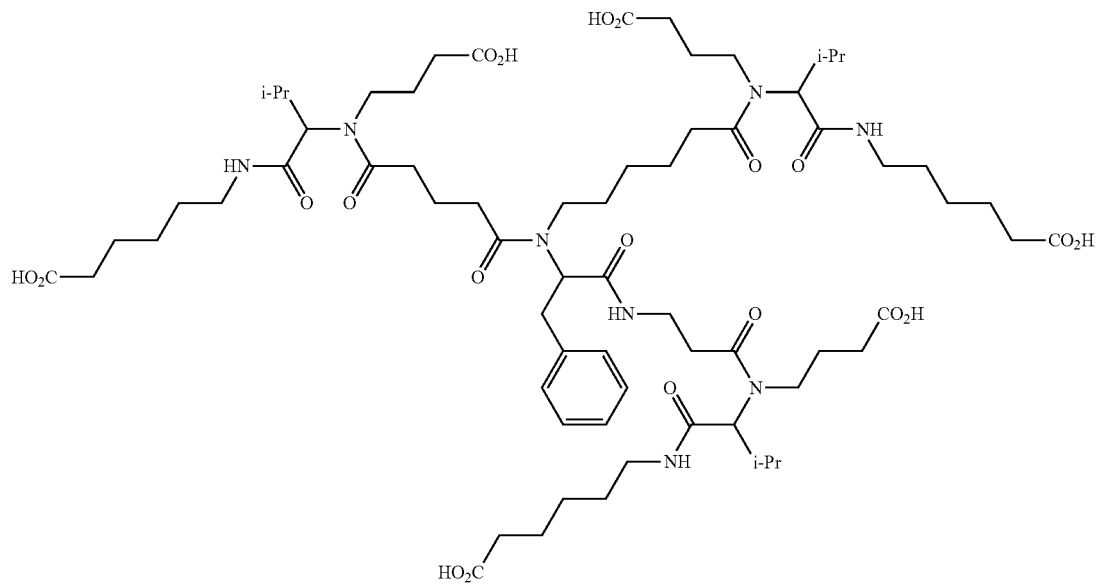 [SMILES: CC(C)C(C(=O)NCCCCCC(=O)O)N(CCCC(=O)O)C(=O)CCCCCN(C(=O)CCCC(=O)N(CCCC(=O)O)C(C(=O)NCCCCCC(=O)O)C(C)C)C(Cc1ccccc1)C(=O)NCCC(=O)N(CCCC(=O)O)C(C(=O)NCCCCCC(=O)O)C(C)C]

Saponifying the methyl ester groups of second generation 64 (0.20 g, 0.14 mmol) yields the hexacarboxylic acid derivative 65 as colorless oil (0.17 g, 91%). TLC (ethyl acetate/MeOH/H$_2$O 3:2:1) R$_f$=0.76; $^1$H NMR (CD$_3$OD, 300 MHz) δ=0.80-0.97 (m, 18H, 6CH$_3$), 1.31-1.81 (m, 32H, 16CH$_2$), 2.22-2.67 (m, 23H, 10CH$_2$, 3CH), 3.15-3.68 (m, 18H, 9CH$_2$), 4.49-4.51 (m, 4H, 4CH), 7.19-7.26 (m, 5H, 5CH) ppm; $^{13}$C NMR (CD$_3$OD, 75 MHz) δ=19.19, 19.29, 20.01, 20.74, 24.21, 24.73, 25.66, 26.16, 26.49, 27.51, 28.17, 29.14, 29.86, 30.69, 31.93, 32.80, 33.54, 34.79, 37.01, 40.12, 43.69, 45.56, 64.81, 67.76, 127.69, 129.57, 130.37, 130.59, 171.64, 172.44, 172.56, 175.50, 176.18, 176.29, 176.75, 177.34 ppm; ESI-MS of C$_{68}$H$_{110}$N$_8$O$_{20}$ (M+H$^+$=1359.9; M+Na$^+$=1382.5; M−H$^−$=1358.6); IR (ATR) ν=3306.9, 2940.2, 2831.6, 1712.4 (CO$_2$H), 1620.5 (amide), 1549.0, 1418.0, 1372.9, 1197.7, 1165.3, 1088.8, 1022.4, 701.6 cm$^{-1}$; HRMS of C$_6$H$_{110}$N$_8$O$_{20}$ [M+Na]$^+$ calc. 1381.77341, obs. 1381.77333.

Methyl Ester-Protected Second Generation (1→2 Branching) (66)

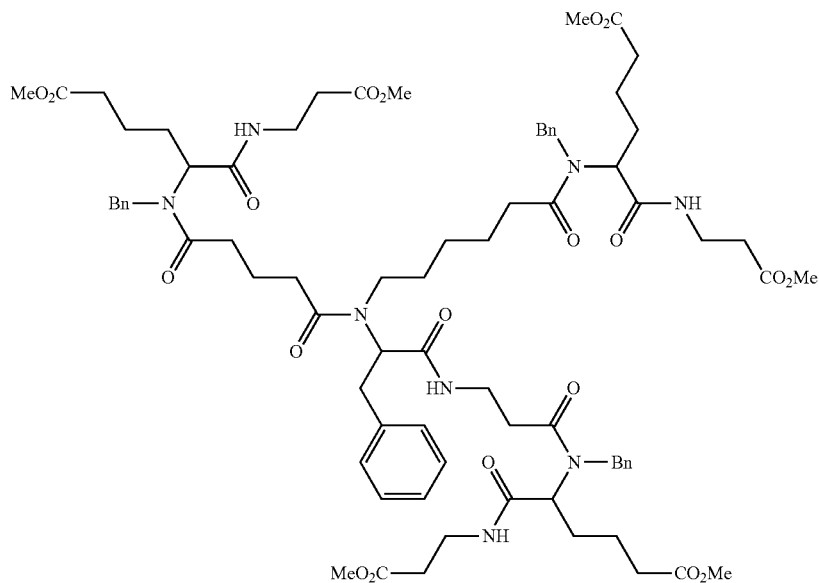 [SMILES: COC(=O)CCCC(C(=O)NCCC(=O)OC)N(Cc1ccccc1)C(=O)CCCCCN(C(=O)CCCC(=O)N(Cc1ccccc1)C(CCCC(=O)OC)C(=O)NCCC(=O)OC)C(Cc1ccccc1)C(=O)NCCC(=O)N(Cc1ccccc1)C(CCCC(=O)OC)C(=O)NCCC(=O)OC]

The threefold Ugi-4CR of tricarboxylic acid core unit 53 (0.18 g, 0.39 mmol) with excesses of methyl 5-oxopentanoate (0.46 g, 3.51 mmol), benzylamine (0.38 g, 3.51 mmol) and methyl 3-isocyanopropionate (0.40 g, 3.51 mmol) yields the methyl ester-protected second generation 66 after column-chromatographic purification (ethyl acetate/MeOH 19:1) as slightly yellowish oil (0.39 g, 68%). TLC (ethyl acetate/MeOH 19:1) $R_f$=0.47; $^1$H NMR (CDCl$_3$, 300 MHz) δ=1.13-2.57 (m, 40H, 20CH$_2$), 2.91-3.51 (m, 12H, 6CH$_2$), 3.60-3.69 (m, 18H, 6CH$_3$), 4.42-4.89 (m, 10H, 3CH$_2$, 4CH), 6.83-6.98 (m, 4H, 4NH), 7.12-7.31 (m, 20H, 20CH) ppm; $^{13}$C NMR (CDCl$_3$, 75 MHz) δ=21.66, 24.60, 27.86, 33.48, 33.72, 34.19, 34.90, 35.13, 48.25, 51.45, 51.66, 53.42, 57.18, 125.78, 125.86, 126.27, 127.19, 128.21, 128.53, 136.95, 137.23, 170.10, 172.08, 173.24, 174.53 ppm; ESI-MS of C$_{77}$H$_{104}$N$_8$O$_{20}$ (M+Na$^+$=1484.0; M+2Na$^{2+}$=754.3); IR (ATR) ν=3314.6, 2949.9, 1731.8 (CO$_2$Me), 1625.5 (amide), 1531.8, 1496.5, 1436.8, 1364.4, 1196.8, 1172.9, 1076.6, 1027.0, 918.3, 886.3, 729.6, 698.7 cm$^{-1}$; HRMS of C$_{77}$H$_{104}$N$_8$O$_{20}$ exact mass=1460.73669 m/z (z=2) [M+2Na]$^{2+}$ calc. 753.35812, obs. 753.35629.

Second Generation as Hexacarboxylic Acid (67)

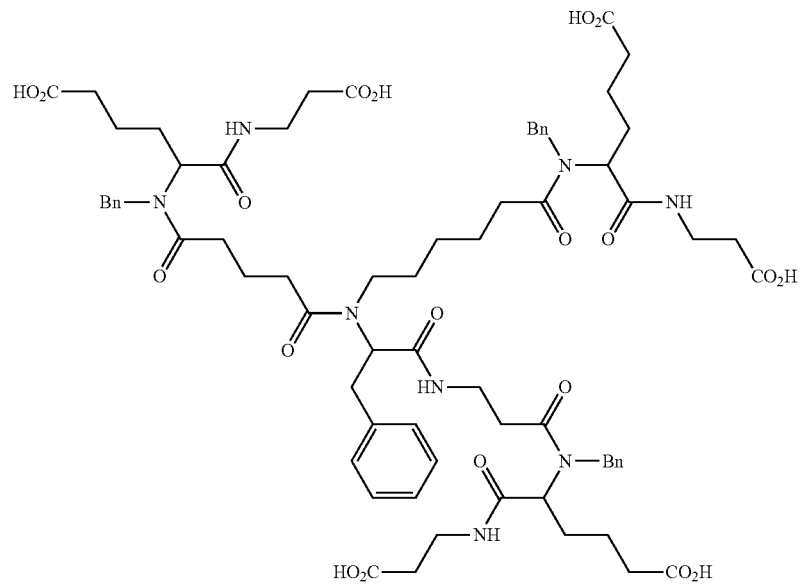 [SMILES: O=C(O)CCCC(C(=O)NCCC(=O)O)N(Cc1ccccc1)C(=O)CCCCCN(C(=O)CCCC(=O)N(Cc1ccccc1)C(CCCC(=O)O)C(=O)NCCC(=O)O)C(Cc1ccccc1)C(=O)NCCC(=O)N(Cc1ccccc1)C(CCCC(=O)O)C(=O)NCCC(=O)O]

Saponifying the methyl ester groups of second generation 66 (0.25 g, 0.17 mmol) yields the hexacarboxylic acid derivative 67 as colorless solid (0.21 g, 92%). TLC (ethyl acetate/MeOH/H$_2$O 3:2:1) $R_f$=0.72; mp. 84-85° C. (ethyl acetate); $^1$H NMR (CD$_3$OD, 300 MHz) δ=0.96-2.51 (m, 40H, 20CH$_2$), 2.96-3.48 (m, 12H, 6CH$_2$), 4.35-4.78 (m, 10H, 3CH$_2$, 4CH), 7.12-7.33 (m, 20H, 20CH) ppm; $^{13}$C NMR (CD$_3$OD, 75 MHz) δ=22.74, 22.81, 25.88, 27.39, 29.64, 29.84, 30.72, 33.97, 34.28, 34.34, 34.55, 36.32, 36.55, 36.79, 58.57, 61.92, 127.41, 127.49, 127.64, 127.91, 128.42, 128.54, 129.29, 129.51, 129.82, 130.37, 130.61, 138.76, 138.84, 139.12, 139.18, 172.45, 175.17, 175.51, 176.41, 176.71, 176.88 ppm; ESI-MS of C$_{71}$H$_{92}$N$_{20}$ (M+H$^+$=1378.1; M+Na$^+$=1399.9; M−H$^-$=1376.3); IR (ATR) ν=2940.3, 1715.6 (CO$_2$H), 1622.1 (amide), 1538.5, 1496.6, 1451.4, 1417.4, 1364.0, 1196.0, 1077.2, 1029.1, 862.2, 732.6, 700.5 cm$^{-1}$; HRMS of C$_{71}$H$_{92}$N$_8$O$_{20}$ [M+Na]$^+$ calc. 1399.63256, obs. 1399.63316.

Methyl Ester-Protected Second Generation (1→2 Branching) (68)

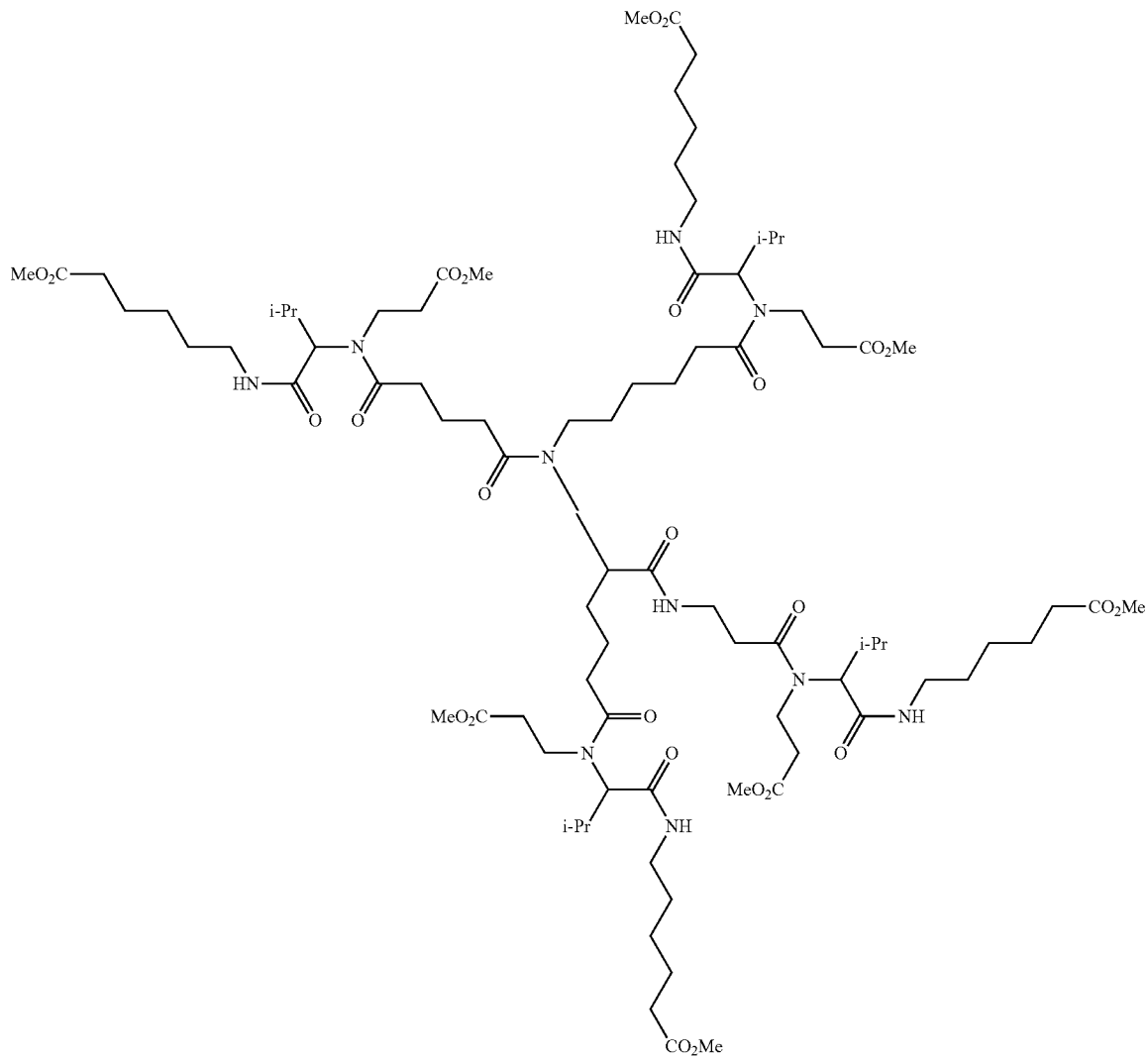 [SMILES: COC(=O)CCCCCNC(=O)C(C(C)C)N(CCC(=O)OC)C(=O)CCCCCN(C(=O)CCCC(=O)N(CCC(=O)OC)C(C(=O)NCCCCCC(=O)OC)C(C)C)C(CCCC(=O)N(CCC(=O)OC)C(C(=O)NCCCCCC(=O)OC)C(C)C)C(=O)NCCC(=O)N(CCC(=O)OC)C(C(=O)NCCCCCC(=O)OC)C(C)C]

The fourfold Ugi-4CR of tetracarboxylic acid core unit 55 (0.18 g, 0.38 mmol) with excesses of isobutyraldehyde (0.33 g, 4.56 mmol), methyl 3-aminopropionate hydrochloride (0.64 g, 4.56 mmol) and methyl 6-isocyanohexanoate (0.71 g, 4.56 mmol) yields the methyl ester-protected second generation 68 after column-chromatographic purification (ethyl acetate/MeOH 19:1) as slightly yellowish oil (0.37 g, 57%). TLC (ethyl acetate/MeOH 19:1) $R_f$=0.46; $^1$H NMR (CDCl$_3$, 300 MHz) δ=0.79-0.96 (m, 24H, 8CH$_3$), 1.24-1.68 (m, 36H, 18CH$_2$), 1.97-2.74 (m, 30H, 13CH$_2$, 4CH), 3.12-3.59 (m, 20H, 10CH$_2$), 3.66, 3.68 (2s, 24H, 8CH$_3$), 4.08-4.41 (m, 5H, 5CH), 6.73-6.98 (m, 5H, 5NH) ppm; $^{13}$C NMR (CDCl$_3$, 75 MHz) δ=18.80, 19.75, 24.45, 26.31, 29.05, 32.47, 33.57, 33.80, 39.00, 51.42, 51.74, 53.41, 170.46, 171.15, 173.63 ppm; ESI-MS of C$_{84}$H$_{144}$N$_{10}$O$_{26}$ (M+Na$^+$=1732.6; M+2Na$^{2+}$=877.6; M−H$^-$=1708.7; M+Cl$^-$=1744.7); IR (ATR) ν=3317.4, 2951.8, 2871.0, 1731.9 (CO$_2$Me), 1624.8 (amide), 1537.4, 1434.7, 1370.2, 1196.2, 1163.3, 987.2, 850.7 cm$^{-1}$; HRMS of C$_{84}$H$_{144}$N$_{10}$O$_{26}$ exact mass=1709.02532 m/z (z=2) [M+2Na]$^{2+}$ calc. 877.50243, obs. 877.50363.

Second Generation as Octacarboxylic Acid (69)

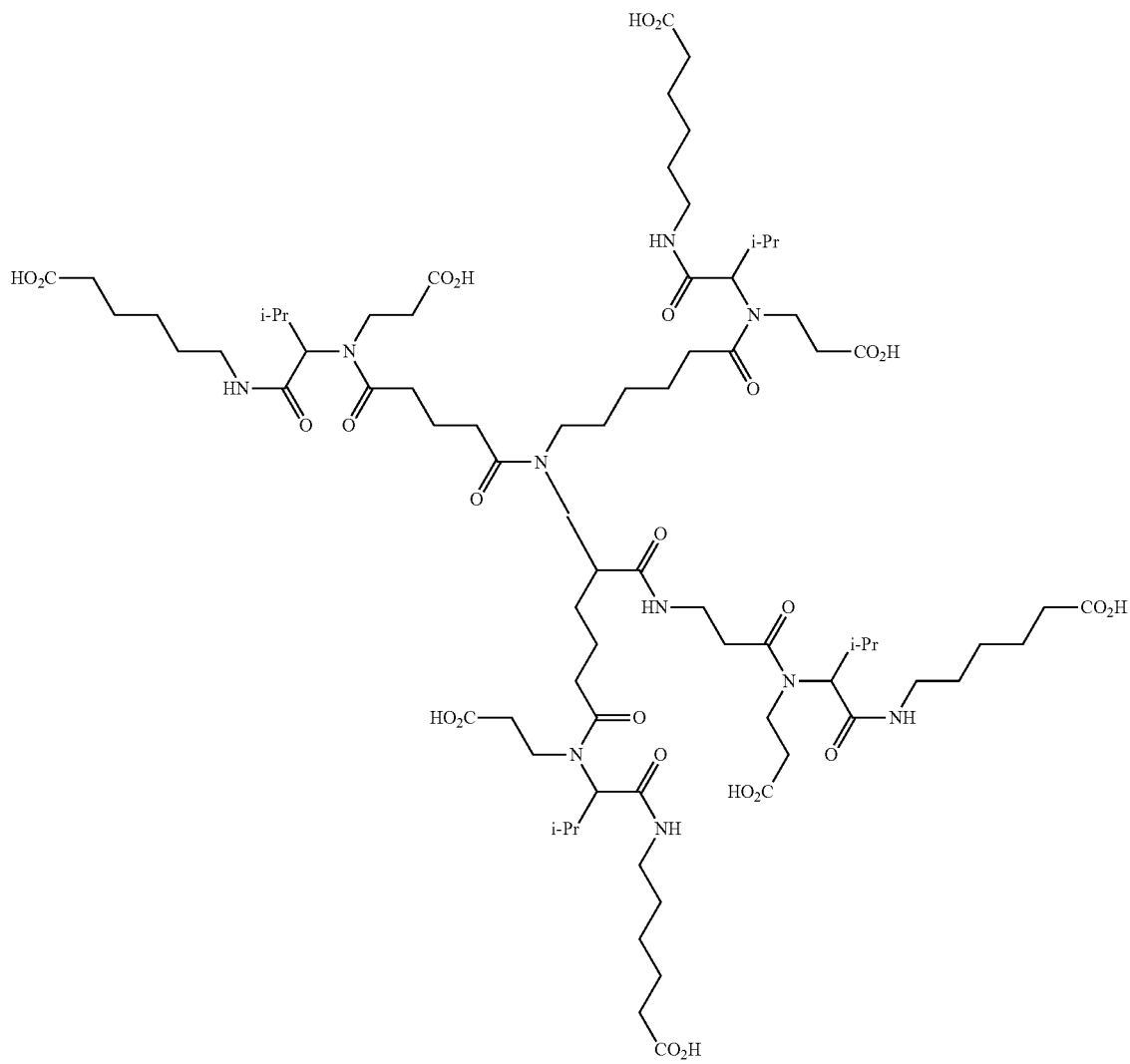 [SMILES: CC(C)C(C(=O)NCCCCCC(=O)O)N(CCC(=O)O)C(=O)CCCCCN(C(=O)CCCC(=O)N(CCC(=O)O)C(C(=O)NCCCCCC(=O)O)C(C)C)C(CCCC(=O)N(CCC(=O)O)C(C(=O)NCCCCCC(=O)O)C(C)C)C(=O)NCCC(=O)N(CCC(=O)O)C(C(=O)NCCCCCC(=O)O)C(C)C]

50

Saponifying the methyl ester groups of second generation 68 (0.25 g, 0.15 mmol) yields octacarboxylic acid derivative 69 as colorless solid (0.23 g, 96%). TLC (ethyl acetate/MeOH/H$_2$O 3:2:1) R$_f$=0.48; mp. 70-71° C. (ethyl acetate); $^1$H NMR (CD$_3$OD, 300 MHz) δ=0.81-0.97 (m, 24H, 8CH$_3$), 1.21-1.99 (m, 36H, 18CH$_2$), 2.27-2.61 (m, 30H, 13CH$_2$, 4CH), 3.10-3.94 (m, 20H, 10CH$_2$), 4.46-4.49 (m, 5H, 5CH) ppm; $^{13}$C NMR (CD$_3$OD, 75 MHz) δ=19.36, 19.78, 20.10, 25.70, 27.52, 27.56, 28.22, 29.23, 29.88, 30.92, 33.30, 33.79, 34.19, 34.78, 40.16, 41.91, 64.88, 67.51, 171.42, 172.30, 174.13, 174.26, 175.26, 177.12 ppm; ESI-MS of C$_{76}$H$_{128}$N$_{10}$O$_{26}$ (M+H$^+$=1597.3; M+Na$^+$=1620.0; M+2Na$^{2+}$= 820.6; M−H$^-$=1596.5); IR (ATR) ν=3344.5, 2942.1, 2833.4, 1712.1 (CO$_2$H), 1622.4 (amide), 1556.0, 1422.2, 1202.4, 1117.7, 1021.0 cm$^{-1}$; HRMS of C$_{76}$H$_{128}$N$_{10}$O$_{26}$ [M+Na]$^+$ calc. 1619.88990, obs. 1619.89041.

Methyl Ester-Protected Second Generation (1→2 Branching) (70)

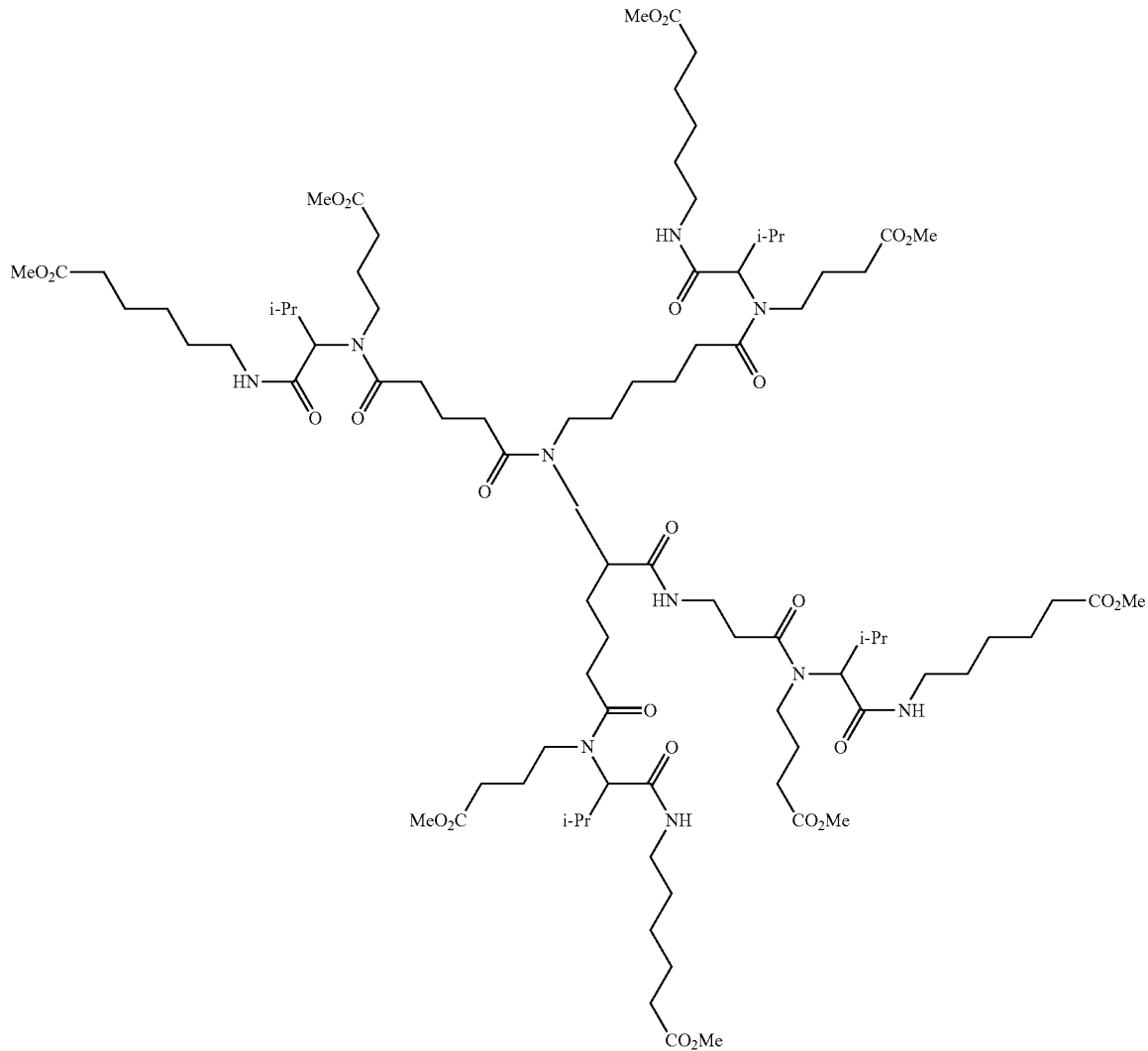 [SMILES: COC(=O)CCCCCNC(=O)C(C(C)C)N(CCCC(=O)OC)C(=O)CCCCCN(C(=O)CCCC(=O)N(CCCC(=O)OC)C(C(=O)NCCCCCC(=O)OC)C(C)C)C(CCCC(=O)N(CCCC(=O)OC)C(C(=O)NCCCCCC(=O)OC)C(C)C)C(=O)NCCC(=O)N(CCCC(=O)OC)C(C(=O)NCCCCCC(=O)OC)C(C)C]

The fourfold Ugi-4CR of tetracarboxylic acid core unit 55 (0.18 g, 0.39 mmol) with excesses of isobutyraldehyde (0.34 g, 4.68 mmol), methyl 4-aminobutyrate hydrochloride (0.72 g, 4.68 mmol) and methyl 6-isocyanohexanoate (0.73 g, 4.68 mmol) yields the methyl ester-protected second generation 70 after column-chromatographic purification (ethyl acetate/MeOH 19:1) as slightly yellowish oil (0.47 g, 68%). TLC (ethyl acetate/MeOH 19:1) $R_f$=0.48; $^1$H NMR (CDCl$_3$, 300 MHz) δ=0.78-0.96 (m, 24H, 8CH$_3$), 1.24-2.05 (m, 44H, 22CH$_2$), 2.25-2.63 (m, 30H, 13CH$_2$, 4CH), 3.12-3.41 (m, 20H, 10CH$_2$), 3.66, 3.68 (2s, 24H, 8CH$_3$), 4.12-4.40 (m, 5H, 5CH), 6.75-6.98 (m, 5H, 5NH) ppm; $^{13}$C NMR (CDCl$_3$, 75 MHz) δ=18.92, 19.82, 24.49, 26.35, 29.09, 30.95, 32.90, 33.86, 39.00, 51.44, 51.68, 53.42, 170.59, 172.91, 173.68 ppm; ESI-MS of C$_{88}$H$_{152}$N$_{10}$O$_{26}$ (M+H$^+$=1767.1; M+Na$^+$=1789.4; M+2Na$^{2+}$=905.7; M−H$^-$=1764.5); IR (ATR) ν=3308.2, 3072.4, 2951.6, 2871.1, 1731.9 (CO$_2$Me), 1621.0 (amide), 1537.2, 1434.9, 1366.6, 1195.8, 1160.6, 1027.2, 923.6, 865.5, 731.1 cm$^{-1}$; HRMS of C$_{88}$H$_{152}$N$_{10}$O$_{26}$ exact mass=1765.08793 m/z (z=2) [M+2Na]$^{2+}$ calc. 905.53373, obs. 905.53281.

Second Generation as Octacarboxylic Acid (71)

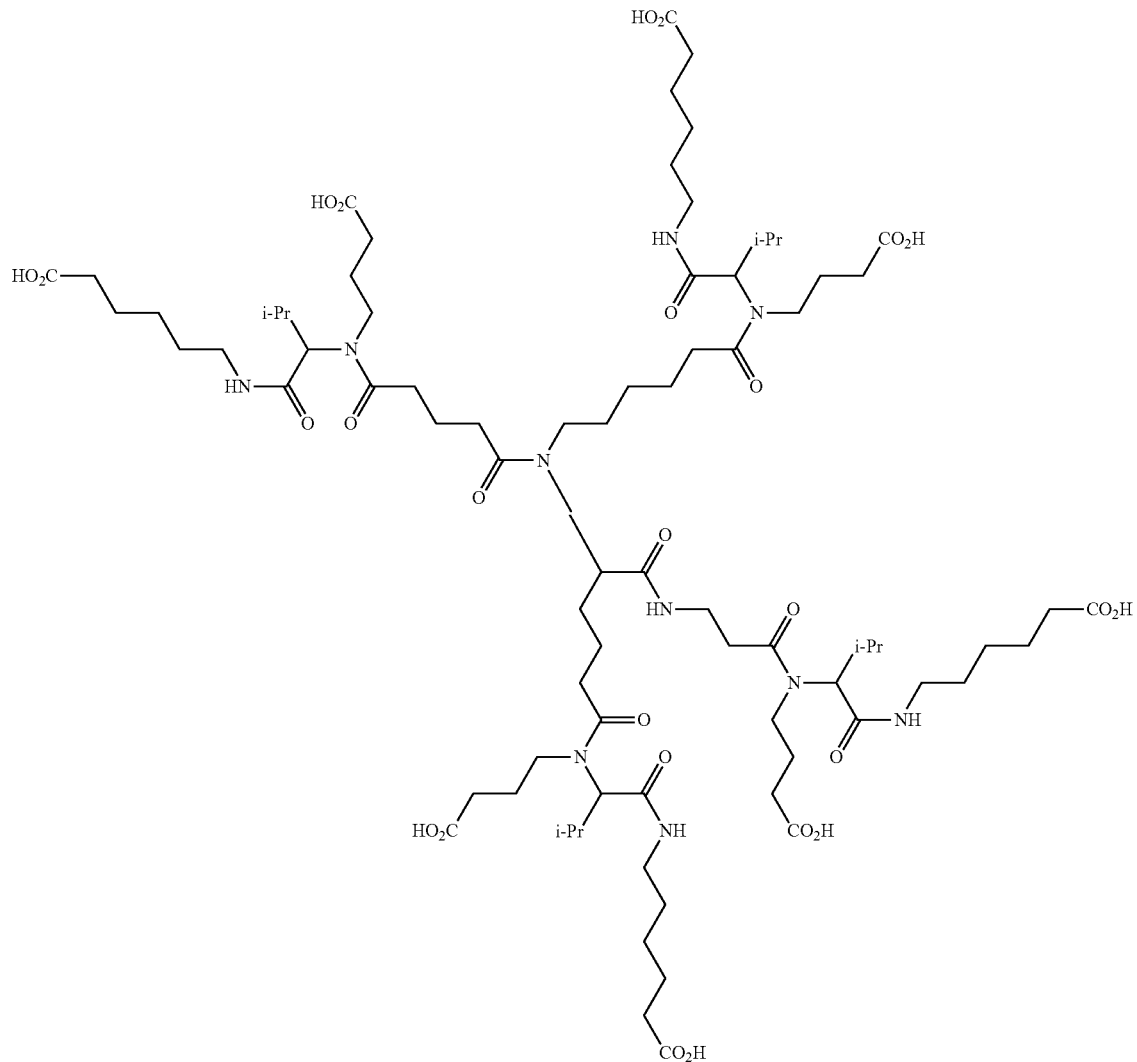 [SMILES: CC(C)C(C(=O)NCCCCCC(=O)O)N(CCCC(=O)O)C(=O)CCCCCN(C(=O)CCCC(=O)N(CCCC(=O)O)C(C(=O)NCCCCCC(=O)O)C(C)C)C(CCCC(=O)N(CCCC(=O)O)C(C(=O)NCCCCCC(=O)O)C(C)C)C(=O)NCCC(=O)N(CCCC(=O)O)C(C(=O)NCCCCCC(=O)O)C(C)C]

50

Saponifying the methyl ester groups of second generation 70 (0.36 g, 0.21 mmol) yields the octacarboxylic acid derivative 71 as colorless solid (0.32 g, 94%). TLC (ethyl acetate/MeOH/H$_2$O 3:2:1) R$_f$=0.50; mp. 67-68° C. (ethyl acetate); $^1$H NMR (CD$_3$OD, 300 MHz) δ=0.80-1.05 (m, 24H, 8CH$_3$), 1.29-2.07 (m, 44H, 22CH$_2$), 2.22-2.73 (m, 30H, 13 CH$_2$, 4CH), 3.15-3.63 (m, 20H, 10CH$_2$), 4.49-4.52 (m, 5H, 5CH) ppm; $^{13}$C NMR (CD$_3$OD, 75 MHz) δ=19.35, 19.86, 20.07, 24.25, 24.75, 25.69, 26.15, 27.51, 27.84, 28.19, 29.15, 29.88, 30.93, 31.84, 31.92, 32.81, 33.80, 34.13, 34.80, 40.13, 45.49, 64.66, 67.64, 171.41, 172.18, 172.29, 175.91, 176.05, 176.53, 177.08 ppm; ESI-MS of C$_{80}$H$_{136}$N$_{10}$O$_{26}$ (M+H$^+$=1655.5; M+Na$^+$=1676.0; M+2Na$^{2+}$=847.3; M−H$^−$=1653.8); IR (ATR) ν=3326.8, 2939.2, 1712.4 (CO$_2$H), 1619.9 (amide), 1552.5, 1417.8, 1373.1, 1273.5, 1197.4, 1164.9, 1088.5, 1022.4 cm$^{-1}$; HRMS of C$_{80}$H$_{136}$N$_{10}$O$_{26}$ [M+Na]$^+$ calc. 1675.95249, obs. 1675.95060.

Methyl Ester-Protected Second Generation (1→2 Branching) (72)

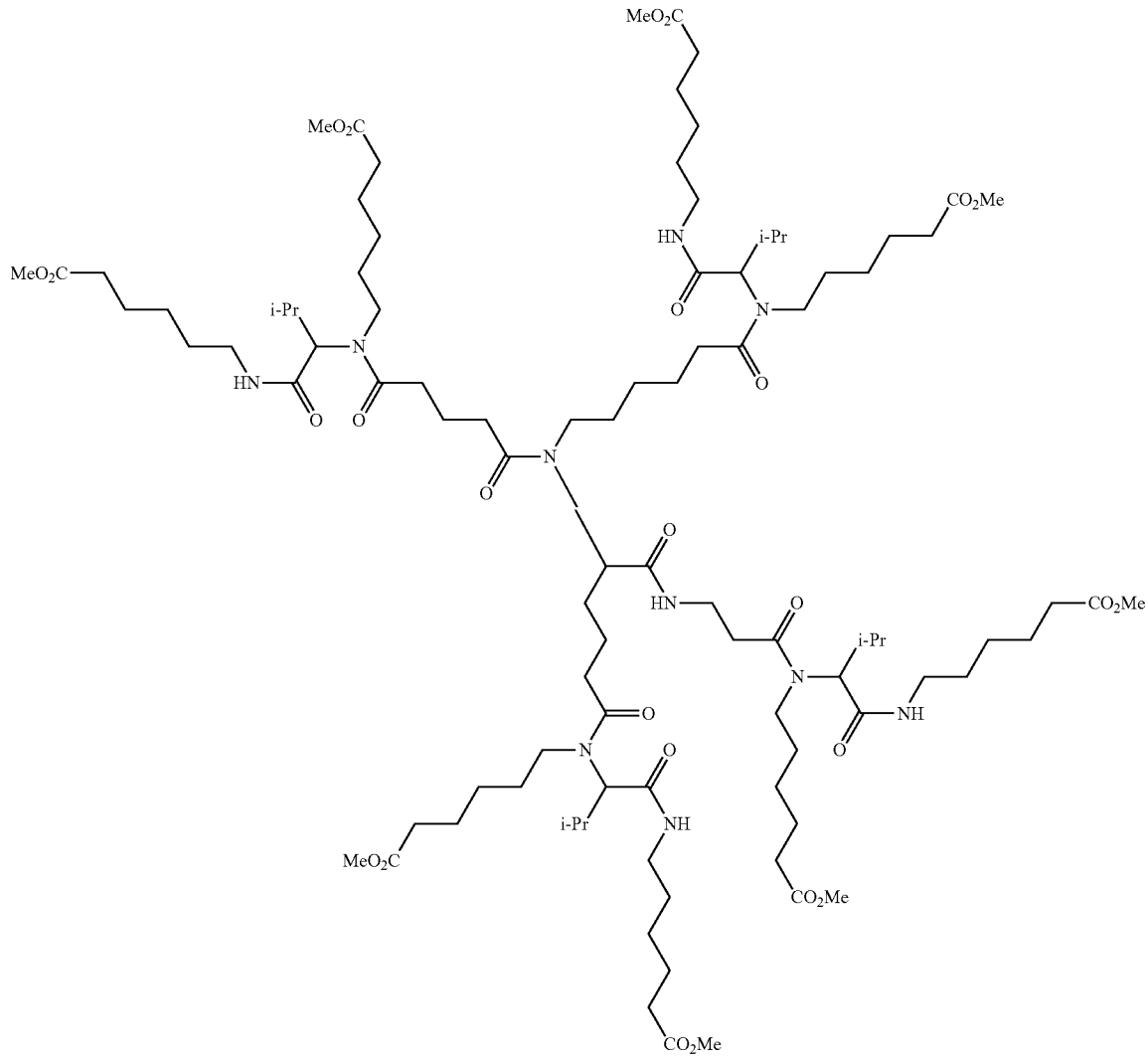 [SMILES: COC(=O)CCCCCNC(=O)C(C(C)C)N(CCCCCC(=O)OC)C(=O)CCCCCN(C(=O)CCCC(=O)N(CCCCCC(=O)OC)C(C(=O)NCCCCCC(=O)OC)C(C)C)C(CCCC(=O)N(CCCCCC(=O)OC)C(C(=O)NCCCCCC(=O)OC)C(C)C)C(=O)NCCC(=O)N(CCCCCC(=O)OC)C(C(=O)NCCCCCC(=O)OC)C(C)C]

The fourfold Ugi-4CR of tetracarboxylic acid core unit (0.18 g, 0.39 mmol) with excesses of isobutyraldehyde (0.34 g, 4.68 mmol), methyl 6-aminohexanoate hydrochloride (0.85 g, 4.68 mmol) and methyl 6-isocyanohexanoate (0.73 g, 4.68 mmol) yields methyl ester-protected second generation 72 after column-chromatographic purification (ethyl acetate/MeOH 19:1) as slightly yellowish oil (0.49 g, 67%). TLC (ethyl acetate/MeOH 19:1) $R_f$=0.47; $^1$H NMR (CDCl$_3$, 300 MHz) δ=0.78-0.99 (m, 24H, 8CH$_3$), 1.21-1.65 (m, 58H, 29CH$_2$), 2.00-2.69 (m, 32H, 14CH$_2$, 4CH), 3.12-3.42 (m, 20H, 10CH$_2$), 3.65, 3.66 (2s, 24H, 8CH$_3$), 4.08-4.20 (m, 5H, 5CH), 6.89-7.06 (m, 5H, 5NH) ppm; $^{13}$C NMR (CDCl$_3$, 75 MHz) δ=17.55, 18.90, 19.59, 19.74, 24.32, 24.42, 24.61, 26.26, 26.38, 26.47, 26.61, 26.93, 29.01, 29.17, 29.40, 29.79, 31.11, 33.77, 38.43, 38.88, 49.24, 51.34, 51.39, 53.37, 68.38, 170.50, 173.47, 173.57 ppm; ESI-MS of C$_{96}$H$_{168}$N$_{10}$O$_{26}$ (M+H$^+$=1878.5; M+Na$^+$=1901.3; M+2Na$^{2+}$=961.9; M+Cl$^-$=1913.9); IR (ATR) ν=3307.6, 2936.1, 2867.3, 1732.3 (CO$_2$Me), 1672.4, 1621.2 (amide), 1537.2, 1434.9, 1367.3, 1196.1, 1163.0, 1100.7, 1010.2, 854.7, 731.7 cm$^{-1}$; HRMS of C$_{96}$H$_{168}$N$_{10}$O$_{26}$ exact mass=1877.21313 m/z (z=2) [M+2Na]$^{2+}$ calc. 961.59633, obs. 961.59395.

Second Generation as Octacarboxylic Acid (73)

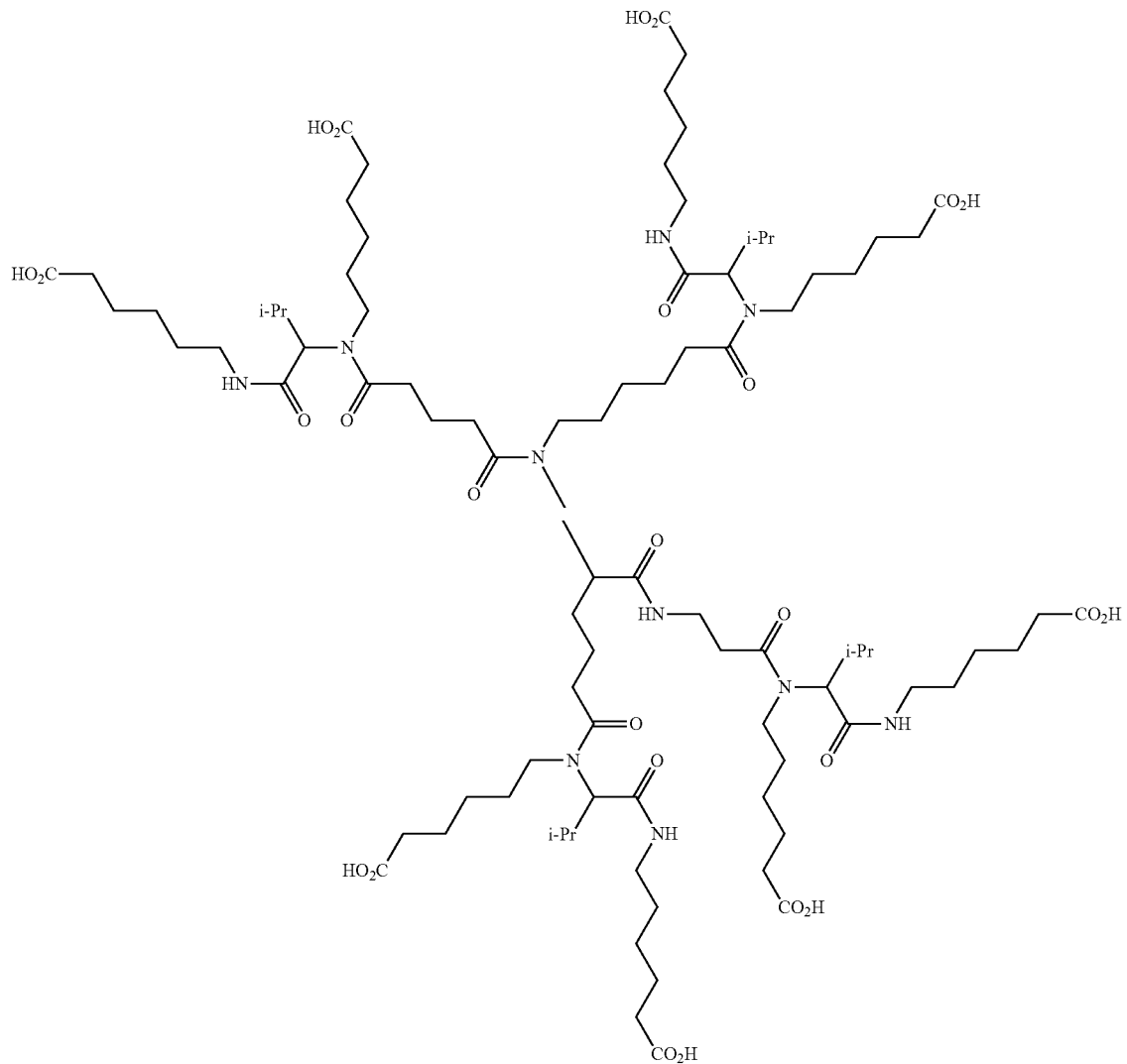

Saponifying the methyl ester groups of second generation 72 (0.38 g, 0.20 mmol) yields the octacarboxylic acid derivative 73 as colorless oil (0.33 g, 94%). TLC (ethyl acetate/MeOH/H$_2$O 3:2:1) R$_f$=0.61; $^1$H NMR (CD$_3$OD, 300 MHz) δ=0.80-1.00 (m, 24H, 8CH$_3$), 1.13-1.99 (m, 60H, 30CH$_2$), 2.15-2.71 (m, 30H, 13CH$_2$, 4CH), 3.15-3.82 (m, 20H, 10CH$_2$), 4.47-4.50 (m, 5H, 5CH) ppm; $^{13}$C NMR (CD$_3$OD, 75 MHz) δ=19.30, 19.82, 20.04, 25.57, 25.67, 25.76, 26.48, 27.53, 27.82, 28.19, 28.66, 29.11, 29.88, 30.65, 33.83, 34.26, 34.79, 40.13, 46.20, 54.82, 64.94, 67.68, 172.42, 172.56, 176.02, 177.27 ppm; ESI-MS of C$_{88}$H$_{152}$N$_{10}$O$_{26}$ (M+H$^+$= 1766.2; M+Na$^+$=1788.4; M+2Na$^{2+}$=905.8; M−H$^−$=1764.5); IR (ATR) ν=3330.6, 2937.1, 2870.1, 1712.5 (CO$_2$H), 1615.1 (amide), 1548.6, 1421.5, 1372.2, 1232.2, 1089.2, 1024.0, 850.3, 731.0 cm$^{-1}$; HRMS of C$_{88}$H$_{152}$N$_{10}$O$_{26}$ [M+Na]$^+$ calc. 1788.07770, obs. 1788.07978.

Preparation of Third Generation Dendrimers

Methyl Ester-Protected Third Generation (80)

Figure 8:
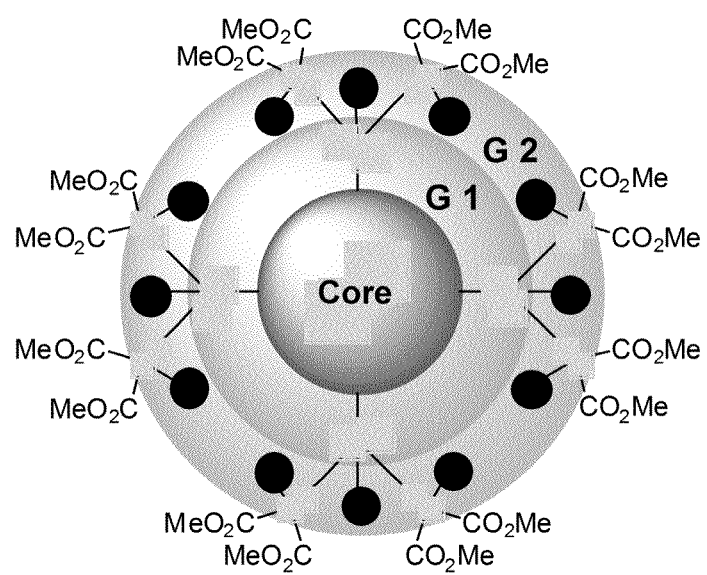
FIG. 8 shows a schematic model of the methyl ester-protected third generation (compound (80)) as prepared in accordance with the present invention.

See FIG. 8

The eightfold Ugi-4CR of second generation octacarboxylic acid 53 (0.40 g, 0.25 mmol) with excesses of methyl 5-oxopentanoate (1.31 g, 10.1 mmol), methyl 4-aminobutyrate hydrochloride (1.55 g, 10.1 mmol) and t-butylisonitrile (0.84 g, 10.1 mmol) yields the methyl ester-protected third generation 80 after column-chromatographic purification (ethyl acetate/MeOH 19:1) as slightly brownish oil (1.00 g, 97%). TLC (ethyl acetate/MeOH 9:1) R$_f$=0.79; $^1$H NMR (CDCl$_3$, 300 MHz) δ=1.23-1.35 (m, 108H, 36CH$_3$), 1.54-2.51 (m, 142H, 71CH$_2$), 3.28-3.36 (m, 26H, 13CH$_2$), 3.66-

3.68 (m, 48H, 16CH$_3$), 4.67-4.88 (m, 13H, 13CH), 6.40-6.77 (m, 13H, 13NH) ppm; $^{13}$C NMR (CDCl$_3$, 75 MHz) δ=20.97, 21.42, 22.14, 24.70, 25.34, 27.29, 28.45, 28.60, 30.29, 30.80, 31.85, 32.88, 32.99, 33.44, 43.62, 47.97, 50.20, 50.80, 51.38, 51.58, 53.36, 56.94, 169.86, 172.61, 172.72, 173.15, 173.38, 173.46, 173.68 ppm; ESI-MS of C$_{203}$H$_{350}$N$_{26}$O$_{58}$ (M+2Na$^{2+}$= 2064.8; M+3Na$^{3+}$=1384.8; M+2Cl$^{2-}$=2077.1); IR (ATR) ν=3323.0, 2954.8, 2248.1, 1731.7 (CO$_2$Me), 1673.0 (amide), 1624.8 (amide), 1536.6, 1453.6, 1435.5, 1416.1, 1364.0, 1258.7, 1197.9, 1170.1, 1073.8, 914.1, 726.6 cm$^{-1}$; HRMS of C$_{203}$H$_{350}$N$_{26}$O$_{58}$ exact mass=4080.52373 m/z (z=3) [M+4H]$^{3+}$ calc. 1361.51835 obs. 1361.51388; MALDITOF-MS of C$_{203}$H$_{350}$N$_{26}$O$_{58}$ [M+Na]$^+$ calc. 4103.514 obs. 4102.949; [M+K$^+$] calc. 4119.487 obs. 4118.936.

Third Generation as Polycarboxylic Acid (81)

Figure 9:
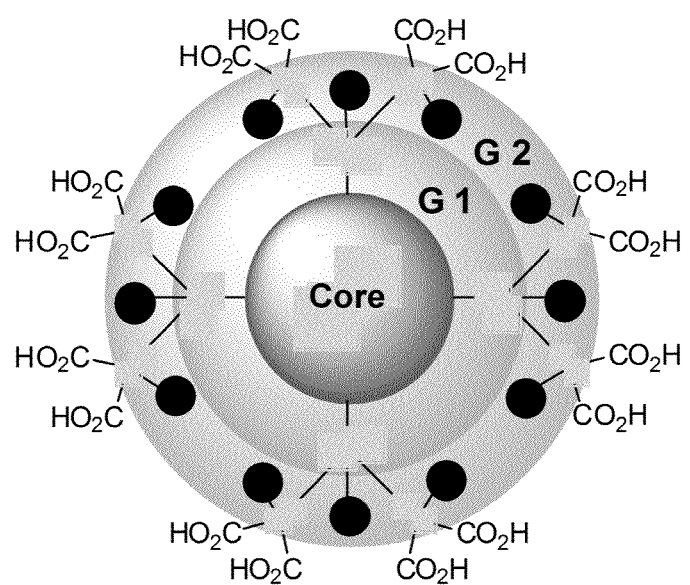
FIG. 9 shows the third generation as polycarboxylic acid (compound (81)) as prepared in accordance with the present invention.

See FIG. 9

Saponifying the methyl ester groups of third generation (0.86 g, 0.21 mmol) yields the polycarboxylic acid derivative 81 as colorless solid (0.75 g, 92%). TLC (ethyl acetate/MeOH/H$_2$O 2:2:1) R$_f$=0.85; mp. 131-132° C. (ethyl acetate); $^1$H NMR (CD$_3$OD, 300 MHz) δ=1.22-1.40 (m, 108H, 36CH$_2$), 1.52-2.56 (m, 142H, 71CH$_2$), 3.29-3.41 (m, 26H, 13CH$_2$), 4.70-4.85 (m, 13H, 13CH) ppm; $^{13}$C NMR (CD$_3$OD, 75 MHz) δ=20.85, 22.73, 22.91, 23.48, 25.32, 26.36, 28.87, 28.97, 29.36, 29.89, 31.14, 31.44, 31.78, 32.72, 33.86, 34.39, 45.51, 52.14, 52.50, 58.96, 61.73, 171.92, 175.22, 176.02, 176.49, 176.60 ppm; ESI-MS of C$_{187}$H$_{318}$N$_{26}$O$_{58}$ (M+2Na$^{2+}$=1952.0; M+3Na$^{3+}$=1307.3; M-2H$^{2-}$=1928.6); IR (ATR) ν=3342.2, 2965.1, 1712.6 (CO$_2$H), 1659.7 (amide), 1614.5 (amide), 1538.7, 1454.8, 1417.5, 1393.5, 1365.1, 1264.2, 1218.3, 1023.9, 865.3 cm$^{-1}$; HRMS of C$_{187}$H$_{318}$N$_{26}$O$_{58}$ exact mass=3856.27333 m/z (z=3) [M-3H]$^{3-}$ calc. 1284.41662 obs. 1284.42075; MALDITOF-MS of C$_{187}$H$_{318}$N$_{26}$O$_{58}$ [M+Na]$^+$ calc. 3879.263 obs. 3879.021; [M+K]$^+$ calc. 3895.237 obs. 3895.102.

Methyl Ester-Protected Linear-Prolongated Third Generation Product (82)

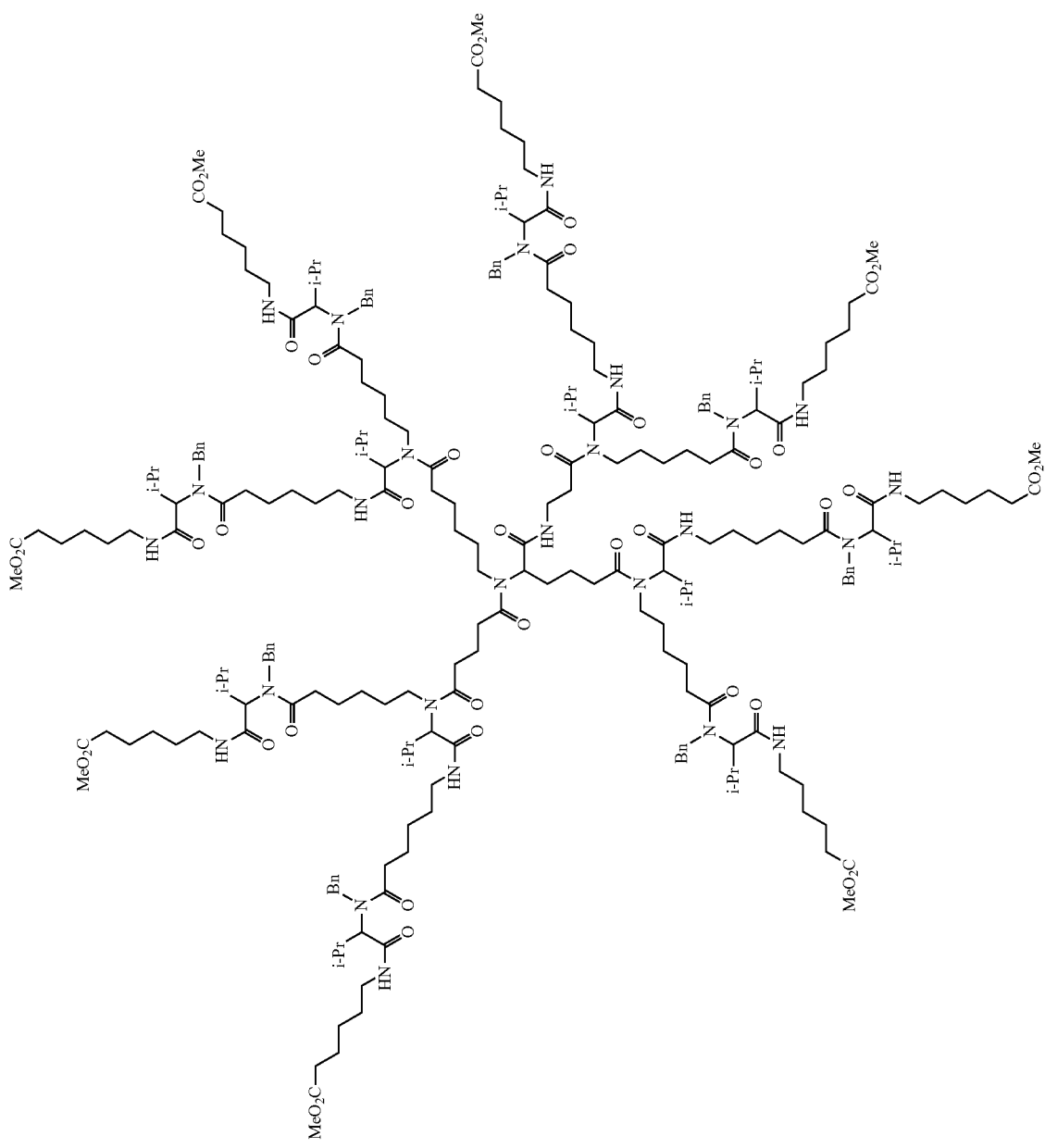

The eightfold Ugi-4CR of octacarboxylic acid 73 (0.08 g, 0.05 mmol) with excesses of isobutyraldehyde (0.14 g, 1.88 mmol), benzylamine (0.20 g, 1.88 mmol) and methyl 6-isocyanohexanoate (0.29 g, 1.88 mmol) yields the unbranched methyl ester-protected third generation 82 after column-chromatographic purification (ethyl acetate/MeOH 19:1) as slightly yellowish oil (0.17 g, 86%). TLC (ethyl acetate/MeOH 19:1) $R_f$=0.52; $^1$H NMR (CDCl$_3$, 500 MHz) δ=0.74-0.94 (m, 72H, 24CH$_3$), 1.18-1.64 (m, 108H, 54CH$_2$), 2.13-240 (m, 54H, 21CH$_2$, 12CH), 2.95-3.18 (m, 36H, 18CH$_2$), 3.65 (s, 24H, 8CH$_3$), 4.53-4.59 (m, 16H, 8CH$_2$), 4.75-4.78 (m, 13H, 13CH), 6.82-7.05 (m, 13H, 13NH), 7.11-7.34 (m, 40H, 40CH) ppm; $^{13}$C NMR (CDCl$_3$, 125 MHz) δ=18.73, 19.51, 24.14, 24.29, 24.45, 24.53, 26.19, 26.48, 26.85, 28.68, 28.83, 29.09, 29.25, 33.65, 33.86, 38.83, 38.96, 48.49, 51.27, 125.87, 126.93, 127.81, 128.34, 137.45, 169.71, 173.74, 174.93, 175.12 ppm; ESI-MS of $C_{240}H_{376}N_{26}O_{42}$ (M+2Na$^{2+}$=2171.5; M+3Na$^{3+}$=1455.3); IR (ATR) ν=3307.8, 2936.4, 2869.7, 1736.8 (CO$_2$Me), 1626.5 (amide), 1541.4, 1452.3, 1368.8, 1234.2, 1203.4, 1168.0, 1102.5, 1029.7, 971.3, 854.3, 731.5, 696.8 cm$^{-1}$; HRMS of $C_{240}H_{376}N_{26}O_{42}$ exact mass=4294.80855 m/z (z=3) [M+3Na]$^{3+}$ calc. 1454.59262 obs. 1454.58922.

Methyl Ester-Protected Third Generation (1→2 Branching) (83)

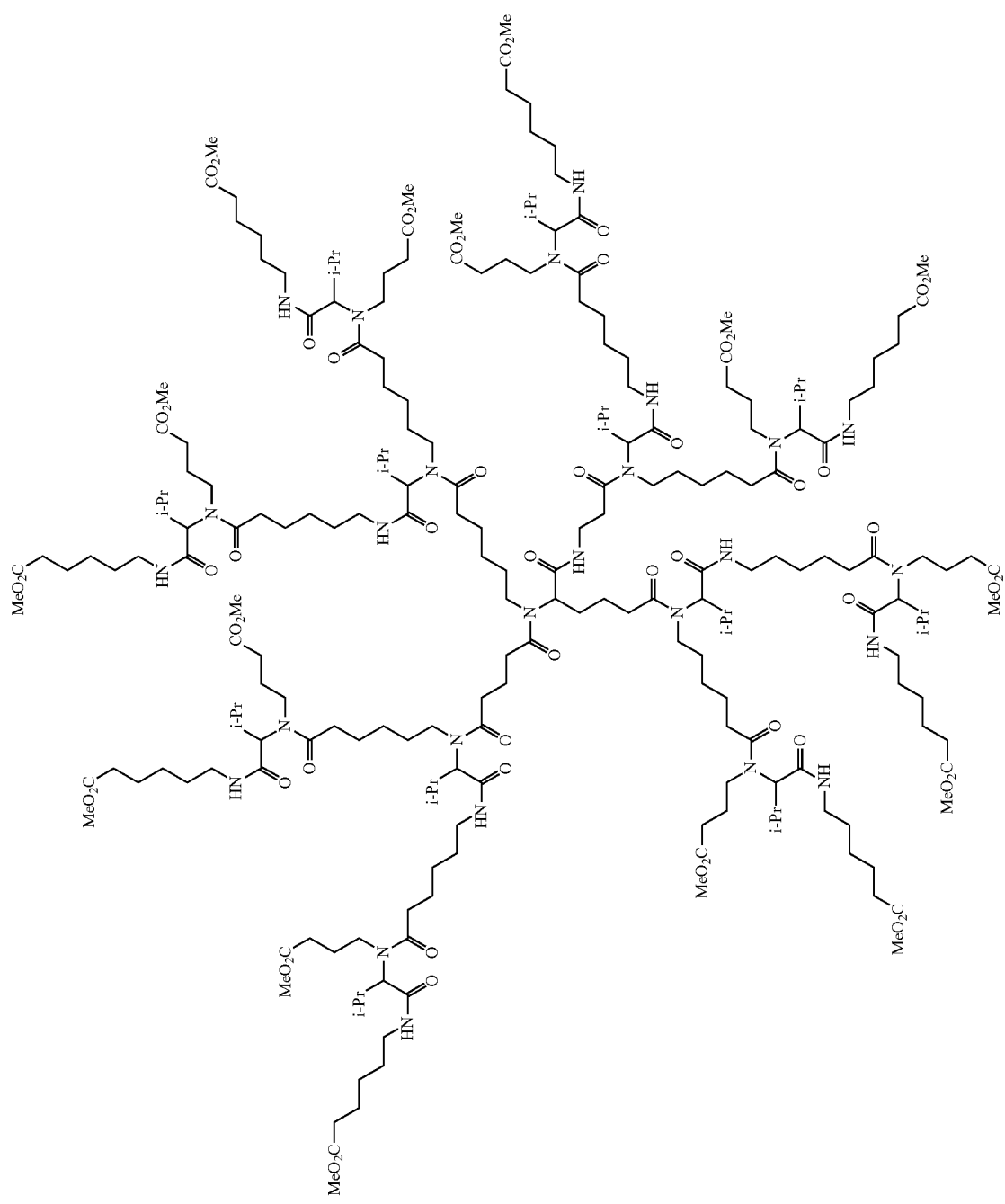

The eightfold Ugi-4CR of octacarboxylic acid 73 (0.076 g, 0.04 mmol) with excesses of isobutyraldehyde (0.12 g, 1.72 mmol), methyl 4-aminobutyrate hydrochloride (0.26 g, 1.72 mmol) and methyl 6-isocyanohexanoate (0.27 g, 1.72 mmol) yields the doubly branched methyl ester-protected third generation 83 after column-chromatographic purification (ethyl acetate/MeOH 19:1) as colorless oil (0.15 g, 81%). TLC (ethyl acetate/MeOH 19:1) $R_f$=0.38; $^1$H NMR (CDCl$_3$, 500 MHz) δ=0.79-1.01 (m, 72H, 24CH$_3$), 1.22-1.89 (m, 124H, 62CH$_2$), 2.25-2.43 (m, 70H, 29CH$_2$, 12CH), 2.91-3.41 (m, 52H, 26CH$_2$), 3.66, 3.67, 3.68 (3s, 48H, 16CH$_3$), 4.20-4.26 (m, 13H, 13CH), 6.83-7.05 (m, 13H, 13NH) ppm; $^{13}$C NMR (CDCl$_3$, 125 MHz) δ=18.68, 19.40, 19.57, 24.25, 24.31, 24.55, 24.88, 26.12, 26.25, 26.40, 26.67, 28.83, 29.03, 29.21, 29.34, 29.42, 30.68, 31.10, 33.05, 33.57, 33.64, 38.78, 39.08, 51.25, 51.39, 51.49, 68.41, 170.66, 170.72, 172.91, 173.51, 173.71, 173.83, 174.31, 174.46 ppm; ESI-Ms of $C_{224}H_{392}N_{36}O_{58}$ (M+2Na$^{2+}$=2211.8; M+3Na$^{3+}$=1482.9); IR (ATR) ν=3305.9, 2935.6, 2870.4, 1732.5 (CO$_2$Me), 1620.5 (amide), 1538.8, 1435.1, 1367.1, 1196.3, 1161.2, 1101.7, 1030.0, 854.8 cm$^{-1}$; HRMS of $C_{224}H_{392}N_{26}O_{58}$ exact mass=4374.85238 m/z (z=3) [M+3Na]$^{3+}$ calc. 1481.27390 obs. 1481.27444.

Methyl Ester-Protected Generation 3 (1→3 Branching) (84)

101 102
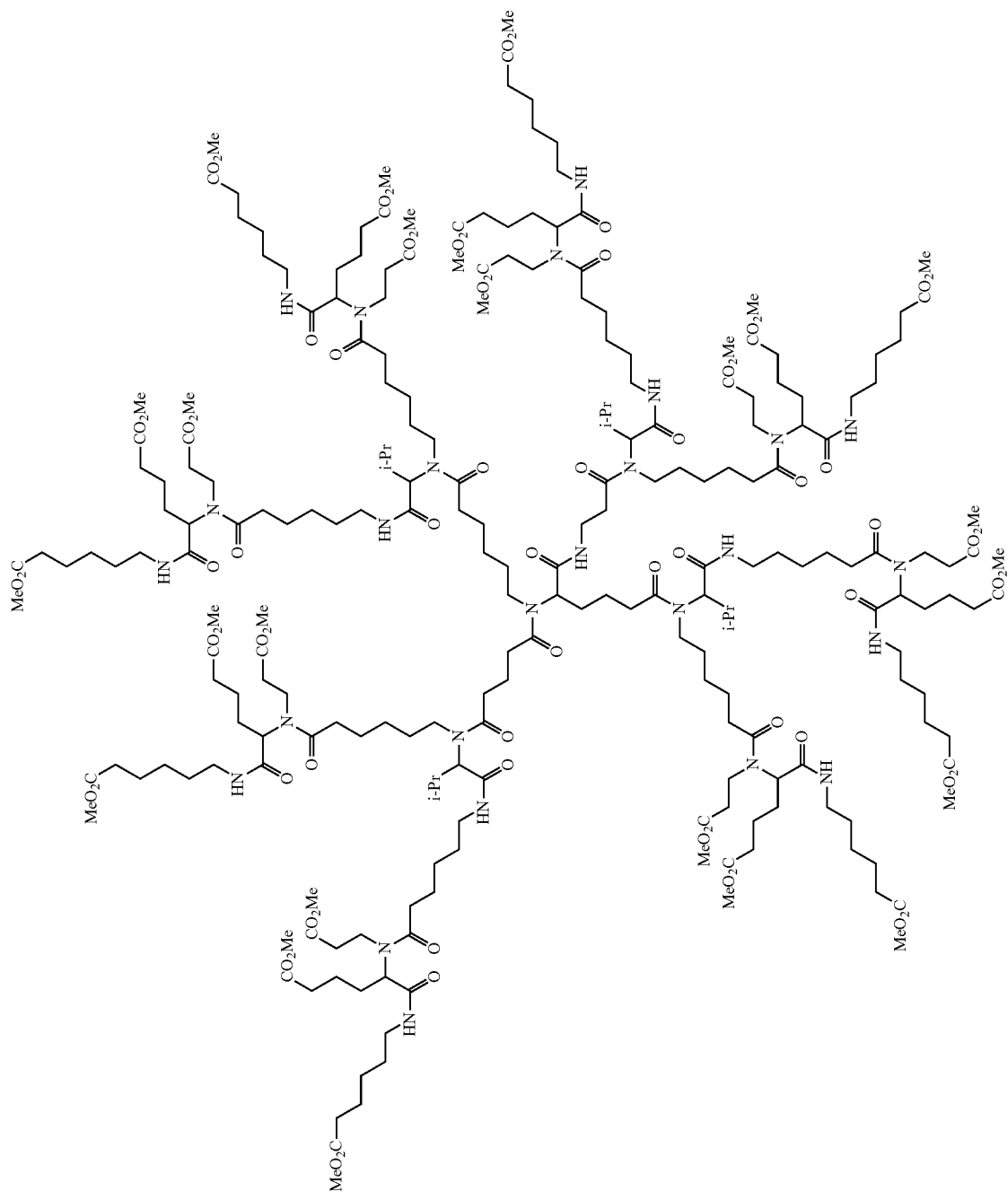

The eightfold Ugi-4CR of octacarboxylic acid 73 (0.08 g, 0.05 mmol with excesses of methyl 5-oxopentanoate (0.24 g, 1.86 mmol), methyl 3-aminopropionate hydrochloride (0.26 g, 1.86 mmol) and methyl 6-isocyanohexanoate (0.29 g, 1.86 mmol) yields the triply branched methyl ester-protected third generation after column-chromatographic purification (ethyl acetate/MeOH 19:1) as slightly yellowish oil (0.19 g, 89%). TLC (ethyl acetate/MeOH 9:1) $R_f$=0.36; $^1$H NMR (CDCl$_2$, 300 MHz) δ=0.79-0.94 (m, 24H, 8CH$_2$), 1.23-2.00 (m, 140H, 70CH$_2$), 2.28-2.91 (m, 78H, 37CH$_2$, 4CH), 3.10-3.41 (m, 52H, 26CH$_2$), 3.66, 3.68 (2s, 72H, 24CH$_3$), 4.68-4.83 (m, 13H, 13CH), 6.80-6.97 (m, 13H, 13NH) ppm; $^{13}$C NMR (CDCl$_3$, 125 MHz) δ=18.63, 19.49, 20.89, 21.26, 21.52, 21.59, 24.04, 24.19, 24.26, 24.44, 24.59, 26.00, 26.07, 26.14, 26.34, 26.53, 27.31, 28.76, 28.88, 28.97, 29.02, 29.22, 32.58, 32.69, 33.02, 33.10, 33.18, 33.30, 33.55, 34.01, 38.43, 38.88, 38.90, 39.25, 40.19, 43.45, 51.20, 51.31, 51.38, 51.44, 51.48, 51.56, 56.73, 169.46, 170.65, 171.13, 173.18, 173.26, 173.34, 173.45, 173.67, 174.01, 174.18 ppm; ESI-MS of $C_{23}2H_{392}N_{26}O_{74}$ (M+2Na$^{2+}$=2386.9; M+3Na$^{3+}$=1600.1); IR (ATR) ν=3307.7, 2948.1, 2865.7, 1731.3 (CO$_2$Me), 1625.3 (amide), 1537.4, 1434.9, 1368.8, 1196.8, 1166.9, 1104.2, 1058.6, 1010.7, 849.2 cm$^{-1}$; HRMS of $C_{222}H_{392}N_{26}O_{74}$ exact mass=4726.77102 m/z (z=3) [M+3Na]$^{3+}$ calc. 1598.58011 obs. 1598.59495.

Methyl Ester-Protected Third Generation (1→3 Branching) (85)

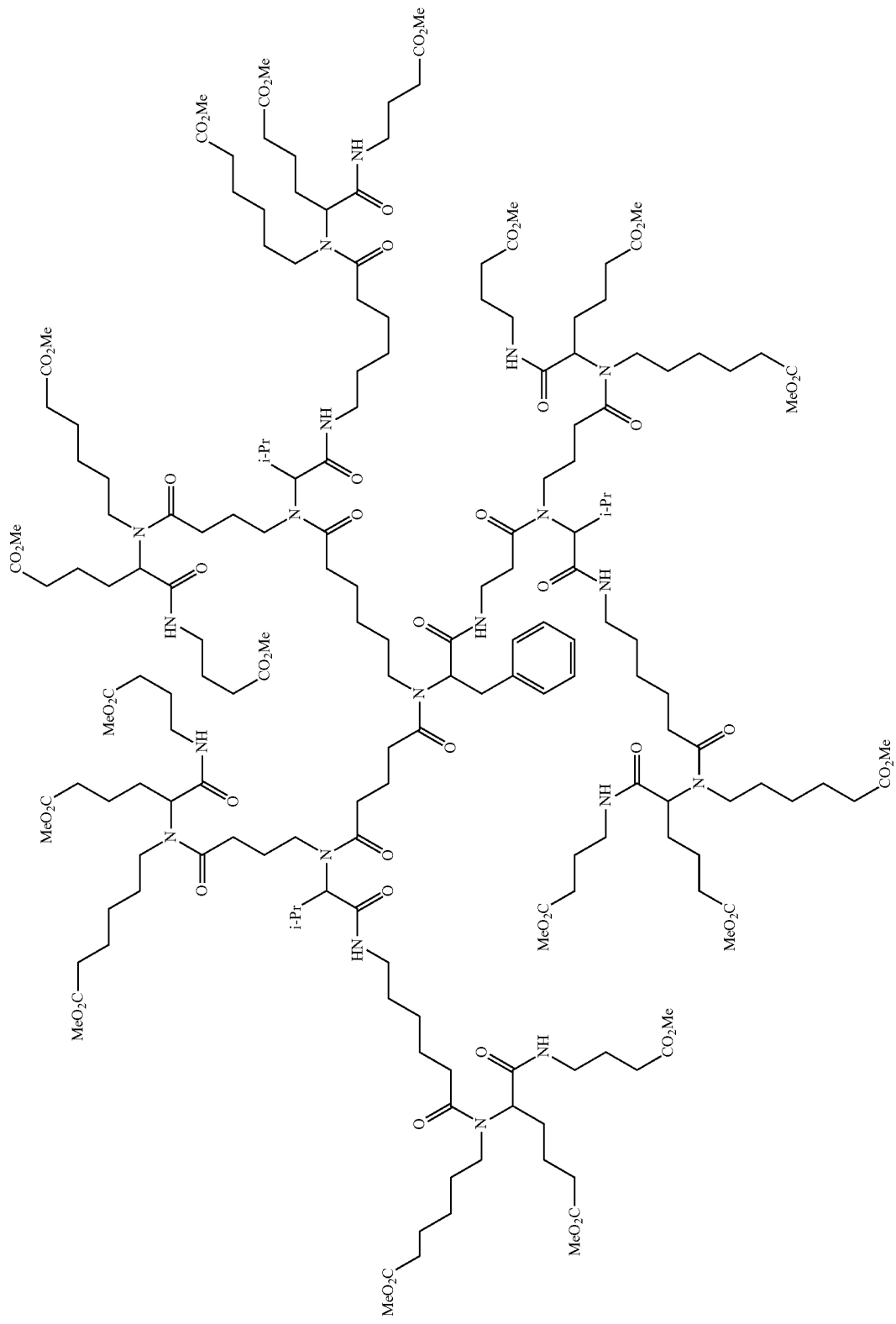

The sixfold Ugi-4CR of hexacarboxylic acid 65 (0.10 g, 0.07 mmol) with excesses of methyl 5-oxopentanoate (0.27 g, 2.10 mmol), methyl 6-aminohexanoate hydrochloride (0.38 g, 2.10 mmol) and methyl 4-isocyanobutyrate (0.27 g, 2.10 mmol) yields the triply branched methyl ester-protected third generation 85 after column-chromatographic purification (ethyl acetate/MeOH 9:1) as brownish oil (0.22 g, 84%). TLC (ethyl acetate/MeOH 9:1) $R_f$=0.59; $^1$H NMR (CDCl$_3$, 300 MHz) δ=0.79-0.95 (m, 18H, 6CH$_3$), 1.18-1.94 (m, 104H, 52CH$_2$), 2.11-2.65 (m, 59H, 28 CH$_2$, 3CH), 2.86-3.57 (m, 42H, 21CH$_2$), 3.66, 3.67 (2S, 54H, 18CH$_3$), 4.75-4.89 (m, 10H, 10CH), 6.91-7.02 (m, 10H, 10NH), 7.19-7.24 (m, 5H, 5CH) ppm; $^{13}$C NMR (CDCl$_3$, 125 MHz) δ=18.48, 19.38, 20.87, 21.21, 21.54, 24.03, 24.20, 24.24, 24.30, 24.42, 24.49, 24.58, 25.28, 25.89, 25.92, 25.94, 26.01, 26.13, 26.18, 26.24, 26.29, 26.47, 27.20, 27.33, 27.51, 28.80, 28.87, 29.08, 29.33, 29.44, 30.93, 30.95, 30.98, 31.06, 31.15, 31.21, 32.68, 32.97, 33.15, 33.23, 33.31, 33.42, 33.48, 33.53, 37.85, 38.23, 38.27, 38.36, 38.80, 40.29, 44.80, 45.39, 45.43, 48.28, 51.11, 51.12, 51.17, 51.20, 51.28, 51.38, 128.05, 128.68, 170.86, 170.90, 173.10, 173.13, 173.17, 173.21, 173.32, 173.37, 173.44, 173.59, 173.67, 173.69, 173.73, 173.95, 174.00 ppm; ESI-MS of C$_{182}$H$_{302}$N$_{20}$O$_{56}$ (M+2Na$^{2+}$=1856.2; M+3Na$^{3+}$=1242.2); IR (ATR) ν=3308.1, 2949.7, 1731.4 (CO$_2$Me), 1626.3 (amide), 1532.0, 1435.4, 1366.5, 1196.4, 1168.4, 1095.0, 1004.0, 883.6, 703.1 cm$^{-1}$; HRMS of C$_{182}$H$_{302}$N$_{20}$O$_{56}$ exact mass=3664.13986 m/z (z=3) [M+3Na]$^{3+}$ calc. 1244.36972 obs. 1244.37251.

Methyl Ester-Protected Third Generation (1→2 Branching) (86)

The sixfold Ugi-4CR of hexacarboxylic acid 67 (0.15 g, 0.11 mmol) with excesses of isobutyraldehyde (0.23 g, 3.24 mmol), methyl 3-aminopropionate hydrochloride (0.45 g, 3.24 mmol) and methyl 6-isocyanohexanoate (0.50 g, 3.24 mmol) yields the doubly branched methyl ester-protected third generation 86 after column-chromatographic purification (ethyl acetate/MeOH 9:1) as slightly yellowish oil (0.26 g, 74%). TLC (ethyl acetate/MeOH 9:1) $R_f$=0.48; $^1$H NMR (CDCl$_3$, 300 MHz) δ=0.76-0.94 (m, 36H, 12CH$_3$), 1.31-1.95 (m, 56H, 28CH$_2$), 2.27-2.68 (m, 50H, 22CH$_2$, 6CH), 3.11-3.85 (m, 36H, 18CH$_2$), 3.65, 3.66 (2s, 36H, 12CH$_3$), 4.18-5.03 (m, 16H, 3CH$_2$, 10CH), 6.83-7.04 (m, 10H, 10NH), 7.24-7.38 (m, 20H, 20CH) ppm; $^{13}$C NMR (CDCl$_3$, 125 MHz) δ=18.48, 19.41, 20.59, 21.67, 21.77, 24.14, 24.29, 24.41, 26.02, 26.53, 27.61, 27.96, 28.09, 28.48, 28.71, 29.03, 29.31, 32.02, 32.16, 32.56, 33.26, 33.51, 33.90, 35.27, 38.43, 38.73, 38.78, 38.95, 40.01, 40.56, 48.07, 51.15, 51.45, 57.03, 66.41, 125.65, 125.75, 126.22, 127.02, 127.20, 127.54, 128.06, 128.23, 128.41, 128.50, 136.91, 137.08, 137.37, 168.96, 170.17, 170.28, 171.09, 172.03, 172.41, 173.05, 173.47, 173.61, 173.93, 174.35 ppm; ESI-MS of C$_{167}$H$_{260}$N$_{20}$O$_{44}$ (M+2Na$^{2+}$=1649.1; M+3Na$^{3+}$=1107.1); IR (ATR) ν=3306.9, 2941.2, 2874.2, 2828.6, 1732.5 (CO$_2$Me), 1625.5 (amide), 1539.3, 1435.7, 1369.1, 1198.6, 1166.2, 1104.8, 1026.0, 731.2, 699.1 cm$^{-1}$; HRMS of C$_{16}$—H$_{260}$N$_{20}$O$_{44}$ exact mass=3249.87223 m/z (z=3) [M+3Na]$^{3+}$ calc. 1106.28051 obs. 1106.28024.

Preparation of a Fourth Generation Dendrimer

Methyl Ester-Protected Fourth Generation (90)

Figure 10:
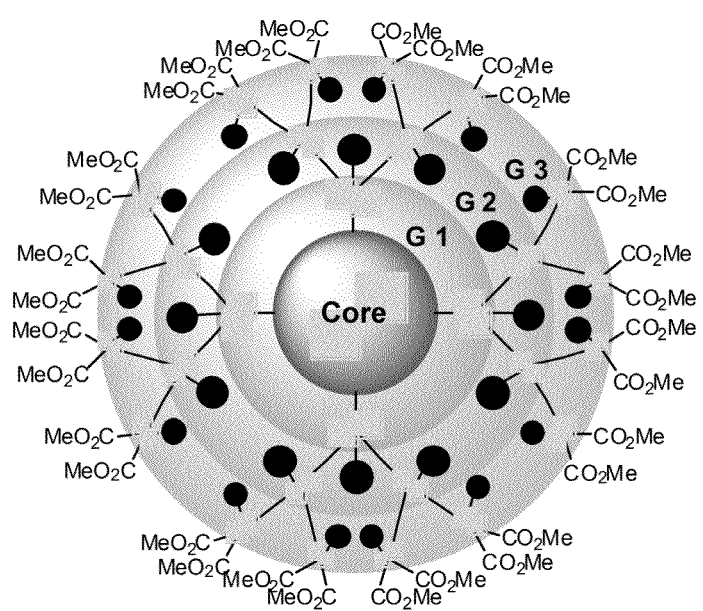
FIG. 10 shows the methyl ester-protected fourth generation (compound (90)) as prepared in accordance with the present invention.

See FIG. 10

The sixteenfold Ugi-4CR of polycarboxylic acid 81 (0.30 g, 0.08 mmol) with excesses of methyl 5-oxopentanoate (0.81 g, 6.22 mmol), methyl 4-aminoburyrate hydrochloride (0.96 g, 6.22 mmol) and t-butylisonitrile (0.52 g, 6.22 mmol) yields the methyl ester-protected fourth generation 90 after column-

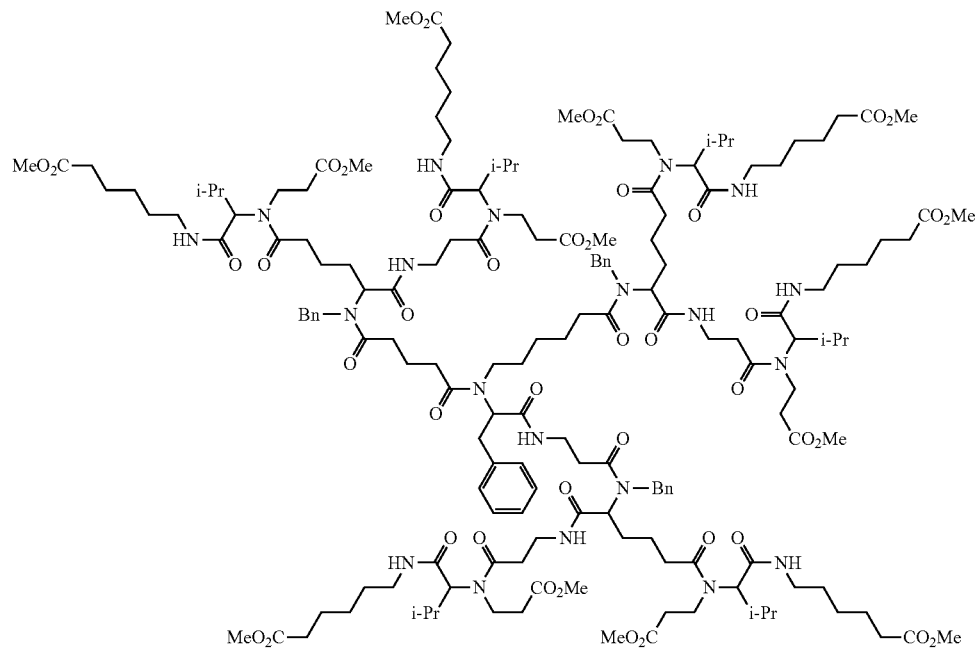 [SMILES: COC(=O)CCCCCNC(=O)C(C(C)C)N(CCC(=O)OC)C(=O)CCCC(C(=O)NCCC(=O)N(CCC(=O)OC)C(C(=O)NCCCCCC(=O)OC)C(C)C)N(Cc1ccccc1)C(=O)CCCCCN(C(=O)CCCC(=O)N(Cc1ccccc1)C(CCCC(=O)N(CCC(=O)OC)C(C(=O)NCCCCCC(=O)OC)C(C)C)C(=O)NCCC(=O)N(CCC(=O)OC)C(C(=O)NCCCCCC(=O)OC)C(C)C)C(Cc1ccccc1)C(=O)NCCC(=O)N(Cc1ccccc1)C(CCCC(=O)N(CCC(=O)OC)C(C(=O)NCCCCCC(=O)OC)C(C)C)C(=O)NCCC(=O)N(CCC(=O)OC)C(C(=O)NCCCCCC(=O)OC)C(C)C]

chromatographic purification (ethyl acetate/MeOH 9:1) as slightly yellowish oil (0.61 g, 88%). TLC (ethyl acetate/MeOH 19:1) $R_f$=0.80; $^1$H NMR (CDCl$_3$, 300 MHz) δ=1.28-1.34 (m, 252H, 84CH$_3$), 1.54-2.46 (m, 302H, 151CH$_2$), 3.27-3.43 (m, 58H, 29CH$_2$), 3.65-3.67 (m, 96H, 32CH$_3$), 4.65-4.93 (m, 29H, 29CH), 6.45-6.81 (m, 29H, 29NH) ppm; $^{13}$C NMR (CDCl$_3$, 75 MHz) δ=20.78, 21.43, 22.13, 24.76, 27.38, 28.47, 29.85, 30.84, 32.86, 33.47, 42.07, 43.63, 50.86, 51.43, 51.63, 53.38, 56.95, 169.85, 172.70, 172.86, 173.22, 173.71 ppm; ESI-MS of $C_{443}H_{766}N_{58}O_{122}$ (M+4Na$^{4+}$=2237.7); IR (ATR) ν=3315.9, 2958.8, 1732.4 (CO$_2$Me), 1673.7 (amide), 1621.4 (amide), 1537.1, 1453.4, 1434.8, 1391.9, 1363.8, 1259.3, 1223.0, 1198.1, 1170.3, 1072.6, 885.1 cm$^{-1}$; HRMS of $C_{443}H_{166}N_{58}O_{122}$ exact mass=8851.55185 m/z (z=4) [M+4Na]$^{4+}$ calc. 2235.87773 exact mass could not be identified; MALDITOF-MS of $C_{443}H_{766}N_{58}O_{122}$ [M+Na]$^+$ calc. 8874.541 obs. 8880.963; [M+K]$^+$ calc. 8896.479 obs. 8890.516.

Fourth Generation as Polycarboxylic Acid (91)

Figure 11:
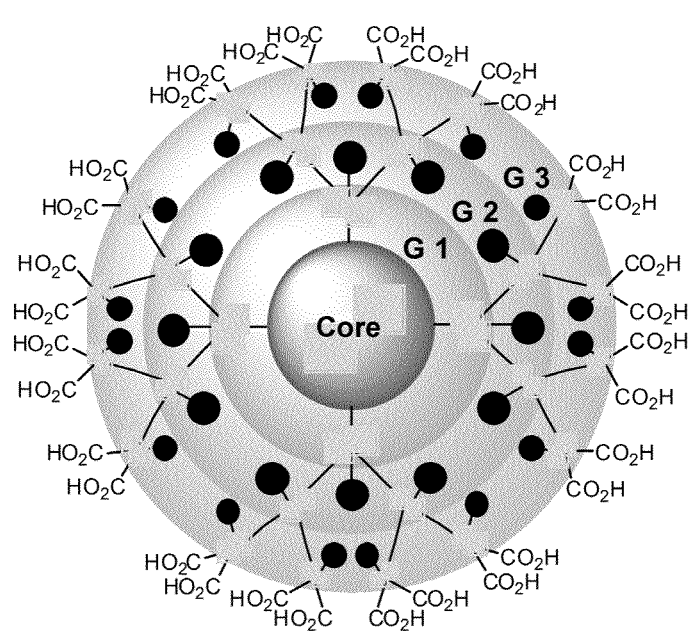
FIG. 11 shows the fourth generation as polycarboxylic acid (compound (91)) as prepared in accordance with the present invention.

See FIG. 11

Saponifying the methyl ester groups of fourth generation 90 (0.49 g, 0.06 mmol) yields the polycarboxylic acid derivative 91 as colorless solid (0.37 g, 80%). TLC (ethyl acetate/MeOH/H$_2$O 2:2:1) R$_f$=0.91; mp. 109-110° C. (ethyl acetate); $^1$H NMR (CD$_3$OD, 300 MHz) δ=1.21-1.35 (m, 252H, 84CH$_3$), 1.53-2.56 (m, 302H, 151CH$_2$), 3.30-3.42 (m, 58H, 29CH$_2$), 4.68-4.84 (m, 29H, 29CH) ppm; $^{13}$C NMR (CD$_3$OD, 75 MHz) δ=20.83, 22.77, 22.93, 23.56, 26.41, 28.95, 29.38, 29.89, 30.74, 30.92, 31.20, 31.50, 31.82, 32.21, 32.76, 33.89, 34.43, 45.55, 52.16, 52.52, 58.96, 61.78, 171.94, 174.93, 175.23, 175.94, 176.55 ppm; ESI-MS of $C_{411}H_{702}N_{58}O_{122}$ (M−4H$^{4-}$=2101.4); IR (ATR) ν=3335.8, 2964.9, 1716.1 (CO$_2$H), 1620.4 (amide), 1541.6, 1455.3, 1422.0, 1393.7, 1365.7, 1221.5, 1071.6, 871.1, 753.2 cm$^{-1}$; MALDITOF-MS of $C_{411}H_{702}N_{58}O_{122}$ [M+Na]$^+$ calc. 8426.041 obs. 8431.544; [M+K]$^+$ calc. 8442.015 obs. 8446.877.

Surface derivatizing a dendrimer with convertible isonitrile by convergent synthesis (Ugi branching for four generations)

Benzyl {9-[4-(2,2-dimethoxyethyl)-3-(formylamino)-benzoyl]-10-isopropyl-13,13-dimethyl-11-oxo-3,6-dioxa-9,12-diazetetradec-1-yl}carbamate (48)

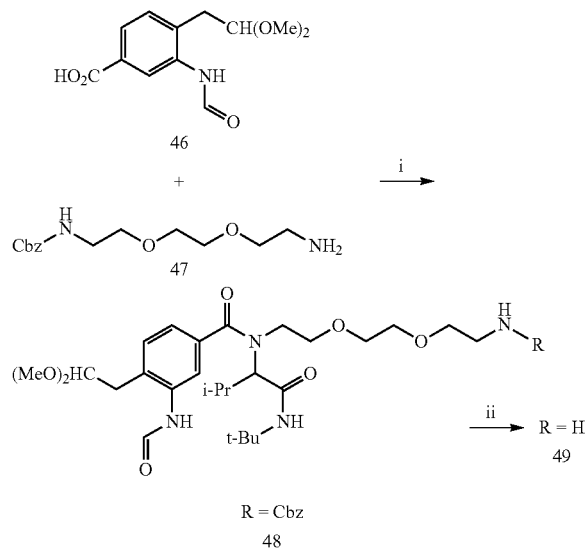

The Ugi-4CR of formamide 46 (1.19 g, 4.70 mmol) with isobutyraldehyde (0.34 g, 4.70 mmol), amine derivative (1.33 g, 4.70 mmol) and t-butylisonitrile (0.39 g, 4.70 mmol) yields the Cbz-protected amine derivative 48 after column-chromatographic purification (ethyl acetate/MeOH 19:1) as slightly yellowish oil (1.93 g, 68%). TLC (ethyl acetate) R$_f$=0.38; $^1$H NMR (CDCl$_3$, 300 MHz, s-cis (minor) and s-trans (major) isomer) δ=0.73, 0.95-1.01 (t, J=6.0 Hz, m, 6H, 2CH$_3$), 1.35, 1.39 (2s, 9H, 3CH$_3$), 2.56-2.77 (m, 1H, CH), 2.93 (t, J=4.9 Hz, 2H, CH$_2$), 3.39, 3.41 (2s, 6H, 2CH$_3$), 3.45-3.96 (m, 13H, 6CH$_2$, CH), 4.42-4.47 (m, 1H, CH), 5.08 (s, 2H, CH$_2$), 5.67, 5.87 (br, 2s, 1H, NH), 7.14-7.33 (m, 8H, 8CH), 7.70, 8.02 (2s, 1H, NH), 8.38, 8.53 (s, d, J=11.3 Hz, 1H, CHO), 8.76-8.90 (m, 1H, NH) ppm; $^{13}$C NMR (CDCl$_3$, 75 MHz, s-cis (minor) and s-trans (major) isomer) δ=18.99, 19.72, 19.80, 26.46, 28.50, 36.32, 36.75, 40.78, 41.30, 50.81, 51.83, 53.34, 54.03, 54.49, 66.36, 67.91, 68.22, 69.94, 70.14, 105.69, 106.45, 119.88, 122.26, 123.59, 127.89, 128.31, 129.01, 130.07, 131.29, 131.89, 135.73, 136.59, 156.44, 159.09, 163.05, 168.51, 169.78, 169.97, 172.75, 173.15 ppm; ESI-MS of $C_{35}H_{52}N_4O_9$ (M+H$^+$=673.7; M+Na$^+$=695.4; 2M+Na$^+$=1367.8; M−H$^-$=671.8); IR (ATR) ν=3314.9, 2963.6, 1668.0 (amide), 1612.8 (amide), 1573.5, 1531.2, 1454.5, 1416.9, 1364.0, 1250.3, 1114.9, 1067.6, 1026.3, 924.6, 823.8, 736.9, 697.0 cm$^{-1}$; HRMS of $C_{35}H_{52}N_4O_9$ [M+Na]$^+$ calc. 695.36320 obs. 695.36354.

N-{2-[2-(2-Aminoethoxy)ethoxy]ethyl}-N-{1-[(tert-butylamino)carbonyl]-2-methylpropyl}-4-(2,2-dimethoxyethyl)-3-(formylamino)benzamide (49) (Formamide-Dendron Amino-URG, Precursor of Convertible Isonitrile)

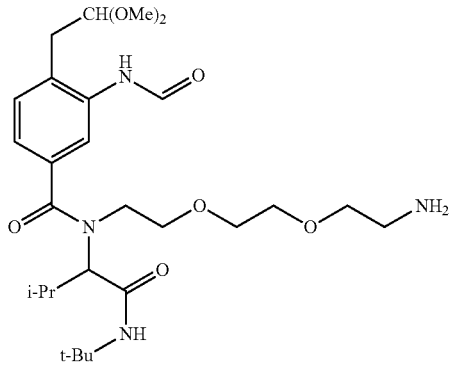

The Cbz-protected amine derivative 48 (1.93 g, 2.87 mmol) in MeOH (50 ml) is admixed with a spatula tip of Pd(OH)$_2$ (20% on activated carbon). The reaction under H$_2$ is allowed to proceed at room temperature under vigorous agitation for a prolonged period. After three hours, the TLC check (ethyl acetate) indicates complete detachment of the Cbz protective group. The catalyst is then filtered off on Celite® and the colorless solution is concentrated to dryness in vacuo. Amine derivative 49 is obtained as slightly yellowish oil (1.44 g, 93%). TLC (ethyl acetate/MeOH/H$_2$O 2:2:1) R$_f$=0.38; $^1$H NMR (CDCl$_3$, 500 MHz, s-cis (minor) and s-trans (major) isomer) δ=0.76, 0.99-1.01 (t, J=6.1 Hz, m, 6H 2CH$_3$), 1.37, 1.40 (2s, 9H, 3CH$_3$) 1.82 (br, s, 2H, NH$_2$), 2.64-2.89 (m, 2H, CH$_2$), 2.94-2.97 (m, 1H, CH), 3.40, 3.42 (2s, 6H, 2CH$_3$), 3.43-4.03 (m, 13H, 6CH$_2$, CH), 4.42-4.49 (m, 1H, CH), 7.17-7.32 (m, 3H, 3CH), 7.70, 8.01 (2s, 1H, NH), 8.42, 8.52 (2s, 1H, CHO), 8.68, 8.95 (2s, 1H, NH) ppm; $^{13}$C NMR (CDCl$_3$, 125 MHz, s-cis (minor) and s-trans (major) isomer) δ=18.62, 18.98, 19.77, 19.84, 26.47, 26.55, 28.49, 28.76, 36.28, 36.72, 41.29, 41.53, 41.57, 50.79, 50.82, 51.81, 53.34, 53.81, 53.94, 54.01, 54.44, 67.82, 67.98, 68.13, 68.27, 69.85, 69.97, 70.05, 70.12, 73.05, 73.15, 105.64, 106.37, 106.74, 119.97, 122.21, 122.82, 123.67, 123.95, 125.39, 129.09, 129.77, 130.29, 131.28, 131.83, 131.95, 134.23, 135.23, 135.62, 135.72, 136.37, 136.64, 159.05, 159.29, 162.80, 168.49, 169.74, 169.93, 171.73, 172.72, 173.12 ppm; ESI-MS of $C_{27}H_{46}N_4O_7$ (M+H$^+$=539.0; M+Na$^+$= 561.1; M−H$^−$=537.8); IR (ATR) ν=3309.1, 2963.7, 2933.0, 2871.5, 2830.9, 2358.8, 2338.3, 1668.1 (amide), 1613.1 (amide), 1573.4, 1530.9, 1454.1, 1417.1, 1388.9, 1362.7, 1307.2, 1295.7, 1270.6, 1245.2, 1224.9, 1189.6, 1168.9, 1115.1, 1067.1, 1038.6, 1002.4, 978.2, 919.0, 859.0, 823.5, 793.9, 750.5, 729.0, 665.0 cm$^{-1}$; HRMS of $C_{27}H_{46}N_6O_7$ [M+Na]$^+$ calc. 539.34448 obs. 539.34383.

R =

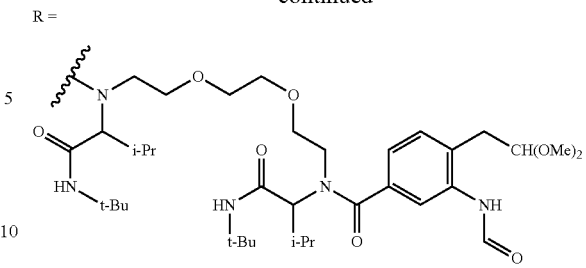

Formamide Dendron Modified Dendrimer Surface of First Generation (95)

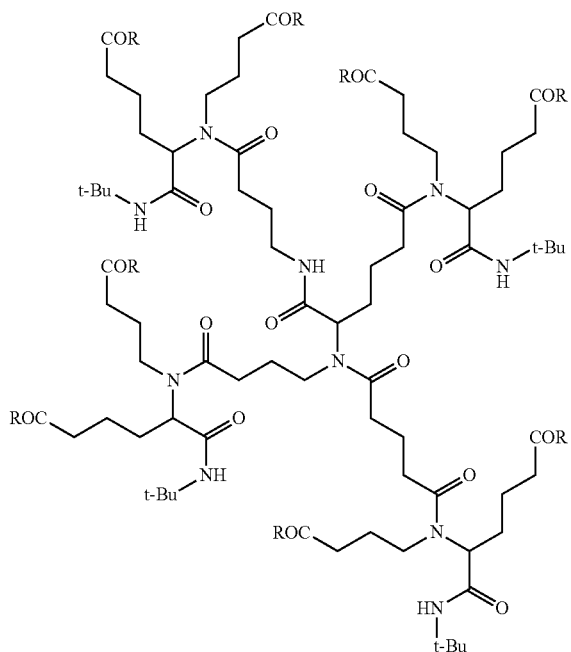

The eightfold Ugi-4CR of octacarboxylic acid 61 (0.10 g, 0.06 mmol) with excesses of isobutyraldehyde (0.11 g, 1.52 mmol), the amine derivative 49 (0.82 g, 1.52 mmol) and t-butylisonitrile (0.13 g, 1.52 mmol) yields the formamide surface derivatized dendrimer 95 (four generations of Ugi branching points) after column-chromatographic purification (ethyl acetate/MeOH 4:1) as colorless solid (0.32 g, 72%). TLC (ethyl acetate/MeOH 4:1) R$_f$=0.68; $^1$H NMR (CDCl$_3$, 300 MHz, δ=0.75-1.03 (m, 96H, 32CH$_3$), 1.24-1.39 (m, 180H, 60CH$_3$), 1.57-1.89 (m, 34H, 17CH$_2$), 2.41-2.63 (m, 40H, 12CH$_2$, 16CH), 2.86-3.00 (m, 18H, 9CH$_2$), 3.31-4.50 (m, 185H, 16CH$_3$, 54CH$_2$, 29CH), 6.42-7.05 (m, 21H, 21NH), 7.16-7.32 (m, 24H, 24CH), 8.42, 8.50 (s, d, J=11.4 Hz, 8H, 8 CHO), 8.87-8.94 (m, 8H, 8NH), ppm; $^{13}$C NMR (CDCl$_3$, 125 MHz, δ=18.63, 19.01, 19.64, 19.77, 19.85, 22.12, 25.17, 26.46, 26.55, 28.41, 28.49, 28.74, 29.52, 30.34, 33.11, 36.20, 36.64, 41.20, 43.96, 48.16, 50.74, 50.79, 51.80, 53.79, 54.00, 54.42, 55.84, 57.27, 67.74, 67.99, 68.13, 68.23, 68.81, 69.68, 69.84, 70.15, 70.29, 76.57, 77.20, 105.62, 106.32, 106.70, 119.74, 122.17, 122.84, 123.60, 124.00, 125.41, 129.20, 129.82, 130.43, 131.36, 131.96, 134.19, 135.21, 135.51, 135.72, 136.25, 136.63, 159.13, 159.30, 162.69, 168.45, 168.88, 169.69, 169.89, 170.02, 170.99, 171.66, 172.64, 173.09, 173.47, 174.33 ppm; ESI-MS of $C_{363}H_{614}N_{50}O_{82}$ (M+3Na$^{3+}$=2353.5; M+4Na$^{4+}$=1771.0; M+5Na$^{5+}$=1421.3); IR (ATR) ν=3306.4, 3076.1, 2965.4, 2937.6, 2876.3, 2830.2, 2359.9, 2340.5, 1660.9 (amide), 1621.5 (amide), 1572.5, 1543.8, 1455.1, 1418.3, 1391.4, 1364.9, 1313.5, 1297.6, 1273.8, 1248.4, 1223.2, 1191.1, 1170.5, 1116.4, 1070.1, 1025.0, 928.6, 820.9, 795.5, 733.5, 688.3 cm$^{-1}$; HRMS of $C_{363}H_{614}N_{50}O_{82}$ exact mass=6986.54127 m/z (z=4) [M+4Na]$^{4+}$ calc. 1769.62509 exact mass could not be identified; MALDITOF-MS of $C_{363}H_{614}N_{50}O_{82}$ [M+Na]$^+$ calc. 7009.531 obs. 7015.103; [M+K]$^+$ calc. 7025.505 of obs. 7030.729.

Synthesis of Highly Diverse Janus Dendrimers

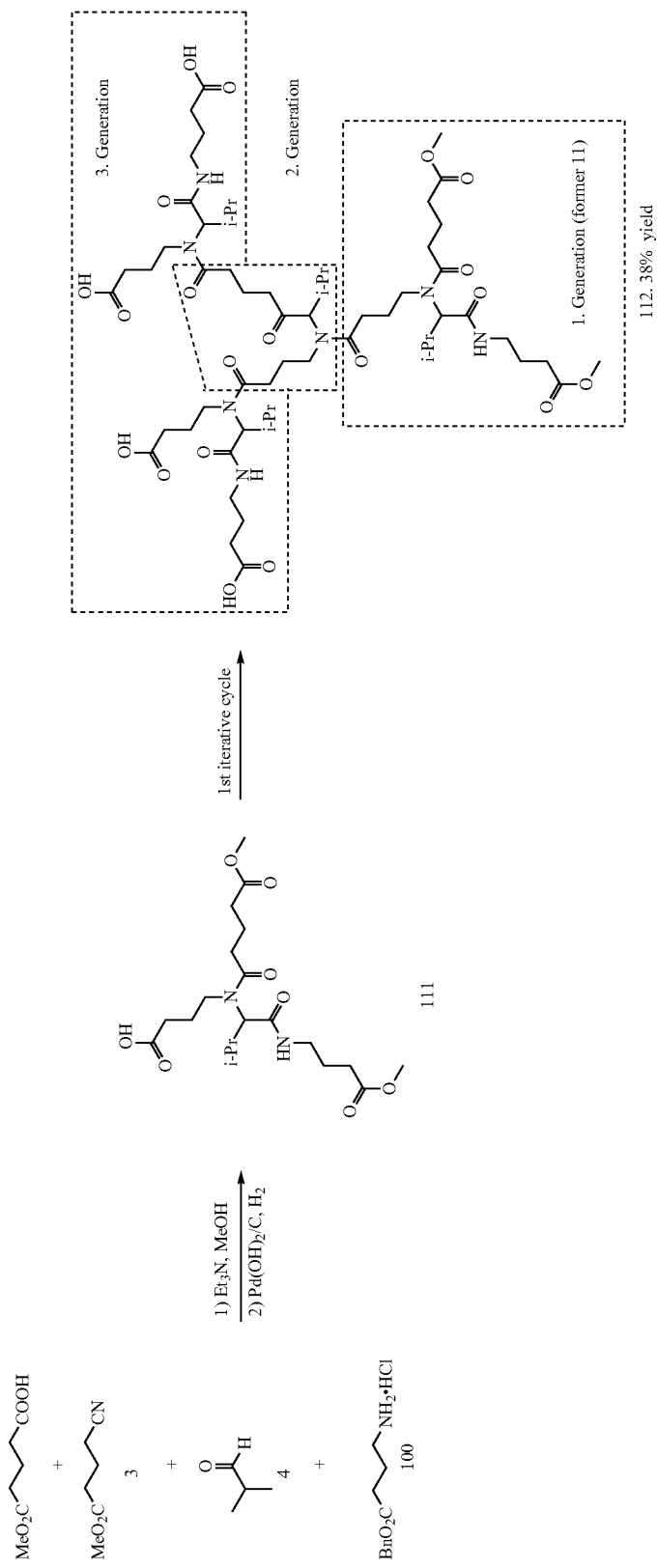

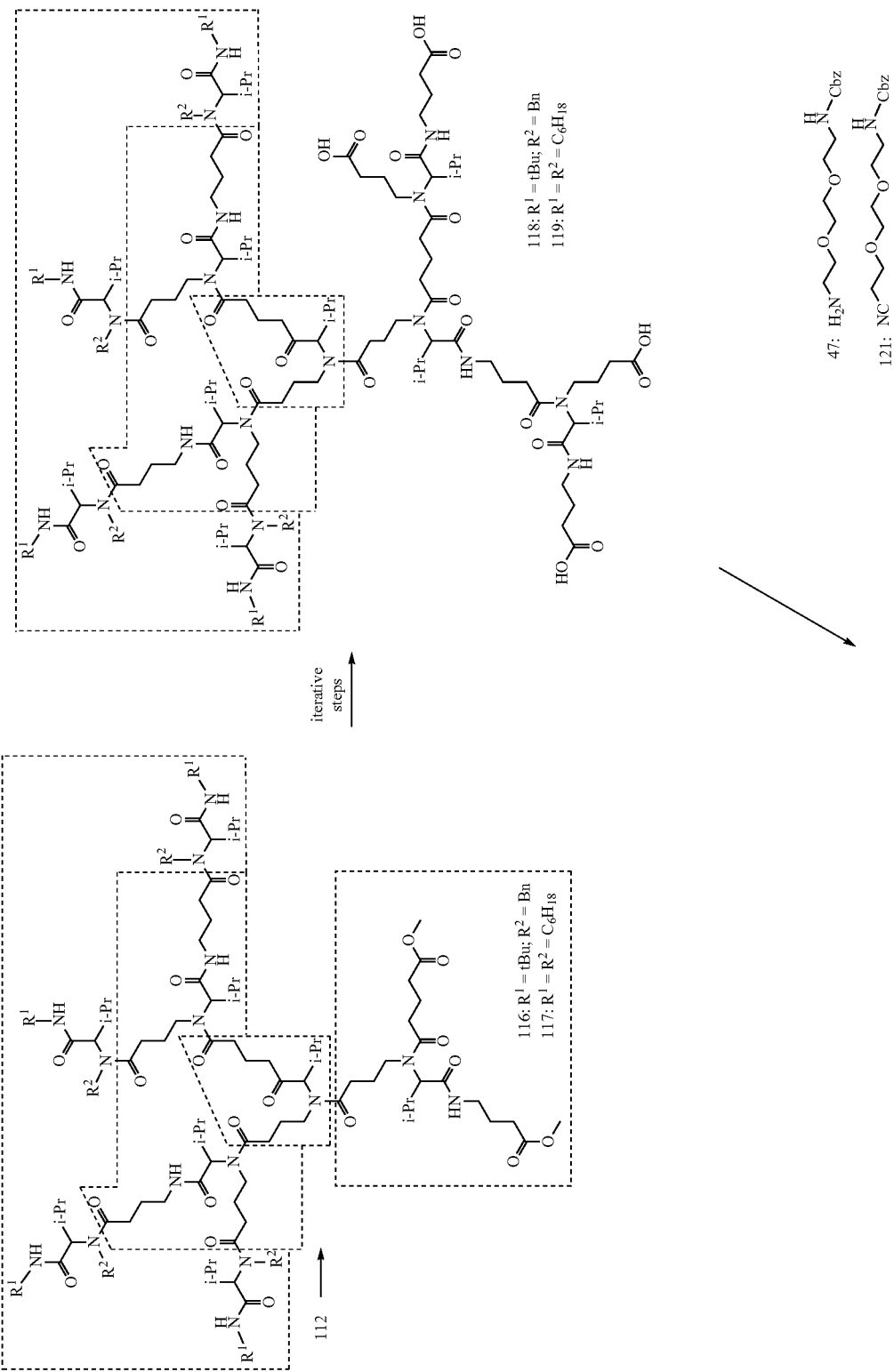

-continued
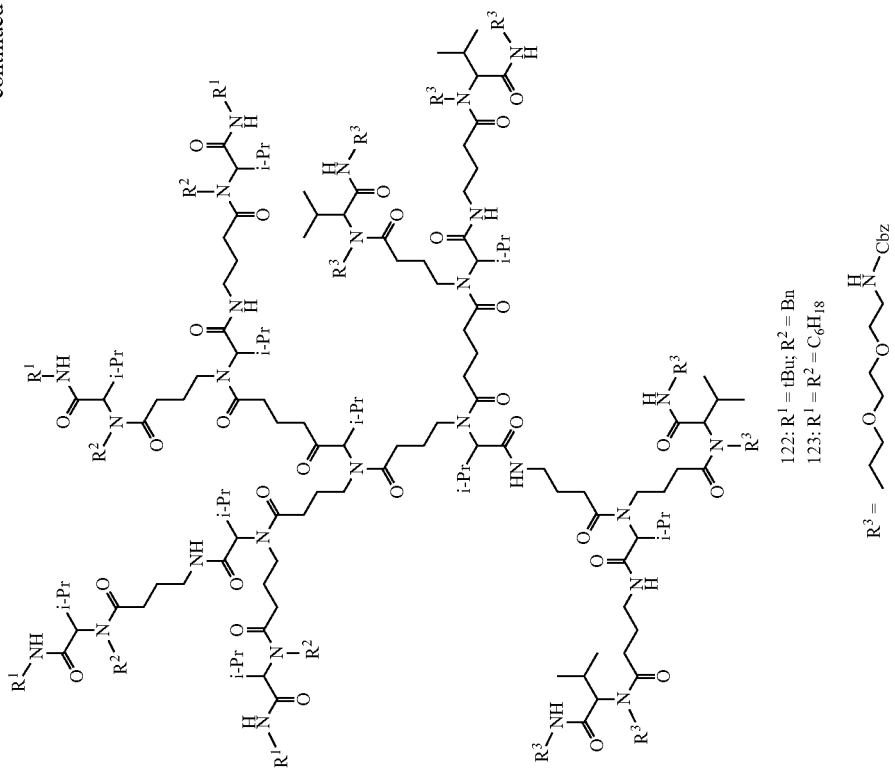

119

First Generation (Protected) 111a

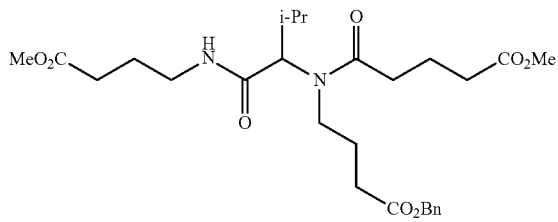 [SMILES: COC(=O)CCCNC(=O)C(C(C)C)N(CCCC(=O)OCc1ccccc1)C(=O)CCCC(=O)OC]

The Ugi-4CR with mono-methyl glutarate (0.95 g, 6.50 mmol), benzyl 4-aminobutyrate hydrochloride 100 (1.50 g, 6.50 mmol), isobutyraldehyde 4 (0.47 g, 6.50 mmol), methyl 4-isocyanobutyrate (0.83 g, 6.50 mmol) and triethylamine (0.66 g, 6.50 mmol) yielded the protected 1st generation 111a after column-chromatographic purification (MeOH/EE, 1:5) as colorless oil (2.16 g, 64%).

ESI-MS: $C_{27}H_{40}N_2O_8$ (M+H$^+$=521.4).

First Generation (Functionalized) 111

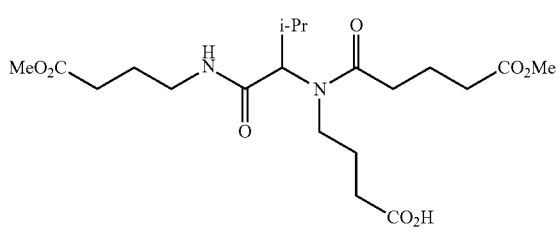 [SMILES: COC(=O)CCCNC(=O)C(C(C)C)N(CCCC(=O)O)C(=O)CCCC(=O)OC]

Cleaving the benzyl ester-protected first generation 111a (2.07 g, 3.97 mmol) yielded 11 as colorless oil (1.70 g, 99%).
ESI-MS of $C_{20}H_{35}N_2O_8$ (M+H$^+$=431.4).

120

Second Generation (Protected) 112a

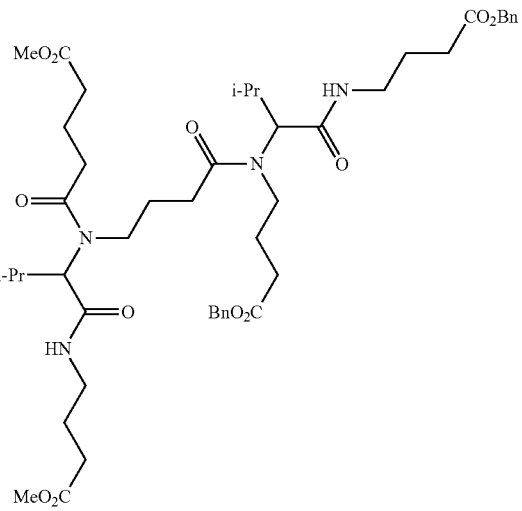

The Ugi-4CR with 111 (0.66 g, 1.50 mmol) with benzyl 4-aminobutyrate hydrochloride 100 (0.66 g, 1.50 mmol), isobutyraldehyde 4 (0.11 g, 1.50 mmol), benzyl 4-isocyanobutyrate (0.31 g, 1.50 mmol) and triethylamine (0.15 g, 1.50 mmol) yields the dibenzyl ester 112a after column-chromatographic purification (EE/hexane, 2:1) as colorless oil (0.81 g, 64%).

ESI-MS: $C_{47}H_{68}N_4O_{12}$ (M+Na$^+$=903.6).

Second Generation (Functionalized) 112b

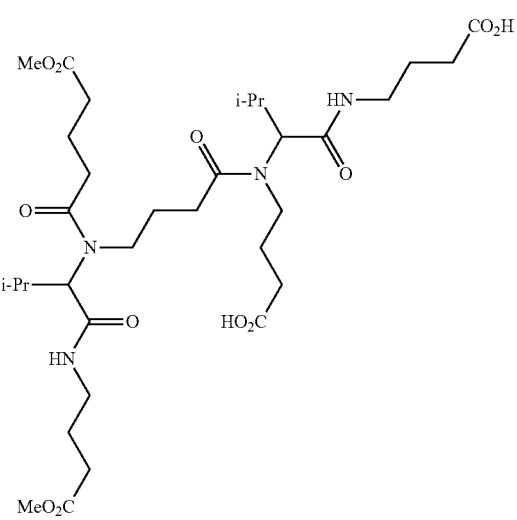 [SMILES: COC(=O)CCCNC(=O)C(C(C)C)N(CCCC(=O)N(CCCC(=O)O)C(C(=O)NCCCC(=O)O)C(C)C)C(=O)CCCC(=O)OC]

Cleaving the dibenzyl ester 112a (0.69 g, 0.79 mmol) yielded 112b as colorless oil (0.55 g, 99%)
ESI-MS: $C_{33}H_{56}N_4O_{12}$ (M+Na$^+$=723.2).

3Rd Generation 112c

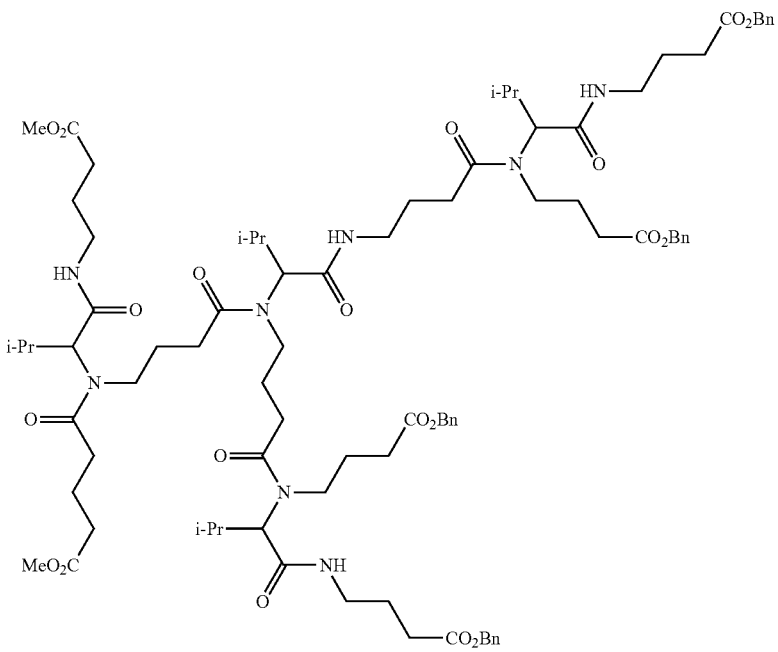 [SMILES: COC(=O)CCCNC(=O)C(C(C)C)N(CCCC(=O)N(CCCC(=O)N(CCCC(=O)OCc1ccccc1)C(C(=O)NCCCC(=O)OCc1ccccc1)C(C)C)C(C(=O)NCCCC(=O)N(CCCC(=O)OCc1ccccc1)C(C(=O)NCCCC(=O)OCc1ccccc1)C(C)C)C(C)C)C(=O)CCCC(=O)OC]

The twofold Ugi-4CR of dicarboxylic acid 112b (0.46 g, 0.65 mmol) with benzyl 4-aminobutyrate hydrochloride 100 (0.46 g, 2.00 mmol), isobutyraldehyde 4 (0.14 g, 2.00 mmol), benzyl 4-isocyanobutyrate (0.41 g, 2.00 mmol) and triethylamine (0.20 g, 2.00 mmol) yielded the tetrabenzyl ester 112c after column-chromatographic purification (EE/hexane, 6:1) as colorless oil (0.76 g, 73%).

ESI-MS: $C_{87}H_{124}N_8O_{20}$ (M+Na$^+$=1625.5).

Tetracarboxylic Acid 112 (HMI 218)

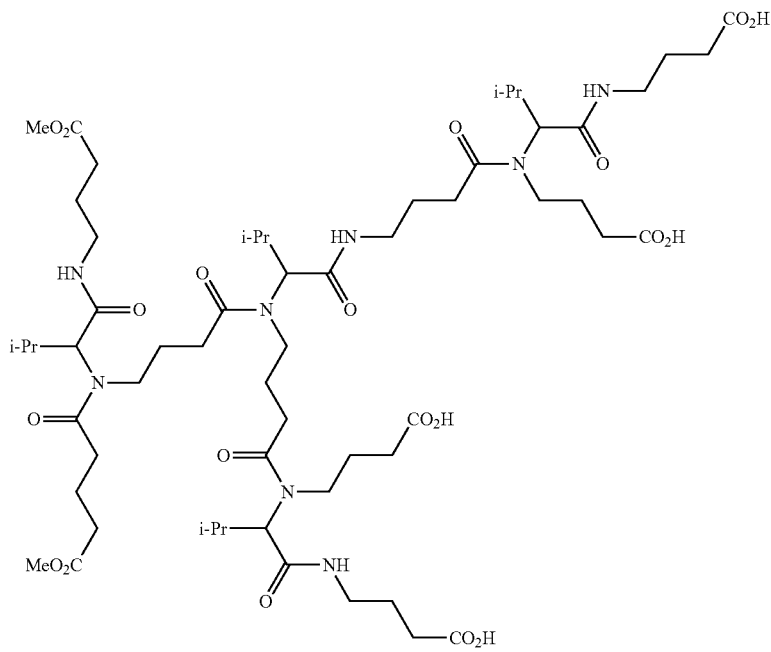 [SMILES: COC(=O)CCCNC(=O)C(C(C)C)N(CCCC(=O)N(CCCC(=O)N(CCCC(=O)O)C(C(=O)NCCCC(=O)O)C(C)C)C(C(=O)NCCCC(=O)N(CCCC(=O)O)C(C(=O)NCCCC(=O)O)C(C)C)C(C)C)C(=O)CCCC(=O)OC]

leaving the tetrabenzyl ester 112c (0.67 g, 0.42 mmol) yielded the tetracarboxylic acid 112 as colorless oil (0.48 g, 92%).

ESI-MS: $C_{59}H_{100}N_8O_{20}$ (M+Na$^+$=1264.1).

Lipophilic Janus Dendrimer (Protected) 116
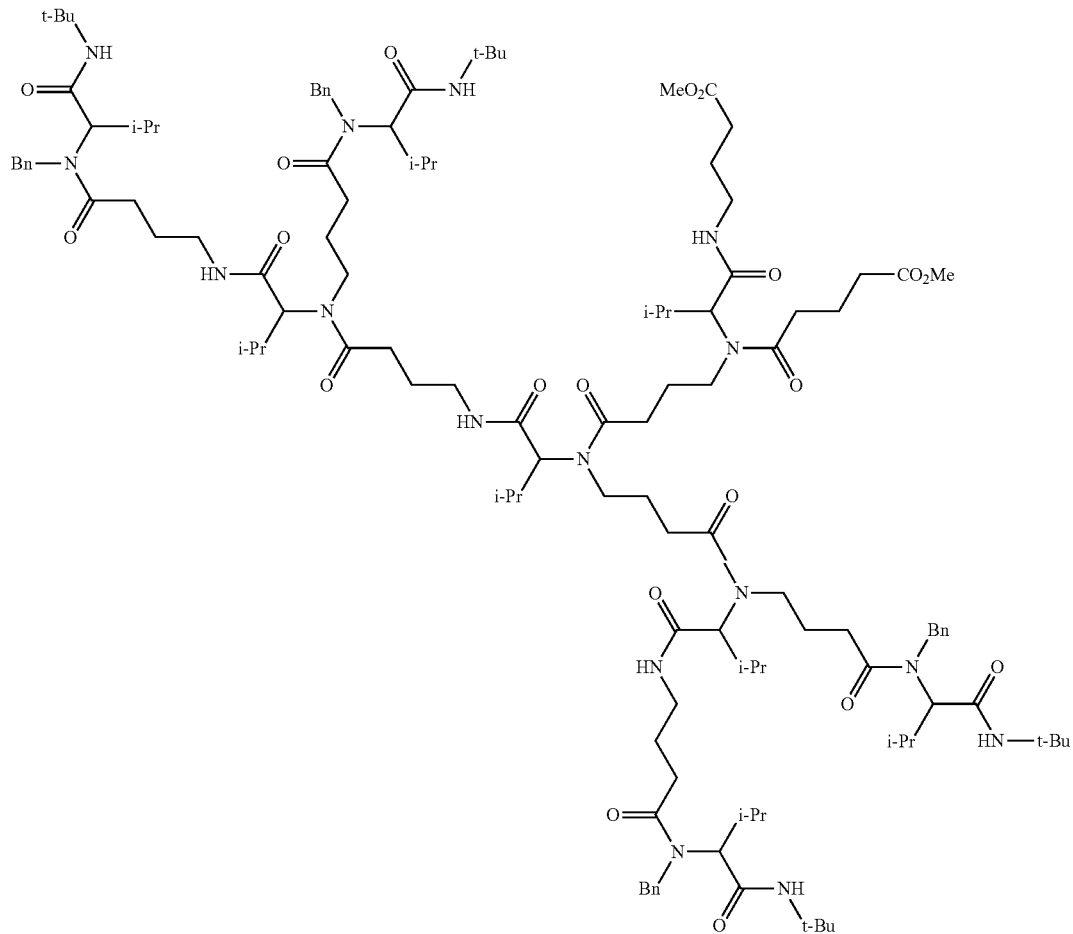 [SMILES: COC(=O)CCCNC(=O)C(C(C)C)N(CCCC(=O)N(CCCC(=O)N(CCCC(=O)N(Cc1ccccc1)C(C(=O)NC(C)(C)C)C(C)C)C(C(=O)NCCCC(=O)N(Cc1ccccc1)C(C(=O)NC(C)(C)C)C(C)C)C(C)C)C(C(=O)NCCCC(=O)N(CCCC(=O)N(Cc1ccccc1)C(C(=O)NC(C)(C)C)C(C)C)C(C(=O)NCCCC(=O)N(Cc1ccccc1)C(C(=O)NC(C)(C)C)C(C)C)C(C)C)C(C)C)C(=O)CCCC(=O)OC]
he fourfold Ugi-4CR of tetracarboxylic acid 112 (0.37 g, 0.30 mmol) with benzylamine (0.64 g, 6.00 mmol), isobutyraldehyde 4 (0.43 g, 6.00 mmol) and t-butylisonitrile (0.50 g, 6.00 mmol) yielded the dimethyl ester 116 after column-chromatographic purification (MeOH/EE, 1:40) as colorless oil (0.42 g, 63%).
ESI-MS: $C_{123}H_{196}N_{16}O_{20}$ (M+2Na$^{2+}$=1132.2).
Janus Dendrimer (Functionalized) 118a
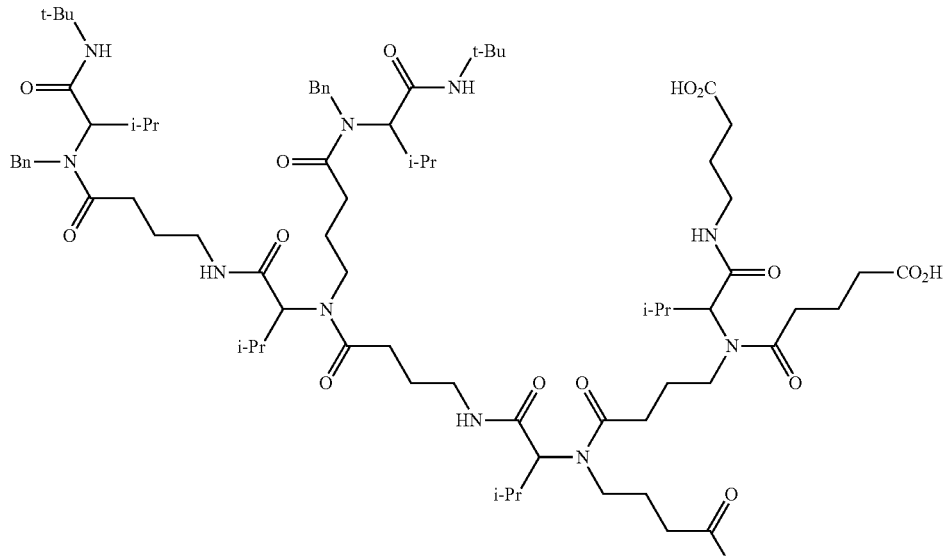

-continued
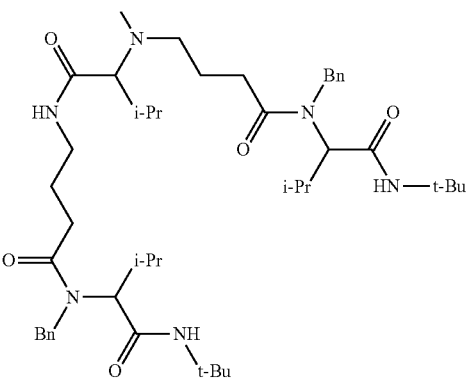
Saponifying the dimethyl ester 116 (0.42 g, 0.19 mmol) with lithium hydroxide monohydrate (0.04 g, 0.95 mmol) yielded the dicarboxylic acid 118a as colorless oil (0.41 g, 99%).
ESI: $C_{121}H_{192}N_{16}O_{20}$ (M+2Na$^{2+}$=1118.5).
Janus Dendrimer (Protected) 118b
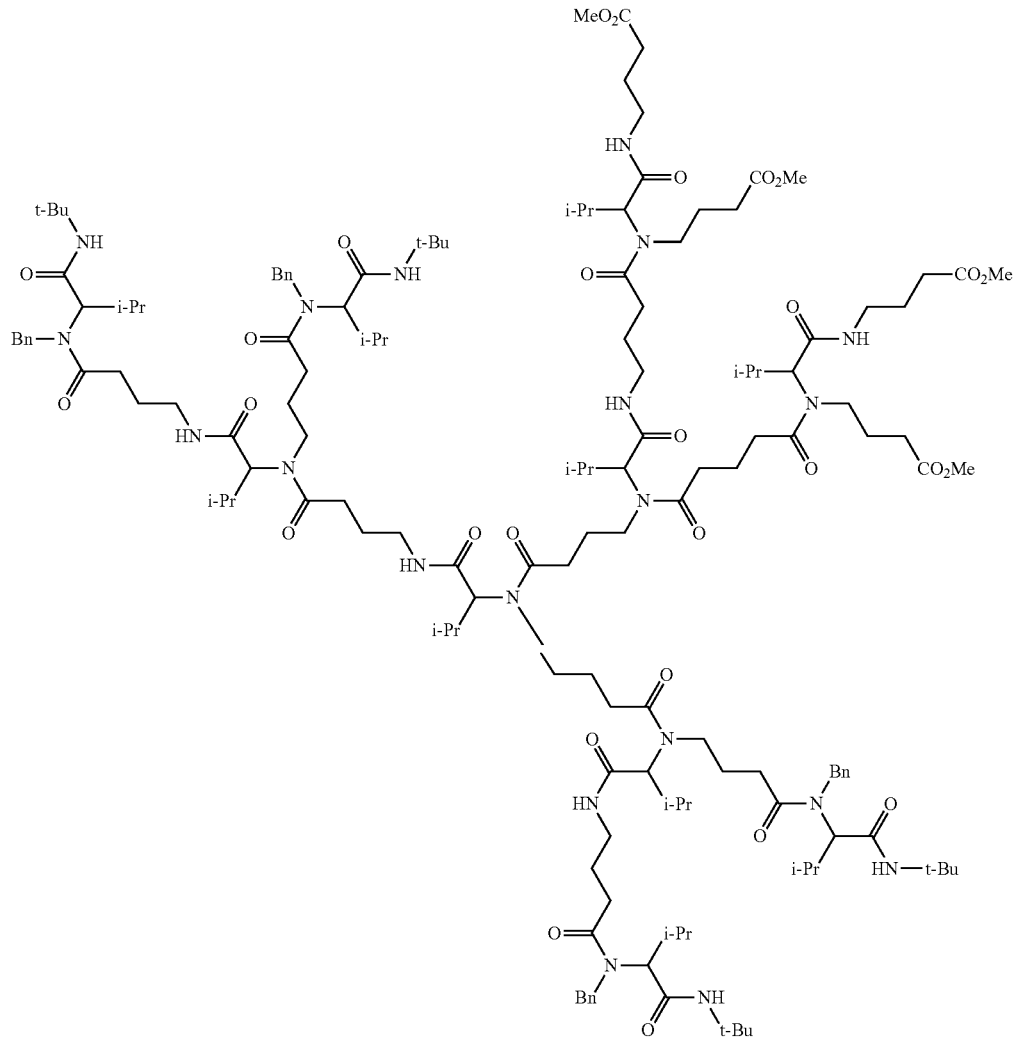 [SMILES: COC(=O)CCCNC(=O)C(C(C)C)N(CCCC(=O)OC)C(=O)CCCNC(=O)C(C(C)C)N(CCCC(=O)N(CCCC(=O)N(CCCC(=O)N(Cc1ccccc1)C(C(=O)NC(C)(C)C)C(C)C)C(C(=O)NCCCC(=O)N(Cc1ccccc1)C(C(=O)NC(C)(C)C)C(C)C)C(C)C)C(C(=O)NCCCC(=O)N(CCCC(=O)N(Cc1ccccc1)C(C(=O)NC(C)(C)C)C(C)C)C(C(=O)NCCCC(=O)N(Cc1ccccc1)C(C(=O)NC(C)(C)C)C(C)C)C(C)C)C(C)C)C(=O)CCCC(=O)N(CCCC(=O)OC)C(C(=O)NCCCC(=O)OC)C(C)C]

The twofold Ugi-4CR of dicarboxylic acid 118a (0.41 g, 0.19 mmol) with methyl 4-aminobutyrate hydrochloride (0.09 g, 0.56 mmol), isobutyraldehyde 4 (0.04 g, 0.56 mmol), methyl 4-isocyanobutyrate 3 (0.07 g, 0.56 mmol) and triethylamine (0.06 g, 0.56 mmol) yielded the tetramethyl ester 118b after column-chromatographic purification (MeOH/EE, 1:40) as colorless oil (0.22 g, 71%).

ESI-MS: $C_{151}H_{244}N_{20}O_{28}$ (M+2Na$^{2+}$=1415.9).

Janus Dendrimer (Functionalized) 118

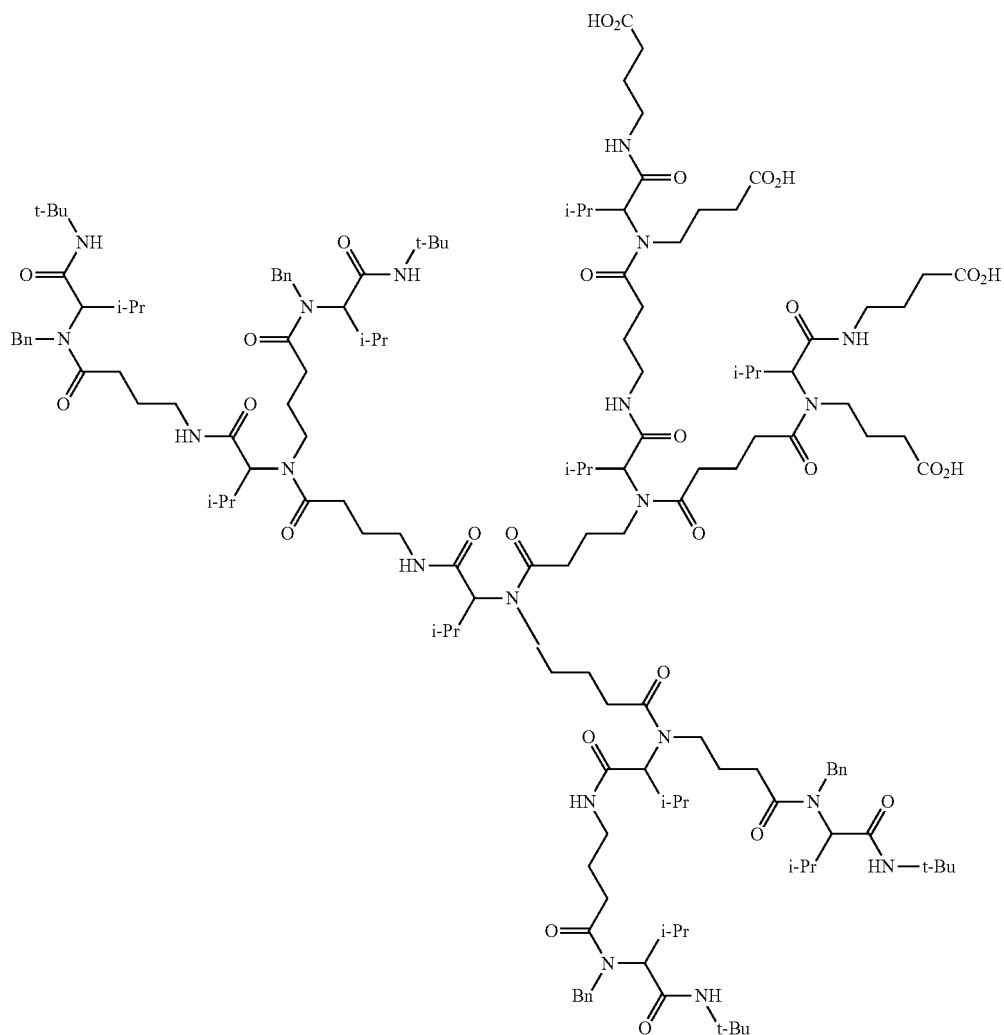 [SMILES: CC(C)C(C(=O)NCCCC(=O)O)N(CCCC(=O)O)C(=O)CCCNC(=O)C(C(C)C)N(CCCC(=O)N(CCCC(=O)N(CCCC(=O)N(Cc1ccccc1)C(C(=O)NC(C)(C)C)C(C)C)C(C(=O)NCCCC(=O)N(Cc1ccccc1)C(C(=O)NC(C)(C)C)C(C)C)C(C)C)C(C(=O)NCCCC(=O)N(CCCC(=O)N(Cc1ccccc1)C(C(=O)NC(C)(C)C)C(C)C)C(C(=O)NCCCC(=O)N(Cc1ccccc1)C(C(=O)NC(C)(C)C)C(C)C)C(C)C)C(C)C)C(=O)CCCC(=O)N(CCCC(=O)O)C(C(=O)NCCCC(=O)O)C(C)C]

Saponifying the tetramethyl ester 118b (0.1 g, 0.04 mmol) with lithium hydroxide monohydrate (0.02 g, 0.38 mmol) yielded the tetracarboxylic acid 118 as colorless oil (0.09 g, 91%). ESI-MS: $C_{147}H_{236}N_{20}O_{28}$ (M+2Na$^{2+}$=1388.5).

Janus Dendrimer (122)

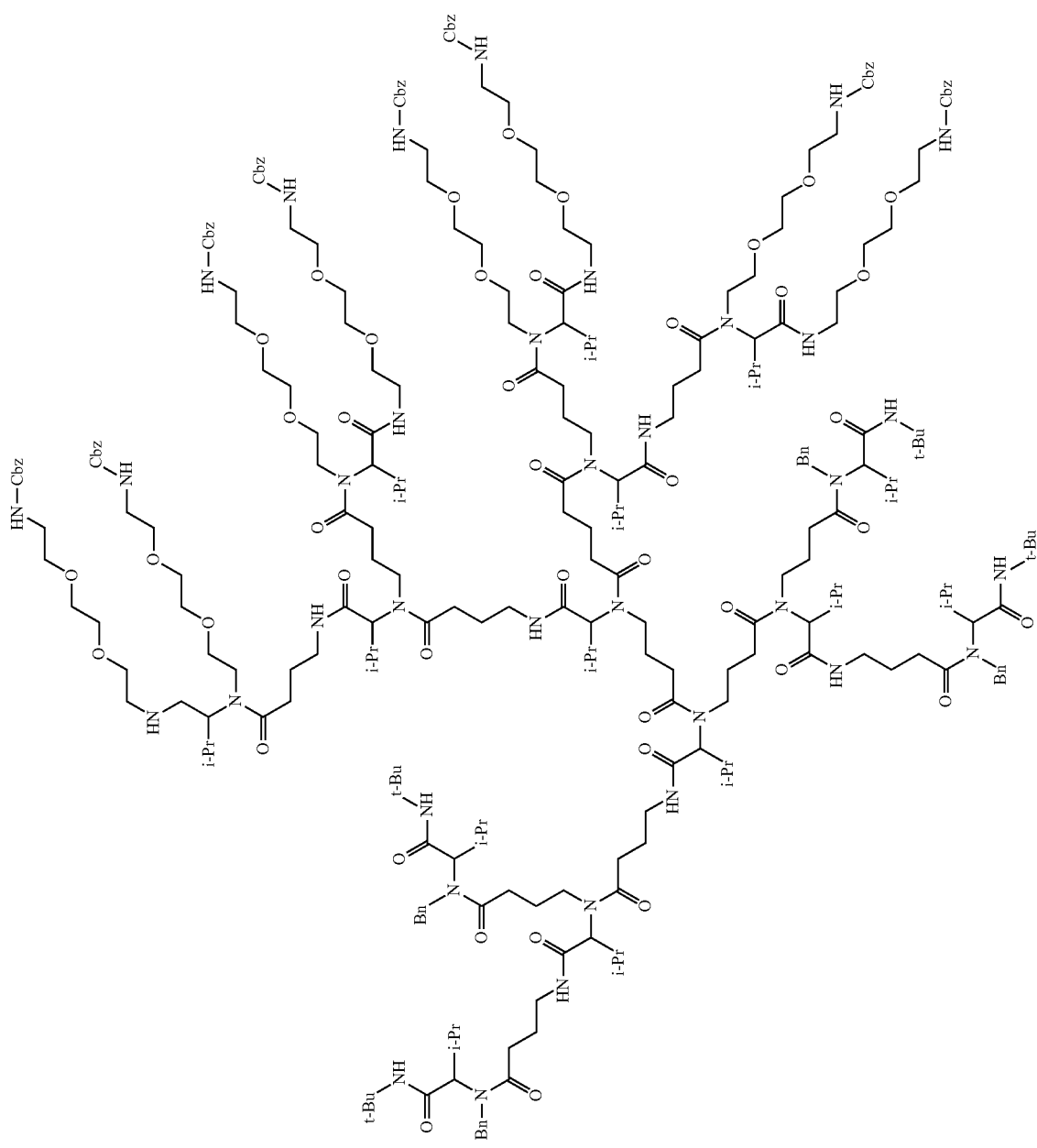

The fourfold Ugi-4CR of tetracarboxylic acid 118 (0.09 g, 0.03 mmol) with benzyl {2-[2-(2-aminoethoxy)-ethoxy]ethyl}carbamate 47 (0.08 g, 0.27 mmol), isobutyraldehyde 4 (0.02 g, 0.27 mmol) and benzyl {2-[2-(2-isocyanoethoxy)ethoxy]ethyl}carbamate 121 (0.08 g, 0.27 mmol) yielded the janus dendrimer 122 after column-chromatographic purification (MeOH/EE, 1:20) as colorless oil (0.12 g, 66%). ESI-MS: $C_{279}H_{428}N_{36}O_{60}$ (M+3Na$^{3+}$=1771.5)

Janus Dendrimer (Protected) 117

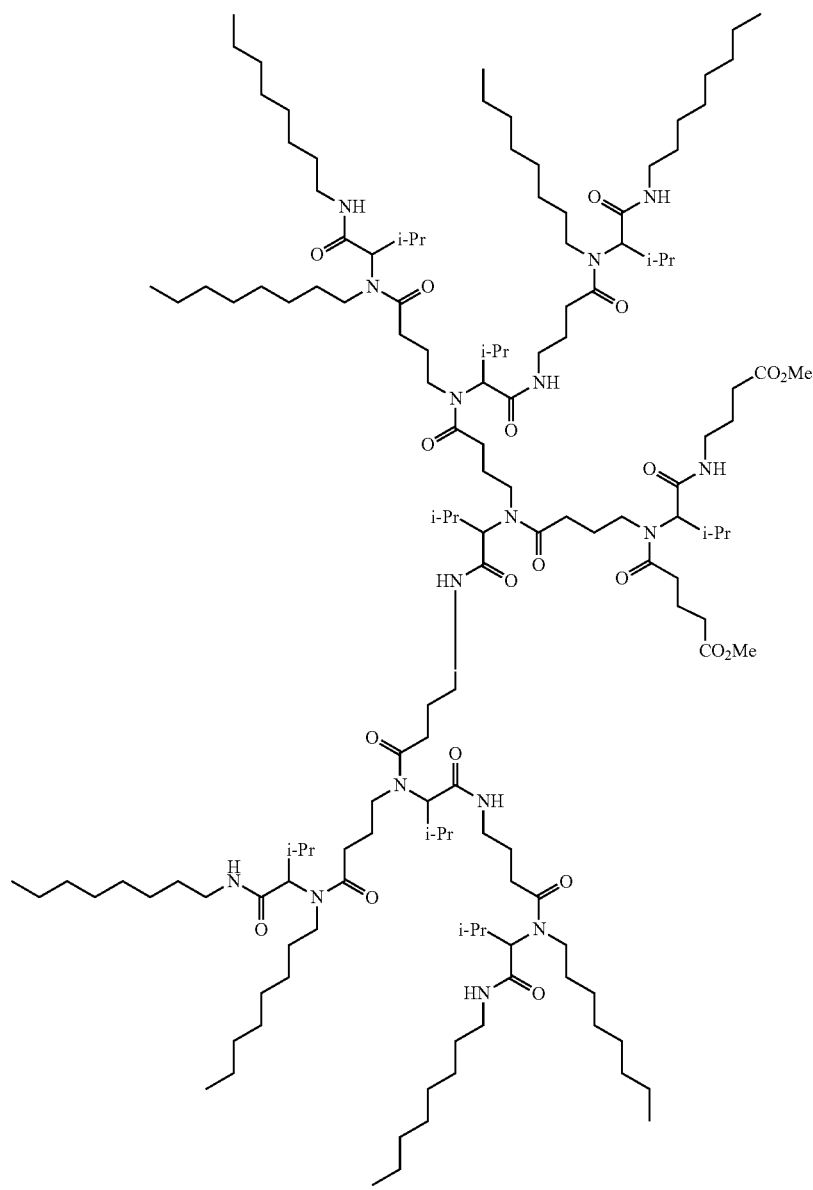 [SMILES: CCCCCCCCNC(=O)C(C(C)C)N(CCCCCCCC)C(=O)CCCNC(=O)C(C(C)C)N(CCCC(=O)N(CCCCCCCC)C(C(=O)NCCCCCCCC)C(C)C)C(=O)CCCNC(=O)C(C(C)C)N(CCCC(=O)N(CCCC(=O)N(CCCCCCCC)C(C(=O)NCCCCCCCC)C(C)C)C(C(=O)NCCCC(=O)N(CCCCCCCC)C(C(=O)NCCCCCCCC)C(C)C)C(C)C)C(=O)CCCN(C(=O)CCCC(=O)OC)C(C(=O)NCCCC(=O)OC)C(C)C]

The fourfold Ugi-4CR of tetracarboxylic acid 112 (0.20 g, 0.16 mmol) with n-octylamine (0.13 g, 0.97 mmol), isobutyraldehyde 4 (0.07 g, 0.97 mmol) and n-octylisonitrile (0.14 g, 0.97 mmol) yielded the dimethyl ester 117 after column-chromatographic purification (MeOH/EE, 1:20) as colorless oil (0.35 g, 86%).

ESI-MS: $C_{143}H_{268}N_{16}O_{20}$ (M+2Na$^{2+}$=1289.1).

Janus Dendrimer (Functionalized) 119a
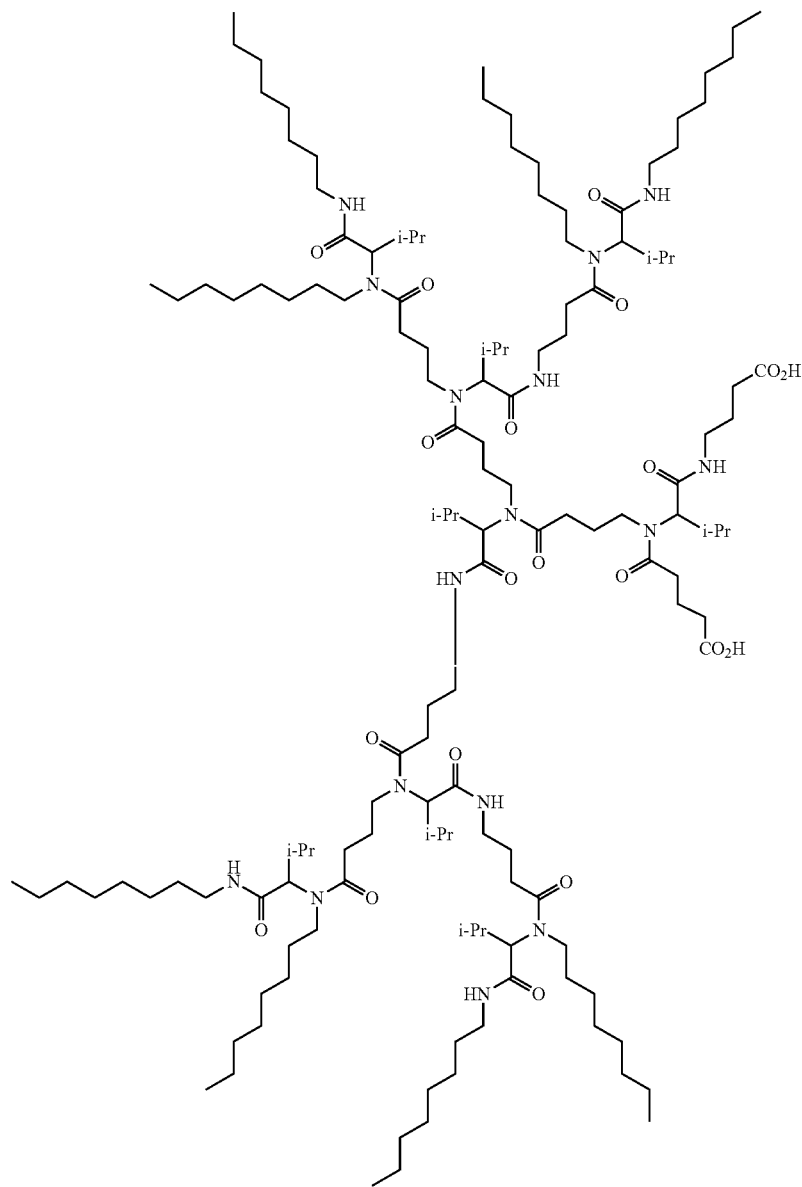 [SMILES: CCCCCCCCNC(=O)C(C(C)C)N(CCCCCCCC)C(=O)CCCNC(=O)C(C(C)C)N(CCCC(=O)N(CCCCCCCC)C(C(=O)NCCCCCCCC)C(C)C)C(=O)CCCNC(=O)C(C(C)C)N(CCCC(=O)N(CCCC(=O)N(CCCCCCCC)C(C(=O)NCCCCCCCC)C(C)C)C(C(=O)NCCCC(=O)N(CCCCCCCC)C(C(=O)NCCCCCCCC)C(C)C)C(C)C)C(=O)CCCN(C(=O)CCCC(=O)O)C(C(=O)NCCCC(=O)O)C(C)C]
Saponifying the tetramethyl ester 117 (0.31 g, 0.12 mmol) with lithium hydroxide monohydrate (0.03 g, 0.62 mmol) yielded the dicarboxylic acid 119a as colorless oil (0.31 g, 98%). ESI-MS: $C_{141}H_{264}N_{16}O_{20}$ (M−2H$^{2-}$=1251.0).

Janus Dendrimer (Protected) 119b
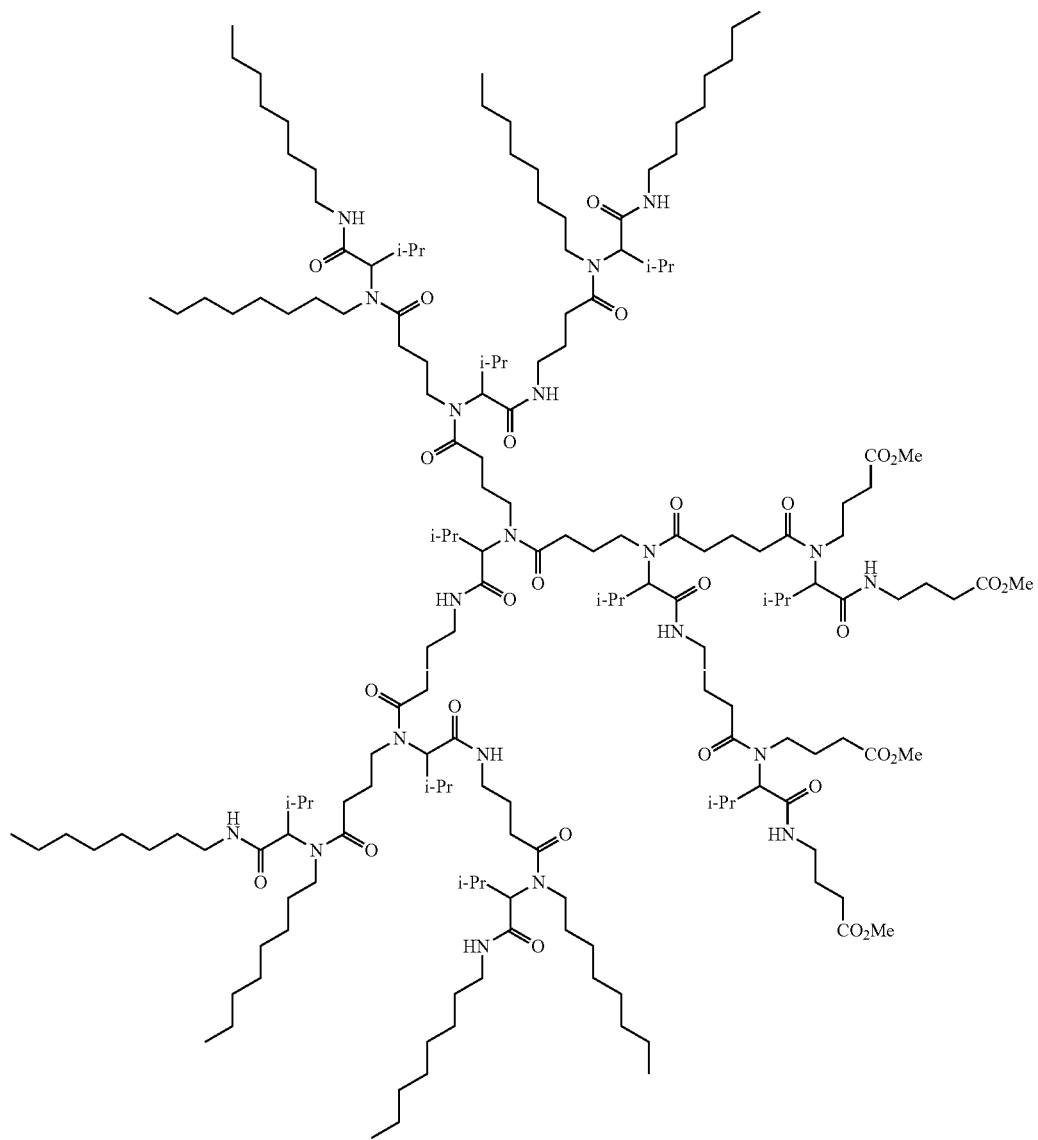 [SMILES: CCCCCCCCNC(=O)C(C(C)C)N(CCCCCCCC)C(=O)CCCNC(=O)C(C(C)C)N(CCCC(=O)N(CCCCCCCC)C(C(=O)NCCCCCCCC)C(C)C)C(=O)CCCNC(=O)C(C(C)C)N(CCCC(=O)N(CCCC(=O)N(CCCCCCCC)C(C(=O)NCCCCCCCC)C(C)C)C(C(=O)NCCCC(=O)N(CCCCCCCC)C(C(=O)NCCCCCCCC)C(C)C)C(C)C)C(=O)CCCN(C(=O)CCCC(=O)N(CCCC(=O)OC)C(C(=O)NCCCC(=O)OC)C(C)C)C(C(=O)NCCCC(=O)N(CCCC(=O)OC)C(C(=O)NCCCC(=O)OC)C(C)C)C(C)C]
The twofold Ugi-4CR of dicarboxylic acid 119a (0.26 g, 0.10 mmol) with methyl 4-aminobutyrate hydrochloride (0.05 g, 0.31 mmol), isobutyraldehyde 4 (0.02 g, 0.31 mmol), methyl 4-isocyanobutyrate 3 (0.04 g, 0.31 mmol) and triethylamine (0.03 g, 0.31 mmol) yielded the tetramethyl ester 119b after column-chromatographic purification (MeOH/EE, 1:20) as colorless oil (0.23 g, 70%).
ESI-MS: $C_{171}H_{316}N_{20}O_{28}$ (M+2Na$^{2+}$=1573.4).

Janus Dendrimer (Functionalized) 119
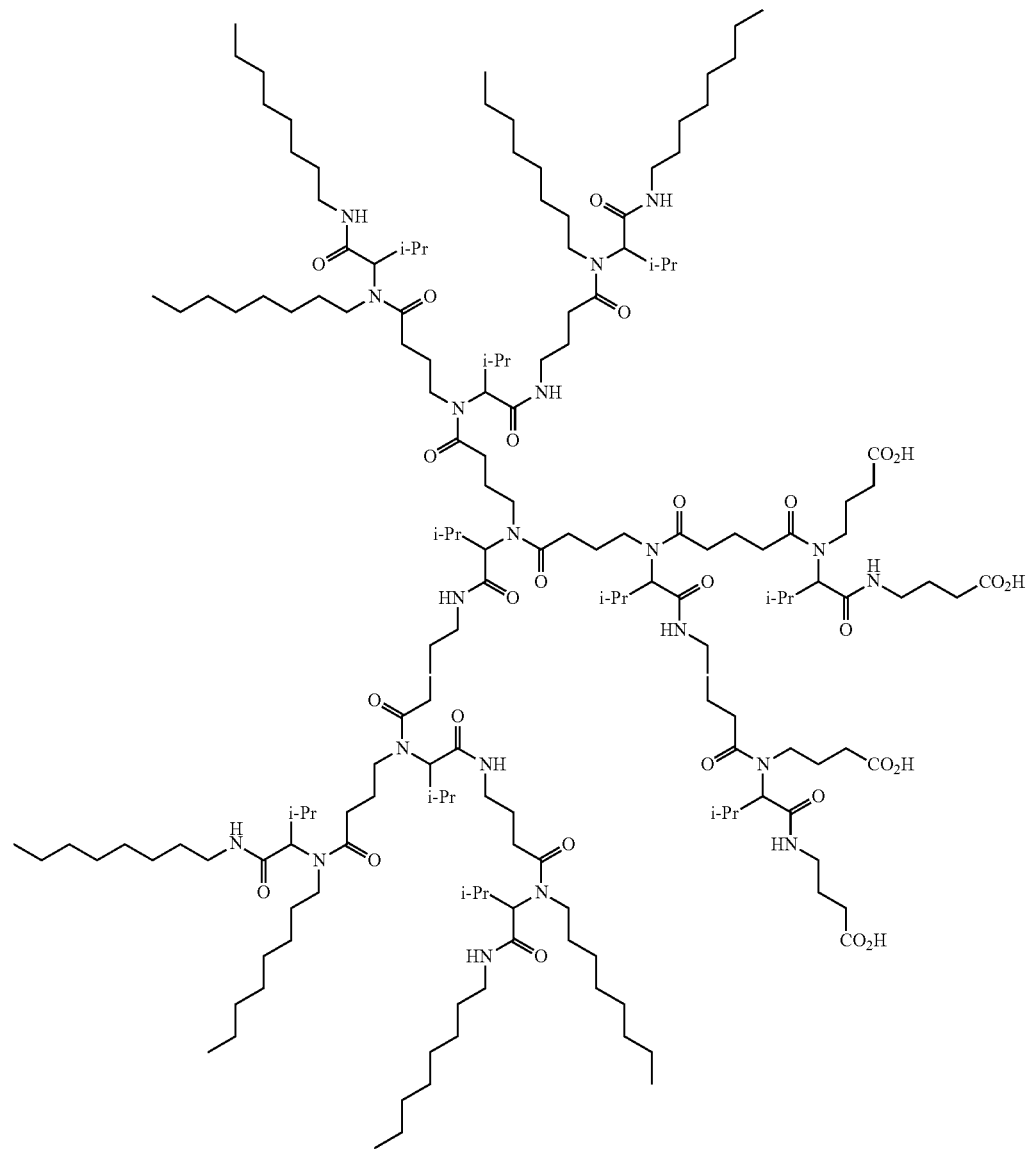 [SMILES: CCCCCCCCNC(=O)C(C(C)C)N(CCCCCCCC)C(=O)CCCNC(=O)C(C(C)C)N(CCCC(=O)N(CCCCCCCC)C(C(=O)NCCCCCCCC)C(C)C)C(=O)CCCNC(=O)C(C(C)C)N(CCCC(=O)N(CCCC(=O)N(CCCCCCCC)C(C(=O)NCCCCCCCC)C(C)C)C(C(=O)NCCCC(=O)N(CCCCCCCC)C(C(=O)NCCCCCCCC)C(C)C)C(C)C)C(=O)CCCN(C(=O)CCCC(=O)N(CCCC(=O)O)C(C(=O)NCCCC(=O)O)C(C)C)C(C(=O)NCCCC(=O)N(CCCC(=O)O)C(C(=O)NCCCC(=O)O)C(C)C)C(C)C]
Saponifying the tetramethyl ester 119b (0.22 g, 0.07 mmol) with lithium hydroxide monohydrate (0.03 g, 0.71 mmol) yielded the tetracarboxylic acid 119 as yellow oil (0.21 g, 98%).
ESI-MS: $C_{167}H_{308}N_{20}O_{28}$ ($M+2Na^{2+}=1545.7$)
Janus Dendrimer (123)

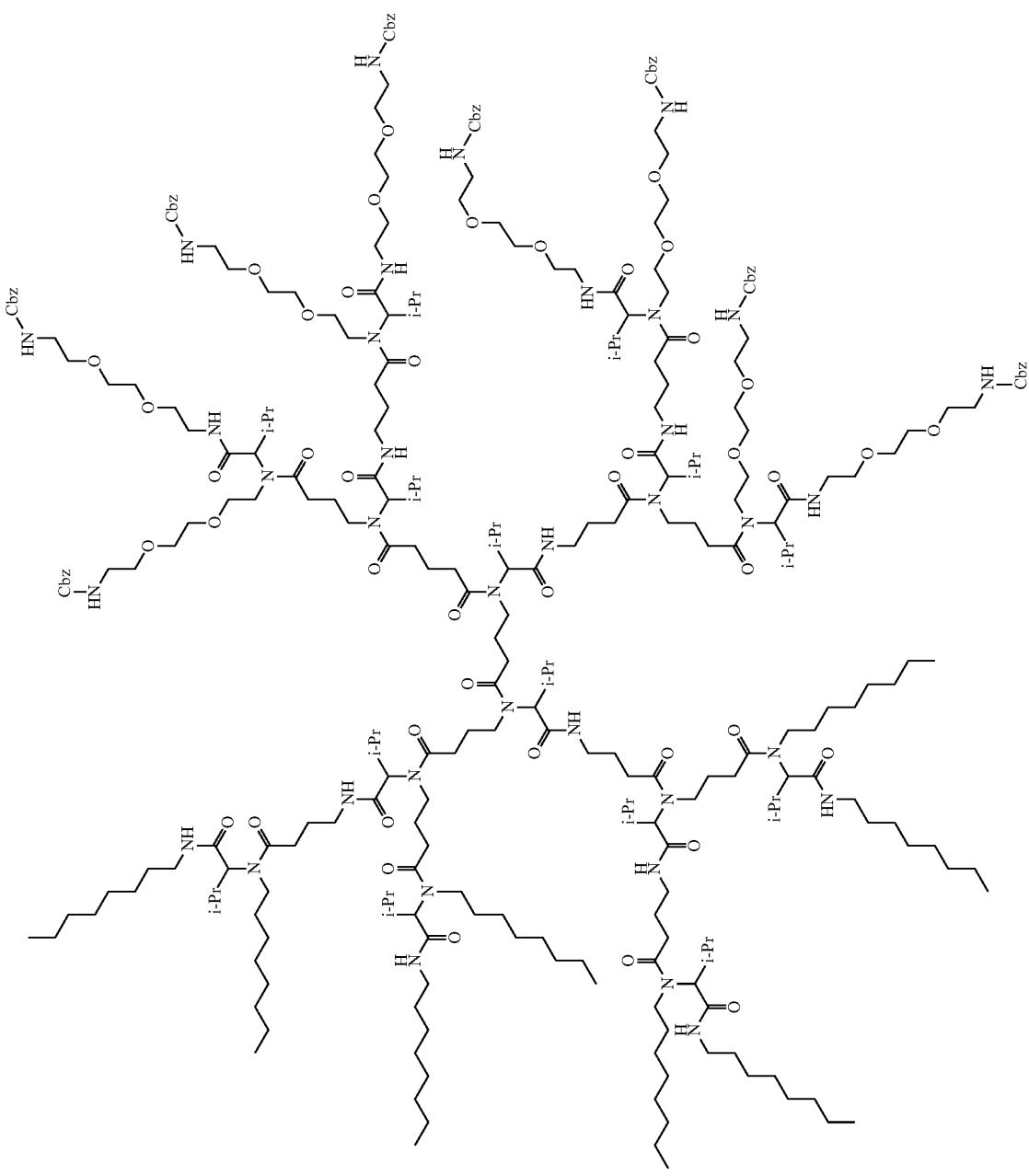

The fourfold Ugi-4CR of tetracarboxylic acid 119 (0.10 g, 0.03 mmol) with benzyl {2-[2-(2-aminoethoxy)-ethoxy]ethyl}carbamate 47 (0.06 g, 0.20 mmol), isobutyraldehyde 4 (0.01 g, 0.20 mmol) and benzyl {2-[2-(2-isocyanoethoxy)ethoxy]ethyl}carbamate 121 (0.06 g, 0.20 mmol) yielded the Janus dendrimer 123 after column-chromatographic purification (MeOH/EE, 1:5) as yellow oil (0.15 g, 82%). ESI-MS: $C_{299}H_{500}N_{36}O_{60}$ (M+3Na$^{3+}$=1876.0).

Dendrimers (127), (128), (129), (130) and (131) Synthesized by Multiple Passerini 3-Component Reaction

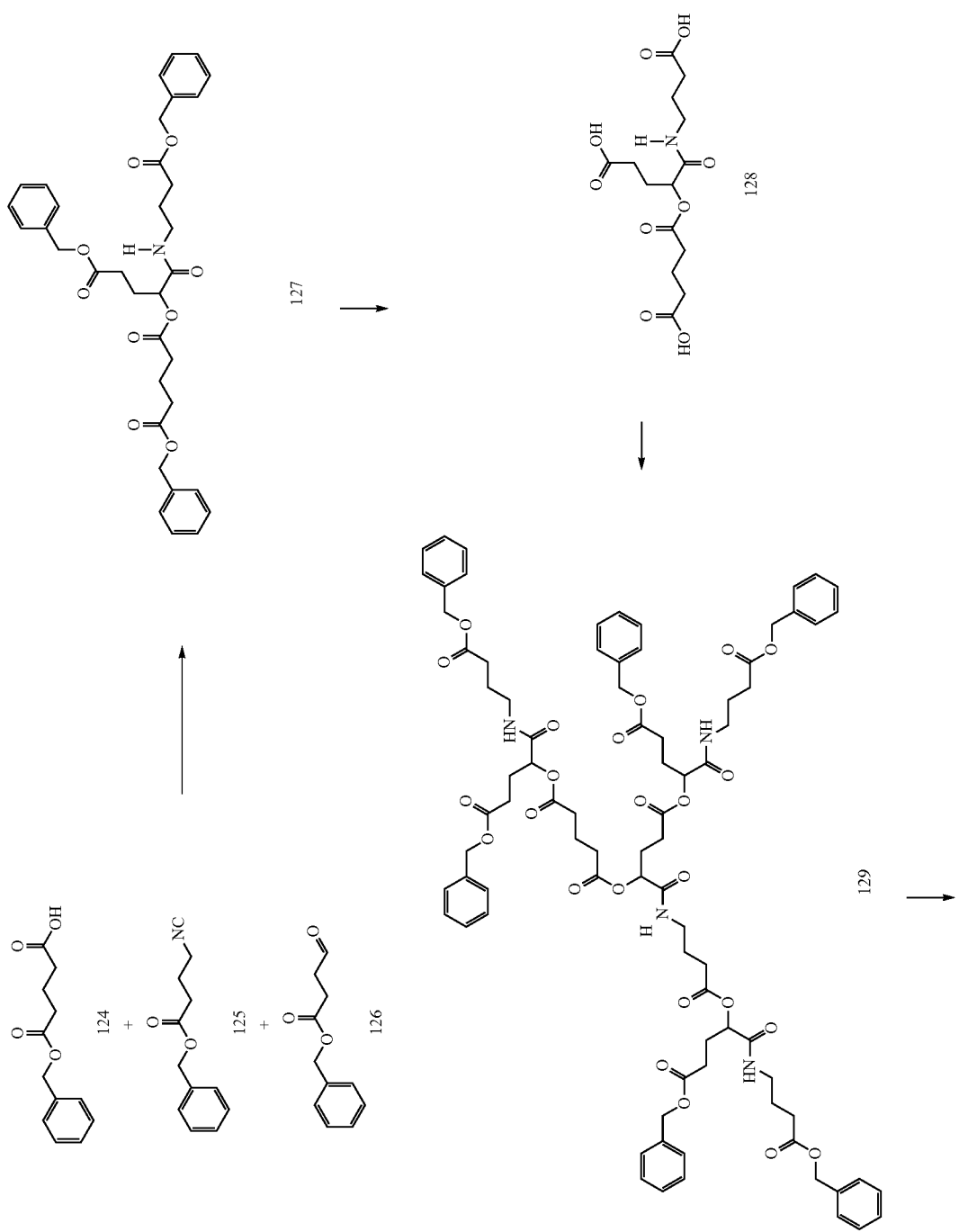

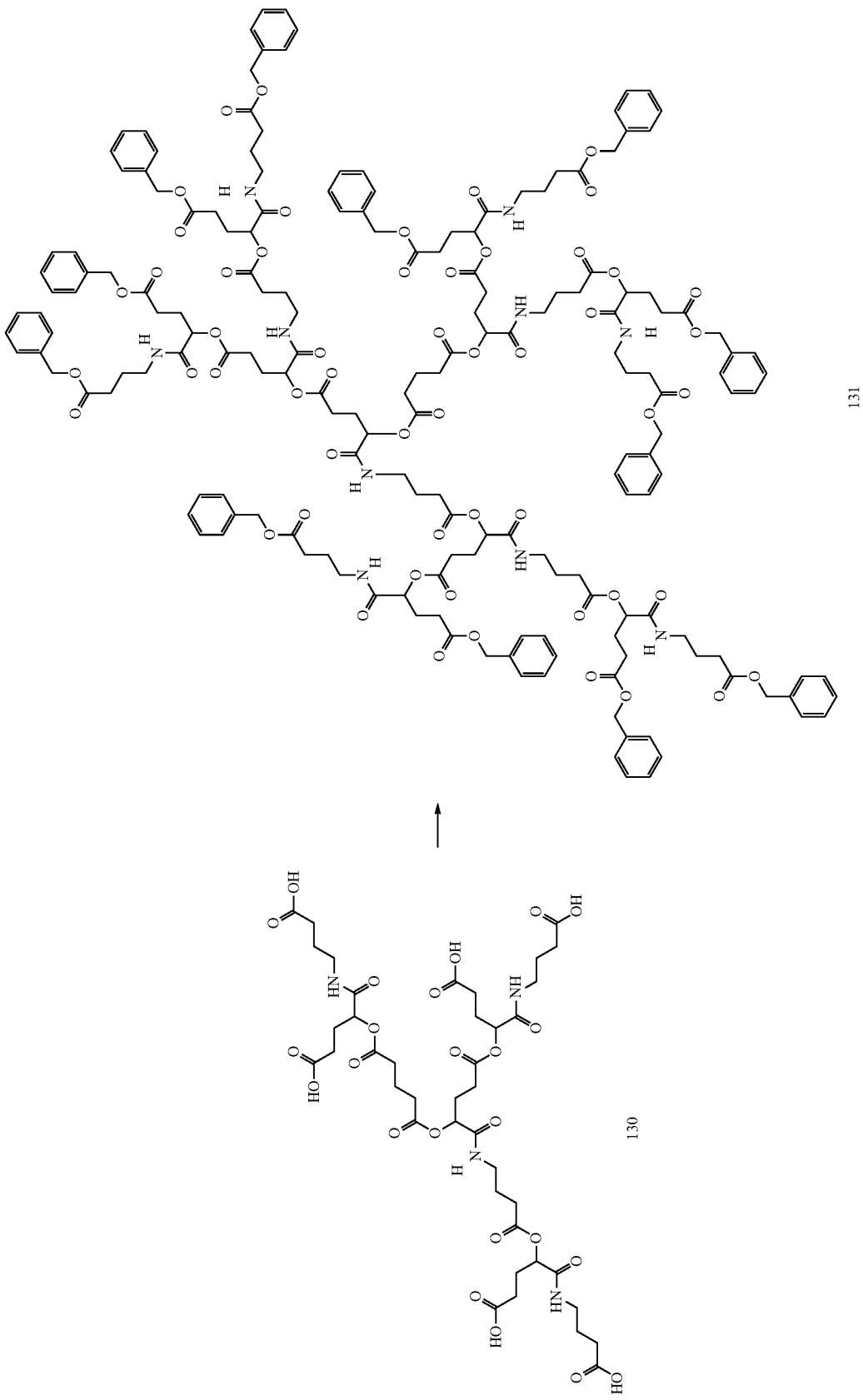

Passerini 1st generation dendrimer—benzyl ester-protected 127 (benzyl 5-(benzyloxy)-1-(4-(benzyloxy)-4-oxobutylamino)-1,5-dioxopentan-2-ylglutarate)

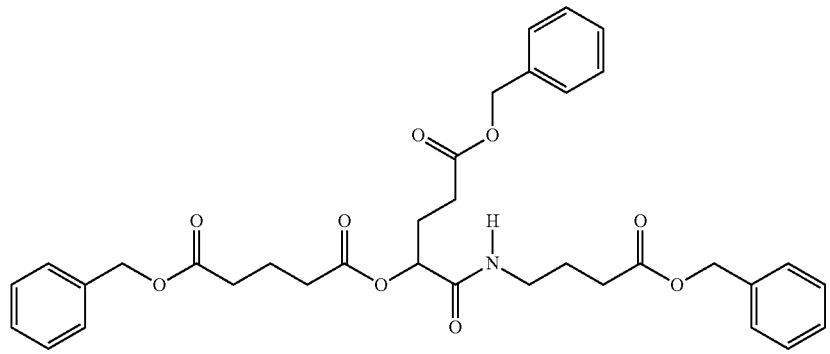 [SMILES: O=C(CCCNC(=O)C(CCC(=O)OCc1ccccc1)OC(=O)CCCC(=O)OCc1ccccc1)OCc1ccccc1]

Benzyl 4-isocyanobutyrate 125 (0.41 g, 2.00 mmol), benzyl 4-oxobutyrate 126 (0.38 g, 2.00 mmol), prepared as described by Ghosez et al. (Tetrahedron, 60, 2004, 7591) and 5-(benzyloxy)-5-oxopentanoic acid 124 (0.44 g, 2.00 mmol), prepared as described by Li et al. (JACS, 117, 1995, 2123), are dissolved in $CH_2Cl_2$ followed by stirring at room temperature for 24 hours. The solvent is removed in a rotary evaporator and the residue purified by column chromatography (hexane:ethyl acetate, 2:1). The product is obtained as yellow oil (0.99 g, 80%). ESI-MS $CH_{35}H_{39}NO_9$ ($M+H^+$=618.13; $M+Na^+$=640.3); HRMS $C_{35}H_{39}NO_9$ $[M+Na]^+$ calc. 640.2523, obs. 640.2517.

Passerini 1st generation dendrimer—carboxylic acid-functionalized 128 (5-(benzyloxy)-1-(4-(benzyloxy)-4-oxobutylamino)-1,5-dioxopentan-2-yl 9,22-bis(3-(benzyloxy)-3-oxopropyl)-3,8,11,16,20,23,28-heptaoxo-1,30-diphenyl-2,10,21,29-tetraoxa-7,15,24-triazatriacontan-17-ylglutarate)

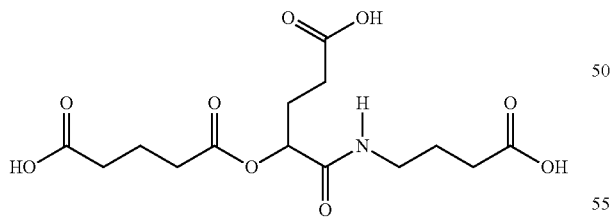

Dendrimer 127 (0.56 g, 1.60 mmol) is dissolved in THF (40 mL). A catalytic amount of $Pd(OH)_2/C$ (50 mg) is added and the reaction solution is stirred at room temperature overnight. The reaction solution is filtered through Celite® and the filtrate is concentrated in a rotary evaporator to obtain the product as colorless oil with a yield of 95%. ESI-MS $C_{14}H_{21}NO_9$ ($M+Na^+$=369.8, $M-H^+$=346.0); HRMS $C_{14}H_{21}NO_9$ $[M+Na]^+$ calc. 370.1114; obs. 370.1109.

Passerini 2nd generation dendrimer—benzyl ester-protected 129 (5-(benzyloxy)-1-(4-(benzyloxy)-4-oxobutylamino)-1,5-dioxopentan-2-yl 9,22-bis(3-(benzyloxy)-3-oxopropyl)-3,8,11,16,20,23,28-heptaoxo-1,30-diphenyl-2,10,21,29-tetraoxa-7,15,24-triaza-tricontan-17-ylglutarate)

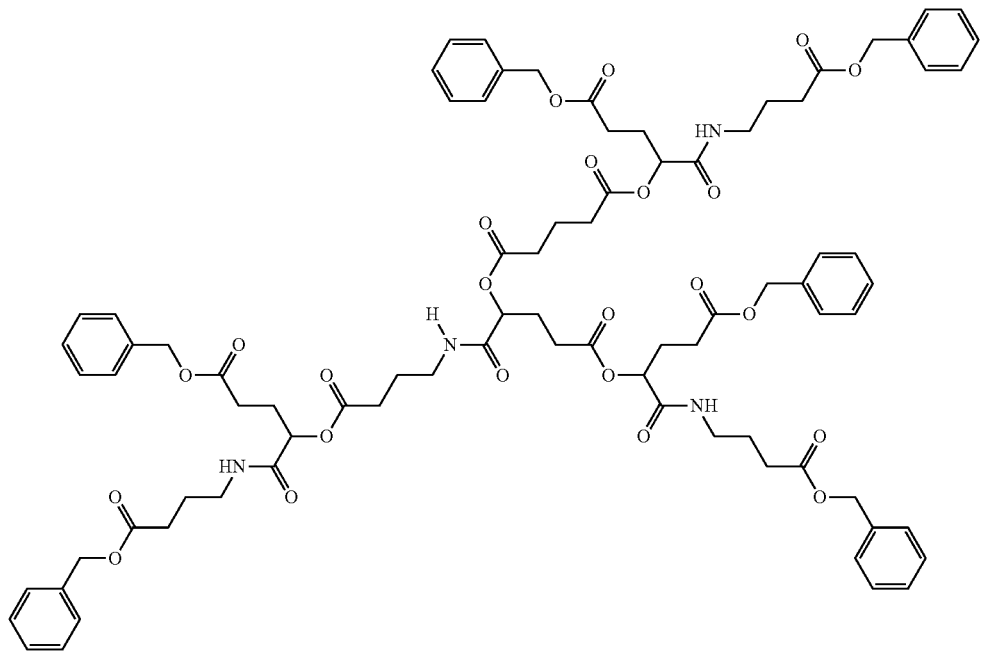 [SMILES: O=C(CCCNC(=O)C(CCC(=O)OCc1ccccc1)OC(=O)CCCNC(=O)C(CCC(=O)OC(CCC(=O)OCc1ccccc1)C(=O)NCCCC(=O)OCc1ccccc1)OC(=O)CCCC(=O)OC(CCC(=O)OCc1ccccc1)C(=O)NCCCC(=O)OCc1ccccc1)OCc1ccccc1]

Benzyl 4-isocyanobutyrate 125 (1.16 g, 5.70 mmol), benzyl 4-oxobutyrate 126 (1.03 g, 5.70 mmol), and 128 (0.44 g, 2.00 mmol) are dissolved in $CH_2Cl_2$ followed by stirring at room temperature for 24 hours. The solvent is removed in a rotary evaporator and the residue purified by column chromatography (hexane:ethyl acetate, 1:1) to obtain the product as yellow oil (1.73 g, 72%). ESI-MS $C_{83}H_{96}N_4O_{24}$ (M+Na$^+$=1556.2); HRMS $C_{83}H_{96}N_4O_{24}$ [M+Na]$^+$ calc. 1555.6312, obs. 1555.6307.

Passerini 2nd generation dendrimer—carboxylic acid-functionalized 130 (15-(3-(4-carboxy-1-(3-carboxy-propylamino)-1-oxobutan-2-yloxy)-3-oxopropyl)-7,23-bis(2-carboxyethyl)-6,9,14,17,21,24-hexaoxo-8,16,22-trioxa-5,13,25-triazanonacosane-1,29-dioic acid)

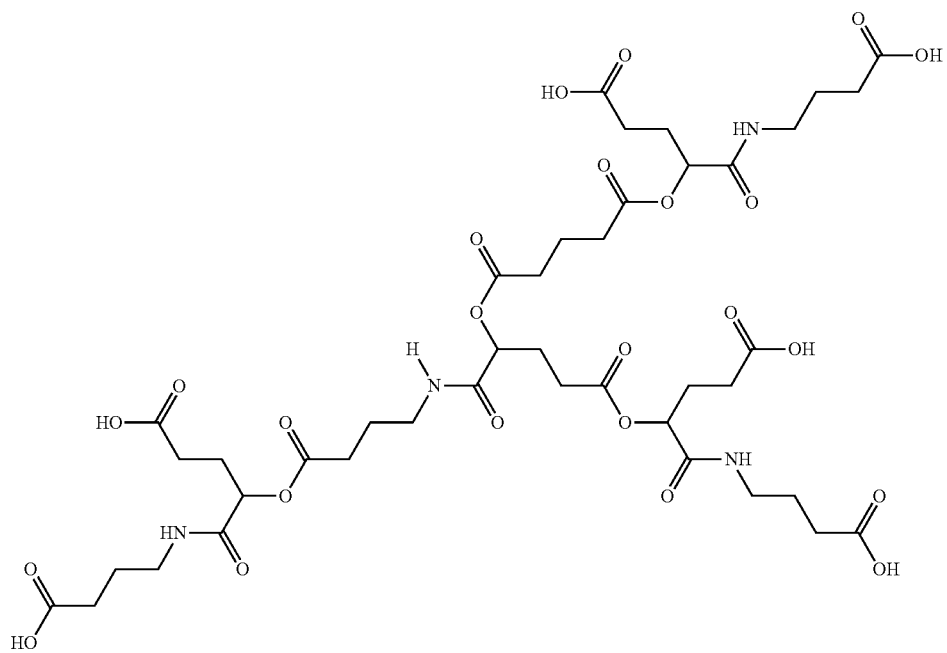 [SMILES: O=C(O)CCCNC(=O)C(CCC(=O)O)OC(=O)CCCNC(=O)C(CCC(=O)OC(CCC(=O)O)C(=O)NCCCC(=O)O)OC(=O)CCCC(=O)OC(CCC(=O)O)C(=O)NCCCC(=O)O]

Dendrimer 129 (1.09 g, 1.10 mmol) is dissolved in THF (40 mL). A catalytic amount of Pd(OH)$_2$/C (50 mg) is added and the reaction solution is stirred at room temperature overnight. The reaction solution is filtered through Celite® and the filtrate is concentrated in a rotary evaporator to obtain the product as colorless oil with a yield of 95%. ESI-MS $C_{41}H_{60}N_4O_{24}$ (M−H$^+$=991.5); HRMS of $C_{41}H_{60}N_4O_{24}$ [M−H]$^+$ calc. 991.3519, obs. 991.3524.

Passerini 3rd generation dendrimer—benzyl ester-protected 131 (17,30-bis(3-(5-(benzyloxy)-1-(4-(benzyloxy)-4-oxobutylamino)-1,5-dioxopentan-2-yloxy)-3-oxopropyl)-9,38-bis(3-(benzyloxy)-3-oxopropyl)-3,8,11,16,19,24,28,31,36,39,44-undecaoxo-1,46-diphenyl-2,10,18,29,37,45-hexaoxa-7,15,23,32,40-pentaazahexa-tetracontan-25-yl 9,22-bis(3-(benzyloxy)-3-oxopropyl)-3,8,11,16,20,23,28-heptaoxo-1,30-diphenyl-2,10,21,29-tetraoxa-7,15,24-triazatriacontan-17-ylglutarate)

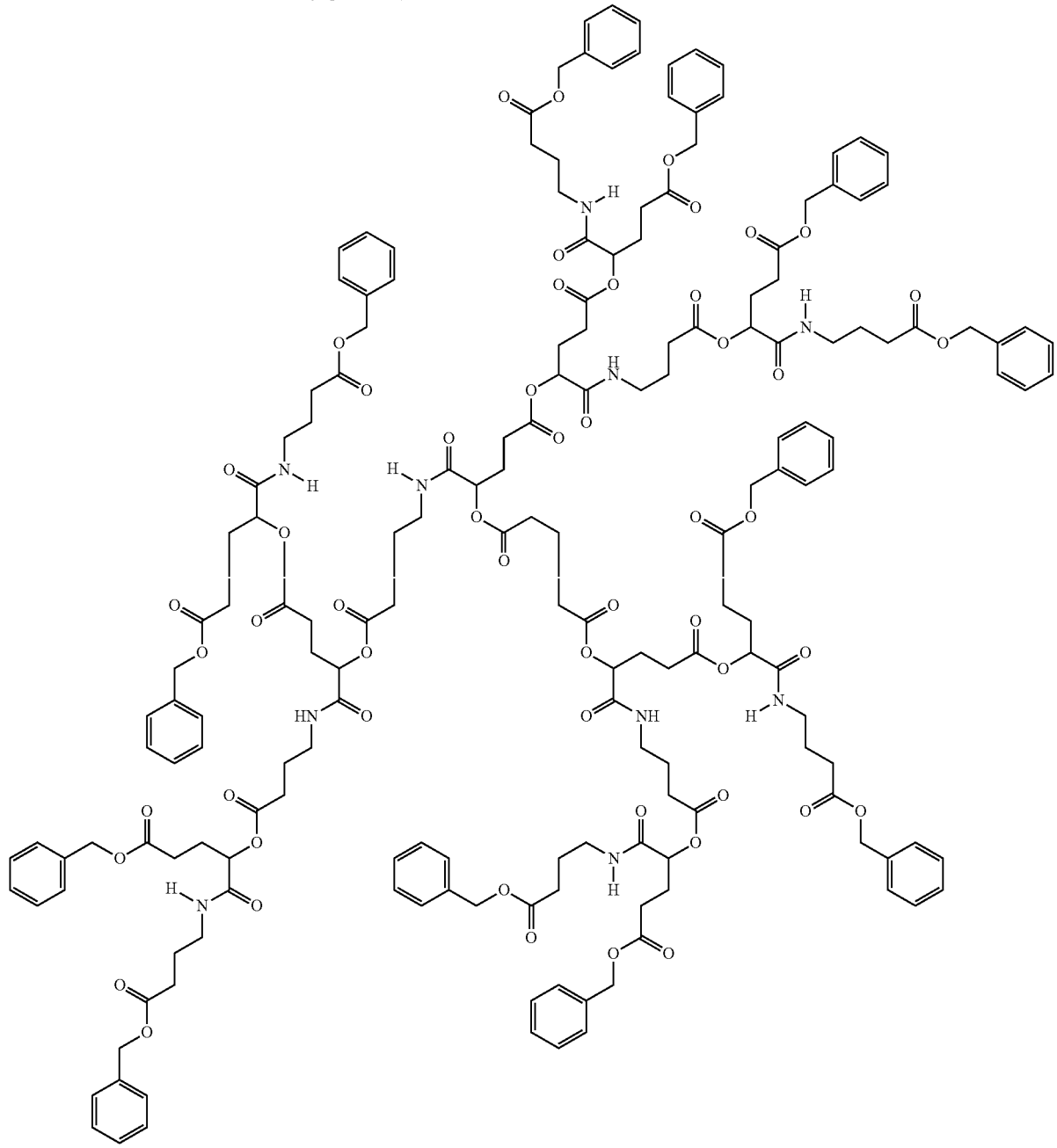 [SMILES: O=C(CCCNC(=O)C(CCC(=O)OCc1ccccc1)OC(=O)CCCNC(=O)C(CCC(=O)OC(CCC(=O)OCc1ccccc1)C(=O)NCCCC(=O)OCc1ccccc1)OC(=O)CCCNC(=O)C(CCC(=O)OC(CCC(=O)OC(CCC(=O)OCc1ccccc1)C(=O)NCCCC(=O)OCc1ccccc1)C(=O)NCCCC(=O)OC(CCC(=O)OCc1ccccc1)C(=O)NCCCC(=O)OCc1ccccc1)OC(=O)CCCC(=O)OC(CCC(=O)OC(CCC(=O)OCc1ccccc1)C(=O)NCCCC(=O)OCc1ccccc1)C(=O)NCCCC(=O)OC(CCC(=O)OCc1ccccc1)C(=O)NCCCC(=O)OCc1ccccc1)OCc1ccccc1]

Benzyl 4-isocyanobutyrate 125 (0.73 g, 3.60 mmol), benzyl 4-oxobutyrate 126 (0.69 g, 3.60 mmol), and 129 (0.50 g, 0.50 mmol) are dissolved in $CH_2Cl_2$ followed by stirring at room temperature for 24 hours. The solvent is removed in a rotary evaporator and the residue purified by column chromatography (hexane:ethyl acetate, 1:1) to obtain the product as yellow oil (0.84 g, 51%). HRMS $C_{179}H_{210}N_{10}O_{54}$ [M+2Na]$^{2+}$ calc. 1704.6895, obs. 1704.6788.

The invention claimed is:

1. A process for preparing chimeric peptide-peptoidic dendrimers by multiple iterative multicomponent reactions, comprising
    reacting a polyfunctionalized core unit with two to six further components which each have different functionalities with different reactivities or protective groups, wherein this multicomponent reaction leads to a branched compound by reactively branching the 3 to 7 components,
    activating the less reactive functionalities and/or deprotecting the protective groups to generate a functionalized first generation of a branched dendrimer,
    reacting the functionalized first generation of the branched dendrimer with further components which each have different functionalities with different reactivities or protective groups, wherein this multicomponent reaction leads to a subsequent branched compound by reactively branching the 3 to 7 components, and
    iteratively repeating the aforementioned steps to obtain peptide-peptoidic dendrimers of higher generations.

2. The process as claimed in claim 1, wherein the multiple iterative multicomponent reaction is a UGI or PASSERINI multicomponent reaction, the polyfunctionalized core unit has UGI-reactive functionalities and is reacted with bifunctional components which each have a first UGI-reactive functionality and a second terminal UGI-reactive functionality which is in protected form (PURG, protected UGI-reactive group) in a UGI or PASSERINI multicomponent reaction, wherein the second protected UGI-reactive functionality is activable after the reaction by deprotecting the PURGs back to UGI-reactive groups.

3. The process as claimed in claim 1, wherein an appropriate UGI (4CR) four-component reaction is used to react an amine derivative, a carbonyl component selected from aldehyde or ketone, a carboxylic acid and an isocyanide derivative (isonitrile) to form an α-aminoacylamide derivative.

4. The process as claimed in claim 1, further comprising the use of bifunctional synthons which comprise a nonbranching unit (NBU) whereby 1→2 branching or linear prolongation is freely generatable in every generation.

5. The process as claimed in claim 1, wherein the polyfunctional core unit is synthesized via one or more UGI or PASSERINI multicomponent reactions to produce di-, tri- or tetrafunctionalized, preferably tri- or tetrafunctionalized, core units or branching sites.

6. The process as claimed in claim 1, wherein appropriate protective-group chemistry is used to specifically activate protected functions selectively in each generation of the divergently constructed dendrimer or in the core unit, wherein the protective groups and reaction conditions are chosen such that other protected functions remain unchanged and do not undergo any secondary reactions.

7. The process as claimed in claim 1, wherein convertible isonitriles are used such that the resulting C-terminal amide group of the UGI unit is converted into a carboxylic acid and thus is in an activated state for participation in relation to the next generation.

8. The process as claimed in claim 1, wherein the resulting N-terminal amide group of the UGI unit is selectively cleaved and converted into a primary amino group and thus is in an activated state for participation in relation to the next generation.

9. The process as claimed in claim 3, further comprising forming stereogenic sites in the α-aminoacylamide derivative.

10. The process as claimed in claim 1, further comprising activating the surface of the resultant higher generation peptide-peptoidic dendrimers in a further UGI-4CR, wherein peptide-peptoidic dendrimers generated have different functionalities at their surface.

11. Chimeric peptide-peptoidic, peptoidic, peptidic, depsipeptidic dendrimers and also corresponding janus dendrimers, obtained by the process as claimed in claim 1.

12. Chimeric peptide-peptoidic dendrimers as claimed in claim 11, obtained by the process wherein the amino component of some or all UGI reactions has emanated from ammonia or an ammonium salt, or from a protected ammonia equivalent which is selectively detachable in the presence of other functional groups of the dendrimer, especially amide groups.

13. First generation peptide-peptoidic dendrimers as claimed in claim 11 based on a core unit as "zero-th generation".

14. The chimeric dendrimer of claim 11 which is peptide-peptoidic.

* * * * *